US012800167B2

(12) United States Patent
Hoyda et al.

(10) Patent No.: US 12,800,167 B2
(45) Date of Patent: Nov. 17, 2026

(54) AIR PURIFICATION SYSTEM

(71) Applicant: Clean Air Zone Inc., Corona, NY (US)

(72) Inventors: Serge B. Hoyda, Great Neck, NY (US); Corey L. Macphee, New Brunswick (CA)

(73) Assignee: Clean Air Zone Inc., Corona, NY (US)

(*) Notice: Subject to any disclaimer, the term of this patent is extended or adjusted under 35 U.S.C. 154(b) by 619 days.

(21) Appl. No.: 17/181,604

(22) Filed: Feb. 22, 2021

(65) Prior Publication Data

US 2021/0270476 A1 Sep. 2, 2021

Related U.S. Application Data

(63) Continuation of application No. 16/231,396, filed on Dec. 22, 2018, now Pat. No. 10,969,125.

(Continued)

(51) Int. Cl.

| | |
|---|---|
| ***F24F 8/133*** | (2021.01) |
| ***A61L 9/04*** | (2006.01) |
| ***B01D 53/78*** | (2006.01) |
| ***B01D 53/84*** | (2006.01) |
| ***B01D 53/96*** | (2006.01) |
| ***F24F 8/10*** | (2021.01) |
| ***F24F 8/175*** | (2021.01) |

(Continued)

(52) U.S. Cl.

CPC ................ *F24F 8/133* (2021.01); *A61L 9/04* (2013.01); *B01D 53/78* (2013.01); *B01D 53/84* (2013.01); *B01D 53/96* (2013.01); *F24F 8/10* (2021.01); *F24F 8/175* (2021.01); *B01D 2258/06* (2013.01); *B01D 2259/4591* (2013.01); *F24F 8/117* (2021.01); *F24F 8/15* (2021.01)

(58) Field of Classification Search

CPC ............... A61L 9/17; A61L 9/145; A61L 9/04

See application file for complete search history.

(56) References Cited

U.S. PATENT DOCUMENTS

| | | | | |
|---|---|---|---|---|
| 1,102,377 A * | 7/1914 | Wilton | ................ | A47G 21/184 221/256 |
| 2,638,644 A | 5/1953 | Rauhut | | |

(Continued)

FOREIGN PATENT DOCUMENTS

| | | |
|---|---|---|
| DE | 101 00 674 A1 | 8/2002 |
| DE | 10 2016 120 534 B3 | 11/2017 |

(Continued)

OTHER PUBLICATIONS

International Search Report of PCT/US2021/18133 mailed Jun. 15, 2021.

(Continued)

*Primary Examiner* — Donald R Spamer

(74) *Attorney, Agent, or Firm* — Collard & Roe, P.C.

(57) ABSTRACT

There is disclosed a system and process for purifying air. The system includes a housing and a plurality of inner and outer chambers. A solution of water and a biological reagent is configured to flow around the inner and outer walls of the inner and outer chambers while air is passed adjacent to this fluid flow. This causes an interaction between the air and the fluid solution to cleanse the air. The air is then discharged from the chamber. There is also disclosed a container having a rolling base allowing the container to be more transportable.

20 Claims, 102 Drawing Sheets

Related U.S. Application Data

(60) Provisional application No. 62/711,297, filed on Jul. 27, 2018, provisional application No. 62/610,092, filed on Dec. 22, 2017.

(51) Int. Cl.
*F24F 8/117* (2021.01)
*F24F 8/15* (2021.01)

(56) References Cited

U.S. PATENT DOCUMENTS

| | | | |
|---|---|---|---|
| 4,689,302 | A | 8/1987 | Goldberg et al. |
| 4,746,336 | A | 5/1988 | Mignot |
| 5,589,132 | A | 12/1996 | Zippel |
| 5,656,242 | A | 8/1997 | Morrow et al. |
| 5,756,899 | A | 5/1998 | Ugai et al. |
| 6,053,968 | A | 4/2000 | Miller |
| 6,500,244 | B2 | 12/2002 | Sanchez |
| 6,589,489 | B2 | 7/2003 | Morrow et al. |
| 6,810,732 | B2 | 11/2004 | Shon |
| 6,916,630 | B2 | 7/2005 | Sofer |
| 7,112,232 | B2 | 9/2006 | Chang et al. |
| 7,147,692 | B2 | 12/2006 | Fornai et al. |
| 7,665,358 | B2 | 2/2010 | Calabrese |
| 7,722,708 | B2 | 5/2010 | Powell, Jr. et al. |
| 8,083,837 | B2 | 12/2011 | Mazzanti et al. |
| 8,357,359 | B2 | 1/2013 | Woo et al. |
| 8,444,922 | B2 | 5/2013 | Kusuura |
| 8,748,167 | B2 | 6/2014 | Greene et al. |
| 9,044,700 | B2 | 6/2015 | Gruenbacher et al. |
| 9,327,223 | B2 | 5/2016 | Gruenbacher et al. |
| 9,573,088 | B2 | 2/2017 | Gruenbacher et al. |
| 9,579,597 | B2 | 2/2017 | Gruenbacher et al. |
| 2004/0184949 | A1 | 9/2004 | Mcellen |
| 2006/0097411 | A1 | 5/2006 | Kim |
| 2006/0169141 | A1 | 8/2006 | Yuen |
| 2007/0122320 | A1 | 5/2007 | Pletcher et al. |
| 2008/0156015 | A1 | 7/2008 | Meyerholtz et al. |
| 2008/0271527 | A1 | 11/2008 | Hewitt |
| 2010/0047117 | A1 | 2/2010 | Bernard |
| 2010/0154534 | A1 | 6/2010 | Hampton |
| 2011/0150814 | A1 | 6/2011 | Woo et al. |
| 2011/0303093 | A1 | 12/2011 | Jeung |
| 2011/0318817 | A1 | 12/2011 | Greene et al. |
| 2012/0167660 | A1 | 7/2012 | Calcote |
| 2012/0183488 | A1 | 7/2012 | Woo et al. |
| 2012/0183489 | A1 | 7/2012 | Woo et al. |
| 2013/0085204 | A1 | 4/2013 | Hollingshead et al. |
| 2014/0208781 | A1 | 7/2014 | Hampton |
| 2015/0004064 | A1* | 1/2015 | Lee .................... B01D 46/0028 165/59 |
| 2015/0266031 | A1 | 9/2015 | Mills et al. |
| 2016/0061646 | A1 | 3/2016 | Mestivier et al. |
| 2017/0122600 | A1 | 5/2017 | Son et al. |
| 2019/0203960 | A1 | 7/2019 | Hoyda et al. |
| 2020/0064175 | A1 | 2/2020 | Krammer et al. |
| 2020/0179873 | A1 | 6/2020 | Hoyda et al. |
| 2022/0397440 | A1 | 12/2022 | Broadbent |

FOREIGN PATENT DOCUMENTS

| | | | |
|---|---|---|---|
| EP | 0 328 782 | A1 | 8/1989 |
| KR | 1997-0030147 | A | 6/1997 |
| WO | 9407122 | A1 | 3/1994 |
| WO | 2004008034 | A1 | 1/2004 |
| WO | 2014162006 | A1 | 10/2014 |
| WO | 2021190749 | A1 | 9/2021 |

OTHER PUBLICATIONS

Notice of Transmittal of the International Search Report of PCT/US2021/18133 mailed Jun. 15, 2021.
Written Opinion of the International Searching Authority of PCT/US2021/18133 mailed Jun. 15, 2021.
International Search Report in PCT/US22/35385 dated Oct. 5, 2022.
Written Opinion in PCT/US22/35385 dated Oct. 5, 2022.
International Search Report in PCT/US23/17771 dated Jun. 21, 2023.
Written Opinion of the Interntional Searching Authority in PCT/US23/17771 dated Jun. 21, 2023.
Notification of Transmittal of the International Search Report and the Written Opinion of the International Searching Authority in PCT/US23/17771 dated Jun. 21, 2023.
Notice of Allowance in Chinese Application No. 201880089590.6 dated Oct. 21, 2022.
Extended European Search Report of European Application No. 18892900.4 dated Oct. 8, 2021.
International Search Report of PCT/US2018/067402, issued Mar. 28, 2019.
Written Opinion of the International Searching Authority of PCT/US2018/067402, issued Mar. 28, 2019.
International Preliminary Report on Patentability with Written Opinion of the International Searching Authority of PCT/US2018/067402, mailed Jul. 2, 2020.
Chinese Office Action in Chinese Application No. 201880089590.6 dated Oct. 27, 2021 with English translation.
International Preliminary Report on Patentability with Written Opinion of the International Searching Authority of PCT/ JS2021/018133 dated Aug. 11, 2022.
Second Chinese Office in Chinese Patent Application 201880089590.6 dated Jun. 29, 2022.
First Examination Report in Indian Office Action No. 202027030194 dated Apr. 7, 2022 with English translation.
U.S. Office Action in U.S. Appl. No. 17/852,341 dated Sep. 12, 2023.
U.S. Office Action in U.S. Appl. No. 16/231,396 dated Oct. 30, 2019.
U.S. Final Office Action in U.S. Appl. No. 16/231,396 dated Apr. 20, 2020.
U.S. Advisory Action in U.S. Appl. No. 16/231,396 dated May 18, 2020.
U.S. Office Action in U.S. Appl. No. 16/231,396 dated Jun. 26, 2020.
U.S. Notice of Allowance in U.S. Appl. No. 16/231,396 dated Oct. 16, 2020.
U.S. Notice of Allowance in U.S. Appl. No. 16/231,396 dated Nov. 23, 2020.
Canadian Examination Report in Canadian Patent Application Serial No. 3, 167,873, dated Oct. 19, 2023.
Canadian Examination Report in Canadian Patent Application Serial No. 3, 127,077, dated Nov. 1, 2023.
Canadian Examiner's Report in Canadian Application No. 3, 127,077 dated Aug. 9, 2024.
U.S. Non-Final Office Action in U.S. Appl. No. 17/715,694 dated Sep. 11, 2024.

* cited by examiner

FIG. 30A
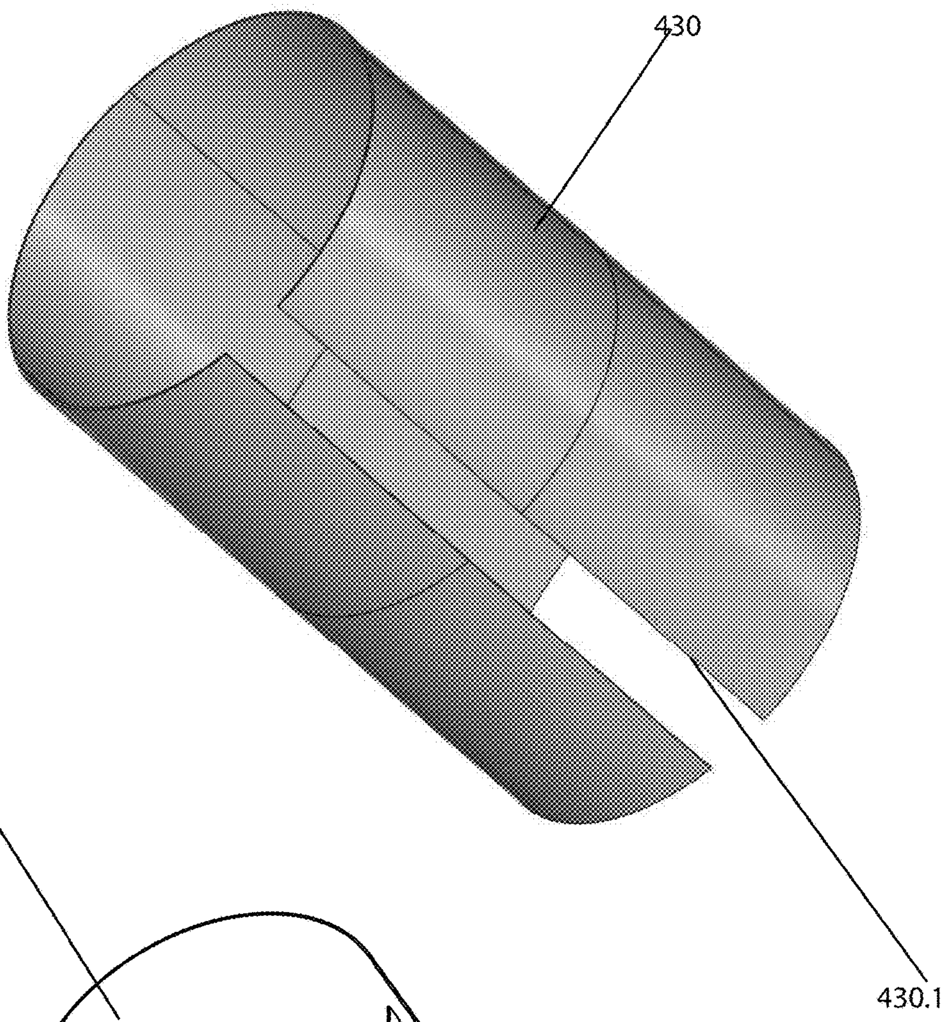
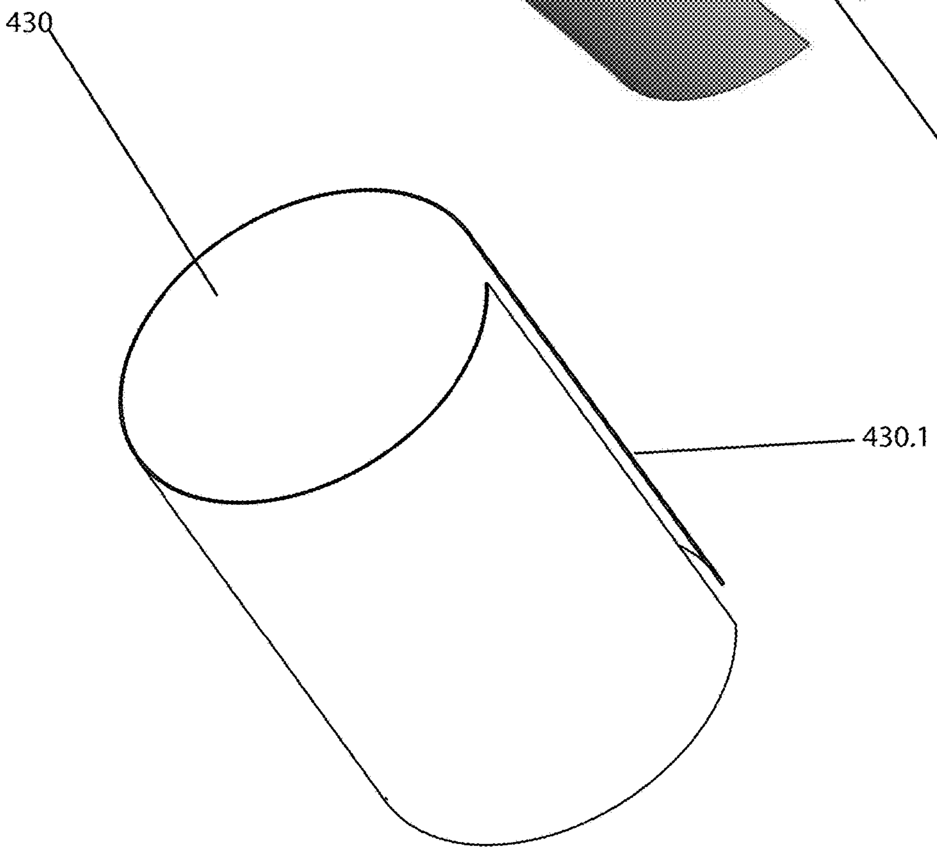
FIG. 30B

FIG. 37A
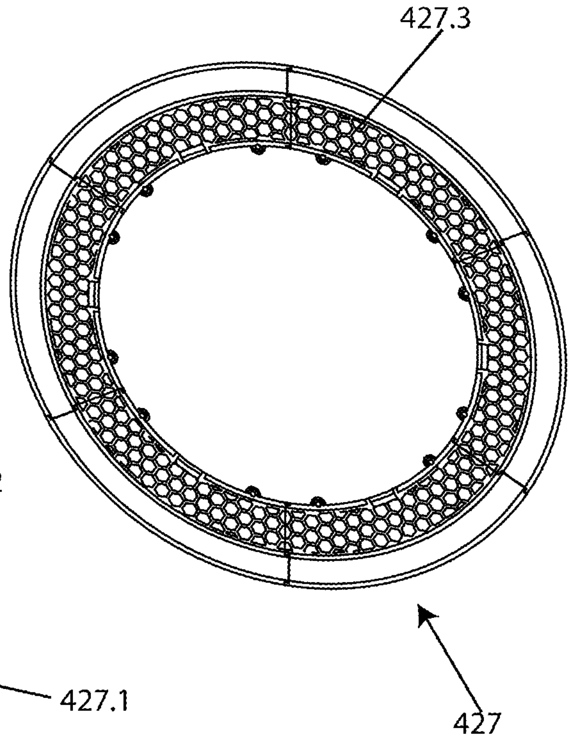
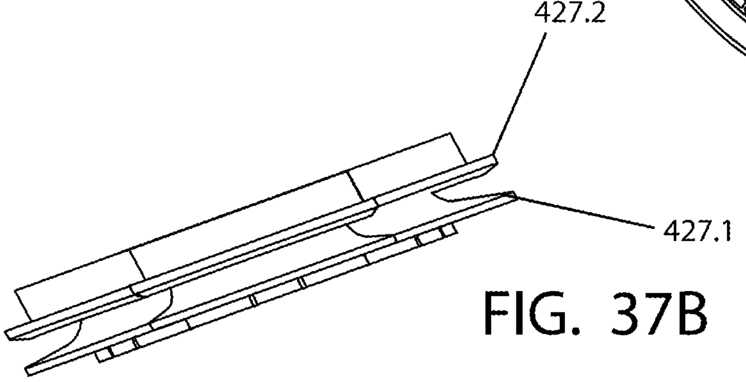
FIG. 37B
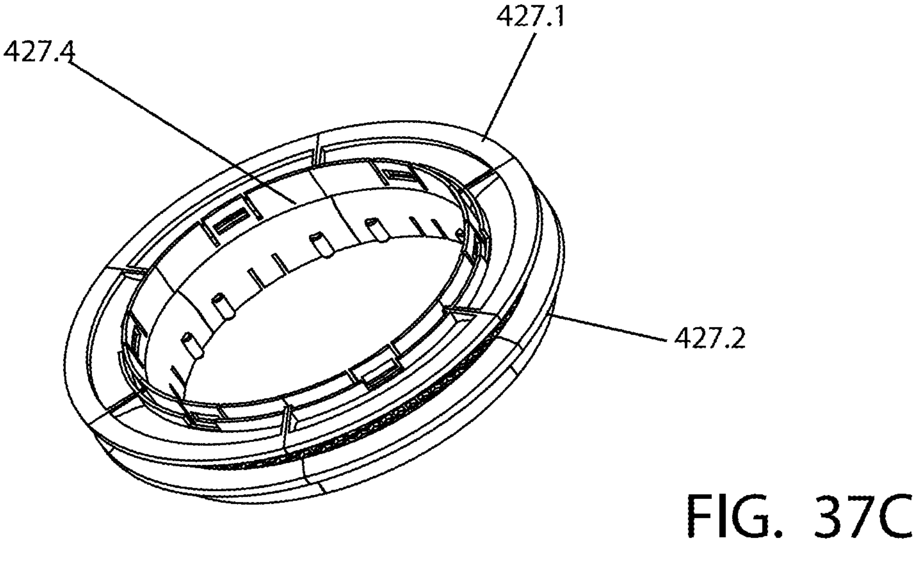
FIG. 37C

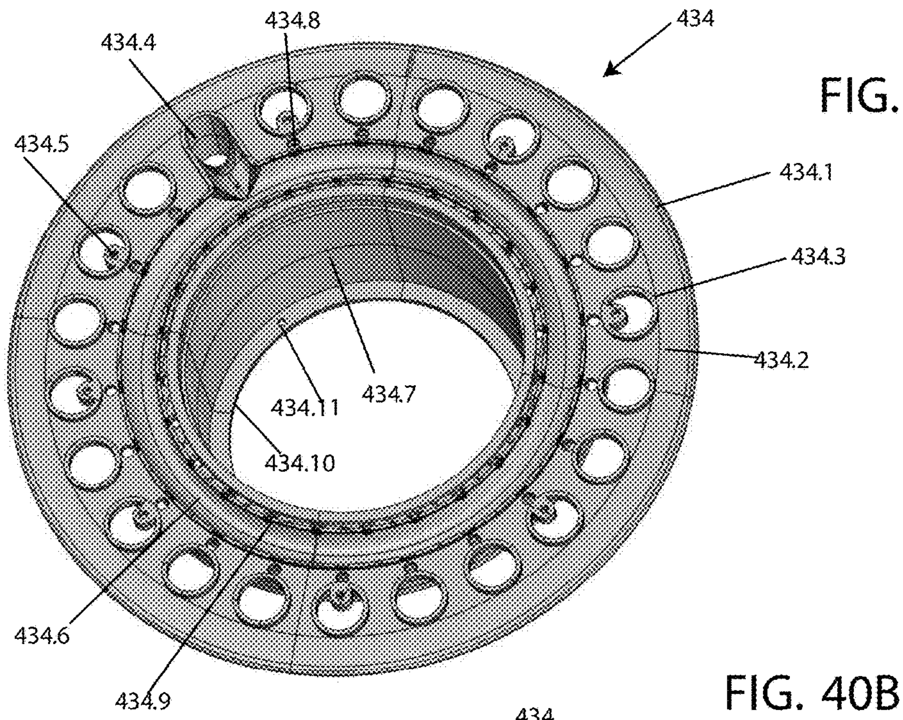
FIG. 40A
FIG. 40B
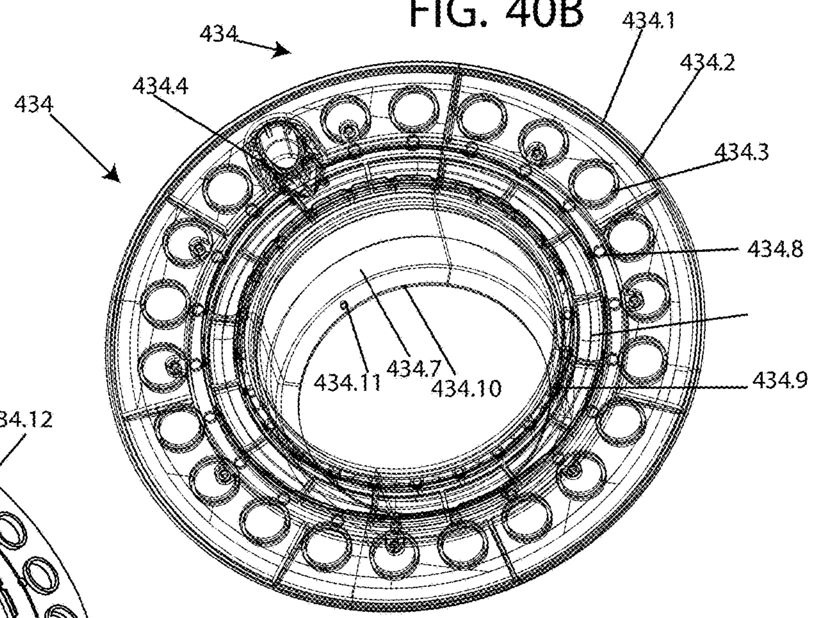
FIG. 40C
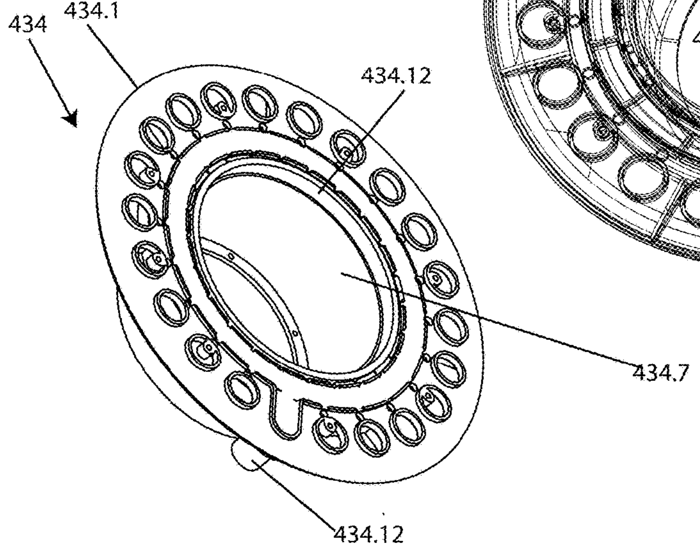

FIG. 43A
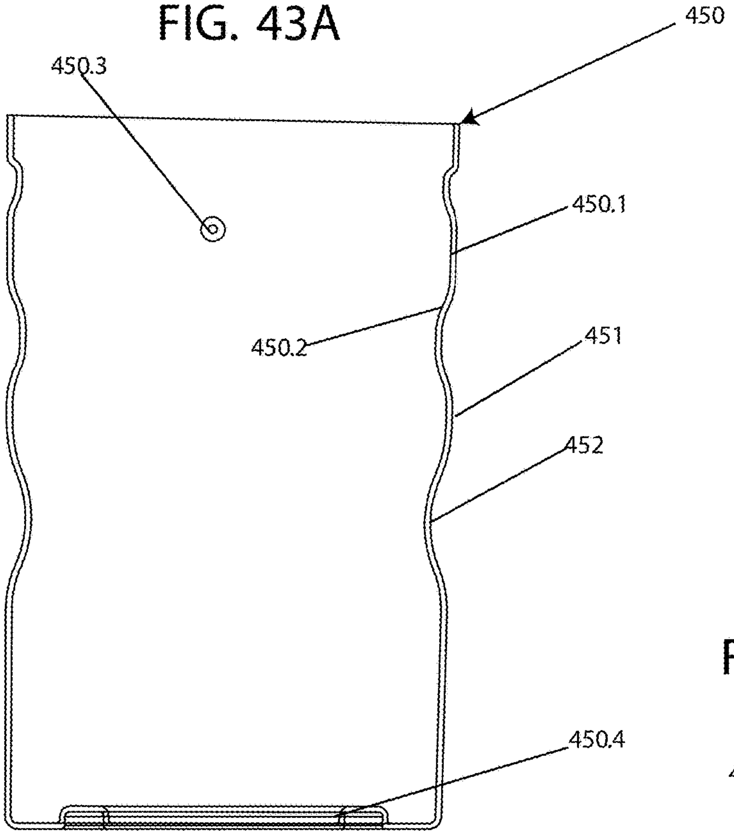
FIG. 43B
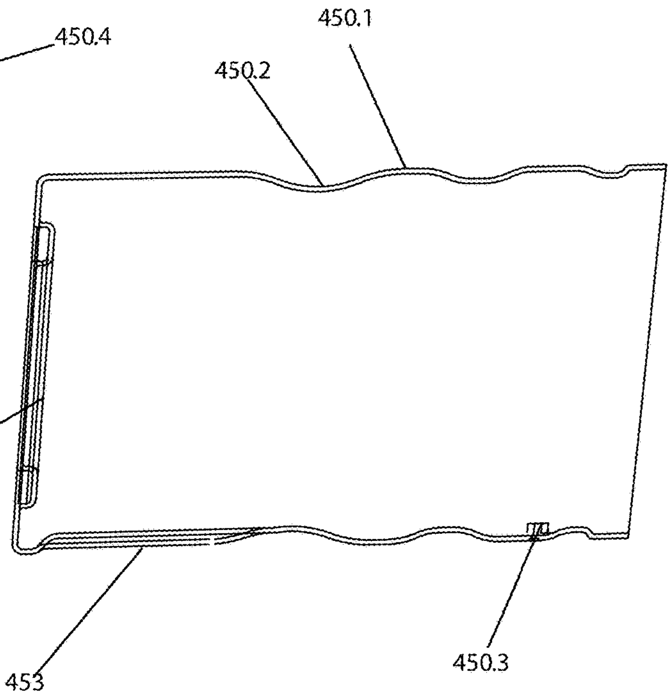
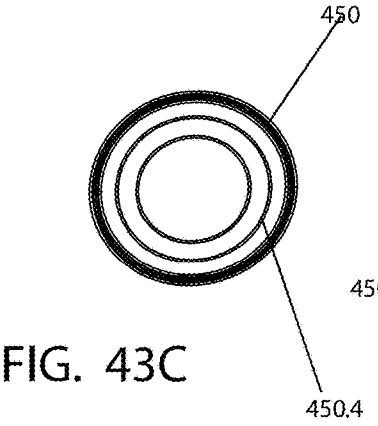
FIG. 43C

FIG. 45A
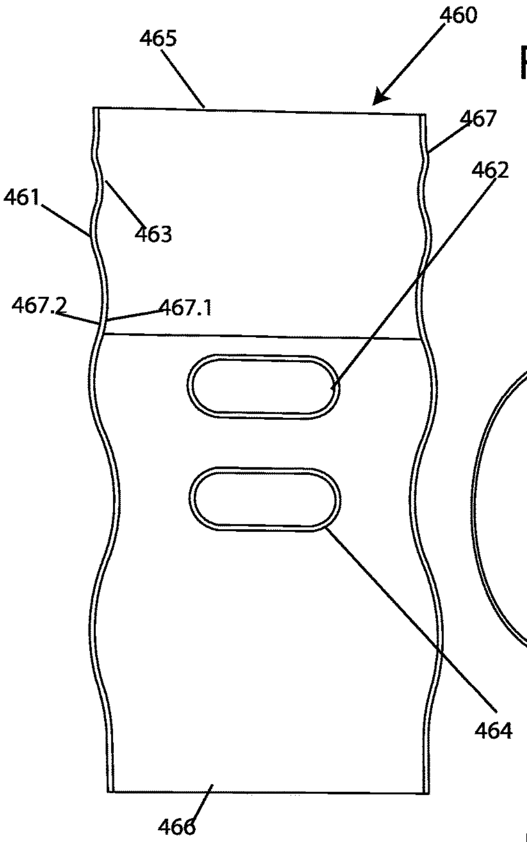
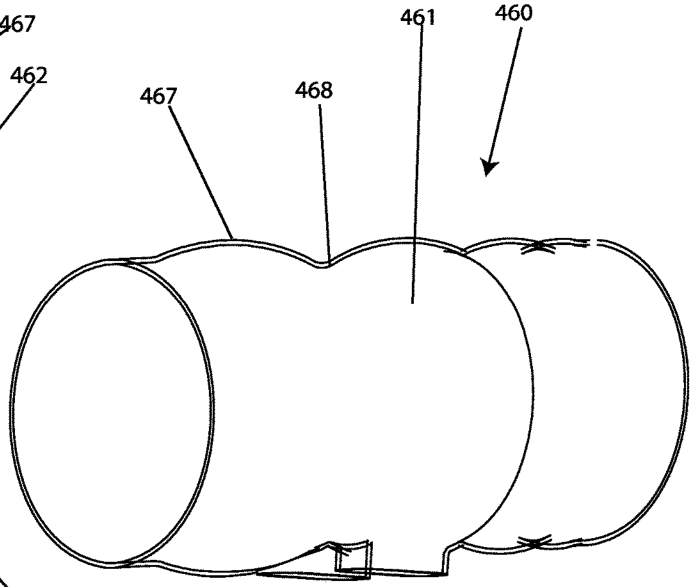
FIG. 45B
FIG. 45C
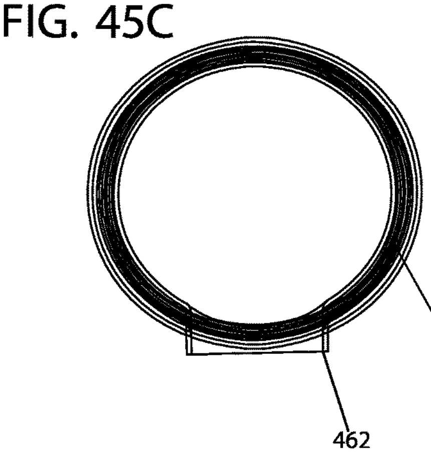
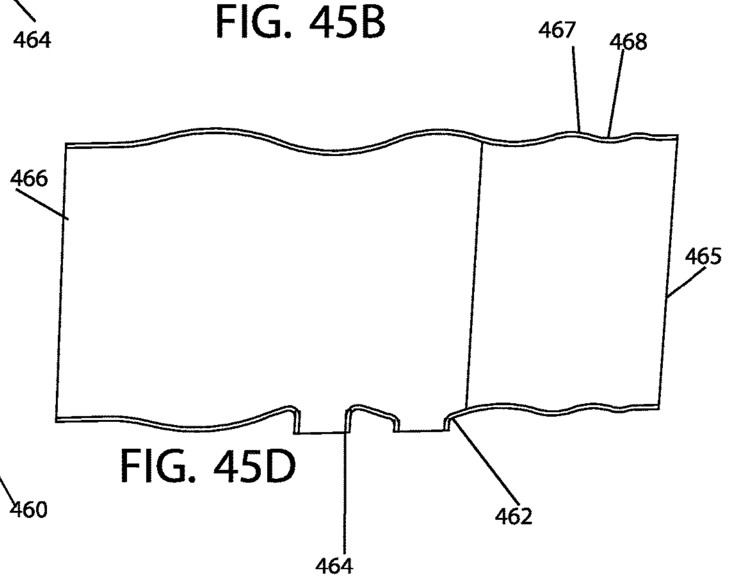
FIG. 45D

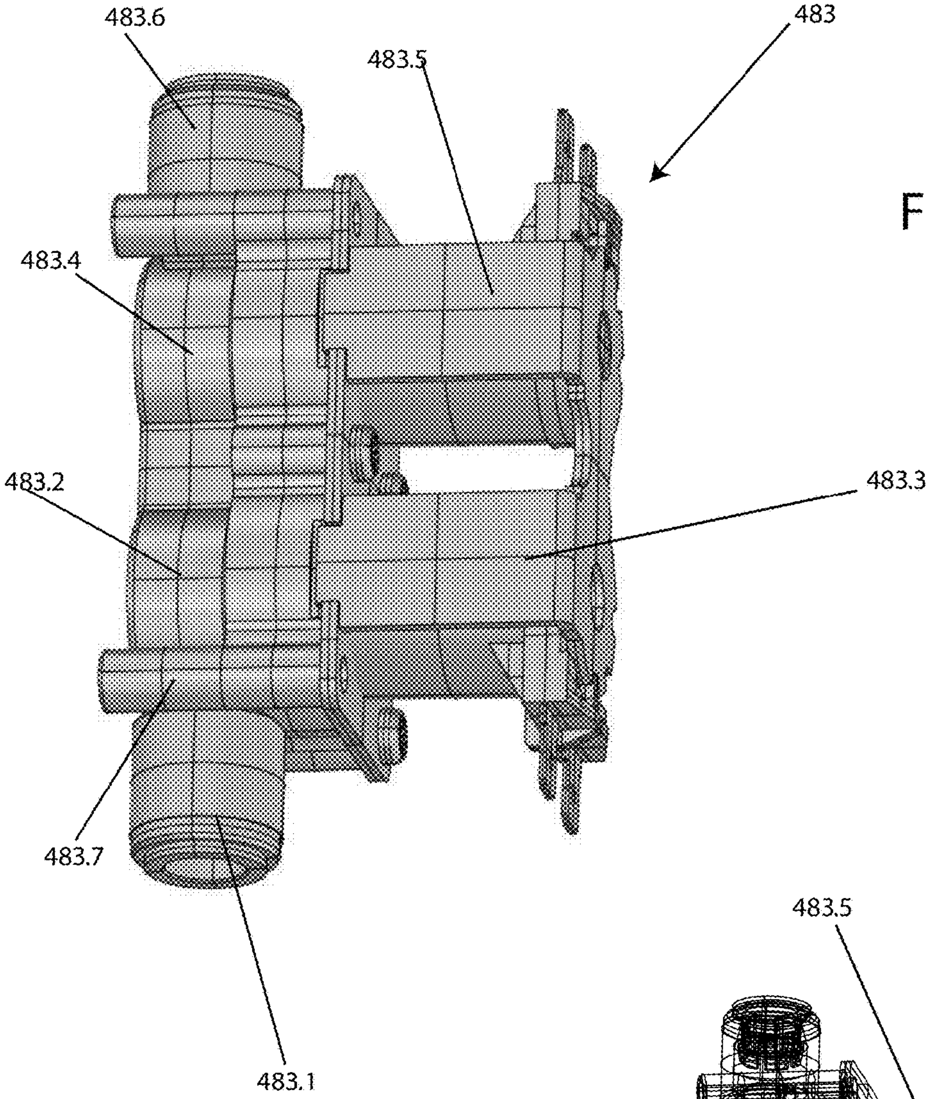
FIG. 52A
FIG. 52B
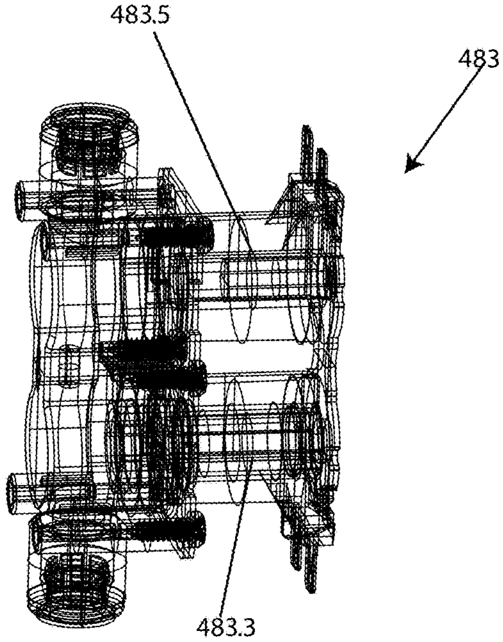

FIG. 62A
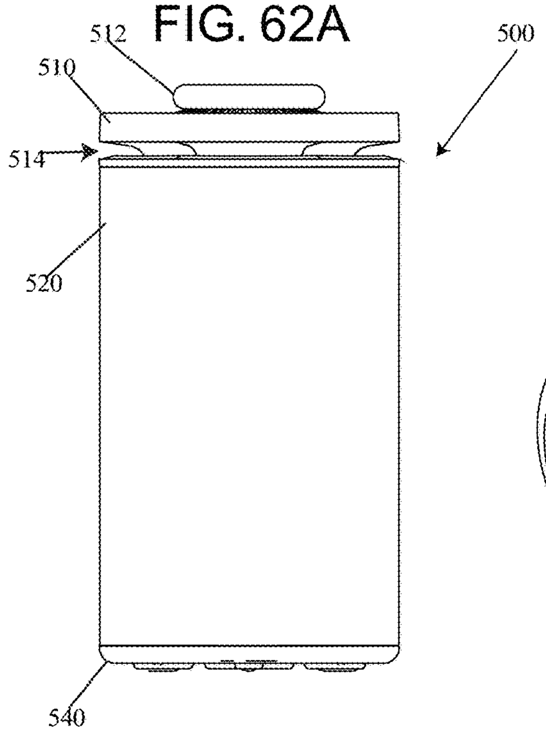
FIG. 62B
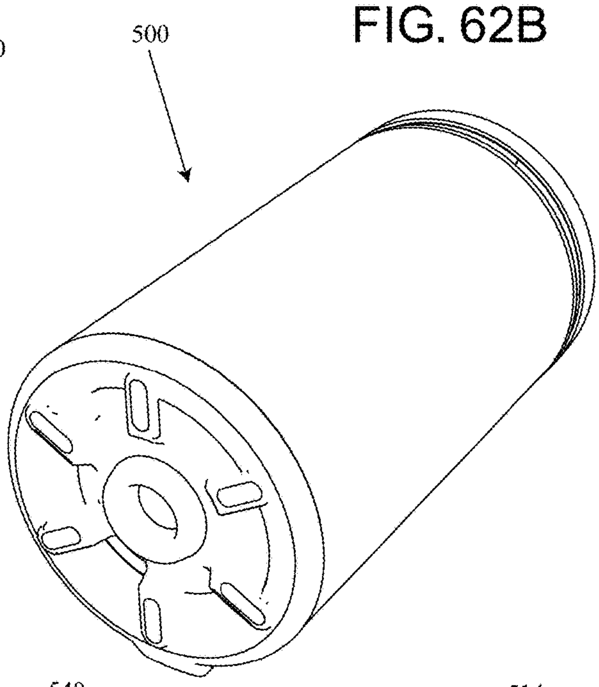
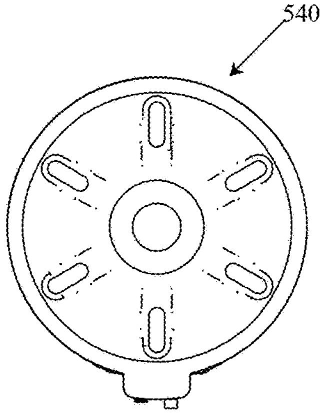
FIG. 62C
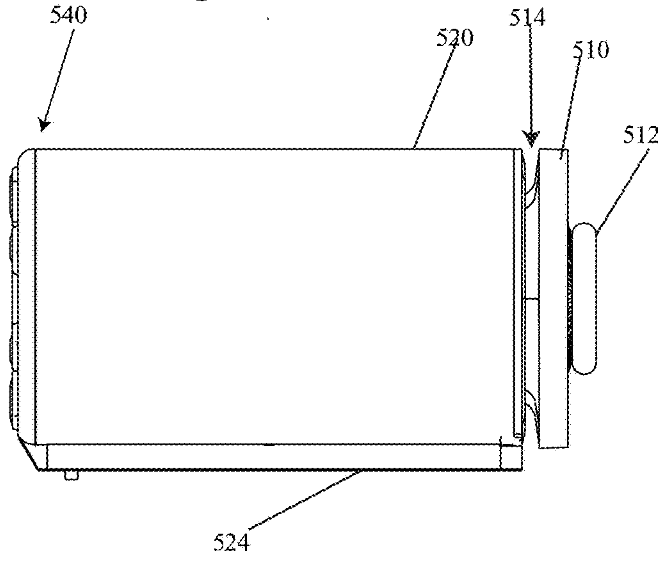
FIG. 62D

FIG. 67A
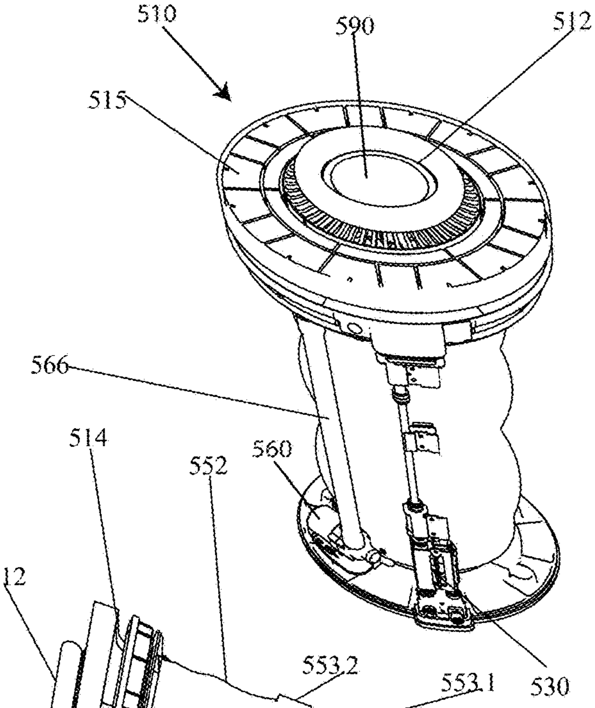
FIG. 67B
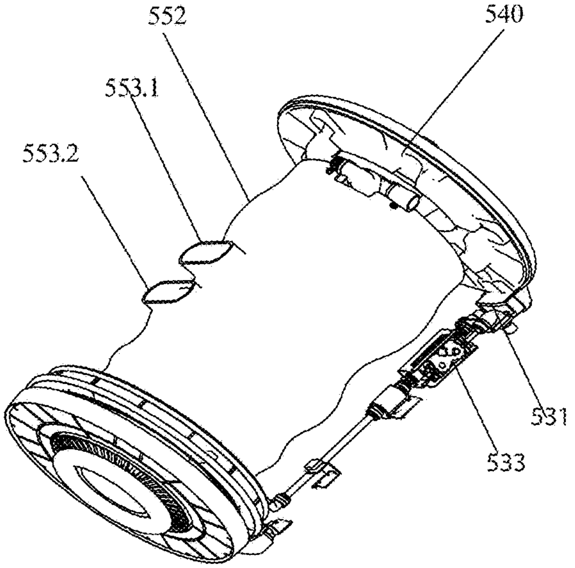
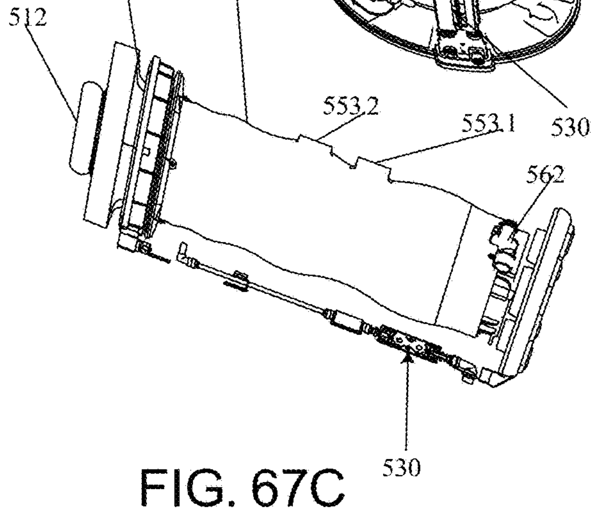
FIG. 67C
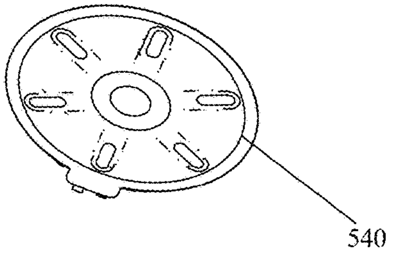
FIG. 67D

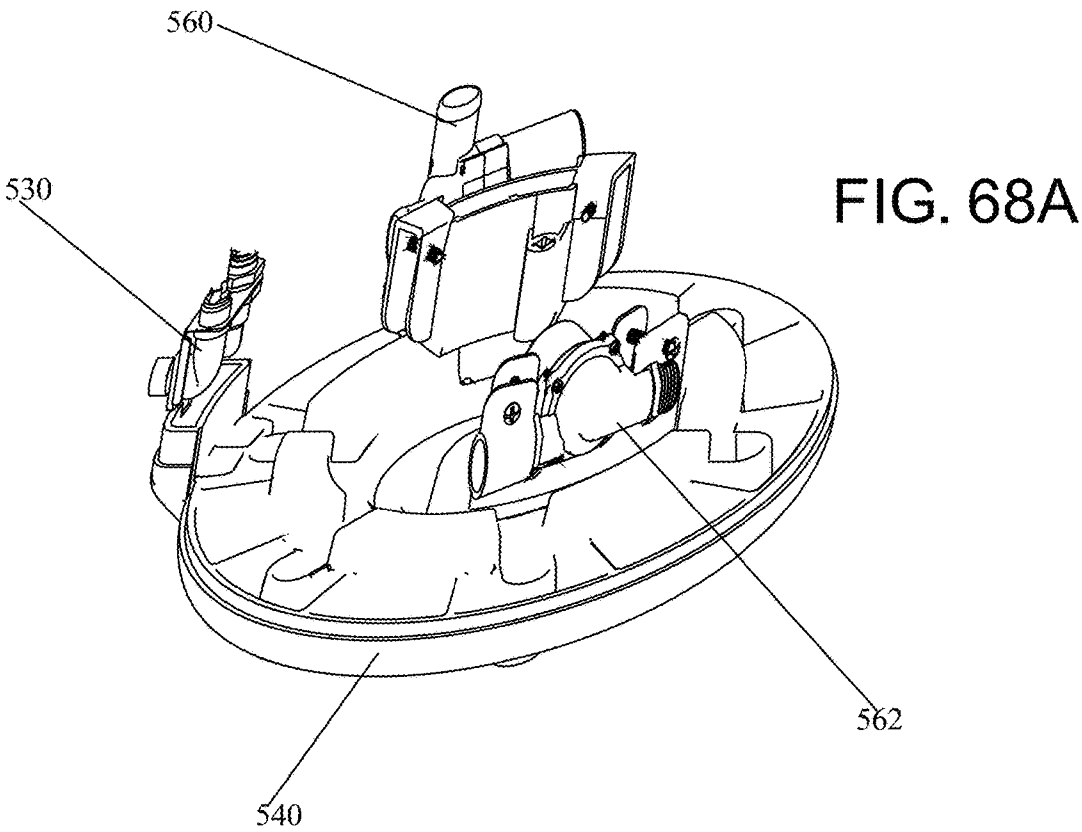
FIG. 68A
FIG. 68B
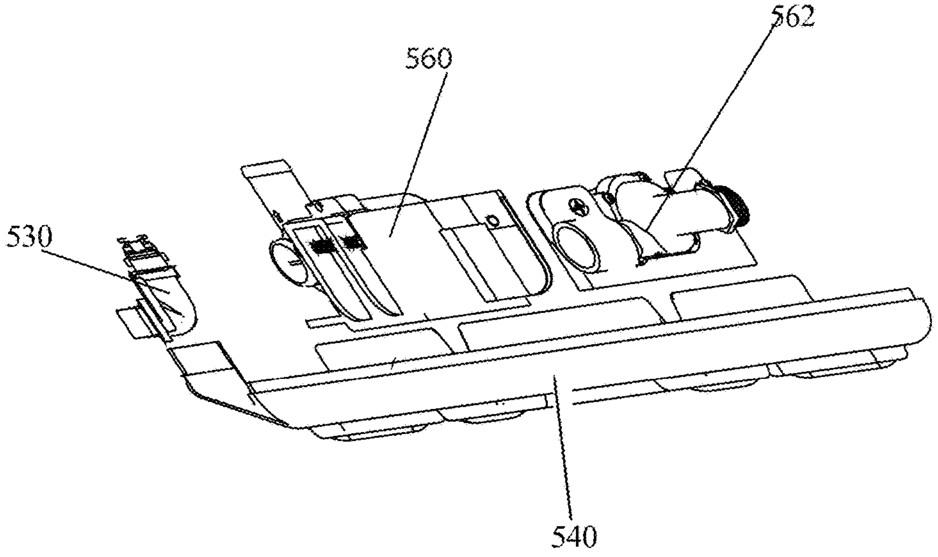

FIG. 85A
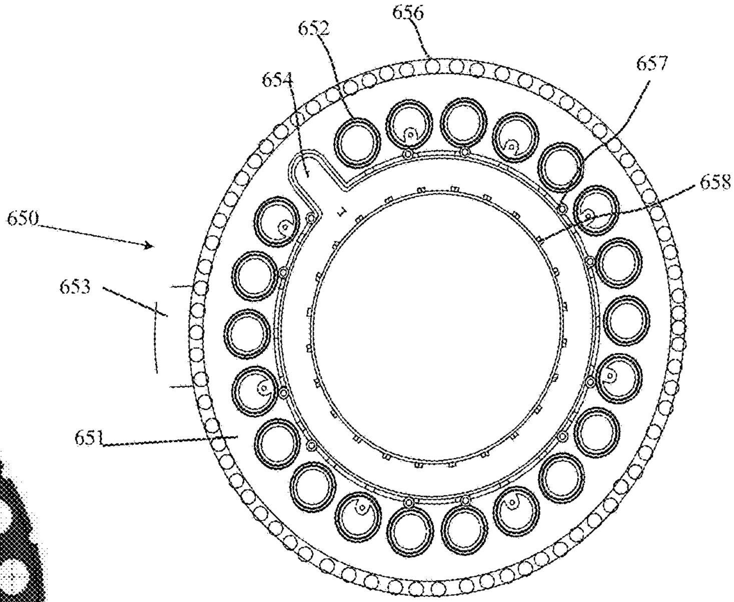
FIG. 85B
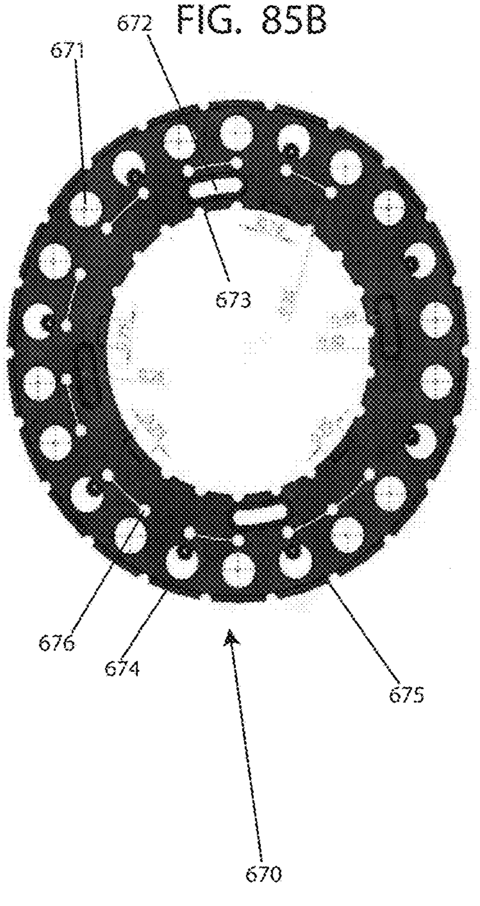
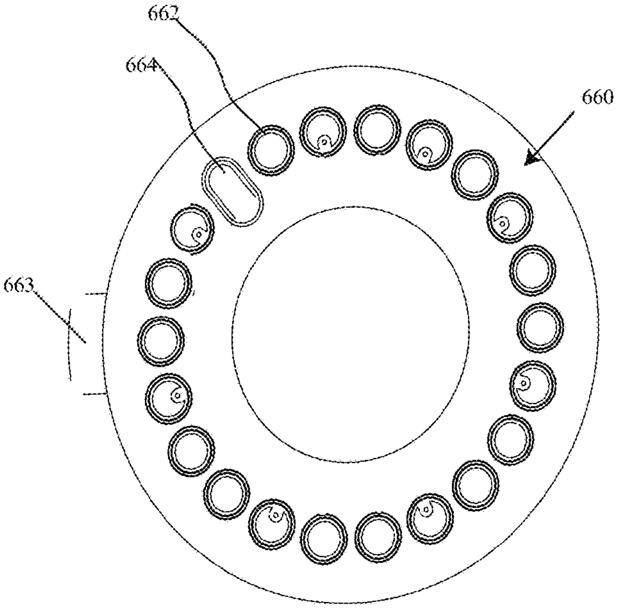
FIG. 85c

AIR PURIFICATION SYSTEM

CROSS REFERENCE TO RELATED APPLICATIONS

This application is a continuation application of U.S. patent application Ser. No. 16/231,396 filed on Dec. 22, 2018, which is a non-provisional application that hereby claims priority from U.S. Provisional Application Ser. No. 62/711,297 filed on Jul. 27, 2018 and U.S. Provisional Application Ser. No. 62/610,092 filed on Dec. 22, 2017 the disclosures of which are hereby incorporated herein by reference in their entirety.

BACKGROUND OF THE INVENTION

At least one embodiment of the invention relates to an air purification system. For example, at least one embodiment of the invention relates to an air purification system which uses at least one biological material which was disclosed in U.S. Pat. No. 6,916,030 invented by Samir Sofer, et al the disclosure of which is hereby incorporated herein by reference.

In at least one embodiment, there can be continuous or batch flow reactors. The technology employed is spun from spiral reactor technology of Goldberg (patent U.S. Pat. No. 4,689,302) the disclosure of which is hereby incorporated herein by reference and others. This prior technology claims that chemical interaction between a fluid (liquid or gas) being convected between channel walls laced with a biological solution in the wall surfaces as well as residing in an aqueous solution in a region towards a bottom region of the tank yields a desired effect or product. The narrower and longer the channel, the more opportunity for interaction and completion of the reaction. Thus, there is a need for a new air purification system which is configured to provide a safe and efficient means for cleaning air.

SUMMARY OF THE INVENTION

In at least one embodiment, there is at least one air purification system which includes a reactor or container which is configured to contain a biological reagent. To create this affect, water containing the dissolved biological reagent in the wall collects impurities in the passing airflow and carries them by gravity effect to a pool of the dissolved reagent below, where the reagent continues working on the impurities. Occasionally, the entire device must be cleaned to remove the solidified and condensed residuals. To reduce the space for a sufficiently long channel multiple housings can be used or in another embodiment a spiral design is chosen.

In at least one embodiment of the invention, a pump is employed to move the solution containing the reagent from the lower collection bin to a porous header above the vertical outer core pipe(s). An exhaust fan draws air down past the outside of the vertical collection wall through and out the exhaust. In one embodiment, the exhaust fan can operate in one direction to create a negative pressure solution. In the negative pressure solution, the fan is disposed adjacent to an exhaust of the container, and operates in a direction to create a negative pressure inside of the container thereby drawing air inside of the container. In another embodiment, the fan can operate such that it revolves in an opposite direction wherein the fan is located towards an inlet port drawing air inside of the container, and thereby driving air inside of the container and pushing existing air outside of the container.

Water vapor collected in the process is replaced by manually refilling the process container. Reagent concentration is maintained by periodically adding concentrated reagent. Waste removal is achieved by cleaning the entire machine periodically.

In at least one modified embodiment, there can be a fluid level control together with a valved water supply. The air flow and water recycling are quite similar to the first application.

In another embodiment of the invention, there can be a water collection capability that is added to reduce water loss and the need for new water. Control of this process permits the device to also act as a room humidifier or dehumidifier. In the case of the dehumidifier, excess water is dynamically captured at the air outlet and is condensed to fall back into the machine water stream. The amount of humidity released to a room is controlled thermally, mechanically, or electrically.

Alternatively, water collection can be performed on the room atmosphere and returned to the machine through a gravity or pump driven process (FIG. 3*b*).

In another embodiment, waste control is maintained using a natural collection method. The biological solution is saturated where the excess is dispersed in the aqueous solution and is heavier than water This causes a natural settling of the excess material which is left undisturbed at the bottom of the tank.

Another collection method Involves Chemical treatment to cause coagulation of the undisturbed material. Over time the coagulant forms a gelatin like substance that can later be removed from the tank bottom.

Alternatively, a horizontal coarse screen can be placed above the zone of precipitation to further lower any movement of the settled material. The screen will act as a reel to trap material to be later removed.

Radial louvres or other form of mechanical closure are attached to the walls at the waste level and manually or automatically controlled for closure to aid in the cleaning process.

To remove the bottommost material, at least one valved exit port at the outer shell at or near the bottom is provided. With the louvres closed and the pump outlet switched from up to down pressurized flow can be made to drive the waste slurry out the exit port.

In another embodiment of the invention, UV light treatment before or/and after the microbiological treatment provides added virus protection to the treated air. Care must be taken to ensure that the microbiological treatment is not exposed to the ultra-violet light.

In another embodiment of the invention, the device and/or air purification process can be applied within a zoned HVAC system to provide clean air at multiple room outlets as part of the heating and air conditioning process.

In another embodiment of the invention, the system can be incorporated into a HVAC system so that it cleans the air while also treating the temperature and the humidity in the air.

In at least one embodiment there is at least one surface that is formed as a corrugated container that is formed by a wavy design or undulating surface.

In all of these designs the size and shape of the machine can be varied, however the above processing can still be used. The processor/motherboard and electronic components can be adapted for use with other air purification machines using a biological reagent in combination with water that is configured to attract particles in the air.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views:

FIG. 30A is a perspective view of the outer cover or skin;

FIG. 30B is another perspective view of the outer cover or skin;

FIG. 37A is a bottom view of an air inlet;

FIG. 37B is a side view of the air inlet;

FIG. 37C is a top perspective view of the air inlet;

FIG. 40A is a top perspective view of the bottom tray;

FIG. 40B is a top perspective view of the bottom tray;

FIG. 40C is another top perspective view of the bottom tray;

FIG. 43A is a side cross-sectional view of the main tank;

FIG. 43B is another side cross-sectional view of the main tank;

FIG. 43C is a top view of the main tank;

FIG. 45A is a side view of the outer core pipe;

FIG. 45B is a side view of the outer core pipe;

FIG. 45C is a top view of the outer core pipe;

FIG. 45D is a side view of the outer core pipe;

FIG. 52A is a side view of the solenoid;

FIG. 52B is a side X-ray view of the solenoid;

FIG. 62A is a side view of another embodiment;

FIG. 62B is a bottom perspective view of the embodiment of FIG. 62A;

FIG. 62C is a bottom view of the embodiment of FIG. 62A;

FIG. 62D is a side view of the embodiment of FIG. 62A;

FIG. 67A is a top side perspective view of the embodiment of FIG. 63 with the skin and cores removed;

FIG. 67B is a side perspective view of the embodiment of FIG. 67A;

FIG. 67C is another side perspective view of the embodiment shown in FIG. 67A;

FIG. 67D is a bottom view of the embodiment of FIG. 67A;

FIG. 68A is a bottom perspective view of a bottom section of the embodiment shown in FIG. 63;

FIG. 68B is a side view of the embodiment shown in FIG. 68A;

FIG. 82A is a view of a first tray;

FIG. 82B is a view of a second tray;

FIG. 83 is a view of the two trays of FIGS. 82A and 82B laid one on top of the other;

FIG. 84 is a view of the two trays placed inside of the outer container;

FIG. 85A is a view of a bottom cover for a tray;

FIG. 85B is an alternative design for a bottom cover tray;

FIG. 85C is a view of a top cover for a tray;

FIG. 86 is an open side view of another embodiment of the invention;

FIG. 87 is an open side view of the embodiment of FIG. 86;

FIG. 88A is an open side view of another embodiment;

FIG. 88B is another view of the embodiment of FIG. 88A

FIG. 89A is an open side view of another embodiment;

Figure 89A:
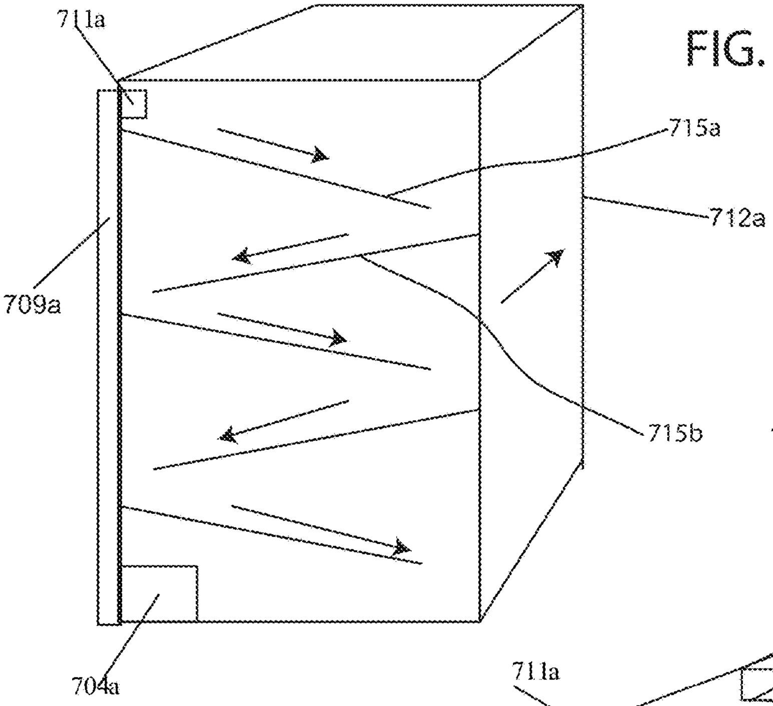
Figure 89B:
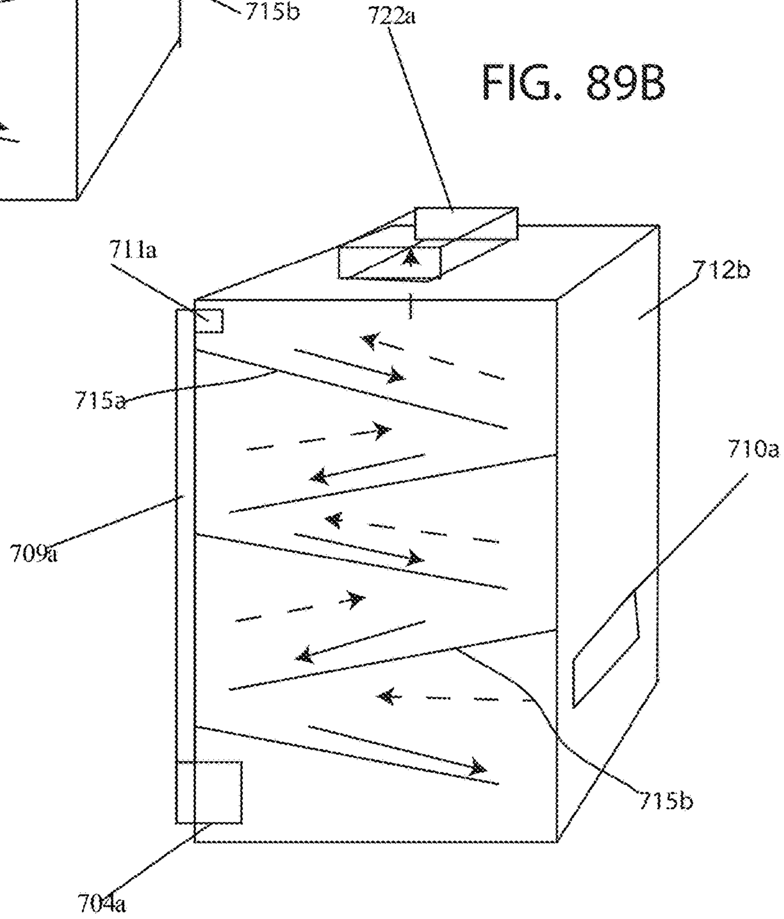
Figure 90:
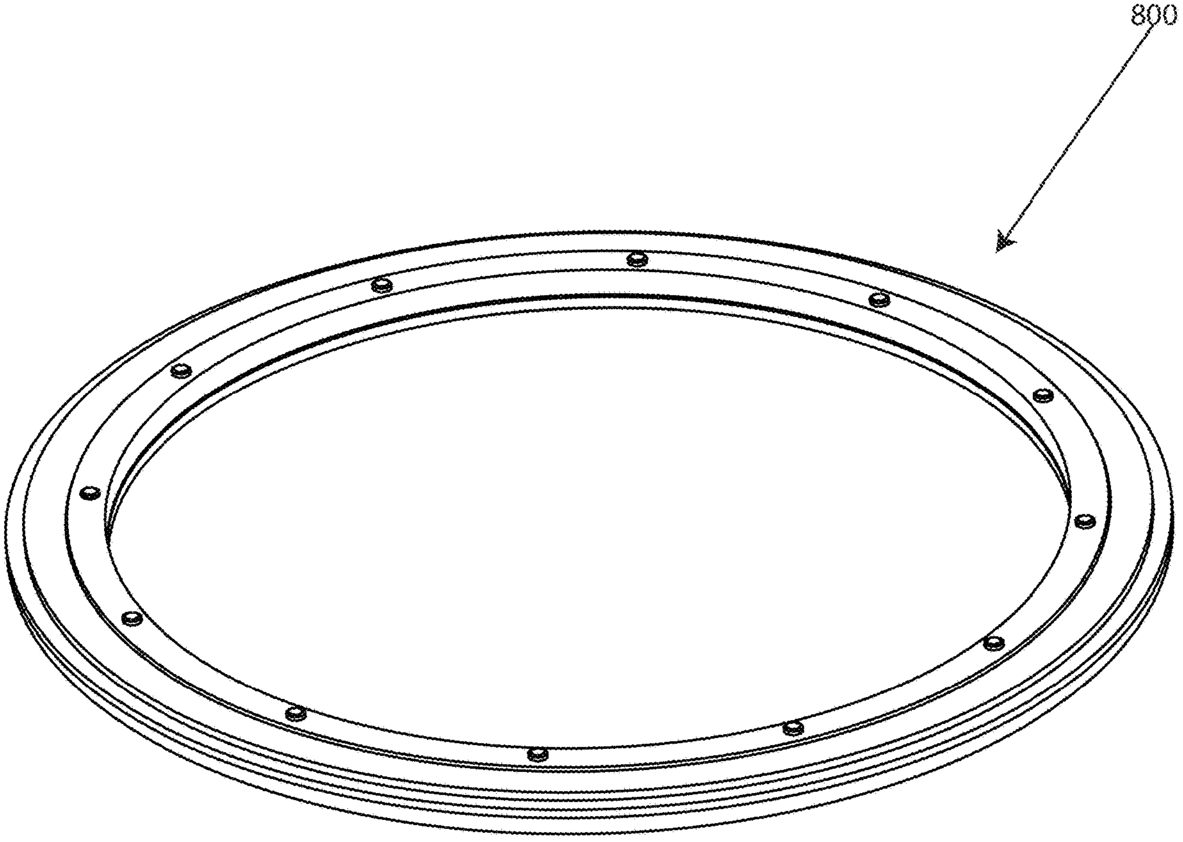
Figure 91:
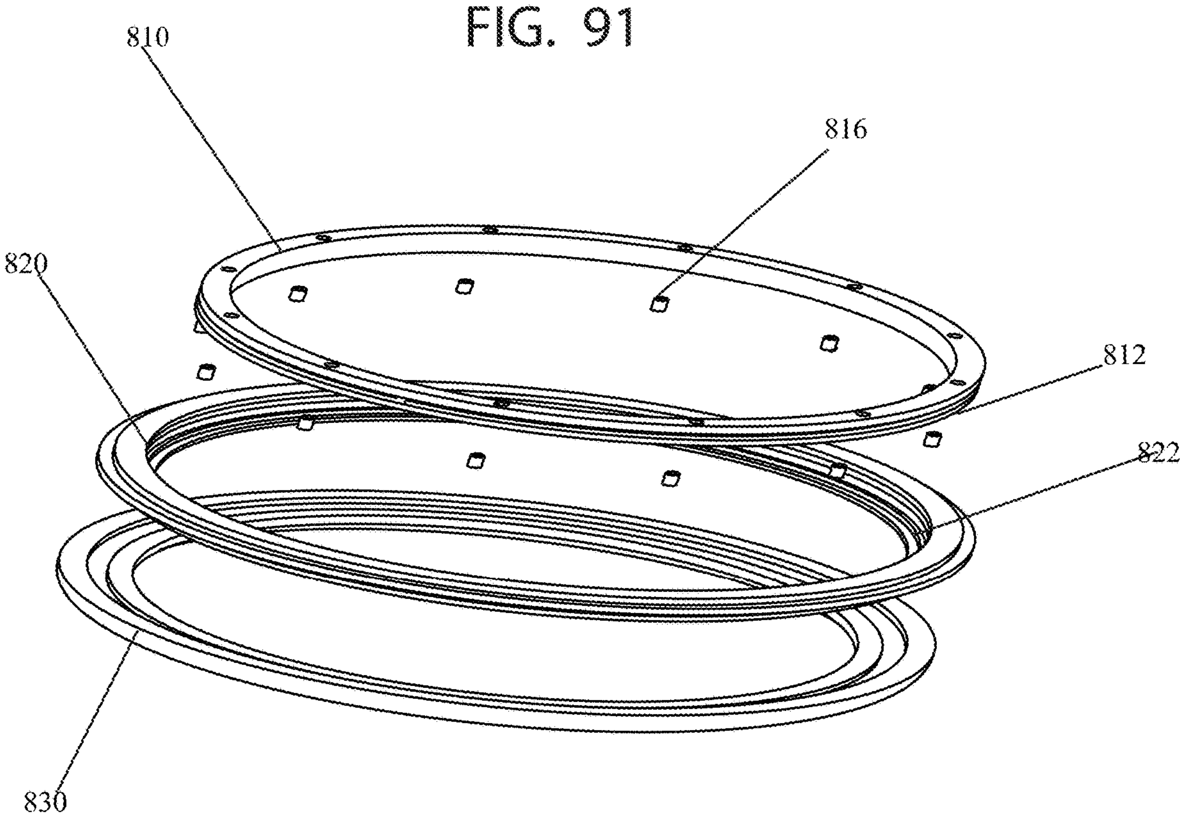
Figure 92:
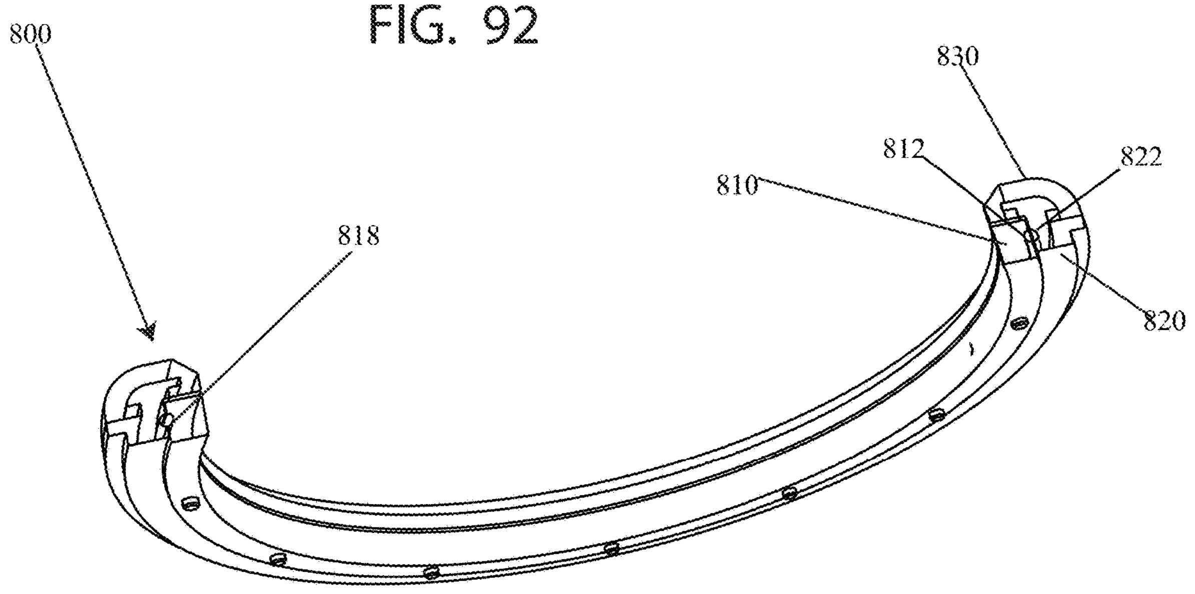
Figure 93:
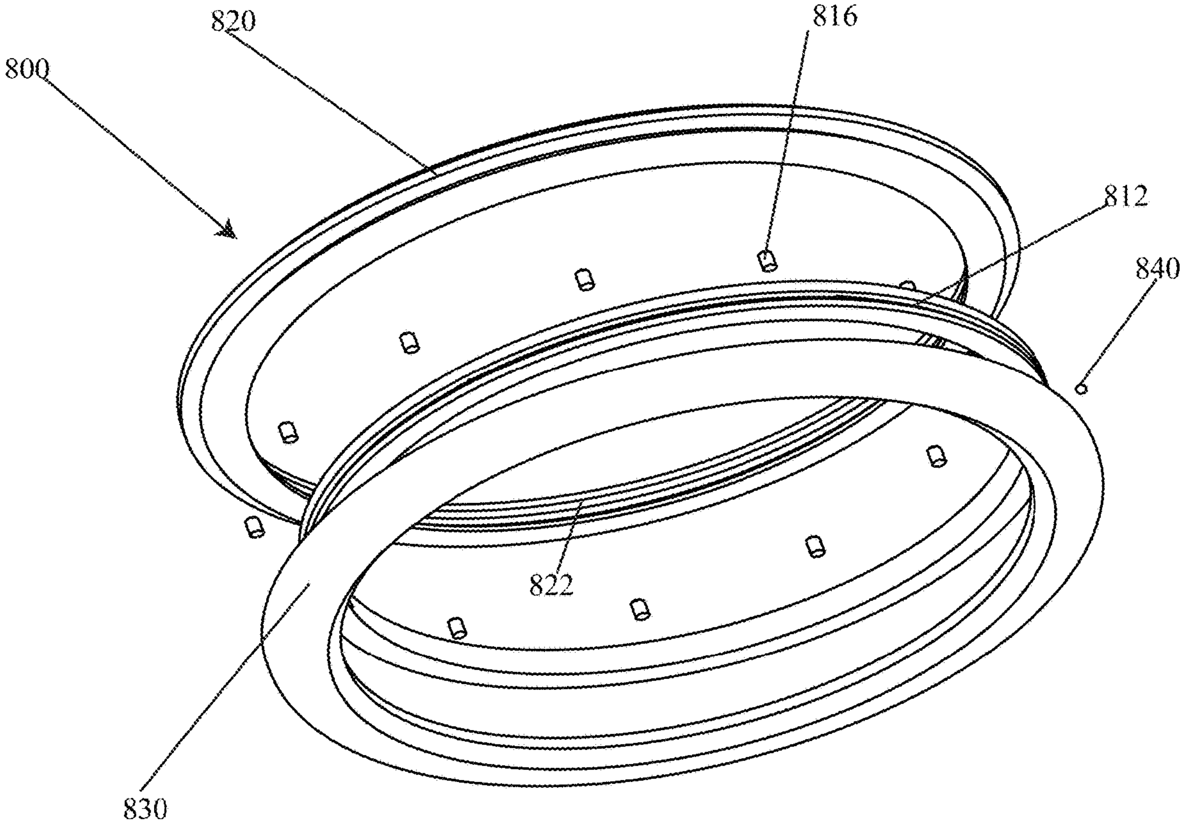
Figure 94:
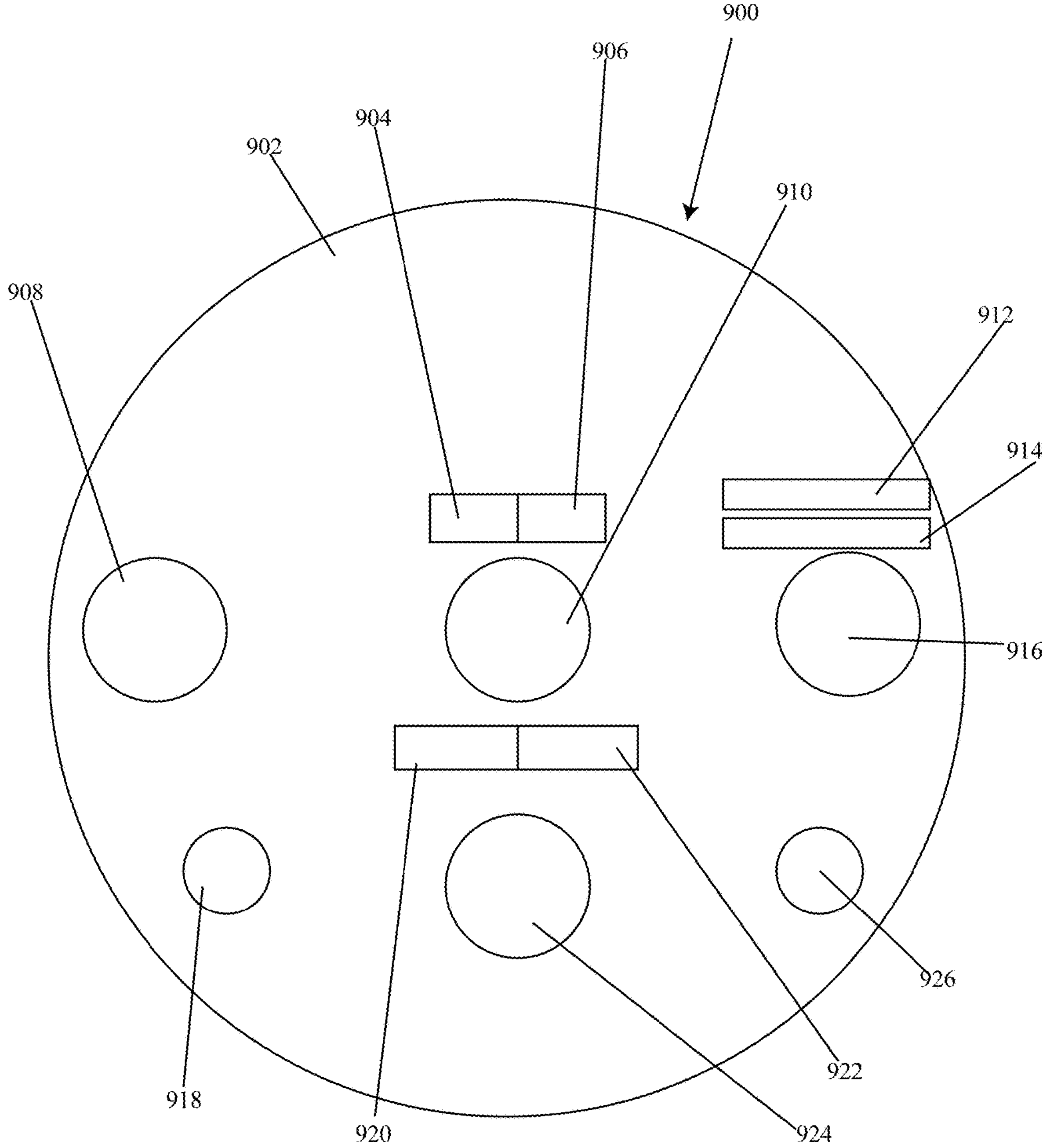

FIG. 89B is a view of another embodiment;

FIG. 90 is a top perspective view of a roller bearing for a bottom section of the invention;

FIG. 91 is an exploded view of the roller bearing;

FIG. 92 is a side cross-sectional view of the assembled roller bearing;

FIG. 93 is an exploded view of the roller bearing showing a ball bearing;

FIG. 94 is a top view of the control panel; and

Figure 95:
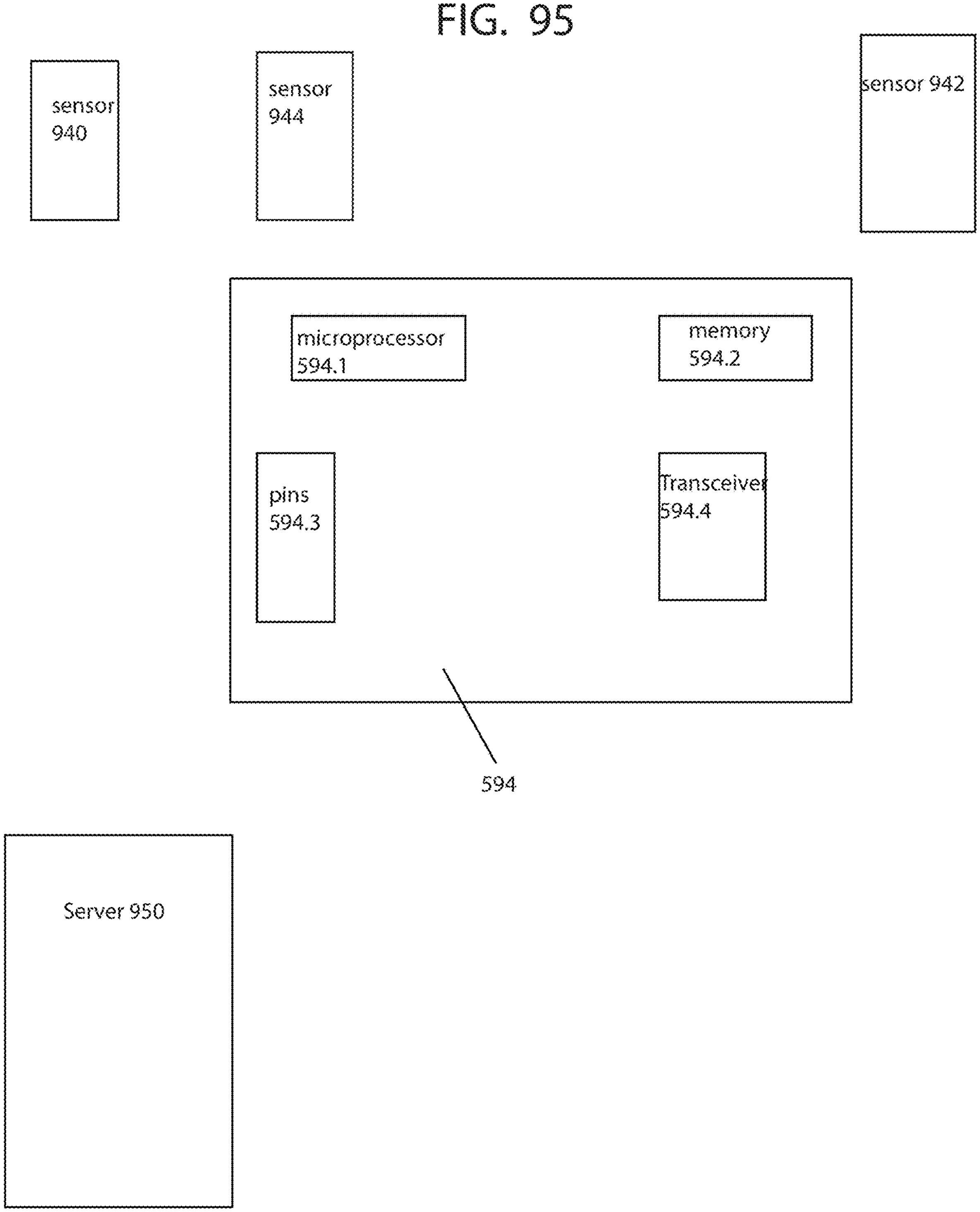
Figure 96A:
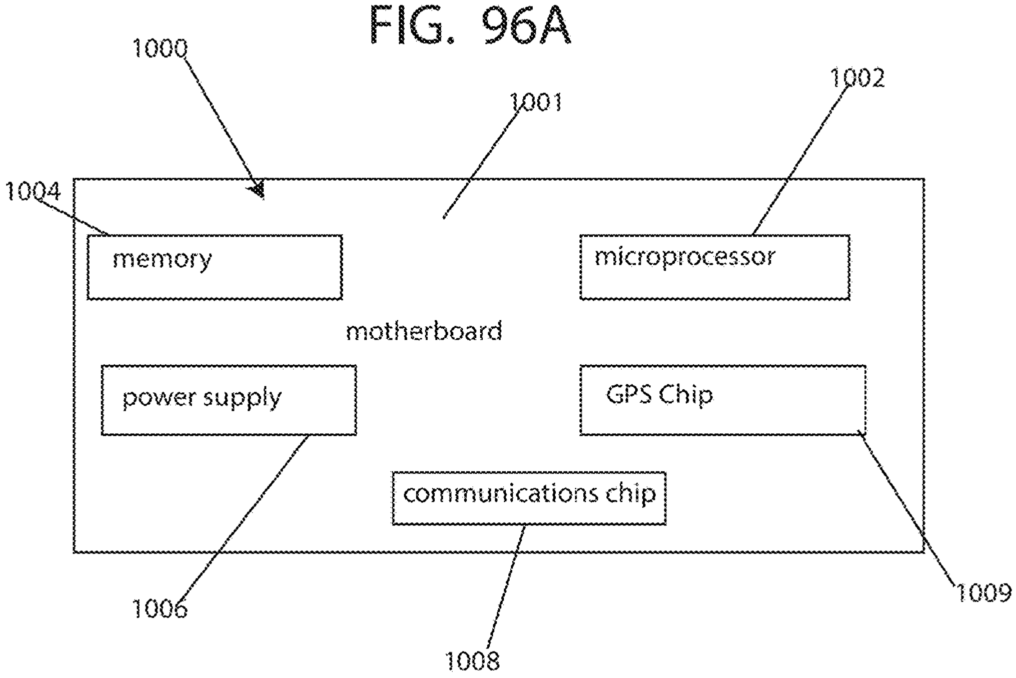
Figure 96B:
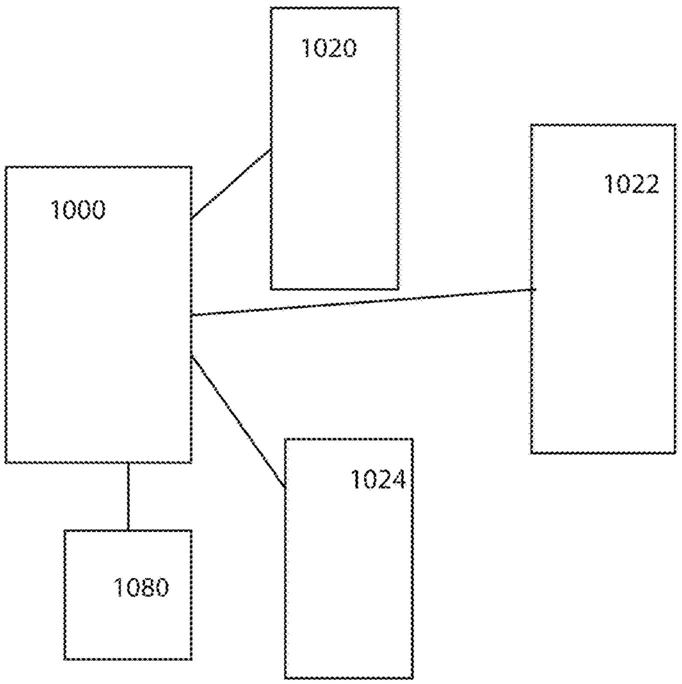
Figure 97:
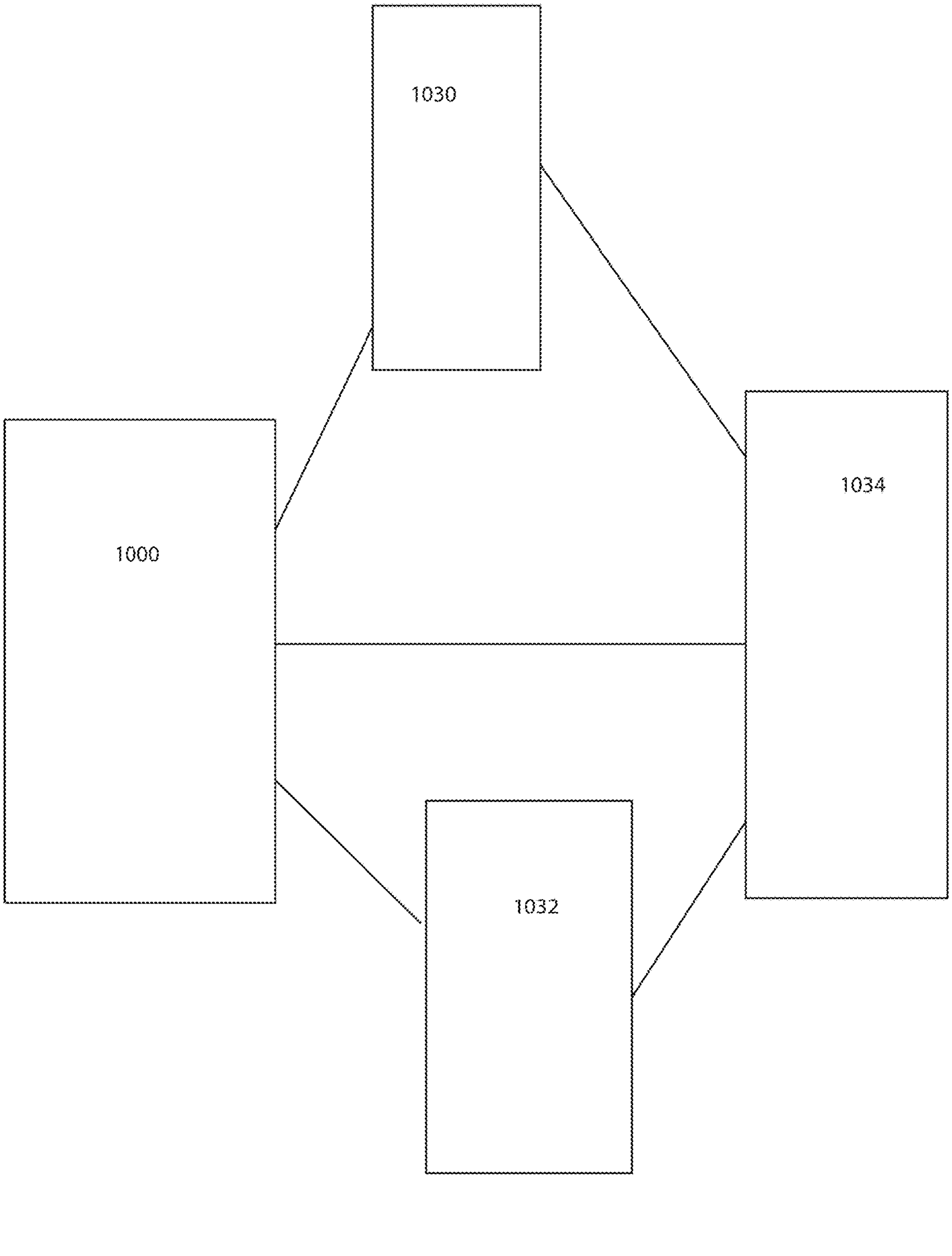
Figure 98A:
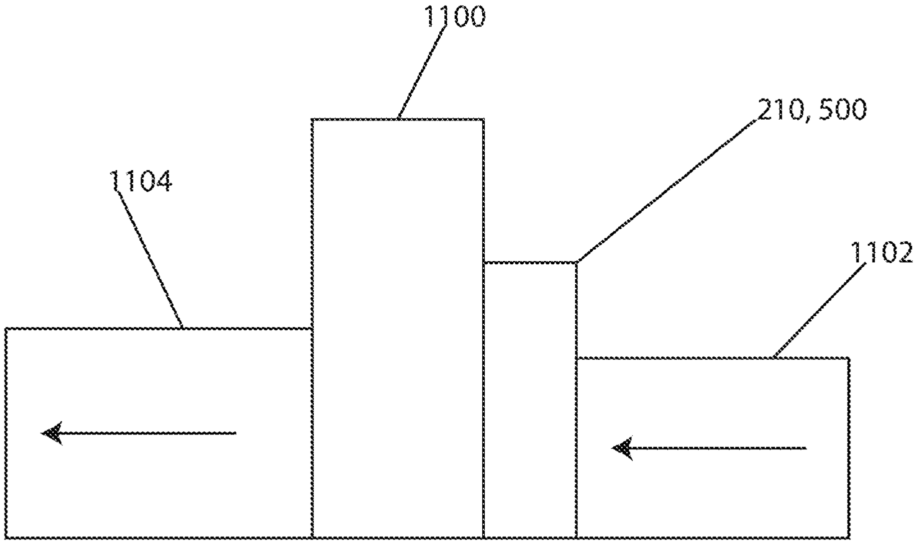
Figure 98B:
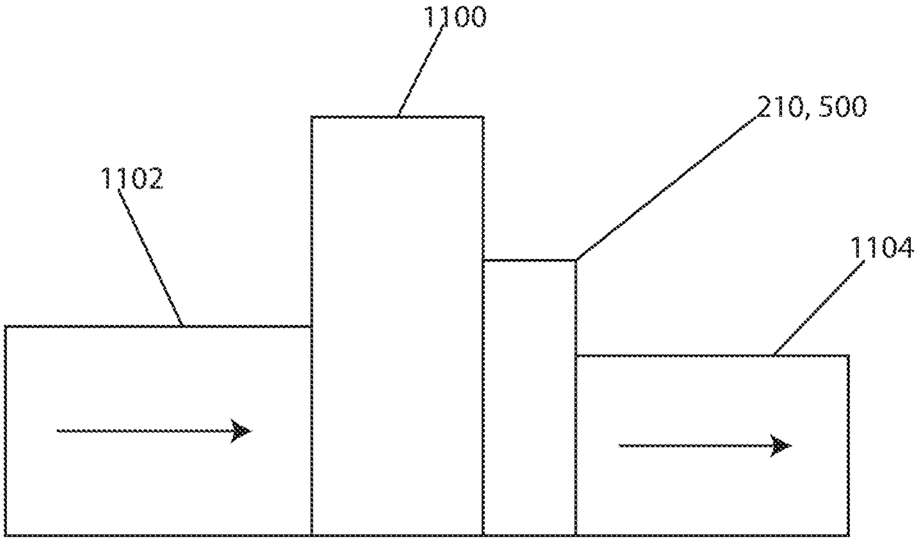
Figure 99:
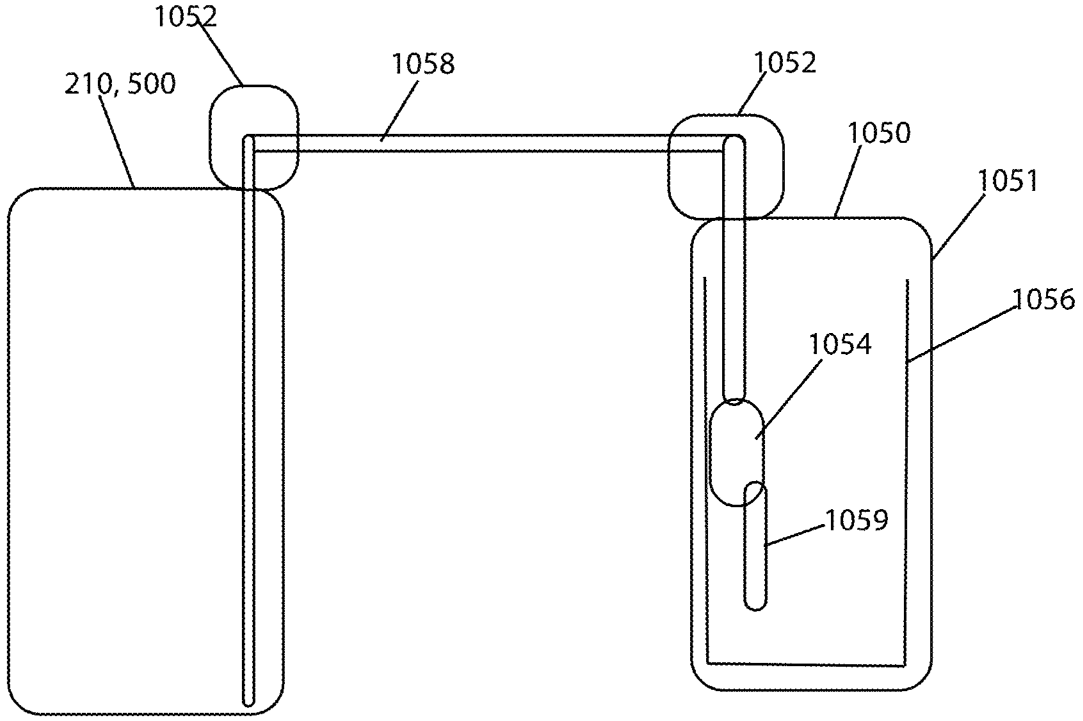
Figure 100:
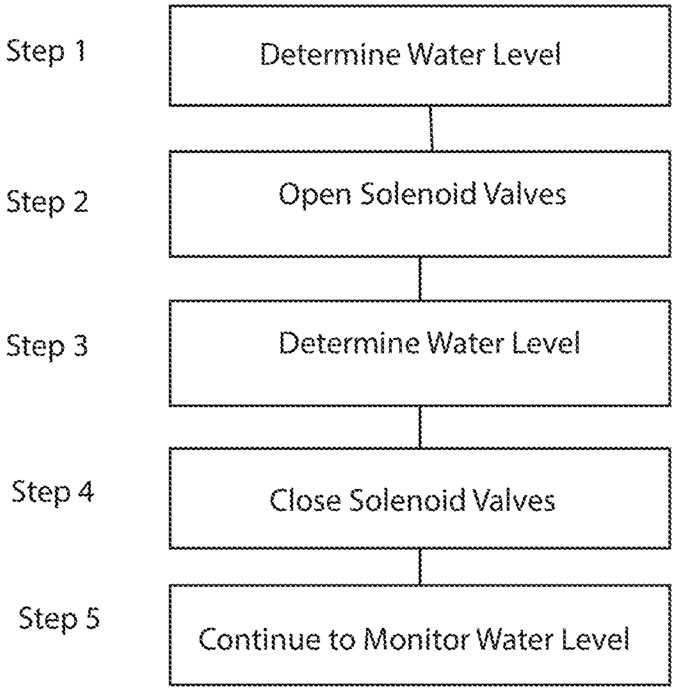
Figure 101:
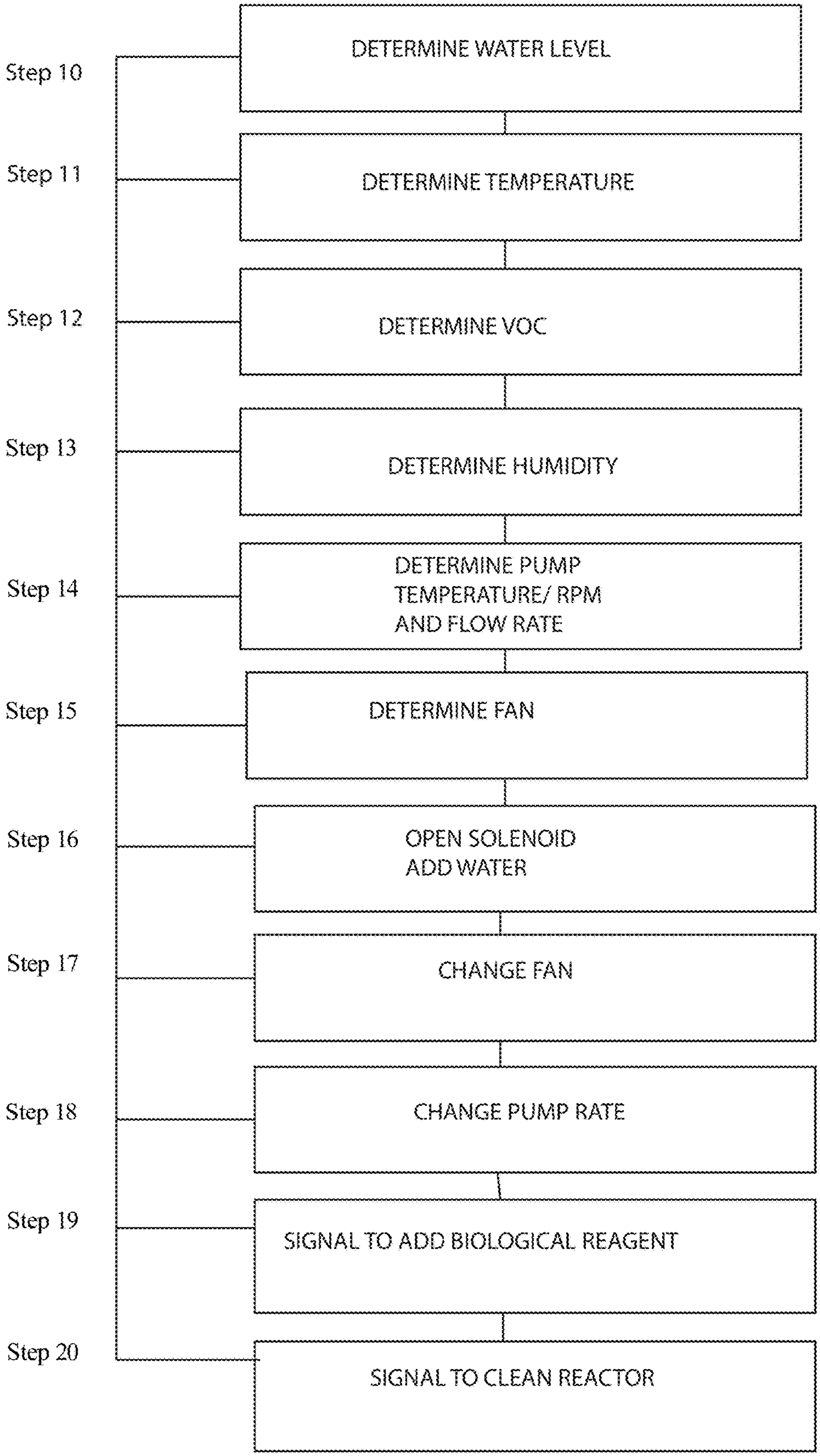
Figure 102:
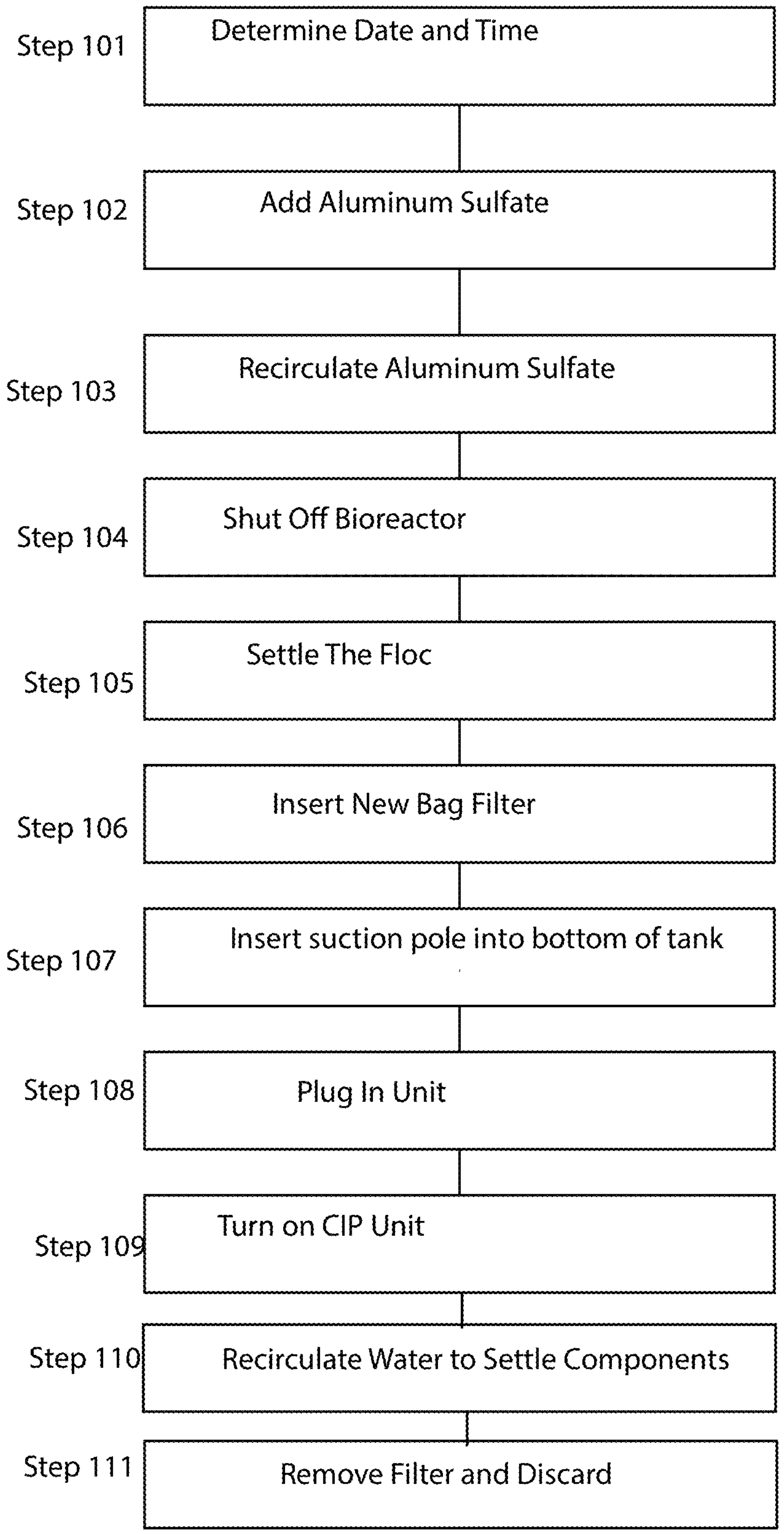

FIG. 95 is a schematic block diagram of one embodiment of a controller;

FIG. 96A is a schematic block diagram of another embodiment of a controller;

FIG. 96B is a schematic block diagram of a controller in communication with sensors and other electronic components;

FIG. 97 is a schematic block diagram of a network layout;

FIG. 98A is a layout of a HVAC system using one embodiment;

FIG. 98B is a view of a layout of a HVAC system working in an opposite direction;

FIG. 99 is a side view of a clean in place system;

FIG. 100 is a first flow chart for filling one embodiment;

FIG. 101 is another flow chart for filling and monitoring one embodiment;

FIG. 102 is another flow chart for cleaning one embodiment.

DETAILED DESCRIPTION OF PREFERRED EMBODIMENTS

Figure 1:
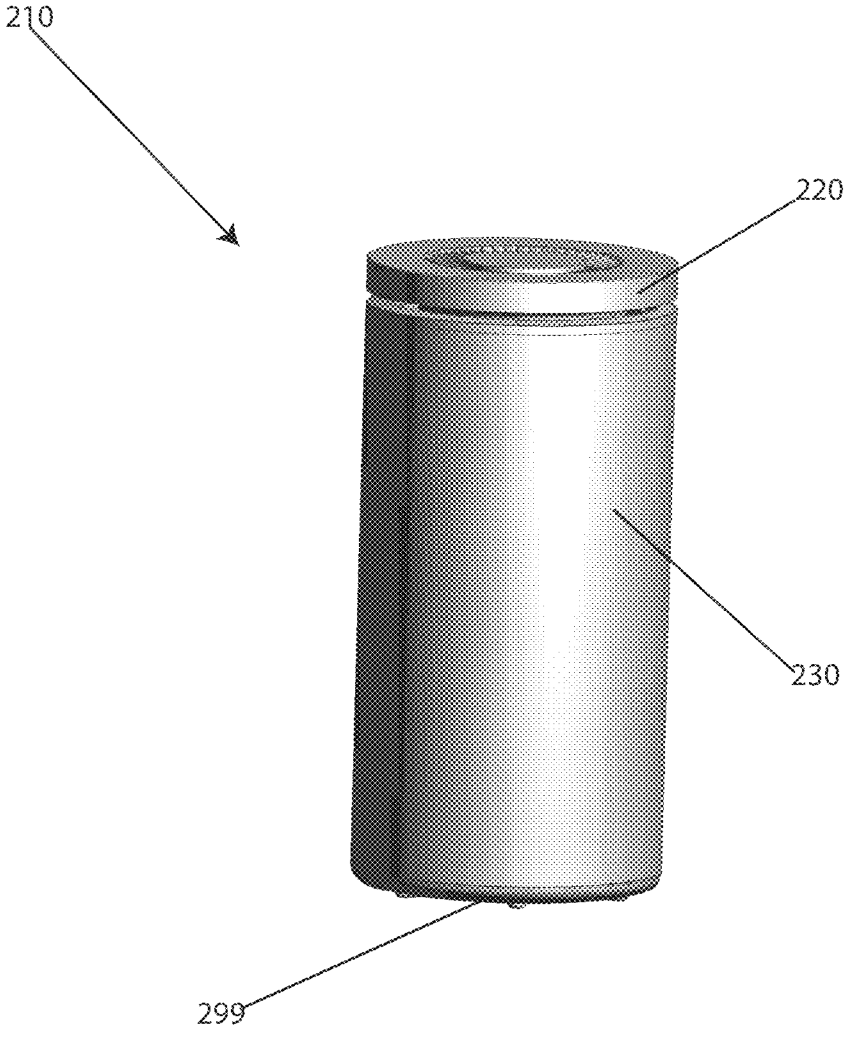
FIG. 1 is a side view of the air purification system.

FIG. 1 shows a front perspective view of an air purification device 210 having a top 220 and a body having an outer cover 230.

Figure 2:
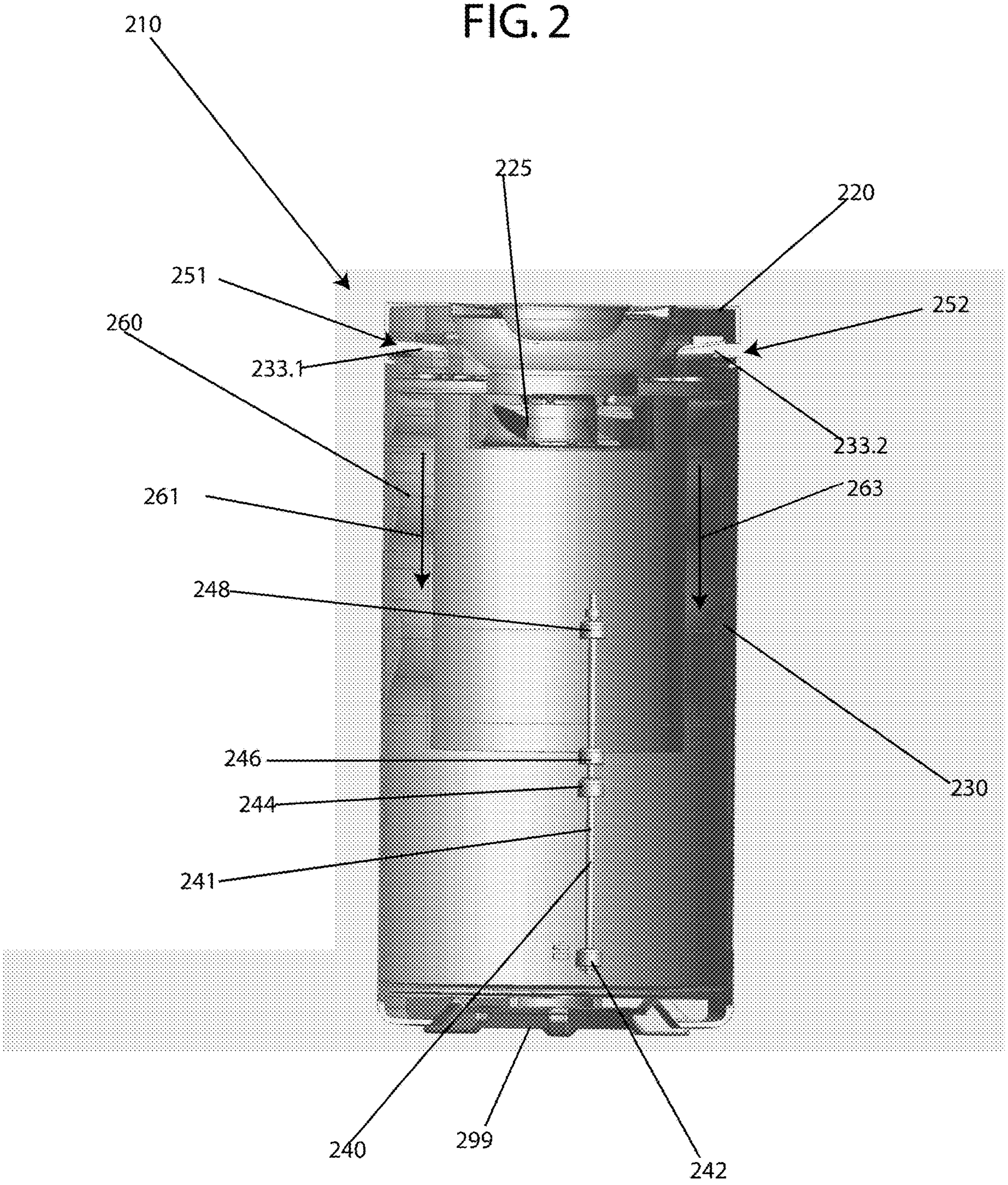
FIG. 2 is a side cross-sectional view of the air purification system taken along line A-A.

FIG. 2 shows a side cross-sectional view of this air purification device 210 showing atop 220, body having cover 230 a fan 225 coupled to top 220, and a fluid level sensor device 240 having a plurality of flotation sensors 242, 244, 246, and 248, disposed along a notation sensing shaft 241. Flotation sensors 242, 244, 246, and 248 are slidable up and down flotation sensing shaft 241. This air purification device 210 includes a plurality of concentric cylinders. For example, there is an outer cover or housing or cover 230, a corrugated substantially cylindrical container 260 having a spillway which has a waving or undulating pattern. In additions there is also a central cylindrical container 250 which is disposed inside of corrugated drip surface 60. As shown adjacent to top 220 there is a fan 225. Fan 225 is configured to pull air through air inlets 233.1 and 233.2 adjacent to top 220. The air then flows along corrugated container 260 into a central region around central cylindrical container 250 in and then back out of top 220. The flow of air provides a circulating air inside of the air purification device 210. Moving along the direction of the air is fluid based solution of water and a purification solution flows down against the fluid flow of the air. The fluid flow of the water in purification solution is down along the corrugated container 260. The interaction of the air with the purification solution cleanses the air of particulate matter, biological material, or any other impurities in the air. The corrugated surface of corrugated container 260 is configured so that the purification solution dripping down from top 220 interacts with this surface, bonds with the surface and forms a coating on the surface. Corrugated container 260 prevents the purification solution from simply freefalling to the bottom. This view shows arrows 261 and 263 which shows the direction of water flow along the inside surface corrugated container 60.

Figure 3:
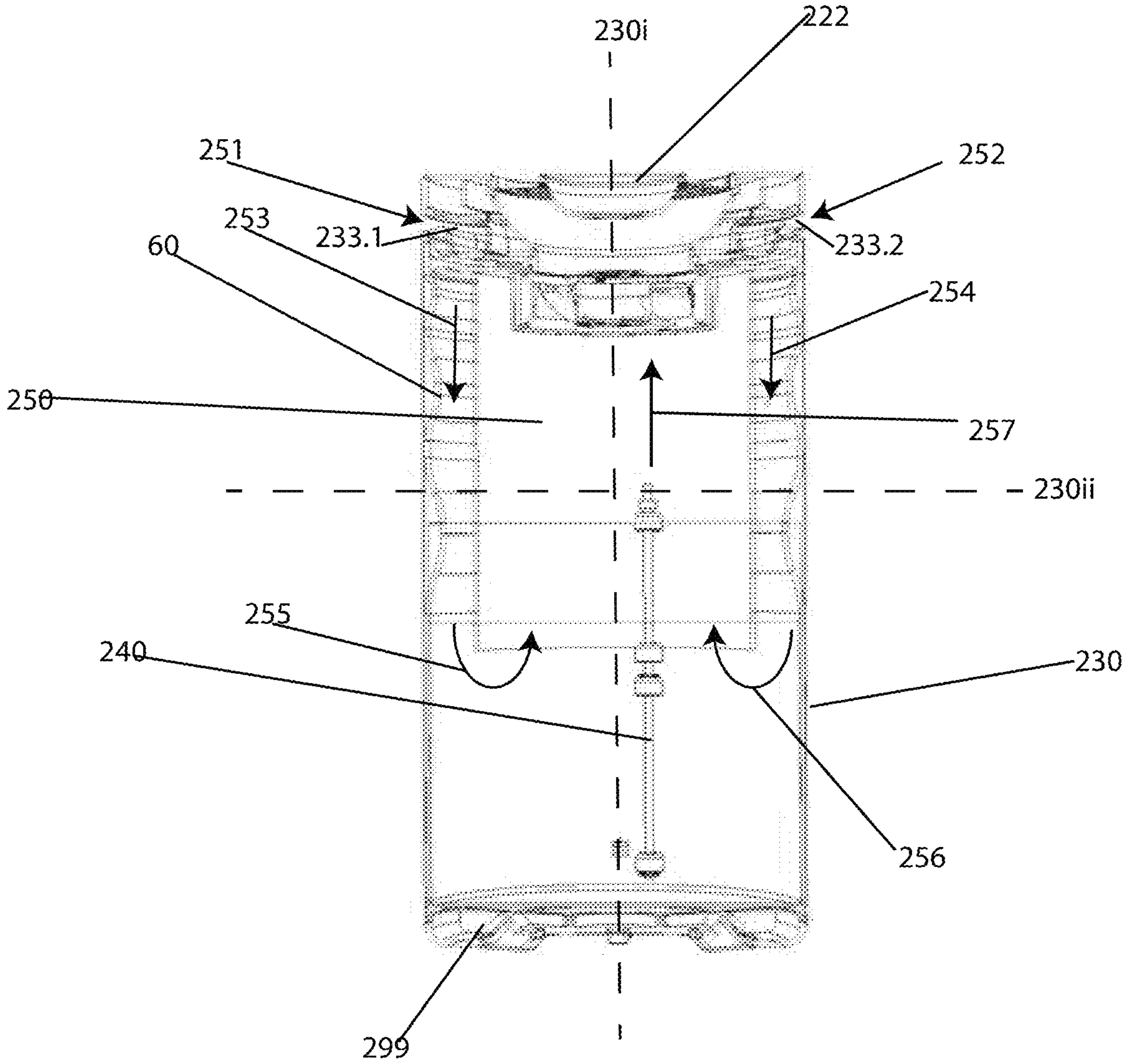
FIG. 3 is a side cross-sectional view of the air purification system.

FIG. 3 shows another view which is a side cross-sectional view as well. This side cross-sectional view shows longitudinal axis 230*i*, and latitudinal axis 230*ii*. Longitudinal axis 230*i* shows that the housing or cover 230 is an elongated cylinder which is longer than it is wide. However, any suitable dimension can be used. Latitudinal axis 230*ii* extends transversely longitudinal axis 230*i*.

There is a top grill 222 which sits above fan 225. Fan 225 pulls air in the direction of arrows 251 and 252 through inlets (See FIG. 3) into the body. The air flows along corrugated container 260 via arrows 253 and 254 towards bottom 299 and is then pulled up around central cylinder 250. The air curls around as shown by arrows 255 and 256 and then flows out of the housing via arrow 257 flowing past fan 225 and out of grill 222. This view also shows fill level sensing system 240 extending substantially along longitudinal axis 230*i*. Fill level sensing system 240 is configured to check for the level of water in the system so that it signals when more water needs to be added.

Figure 4:
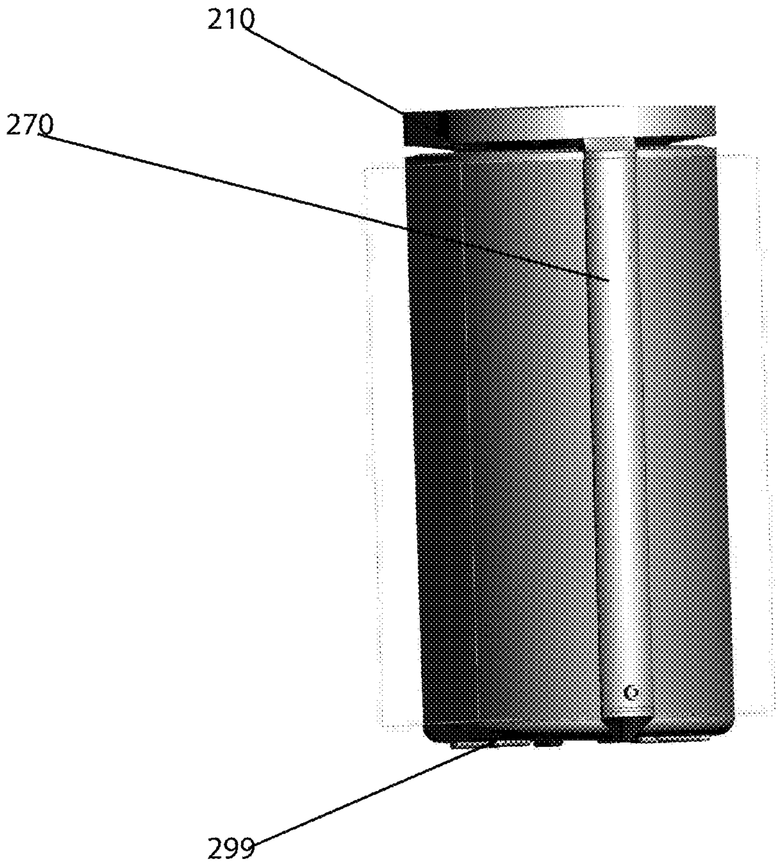
FIG. 4 is a side view of the air purification system with an outer cover shown.
Figure 8:
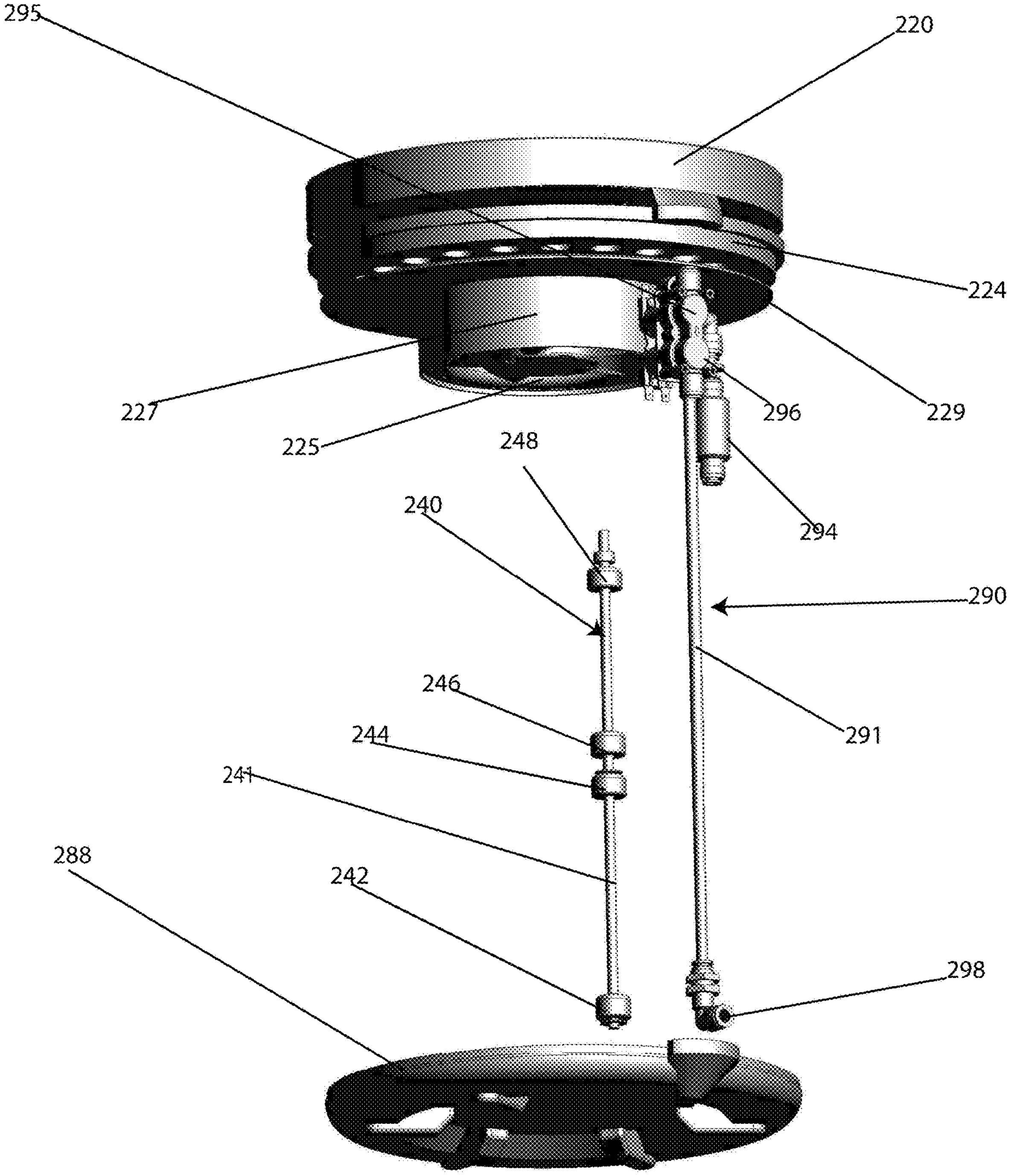
FIG. 8 is a side view showing the top and the bottom, as well as the float sensor system and the fluid transfer system.

FIG. 4 shows a side view of the air purification device 210 with an outer covering 270 covering the purification solution transfer system 290 (See FIG. 8).

Figure 5:
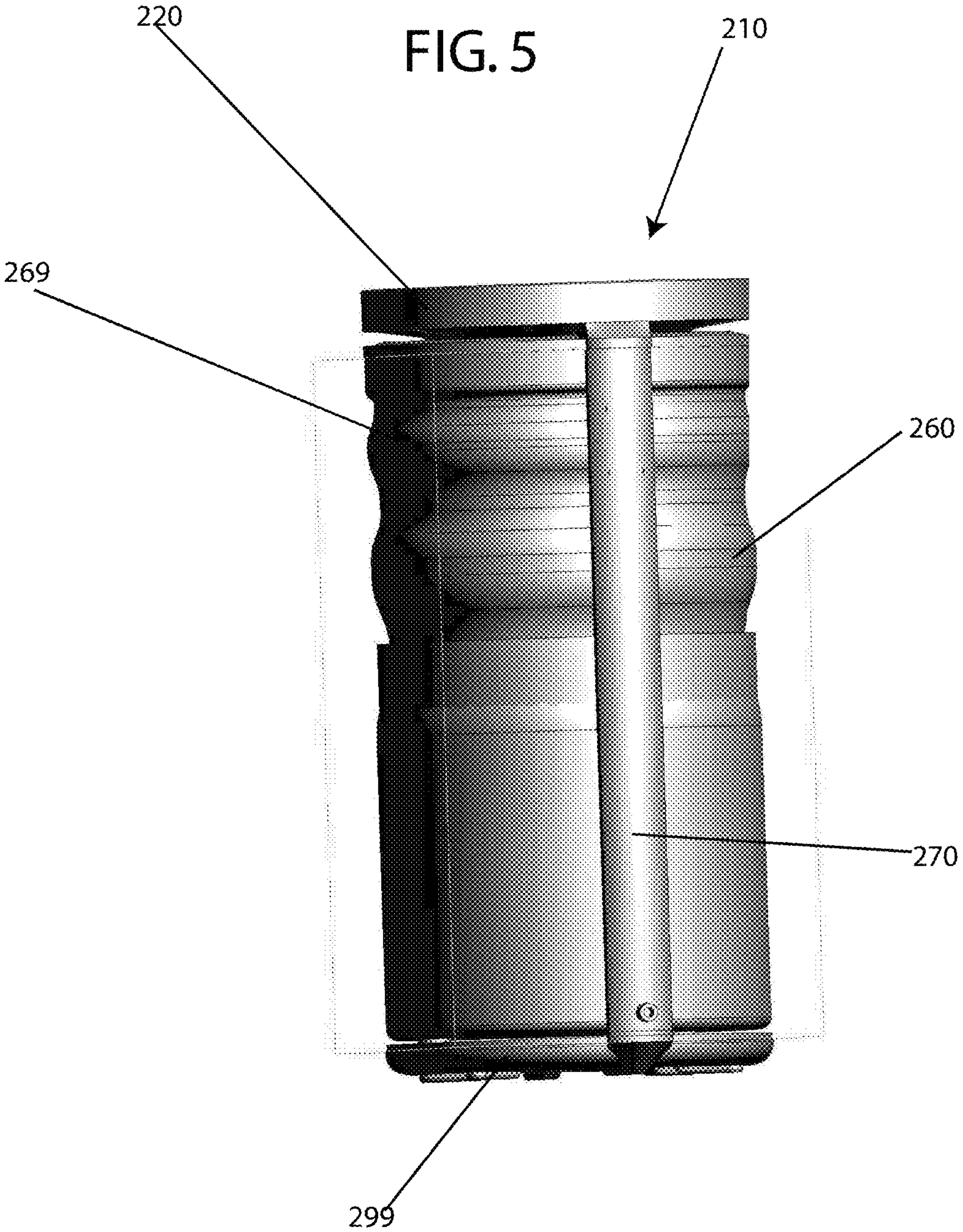
FIG. 5 is a side view of the air purification system with the outer cover removed.

FIG. 5 shows a side view of the device, with cover 30 missing. In this view, there shown top 220 bottom 299, corrugated container 260 having a corrugated portion 269. These corrugated portions are shown as a wavy surface formed in the corrugated container 260. Outer covering 270 is shown extending adjacent to this corrugated container 260 but outside of this corrugated container 260. Outer covering 270 extends from bottom to top 220. As indicated above the wavy portion of the corrugated container 260 is configured to catch falling fluid and is configured to prevent the falling fluid from dropping entirely from a top 220 to a bottom 299 of the device.

Figure 6:
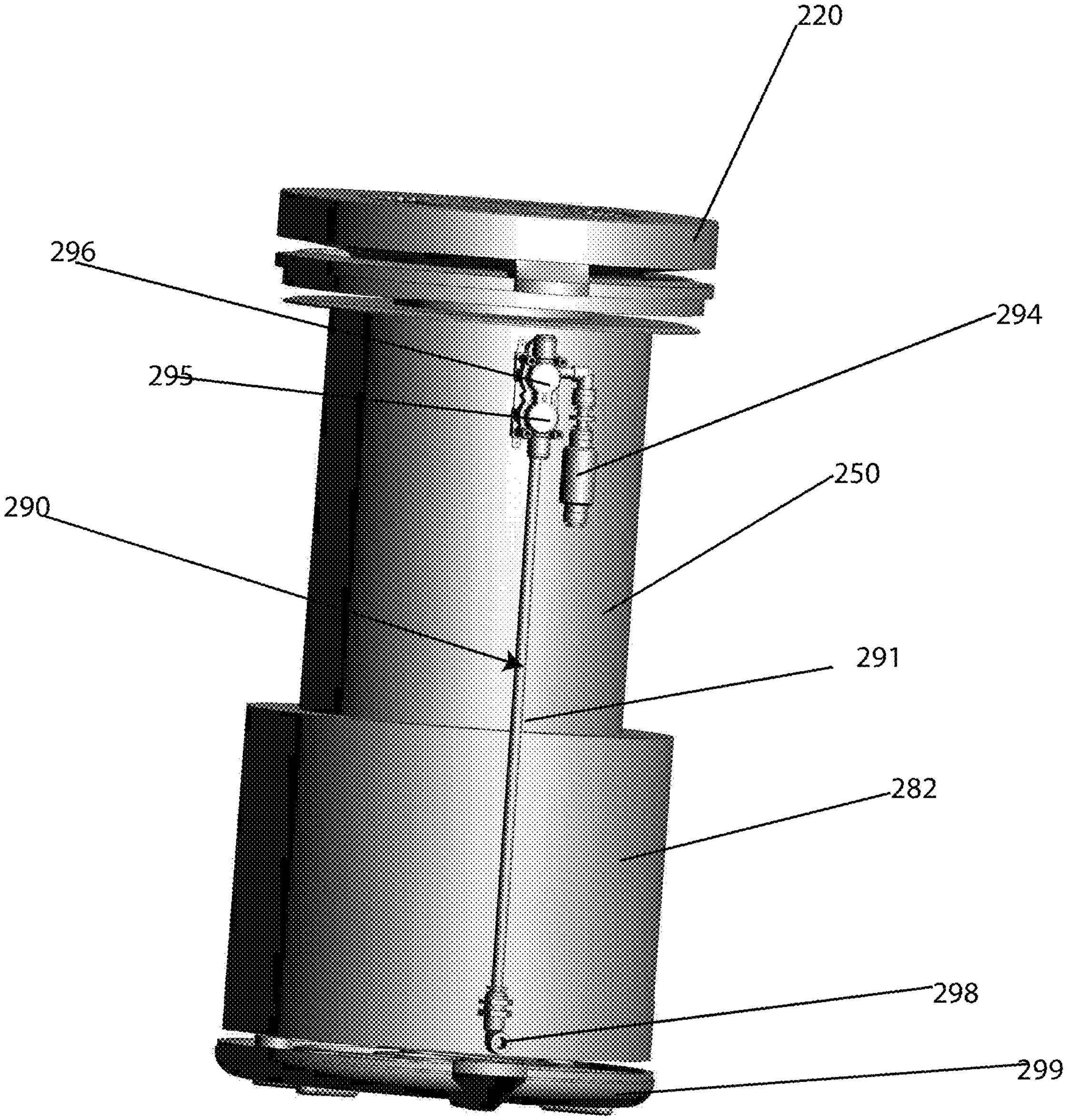
FIG. 6 is a side view of the air purification system as shown in FIG. 1 with the cover and the corrugated container removed.

FIG. 6 shows a side view of the air purification device 210 with the outer covering 270 missing as well as the cover 230 missing. In addition, corrugated container 260 is also missing. This view shows central cylinder 250, another outer cylinder 282, and purification solution transfer system 290. Purification solution transfer system 290 includes an extending pipe or channel 291, a filter 294 and a second distribution outlet 296. There is also an intake 298 disposed adjacent to the bottom 299 of air purification device 210. Purification solution comprising water purification elements such as proprietary biological solution, close up through intake 298 up along outside of corrugated container 260 and then is dispensed inside of corrugated container 260. The purification solution than flows down along inside surface of corrugated container 260 back towards the bottom 299.

Figure 7:
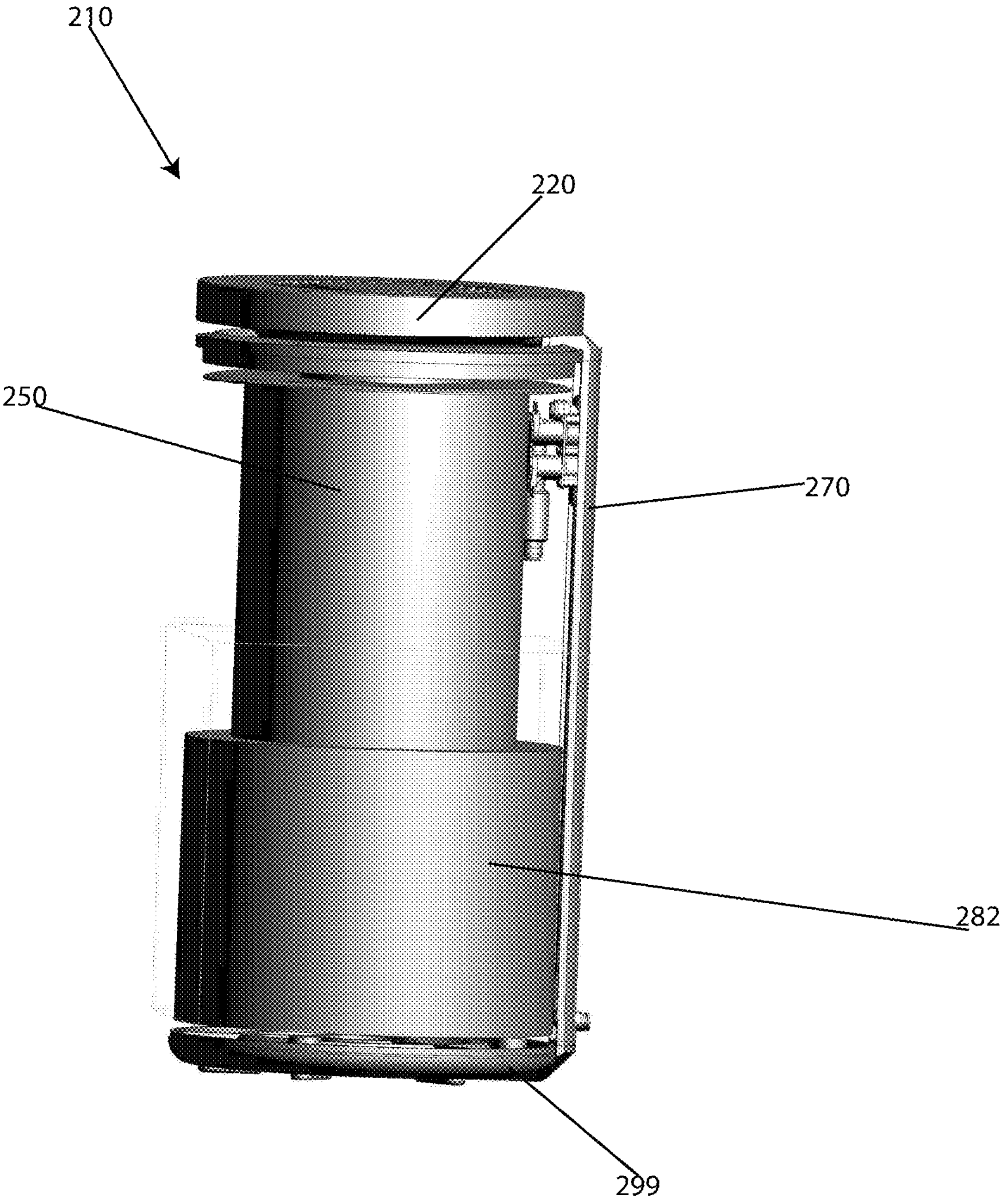
FIG. 7 is a side view with the cover and the corrugated container removed and showing the outer cover.

FIG. 7 shows a side view of the device with cover 230 missing, as well as corrugated container 260 missing as well. Outer cover 270 shown covering over purification solution transfer system 290. Thus, this view shows purification solution transfer system 290 configured to extend up in a longitudinal direction outside of central cylinder 50 but inside of outer cover 270 torn bottom 299 to top 220.

FIG. 8 is a side view of the device with the outer cover missing as well as the central cylinder 250 and the corrugated container 260 as well. This view shows the fill level sensing system 240 having a plurality of float sensors 242, 244, 246, and 248 along shaft 241. There is also shown water input system 290. Water-input system 290 includes an extending pipe or channel 291, a first distribution outlet 295 and a second distribution outlet 296. There is also a filter 294 disposed towards an upper region of this water input system 290. As discussed above, fluid such as water flows up from a bottom region of the chamber through intake 298, it flows through pipe or channel 291 and up through filter 294, and then out of outlets 295 and 296. The fluid then flows into container 260.

Figure 9:
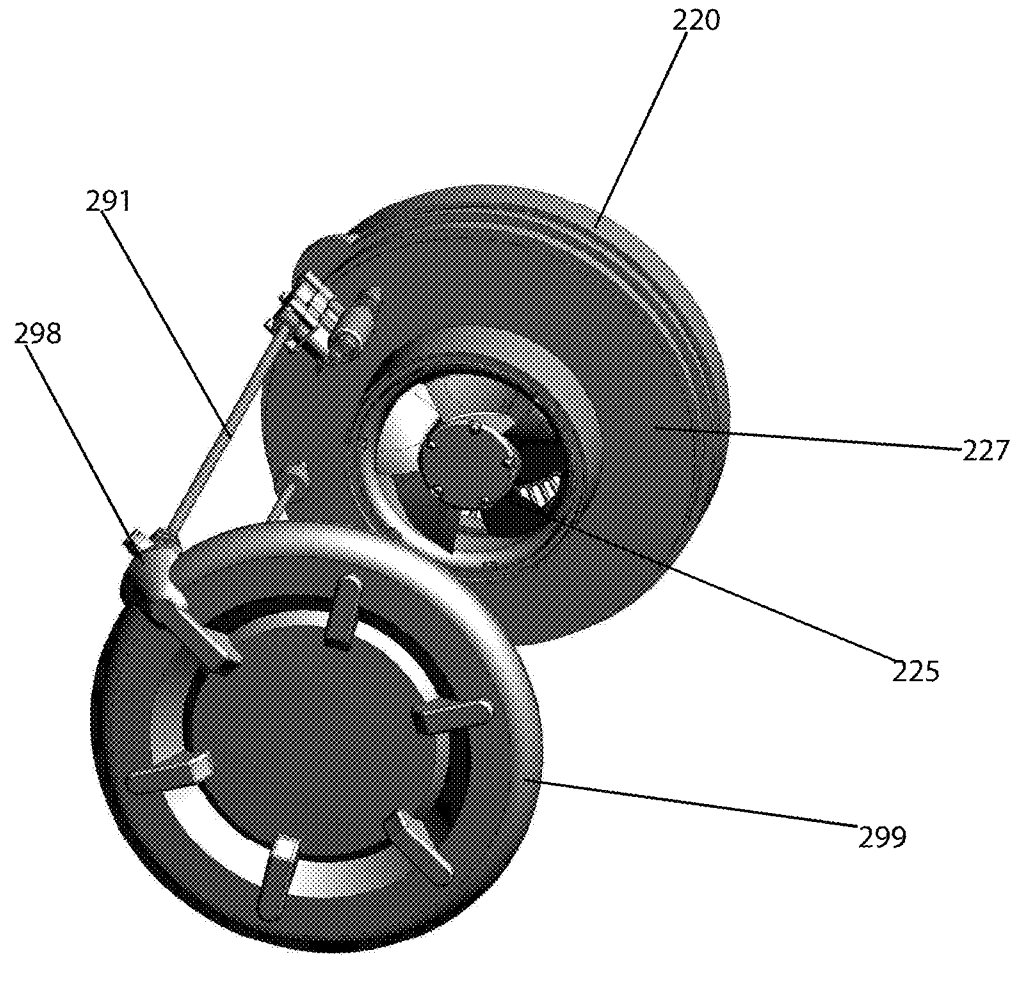
FIG. 9 is an end-side perspective view showing the fluid transfer system.

FIG. 9 is an end view of the device showing the-water input system 290 having an inlet 298 as well as pipe or channel 291 which extends from a bottom 299 to a top 220. There is also shown fan 225 as well as annular catch plate 227.

Figure 10:
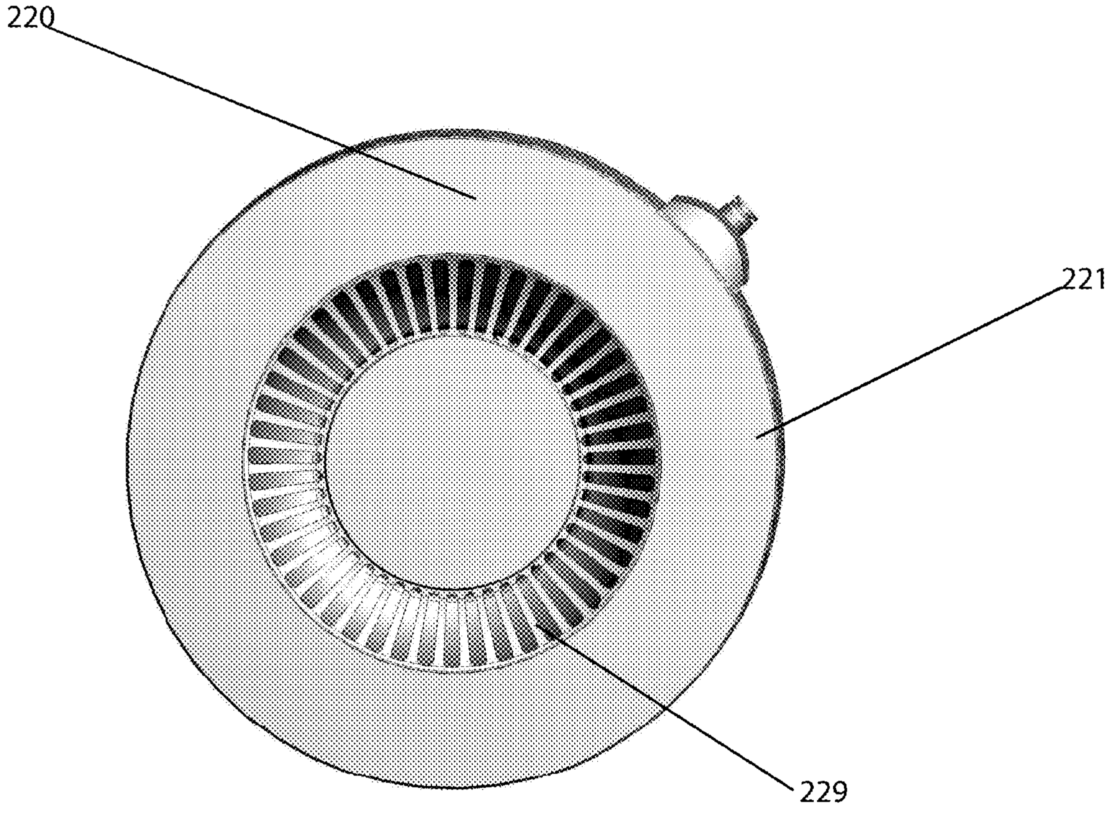
FIG. 10 is a top view of the top of the air purification system.

FIG. 10 is a top view of the device showing top 220, having a cover surface 221 and a louvered region 229. This louvered region allows air to flow through as driven by a fan 225 (see FIG. 9).

Figure 11:
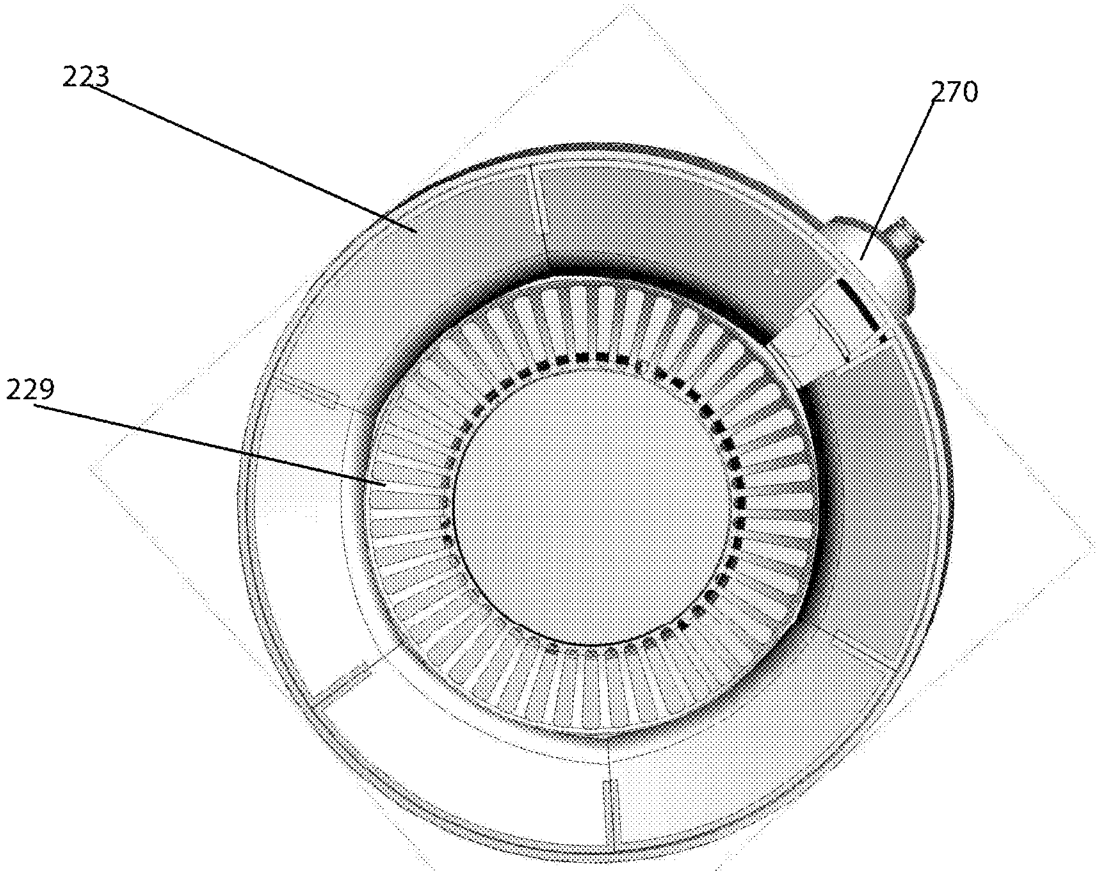
FIG. 11 is a top view of the air purification system with the top cover removed.

FIG. 11 is a top view of the device with cover surface 221 removed. This view shows louvered region 229 as well as cover plates 223 sitting above louvered region. This view also shows an outer cover 270 as well.

Figure 12:
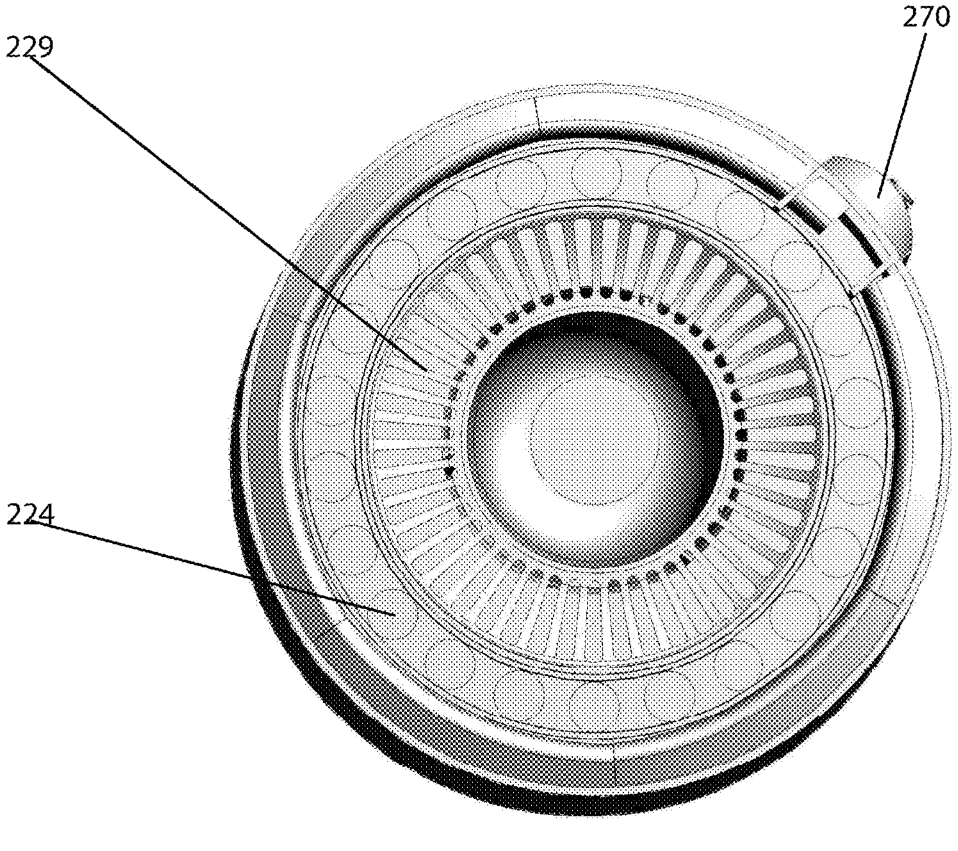
FIG. 12 is a top view of the air purification system with the louvers exposed.

FIG. 12 shows the top view of the device with cover plates 223 removed. This shows spillway 224 which includes a plurality of holes formed in this annular ring-shaped spillway. Spillway 224 has a plurality of holes disposed therein which allow fluid to flow down into the device. This view also shows an outer cover 270 which covers purification solution transfer system 290.

Figure 13:
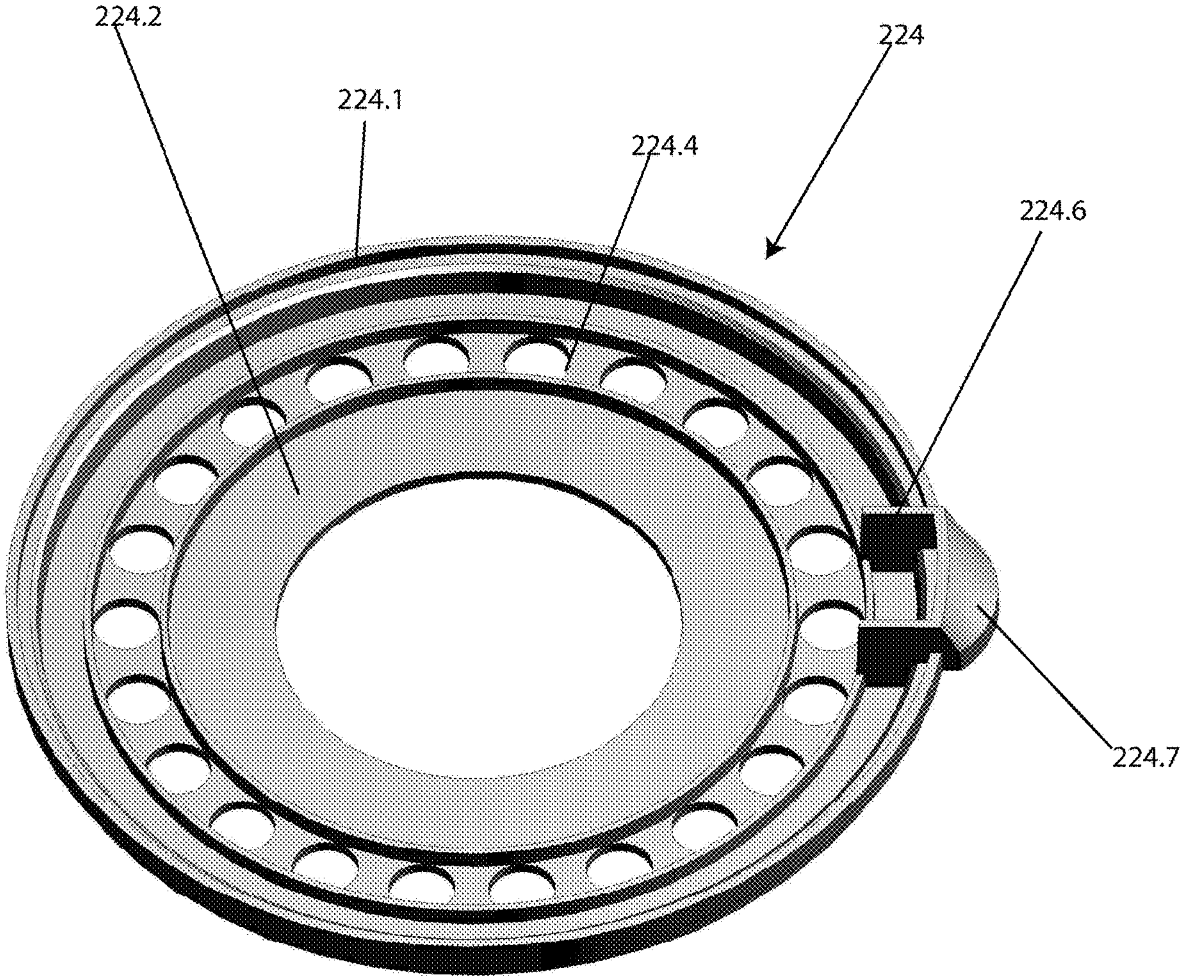
FIG. 13 is a side perspective view of a top tray of the air purification system.

FIG. 13 shows spillway 224 which includes an outer ring 224.1 which forms a side wall, an inner flat ring 224.2, a plurality of holes 224.4, disposed in the spillway 224, a side bracket 224.6 and a tab 224.7. This spillway 224 receives purification solution and then spreads this purification solution around the annular ring 224.2 and in through holes 224.4 so that it drips down relatively evenly onto corrugated container 260. Side bracket 224.6 is configured to receive fluid from purification solution transfer system 90, particularly from outlets 295 and 296.

Figure 14:
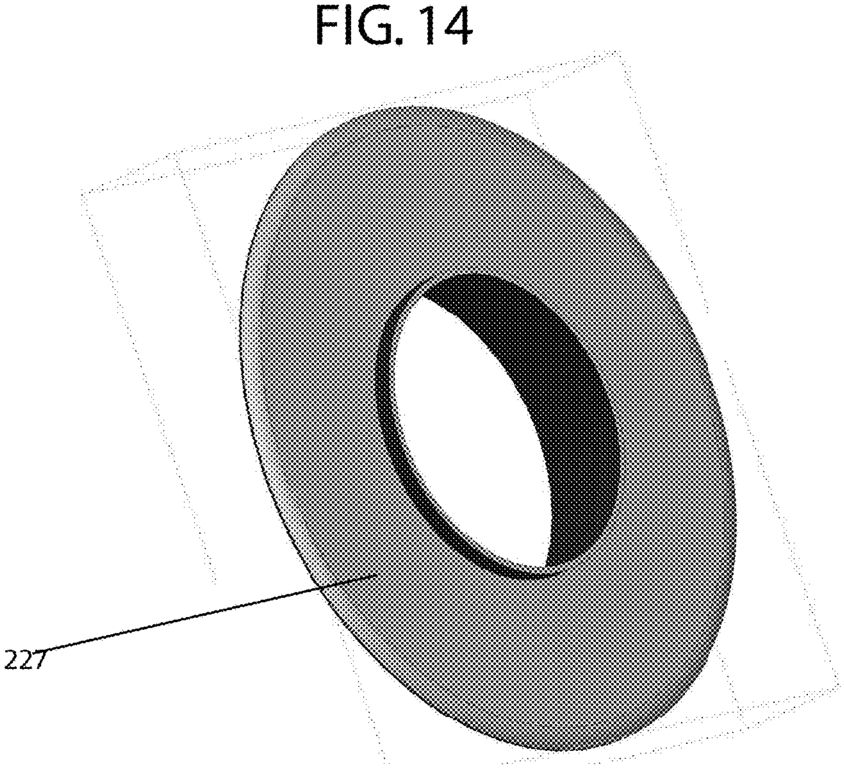
FIG. 14 is a view of an annular plate disposed below the spillway.

FIG. 14 shows an annular catch 227 which is configured to be disposed below spillway 224 in the air purification device 210. This annular catch 227 is configured to catch the purification solution and then pass it onto the corrugated container 60.

Figure 15:
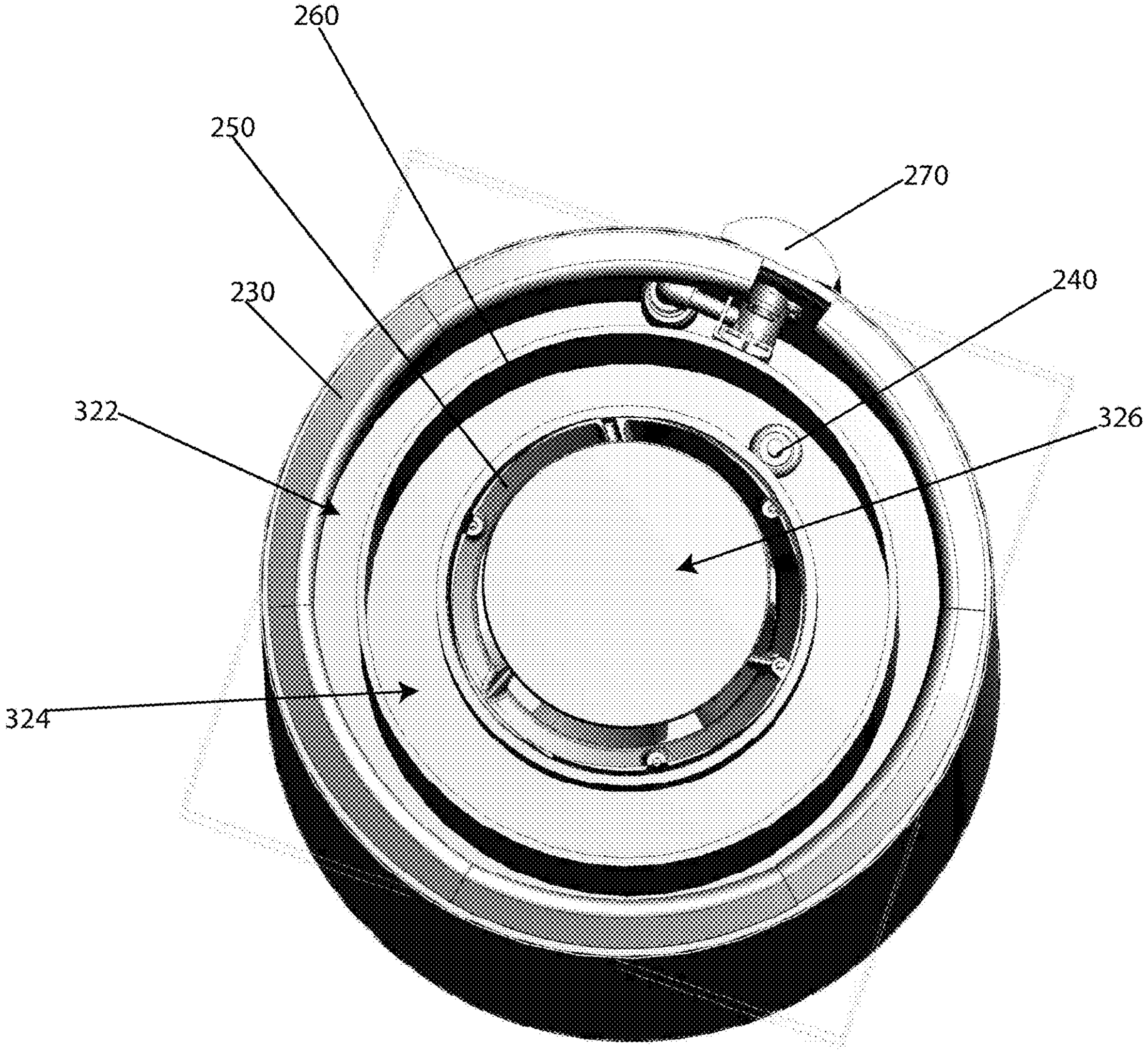
FIG. 15 is a view of the device with the top removed.

FIG. 15 is a top view of the device which shows outer cover 270, positioned outside cover 230. There is also shown spillway 260 as well as central cylinder 250, fill level sensor 240 is also shown along with channel openings 322 and 324, these channel openings are configured to allow fluid to flow up or down in these openings, such as in the form of air being pulled through the system via a fan such as via fan 225 or from purification solution flowing through the system as well.

Figure 16:
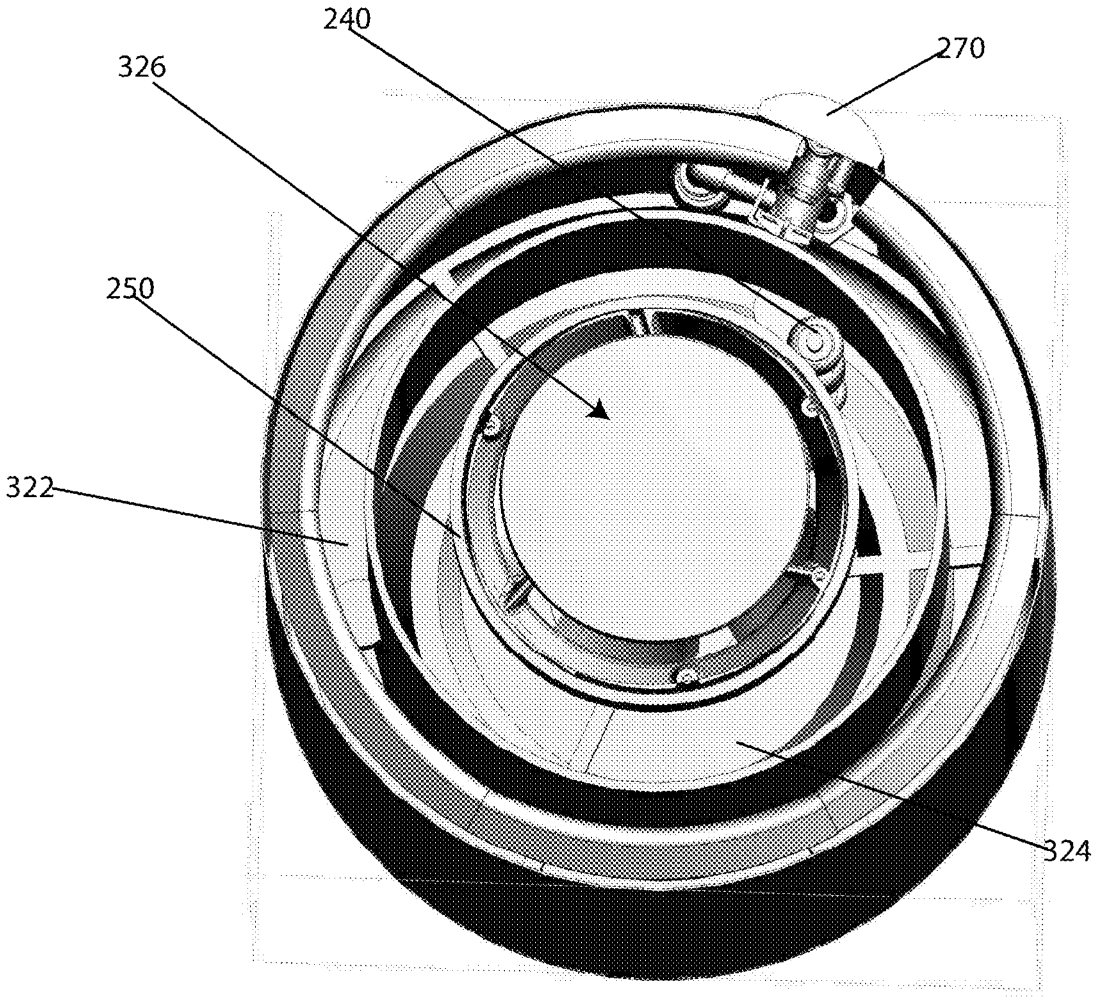
FIG. 16 is another angle of the top view of the devise with the top removed.

FIG. 16 shows another view which shows central cylinder 250, fill level sensor 240, outer cover 270, inner channel opening 326, outer channel opening 322, and channel opening 324 as well.

Figure 17:
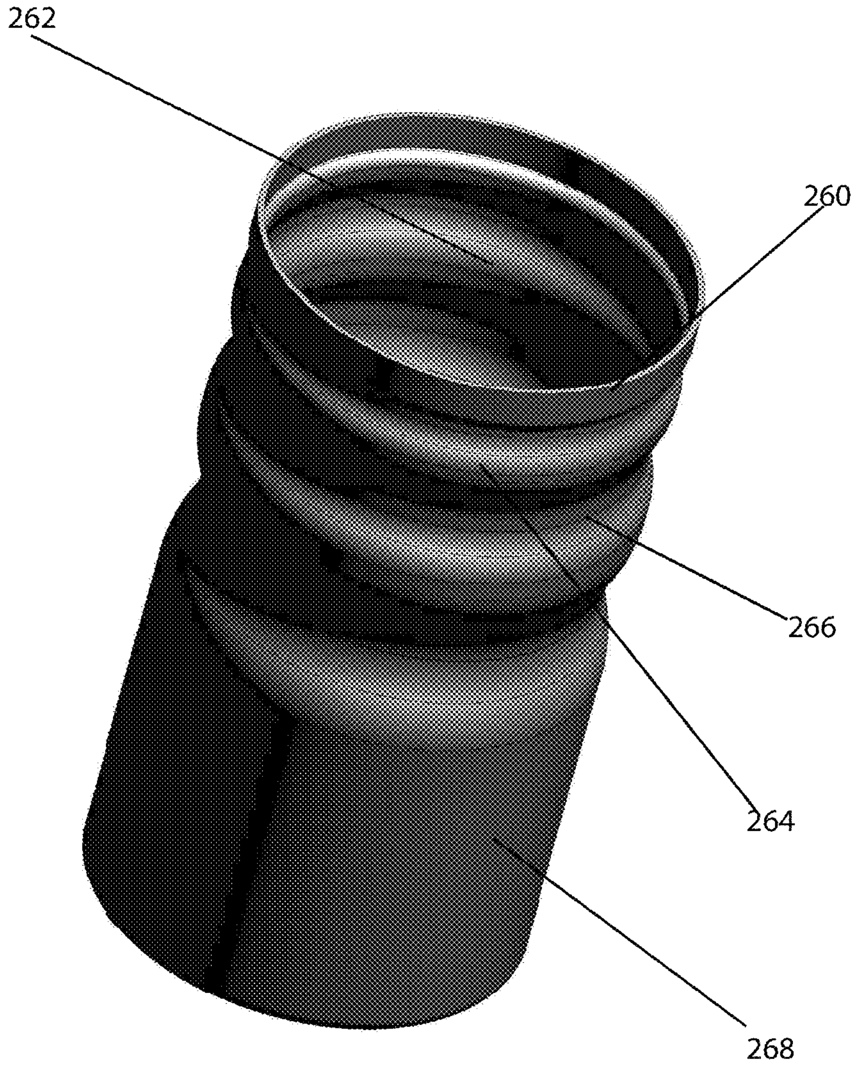
FIG. 17 is a side view of the outer tank.

FIG. 17 shows a perspective view of the corrugated container 260. This corrugated spillway has a plurality of wavy or undulating surfaces include a first inner surface 262, another surface 264, and another surface 266. These varying peaks and troughs form an uneven catch which is configured to catch the falling purification solution which is falling from the spillways 224 and annular catch 227.

Figure 18:
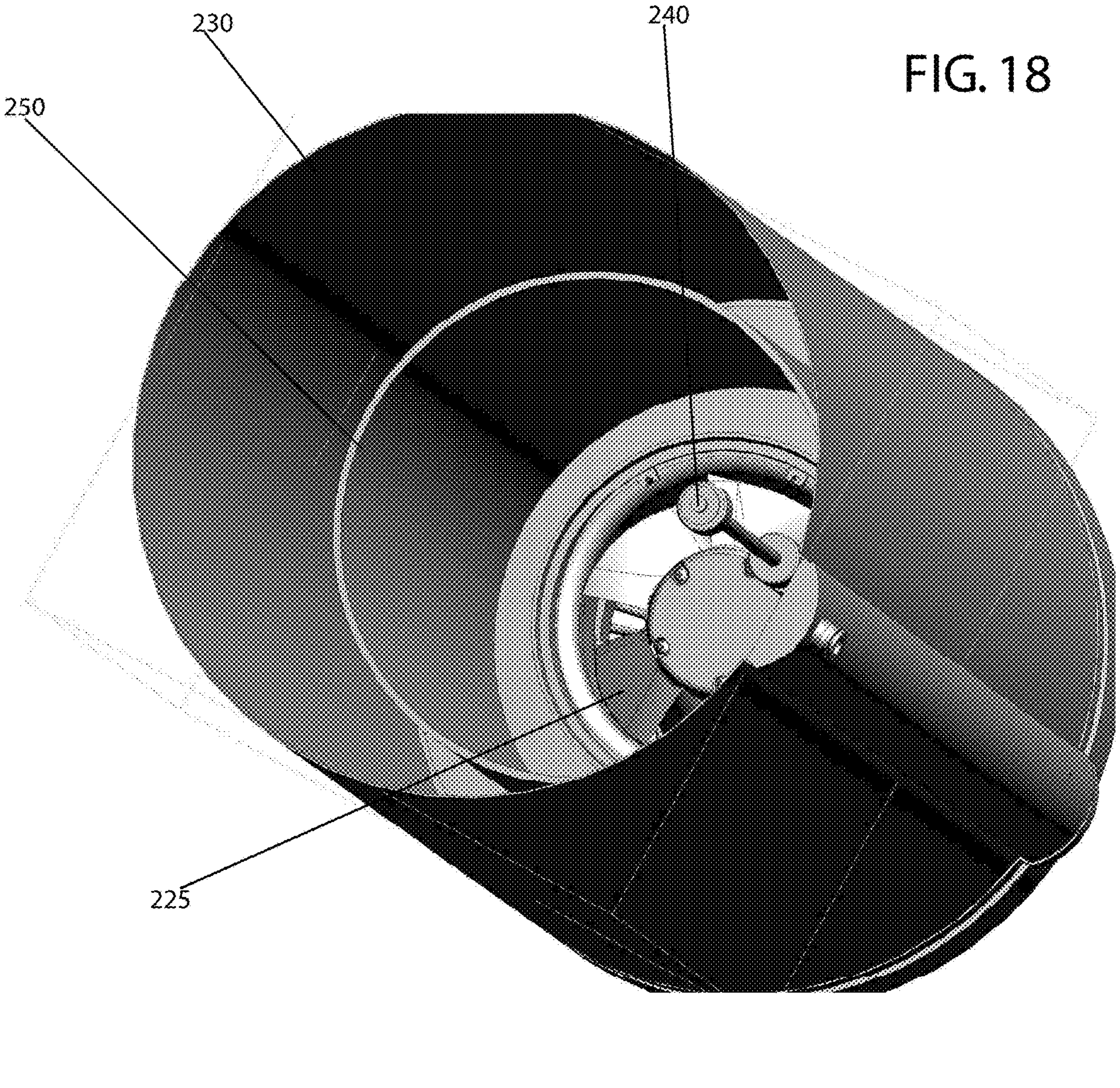
FIG. 18 is a view of the outer cover and the inner cylinder with the outer tank removed.

FIG. 18 is a sided perspective view of outer cover 230 as well as central cylinder 250. This view also shows fan 225 and fluid level sensor 240.

Figure 19:
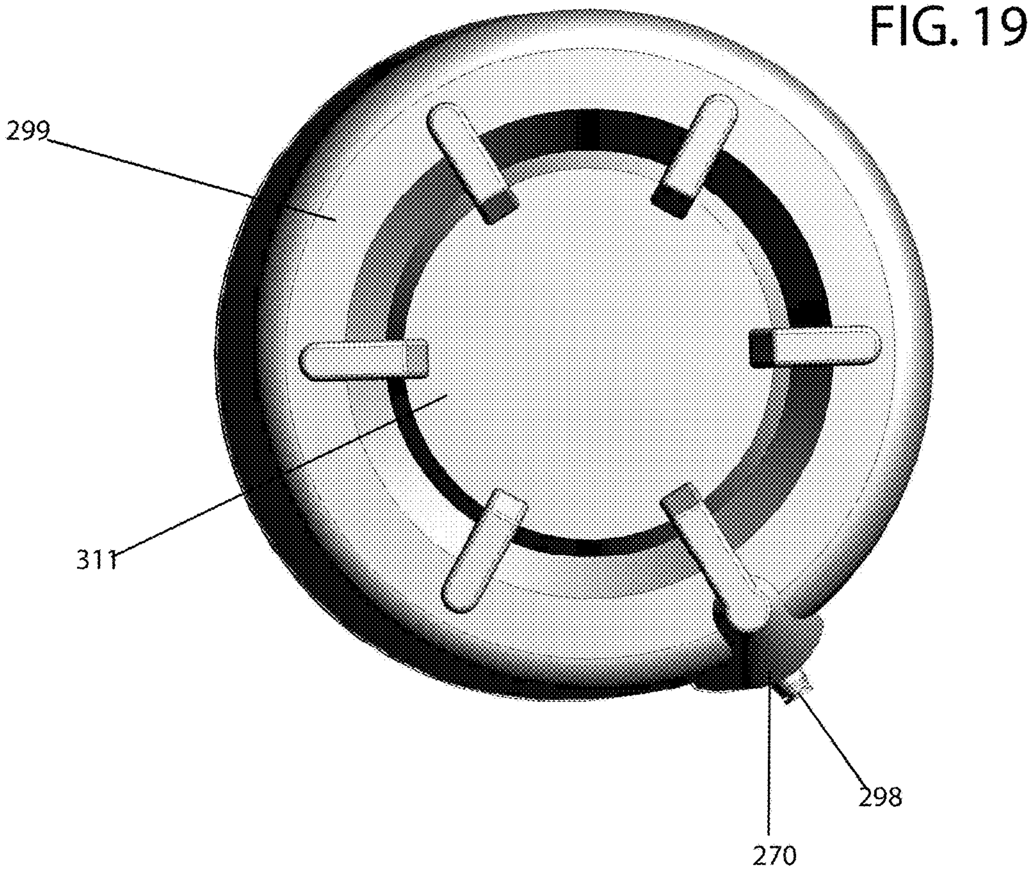
FIG. 19 is a bottom view of the air purifier.

FIG. 19 shows a bottom view of the air purification system which shows bottom 299 as well as a central plate 311. This view shows outer cover 270 as well as intake 298.

Figure 20:
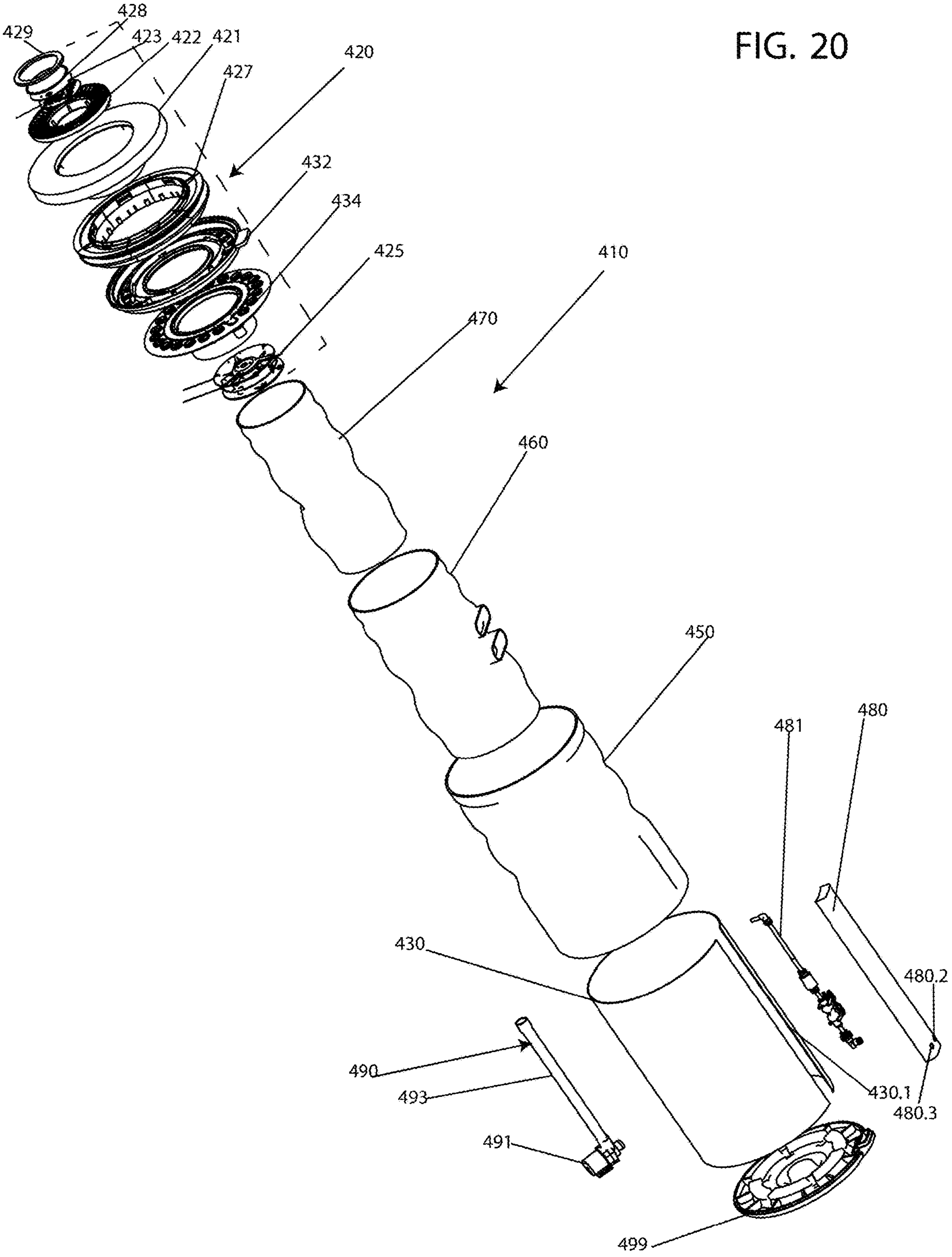
FIG. 20 is a side perspective exploded view of another embodiment of an air purification device.

FIG. 20 is a perspective exploded view of another embodiment comprising an air purifying device 410. Air purifying device 410 comprises a top 420, a skin, 430, a main tank 450, an outer core pipe 460, and an inner core pipe 470. Each of main tank 450 outer core pipe 460 and inner core pipe are in a corrugated or wavy pattern. Skin 430 and bottom 499 are coupled to main tank 450.

A conduit comprising an outer pipe cover 480 is coupled to outer cover or skin 430, wherein outer cover 480 is configured to cover over a water supply sub assembly 481. Outer pipe cover 480 includes a body section 480.1, inlets 480.2 and 480.3 for both electrical and water supply. An intake of water supply sub assembly 481 is coupled to inlet 480.2. There is also a water distribution sub assembly 490 as well. Coupled to main tank 450, and skin 430 is a bottom 499. Purification solution transfer system 490 is configured to pump fluid such as water and a biological reagent from a bottom portion of main tank 460 to an upper portion of main tank 450 towards top 420. The surface of each of main tank 450, outer core pipe 460 and inner core pipe 470

Figure 21:
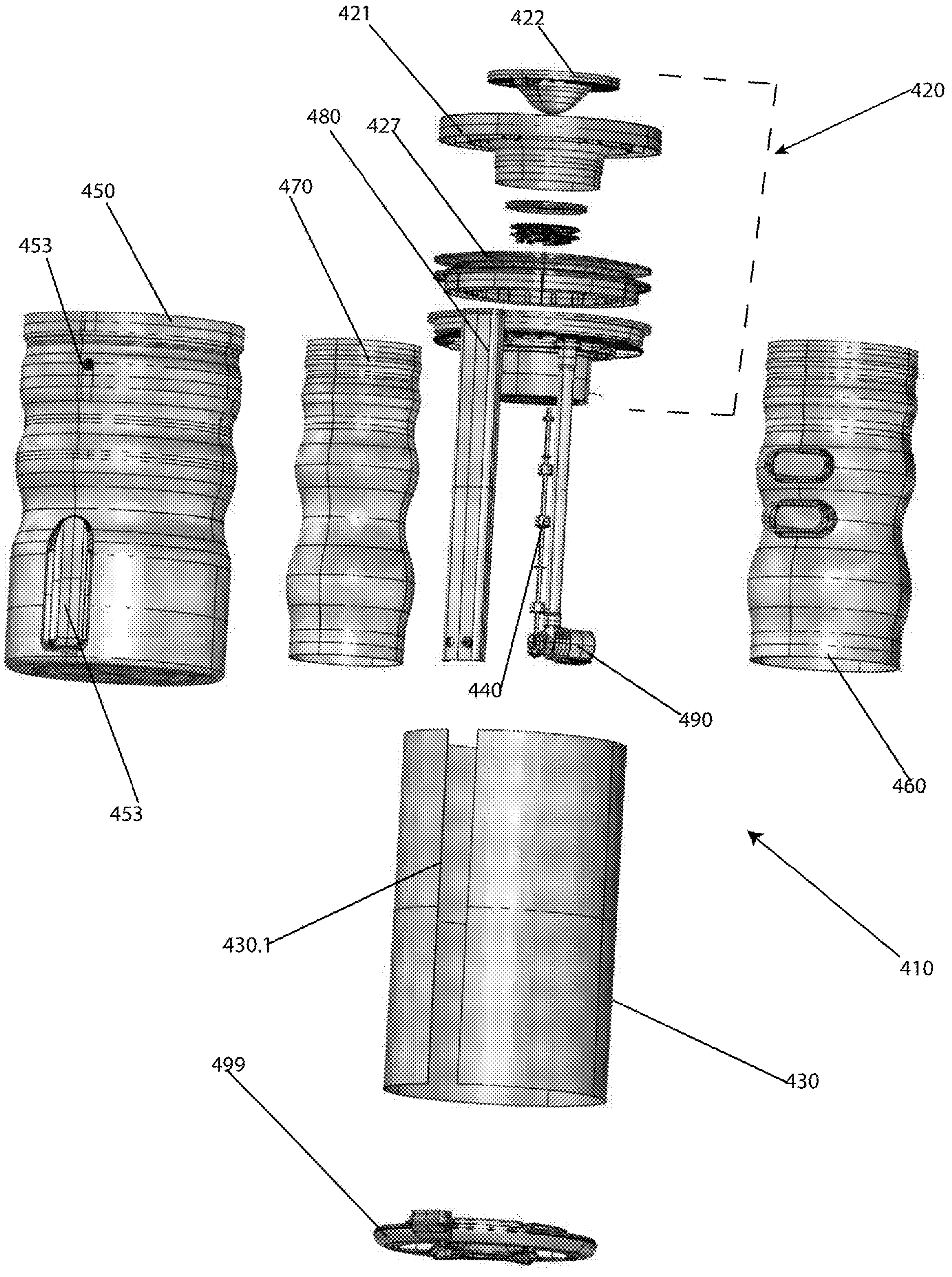
FIG. 21 is a bottom-side perspective exploded view of the embodiment of FIG. 20.

FIG. 21 shows a side exploded view of the embodiment of the air purifying device 410 of FIG. 20, which shows top 420, skin 430 having a slot or channel 430.1. Slot or channel 430.1 is configured to be positioned adjacent with conduit or outer pipe cover or 480. In this view, there is shown main tank 450 having recess or housing 453 configured to receive at least a portion of water supply sub assembly 481 (see FIG. 1). In addition, there is outer core pipe 460, inner core pipe 470, as well as fluid sensing system 440, and water distribution sub assembly aka purification solution transfer system 490. Top section 420 includes PCB housing 422, top cover 421, wherein PCB housing 422 fits inside of top cover 421. Top cover 421 fits on top of and at least partially inside of air inlet 427, while air inlet 427 fits on top of, and at least partially inside of top tray 432 and bottom tray 434. Top tray 432, and bottom tray 434 are coupled together to form a series of fluid channels to distribute fluid that is pumped and/or moved from a bottom of main tank 450 to a top portion into top 420.

Figure 22:
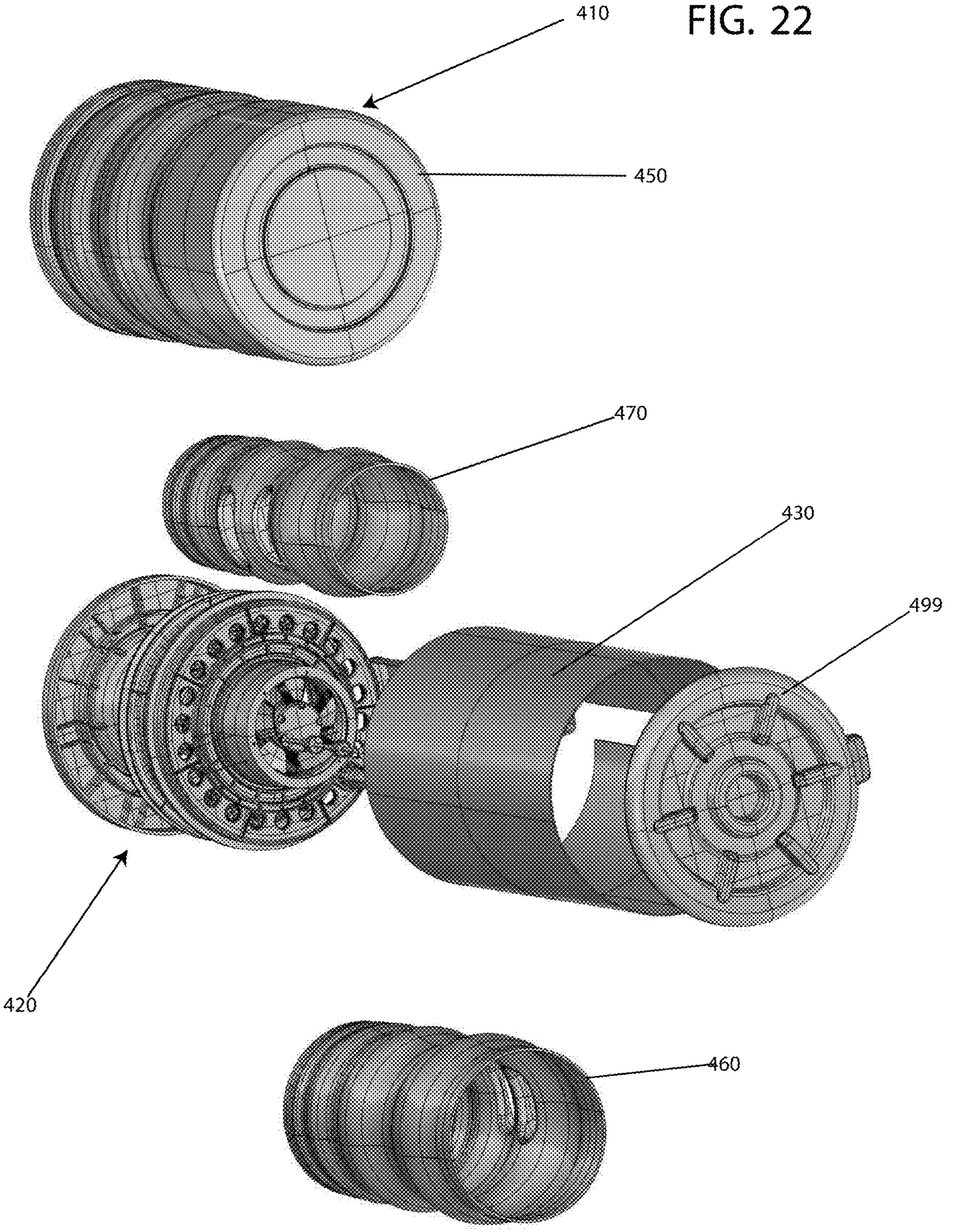
FIG. 22 is a top exploded view of the embodiment of FIG. 20.

FIG. 22 shows an exploded perspective view of the air purifying device 410 with main tank 450 shown along with outer pipe 460, inner pipe 470, and top section 420 also shown Bottom 499 is also shown.

Figure 23:
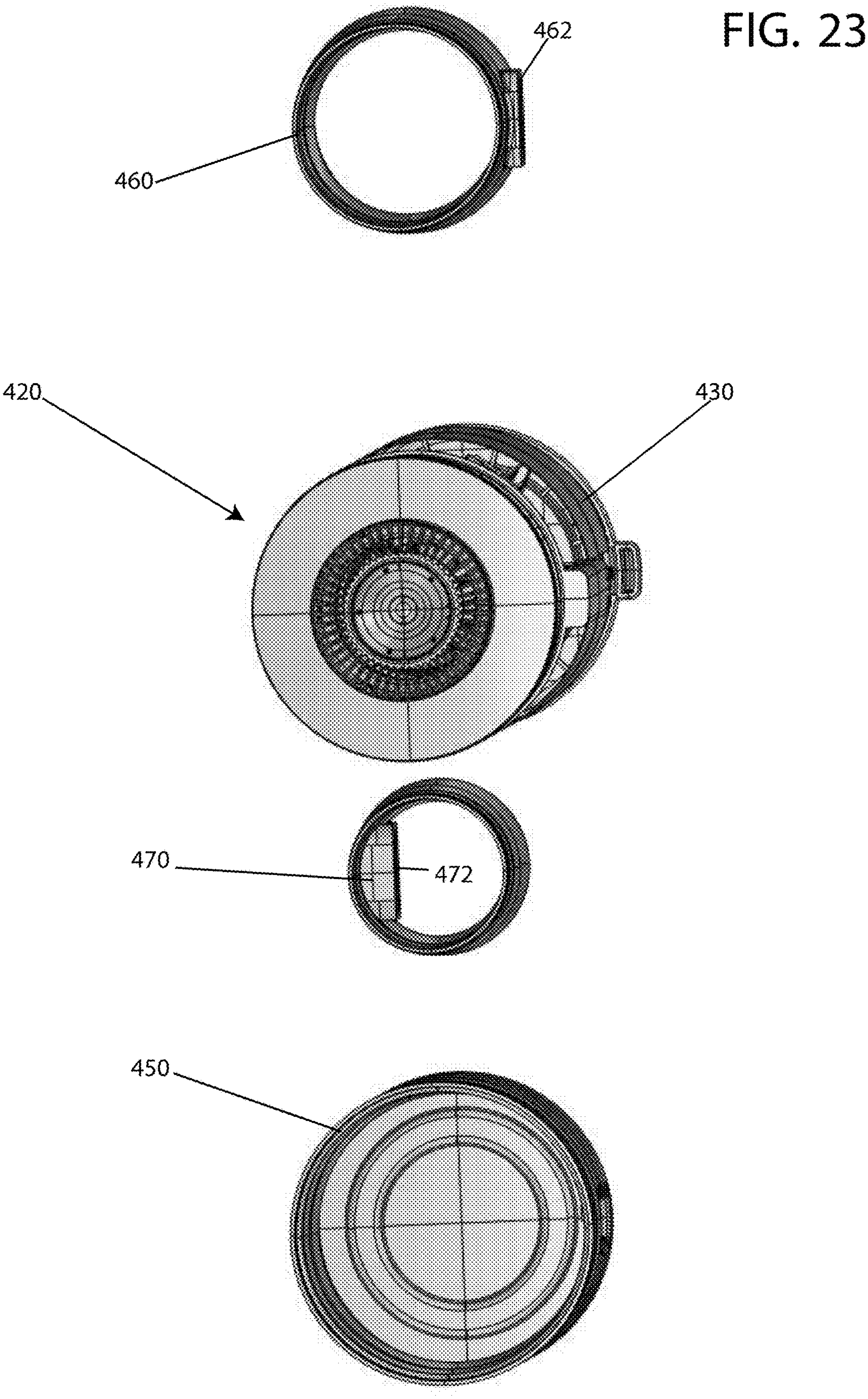
FIG. 23 is a side exploded view of the embodiment of FIG. 20.

FIG. 23 shows a side exploded view of the embodiment of FIG. 20 which shows top 420, skin 430, tank 450 outer core pipe 460 having an outward facing air channel 462, inner-core pipe 470 having an inward facing air channel 472.

Figure 24:
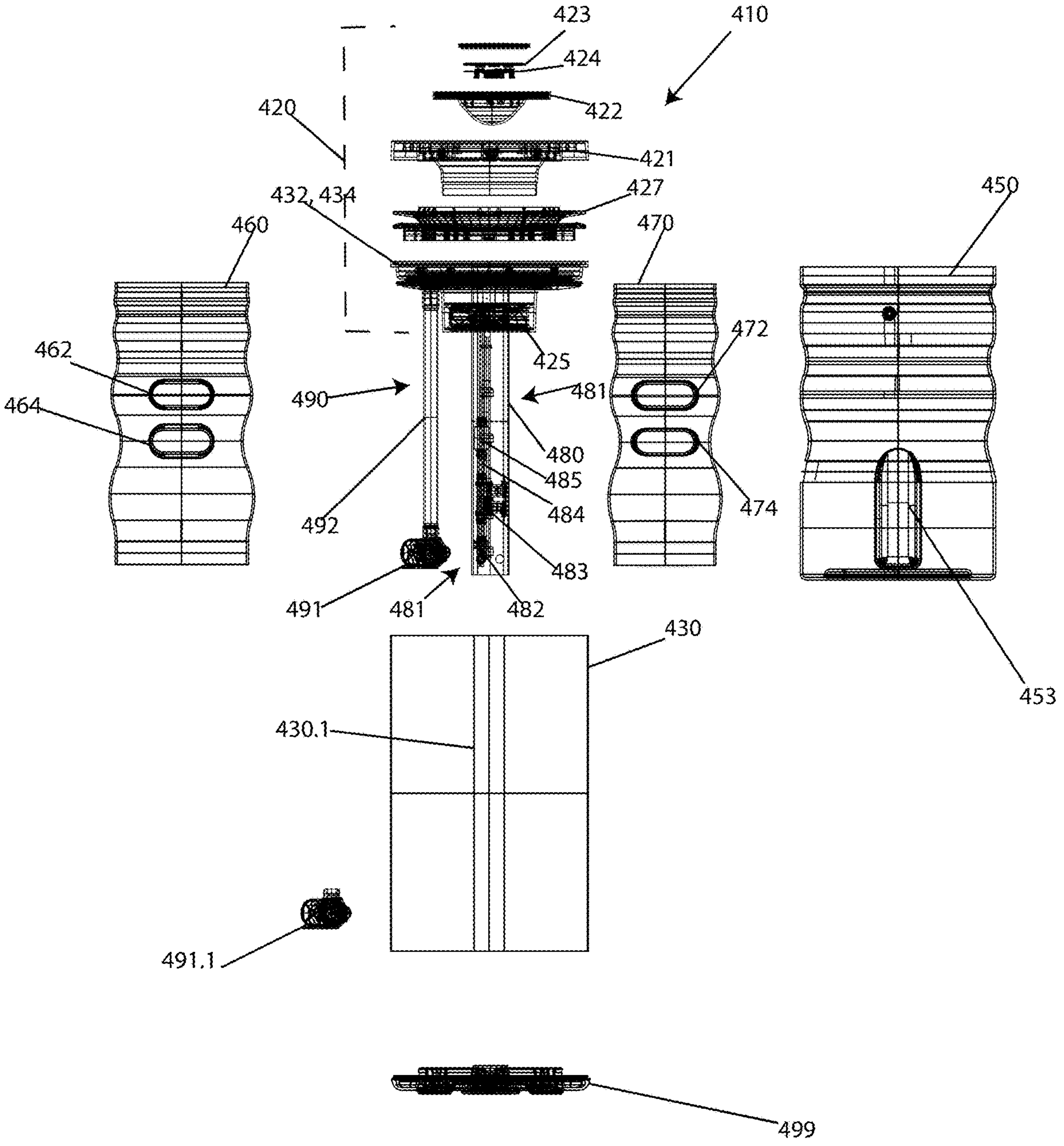
FIG. 24 is a side exploded view of the embodiment of FIG. 20.

FIG. 24 shows a side exploded view of the embodiment of FIG. 20 which shows the air purifying device with a top 420, including top cover 421, PCB housing 422 housing both touch panel 423 and the printed circuit board (PCB) 424. There is also air inlet 427, as well as top and bottom trays 432 and 434. A fan 425 is shown coupled to bottom tray 434.

There is also shown skin 430 having a slot or channel 430.1. Slot or channel 430.1 is configured to be covered by outer pipe cover 480. Disposed inside of skin 430 is outer core pipe 460 which has two air inlets 462 and 464, inner core pipe 470 has two air inlets 472 and 474 as well.

Figure 25:
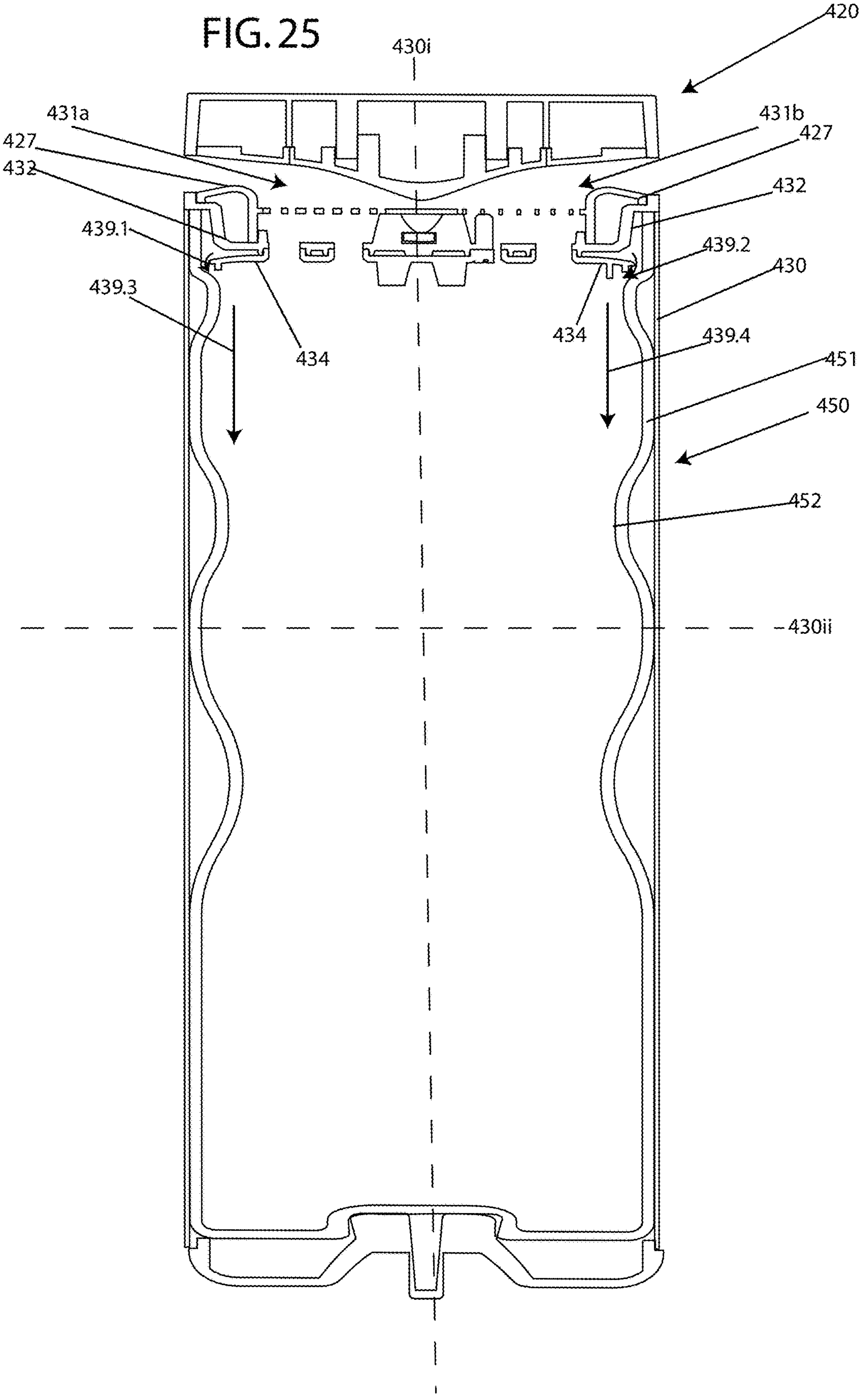
FIG. 25 is a side cross-sectional view of the device taken along a first vertical plane.

FIG. 25 is a cross-sectional view of the air purifying device 410. This view shows top 420 coupled to a body section including skin 430 and main tank 450. Main tank 450 has a body that is shaped in a substantially corrugated or wavy design with alternating outer sections 451 and inner sections 452. These alternating outer and inner sections are alternating along longitudinal axis 430*i*, and are at different depths relative to latitudinal axis 430*ii*. This cross-sectional view also shows air inlet openings showing air flow patterns 431*a* and 431*b* which show air flowing into the system through air inlet 427. Top and bottom trays 432 and 434 are shown coupled to each other as well. Arrows 439.1, and 439.3 show the flow of fluid over bottom tray 434 down into the inner side of main tank 450. In addition, arrows 439.2 and 439.4 also show this flow of fluid from the other side of this housing.

Figure 26:
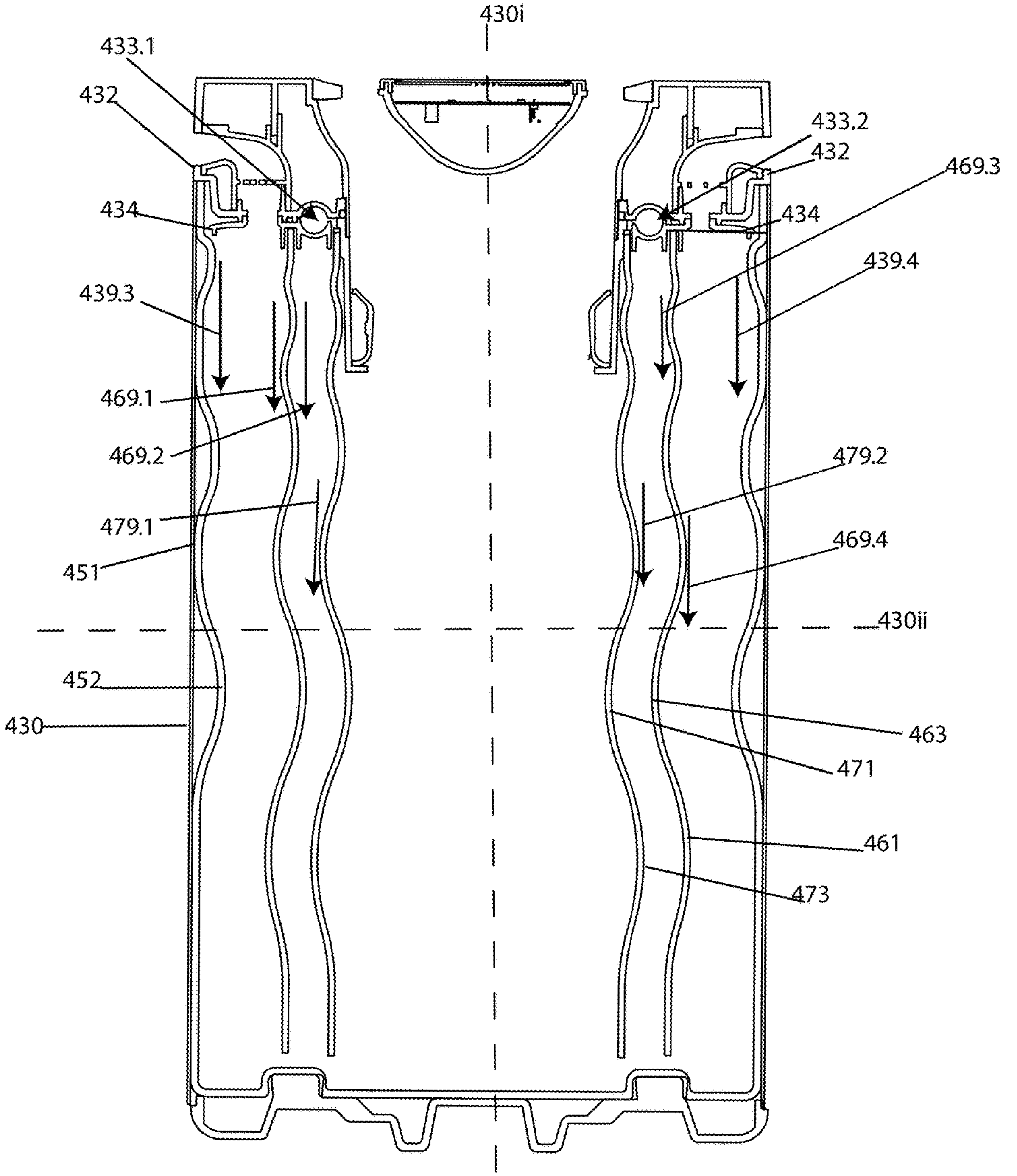
FIG. 26 is a side cross-sectional view of the device taken along a another vertical plane.

FIG. 26 shows another cross-sectional view which shows both skin 430, main tank 450, outer core pipe 460 and inner core pipe 470. With this view there is shown top and bottom trays 432 and 434. Top and bottom trays 432 and 434 when combined form a channel or tube for allowing fluid to flow under mild pressure therein. This channel or tube is shown as channel 433.1 and 433.2 and forms a circular or annular tube around the entire device. Fluid is forced outside of these channels to either inner or outer regions of trays 432 and 434. As disclosed above main tank 450 includes both cuter sections 451 and inner sections 452 such that fluid can flow down these outer and inner sections rather than free-fall down to a bottom portion of the tank. In addition, outer core pipe 460 includes both an outer section 461 and an inner section 463 alternating in a pattern along longitudinal axis 430*i*. Thus, outer section 461 is at a different depth than inner section 463 with respect to latitudinal axis 430*ii*. In addition, along inner core pipe 470 there are both outer sections 471 and inner sections 473. These outer and inner sections 471 and 473 respectively are extending in a pattern along longitudinal axis 430*i* and at varying depths with respect to latitudinal axis 430*ii*. Thus, the flow of fluid along these walls of main tank 450, outer core pipe 460 and inner core pipe 470 is shown by arrows 439.3, and 439.4 down main tank 450. The fluid flows over these walls of varying depth so that the fluid does not free fall to the bottom. The arrows 489.1 and 469.4 show fluid flow down the outer walls of outer core pipe 460. The arrows 469.2 and 469.3 show fluid flow down the inner walls of outer core pipe 460. Furthermore, the arrows 479.1 and 479.2 shows fluid flow down the outer walls of inner core pipe 470.

Figure 27:
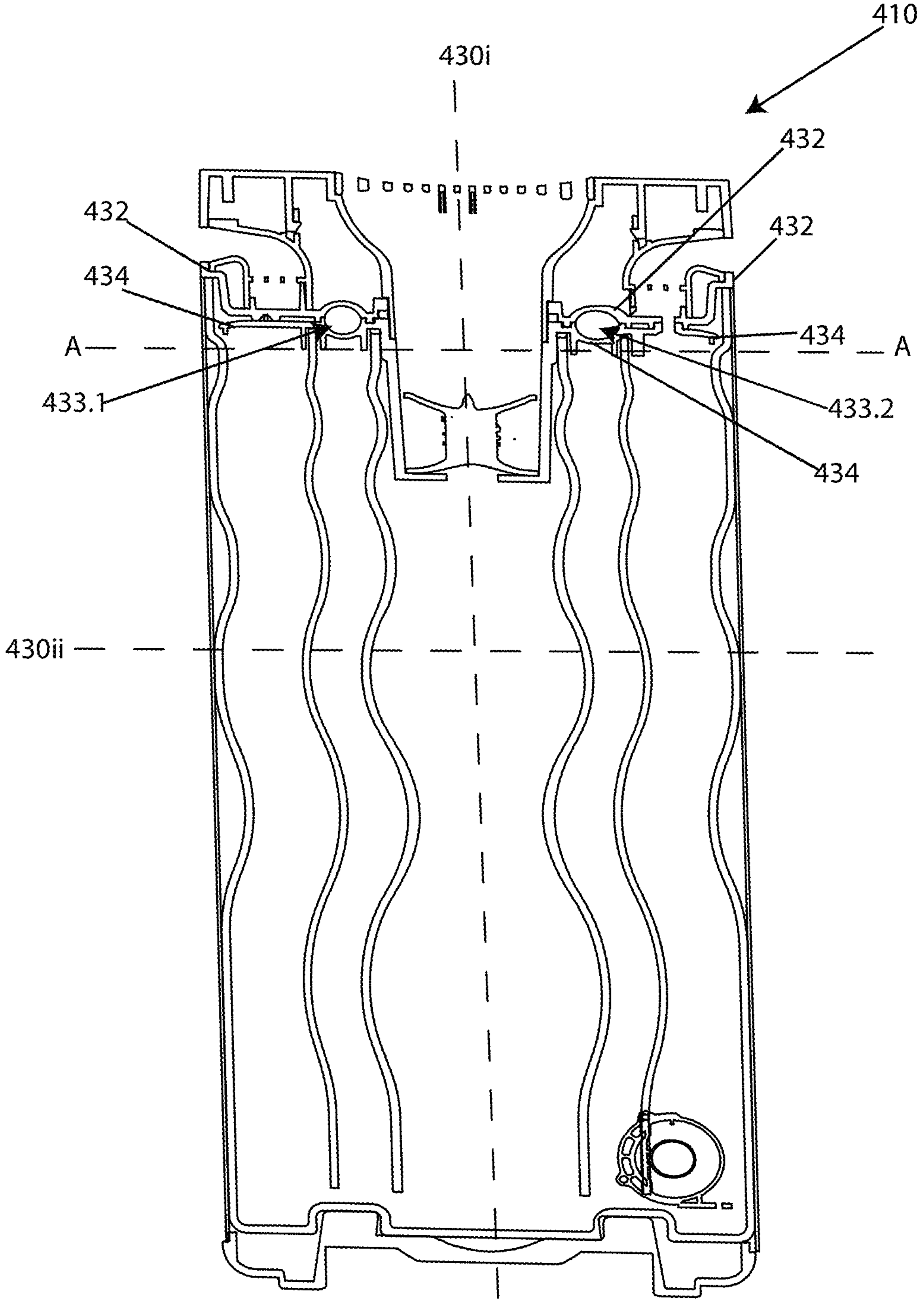
FIG. 27 is another side cross-sectional view taken at a different depth than FIG. 28.

FIG. 27 shows a similar cross-sectional view which shows both longitudinal and latitudinal axes 430*i* and 430*ii*. In addition, there is shown both top tray 432, and bottom tray 434 as wall as channels 433.1 and 433.2 for a fluid path.

Figure 28:
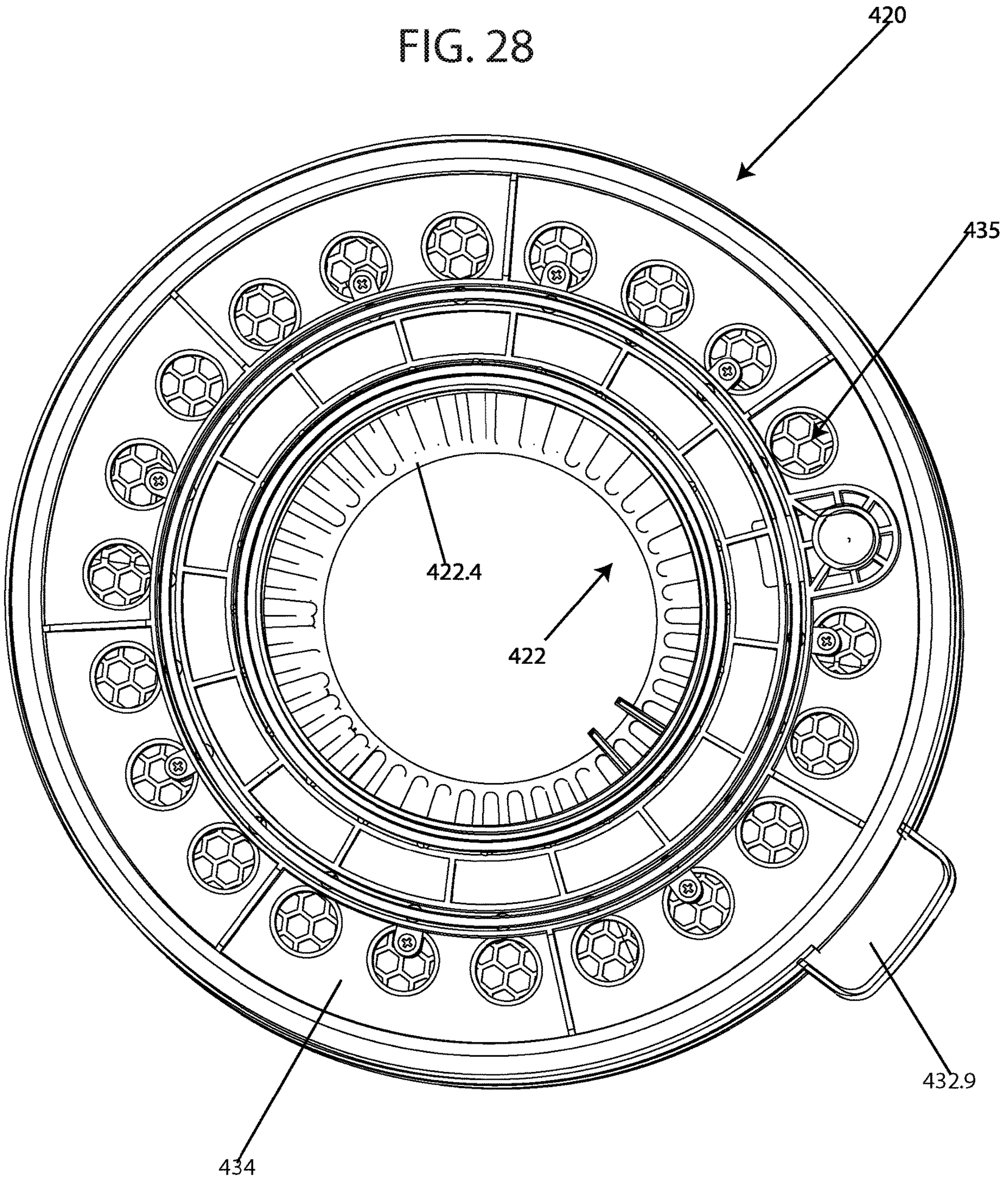
FIG. 28 is a cross-sectional view of the device taken at section line A-A in FIG. 27.

FIG. 28 shows a bottom view taken of top 420 along a cross-sectional line A-A shown in FIG. 27. This view shows Bottom cover 434, having main air inlet 427 for allowing air to flow through. A tab or flange 432.9 is shown extending out from top tray 432. Tab or flange 432.9 is configured to receive a top portion of outer pipe cover 480. In addition, louvers 422.4 on PCB housing 422 are also shown. These louvers 422.4 are configured to allow fluid such as air to flow out from the housing as air flows out of a central core of the housing. Thus, in at least one embodiment, where fan 425 (see FIG. 20) is moving to create negative air pressure inside of the housing, air flowing into the housing flows down through air holes 435 and around the outer core pipe 460 and the inner core pipe 470 and then out and up through louvers 422.4. In an alternative embodiment, fan 425 is reversed thereby creating positive air pressure in the housing drawing air in through louvers 422.4 down through a center of the housing around inner core pipe 470 around outer core pipe 460 and then out through air inlet 427.

Figure 29:
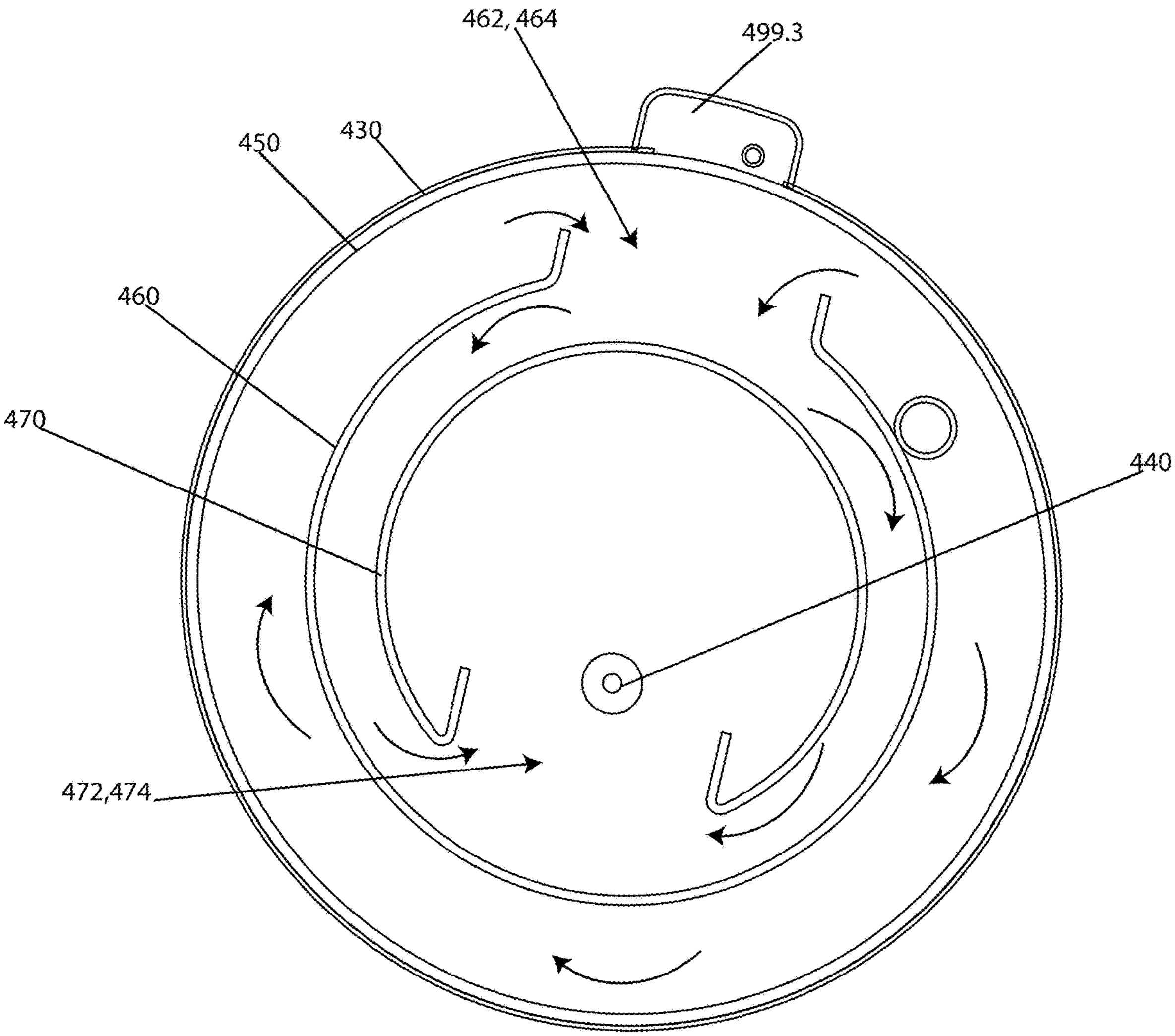
FIG. 29 is a cross-sectional view taken along latitudinal line 430*ii* in FIG. 27.

FIG. 29 shows a cross-sectional view taken along latitudinal axis 430*ii*. This cross-sectional view shows tank 450, outer pipe 460, and inner pipe 470. The arrows show that the air flow starts by flowing through air holes 435 (See FIG. 28), then around outer core pipe 460, through air inlets 462 and 464, and then around inner core pipe 470. The air then flows through air inlets 472 and 474. That air that is now in a central region of the device then flows out and up through or past louvers 422.4 and out of the system. However, with this design, the air comes in contact with the inside surface of main tank 450, the inner and outer surfaces of outer core pipe 460 and the outer and inner surfaces of inner core pipe 470.

FIGS. 30A and 30B show skin 430 in greater detail. There is shown slot or channel 430.1 which runs along a longitudinal axis of skin 430. Skin 430 can be of any suitable material such as but not limited to metal, plastic, wood, composite or any other suitable material. The skin 430 can be of any suitable shape as well.

Figure 31A:
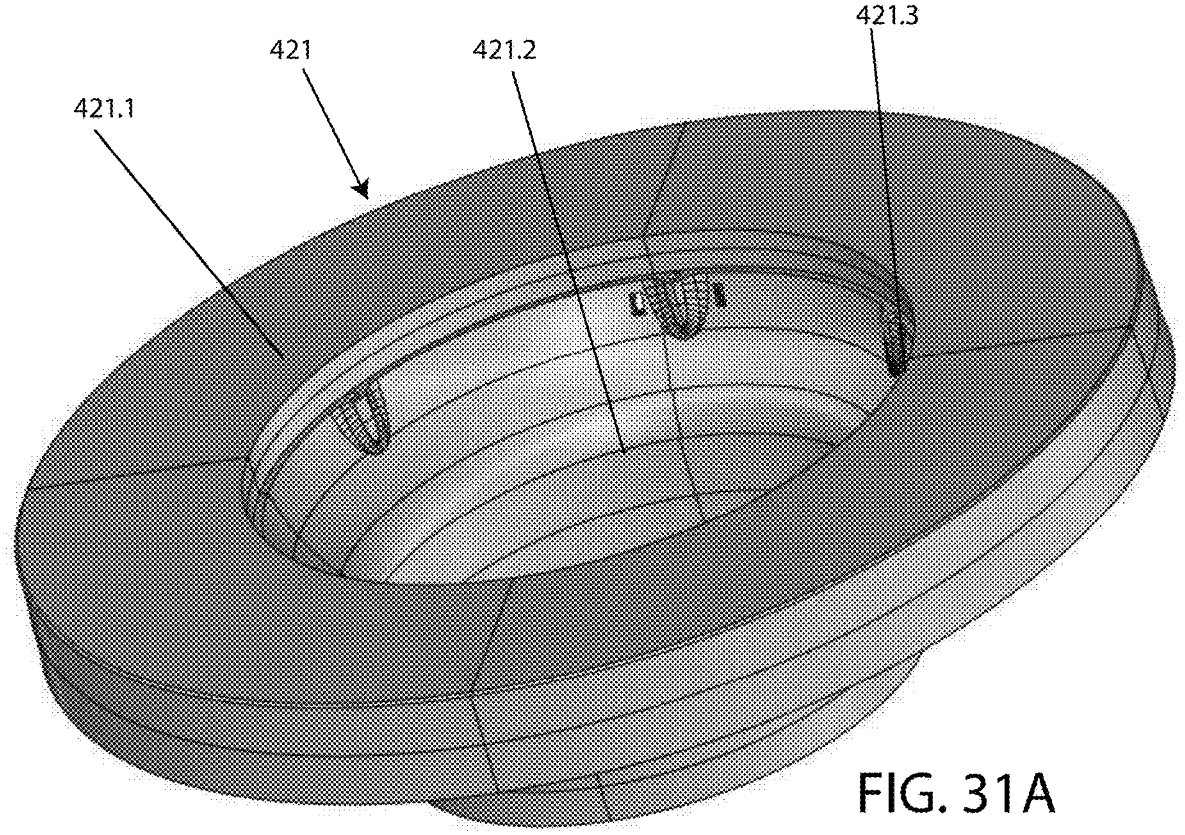
FIG. 31A is a perspective view of the top cover.
Figure 31B:
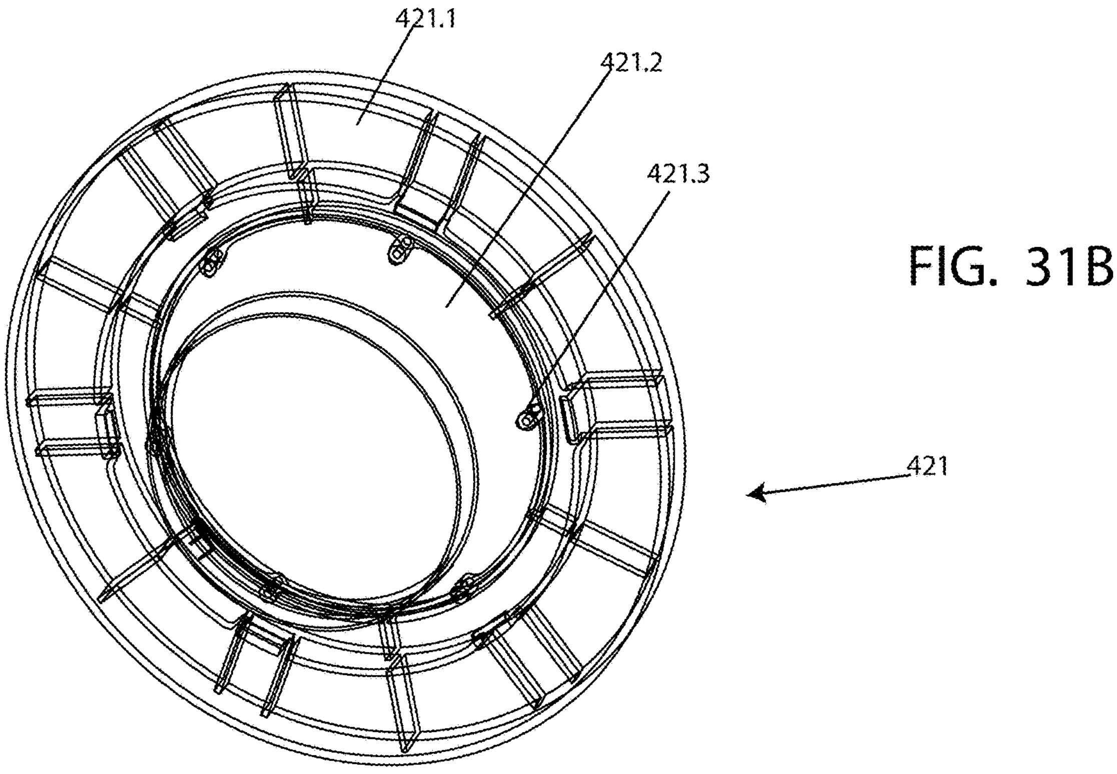
FIG. 31B is another perspective view of the top cover.

FIGS. 31A and 31B show perspective views of cover 421. Cover 421 includes a top cover section 421.1. In addition, there is a channel section 421.2. Channel section 421.2 is substantially cylindrical and is configured to receive PCB housing 422. In addition, there are screw holes configured to receive screws.

Figure 32A:
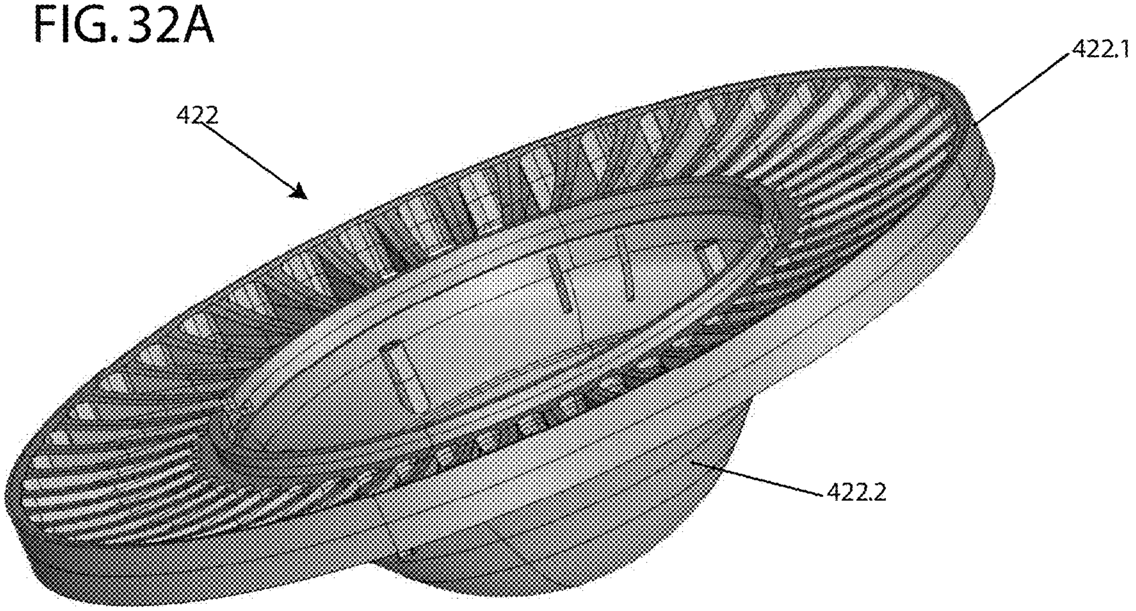
FIG. 32A is a perspective view of the PCB housing.
Figure 32B:
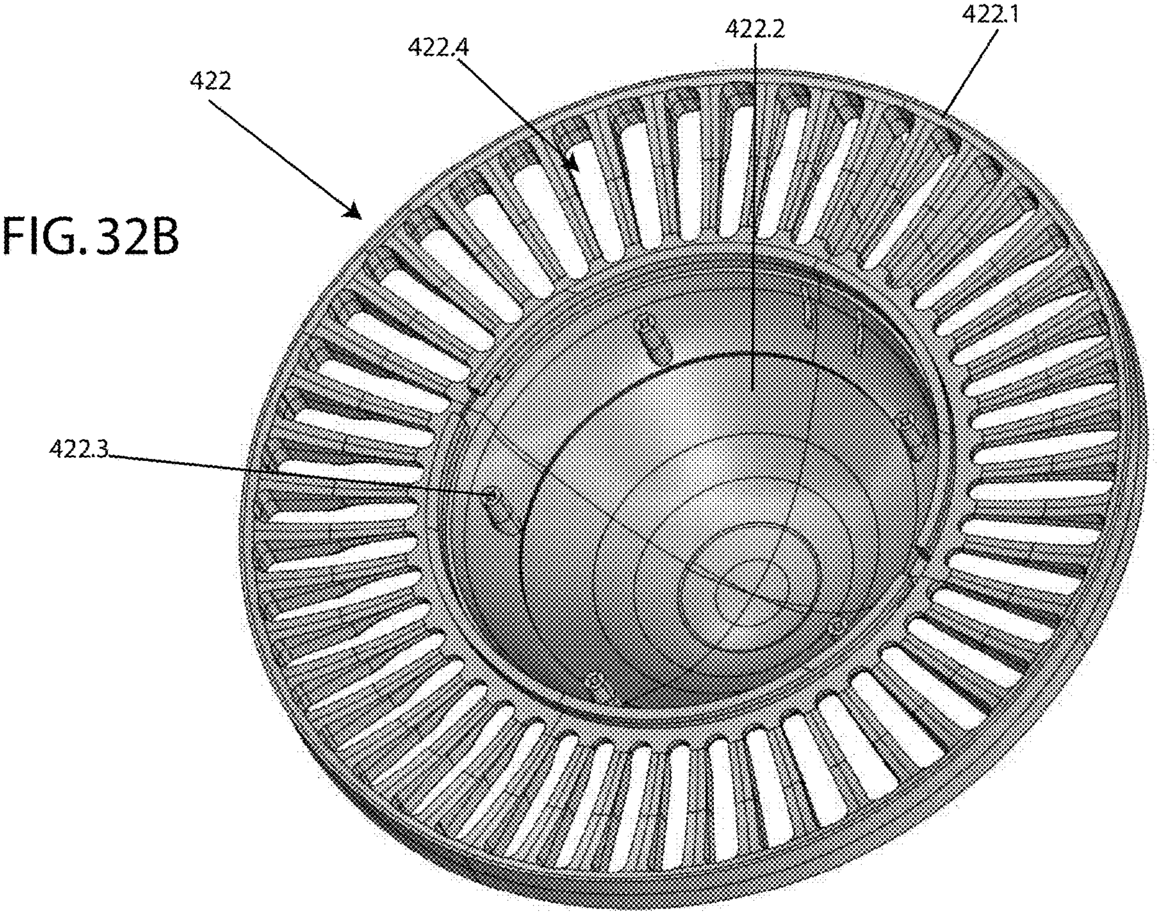
FIG. 32B is another perspective view of the PCB housing.
Figure 33:
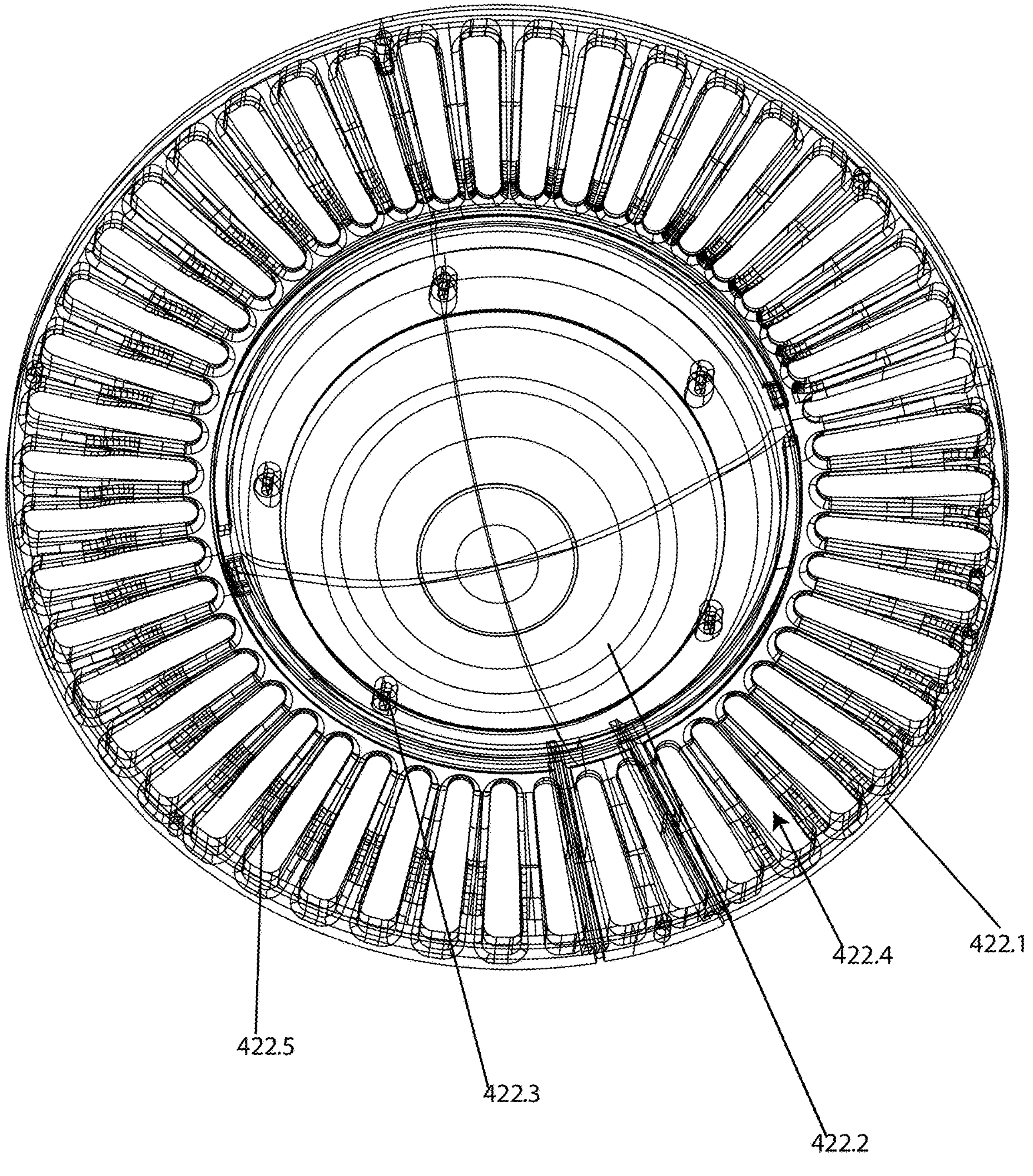
FIG. 33 is a top view of the PCB housing.

FIGS. 32A and 32B are perspective views of PCB housing 422. PCB housing 422 includes a rim 422.1 a bowl or housing section 422.2. There are also screw holes 422.3 disposed inside of the bowl 422.2 wherein a screw can be fed therein to secure PCB housing 422 to cover 421. Bowl 422.2 is shaped as an aerodynamic bowl to deflect air that is fed through the device past or through the louvers 422.4. FIG. 33 shows a top view of this same PCB housing which shows louver arms 422.5 interspersed between the plurality of louver openings.

Figure 34A:
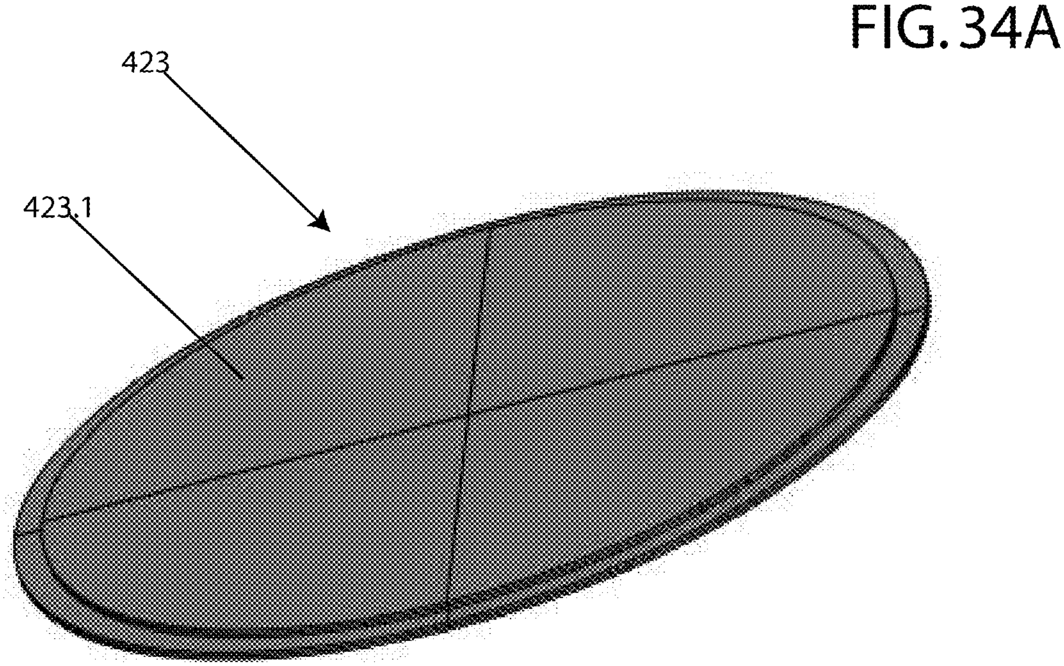
FIG. 34A is a perspective view of a first side of a touch screen.
Figure 34B:
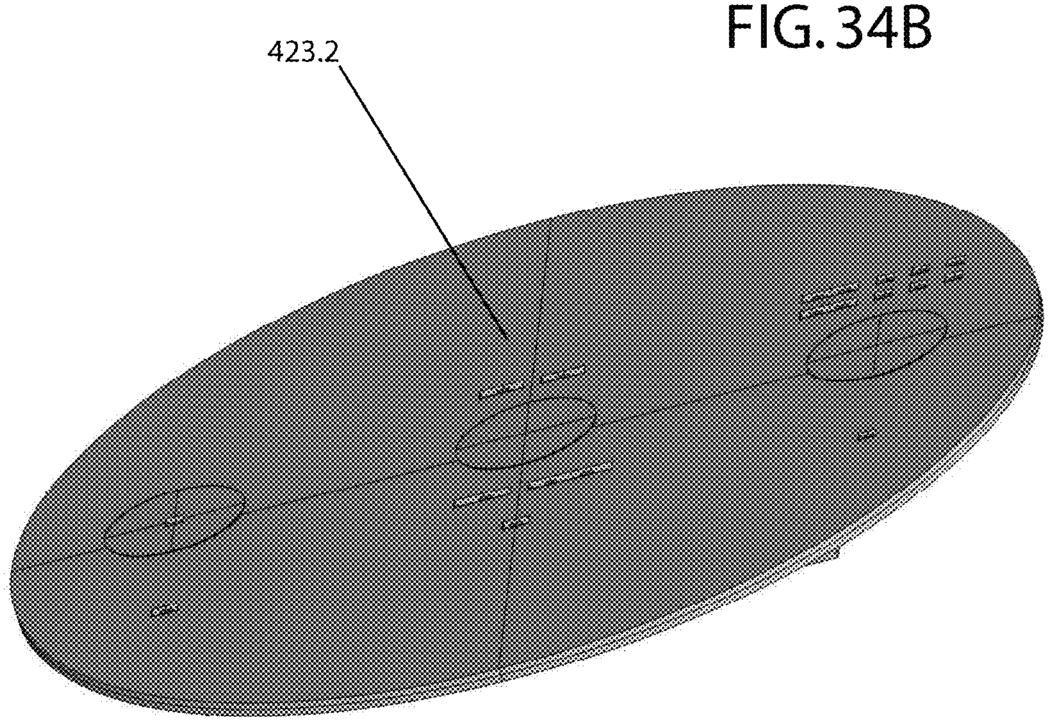
FIG. 34B is a perspective view of an opposite side of a touch screen.

FIGS. 34A and 34B show top and bottom views of a touch screen 423. In the top view of FIG. 34A there is shown top surface 423.1. In the bottom view of FIG. 34B there is shown bottom surface 423.2.

Figure 35A:
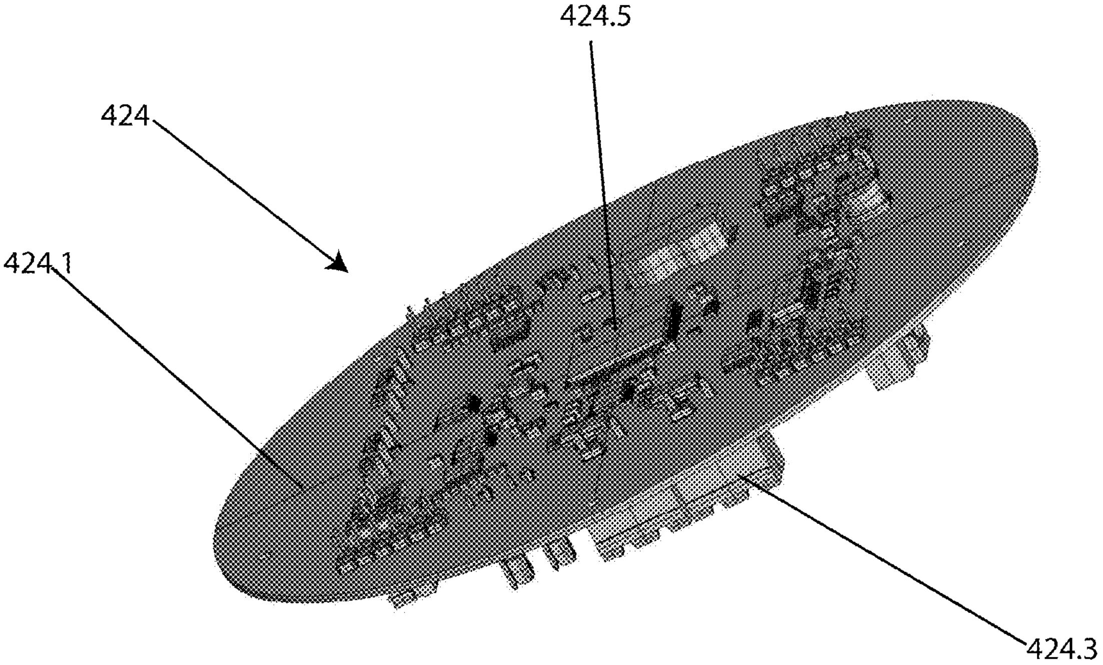
FIG. 35A is a perspective view of a first side of a PCB board.
Figure 35B:
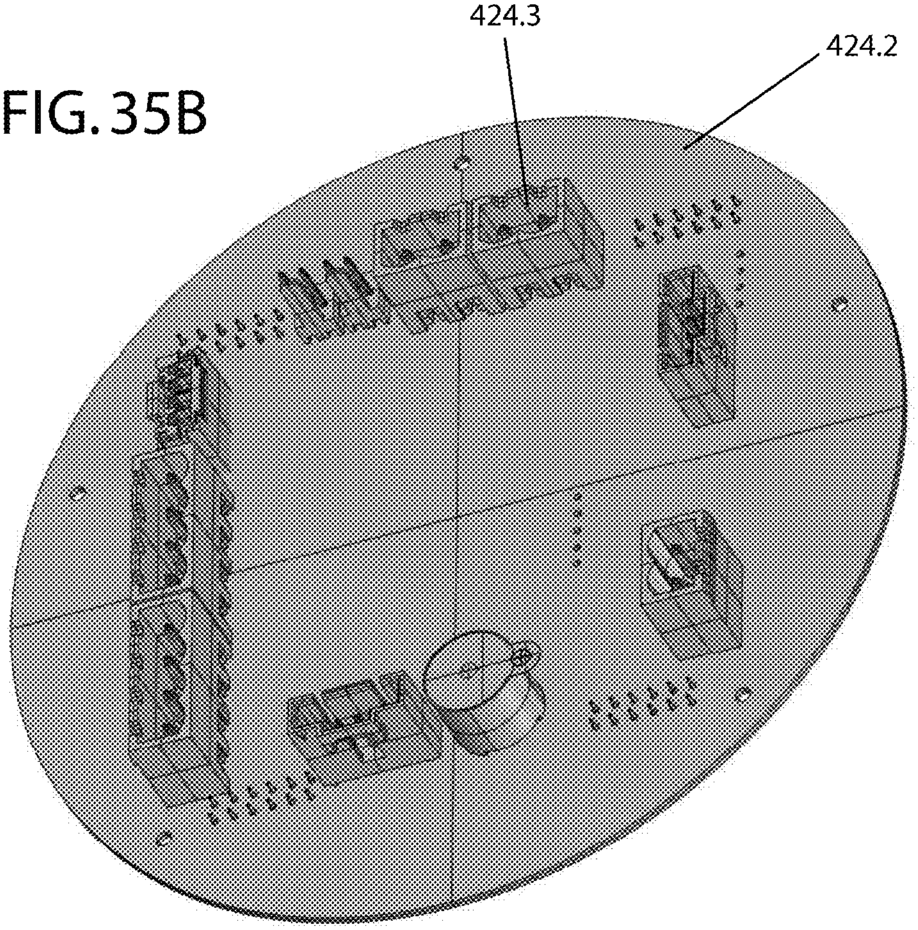
FIG. 35B is a perspective view of an opposite side of a PCB board.

FIGS. 35A and 35B show printed circuit board (PCB) 424 having a first side 424.1 and a second side 424.2. On the second side are connectors 424.3. Connectors 424.3 are configured to connect to sensors housed inside of the device or to other components in communication with the printed circuit board (PCB) 424. The PCB 424 is coupled to and in communication with touch screen 423. Both the touch screen 423 and the PCB 424 are housed inside of PCB housing 422. PCB 424 is essentially a controller that at least includes at least one processor such as a microprocessor shown by way of example by microprocessor 424.5. Microprocessor 424.5 is configured to run at least one program which controls the filling of fluid between two different pre-set heights based upon readings provided by a fluid sensing system 440 including a plurality of different water level sensors such as floatation sensors. Other components associated with the controller can be at least one memory in communication with the microprocessor such as microprocessor 424.5. Furthermore, the controller can also optionally include at least one transceiver so that the controller can communicate with outside components such as a solenoid valve, the fan, pumps, a fill level sensor and any other suitable sensors. This communication can be through a wired or wireless manner.

Figure 36A:
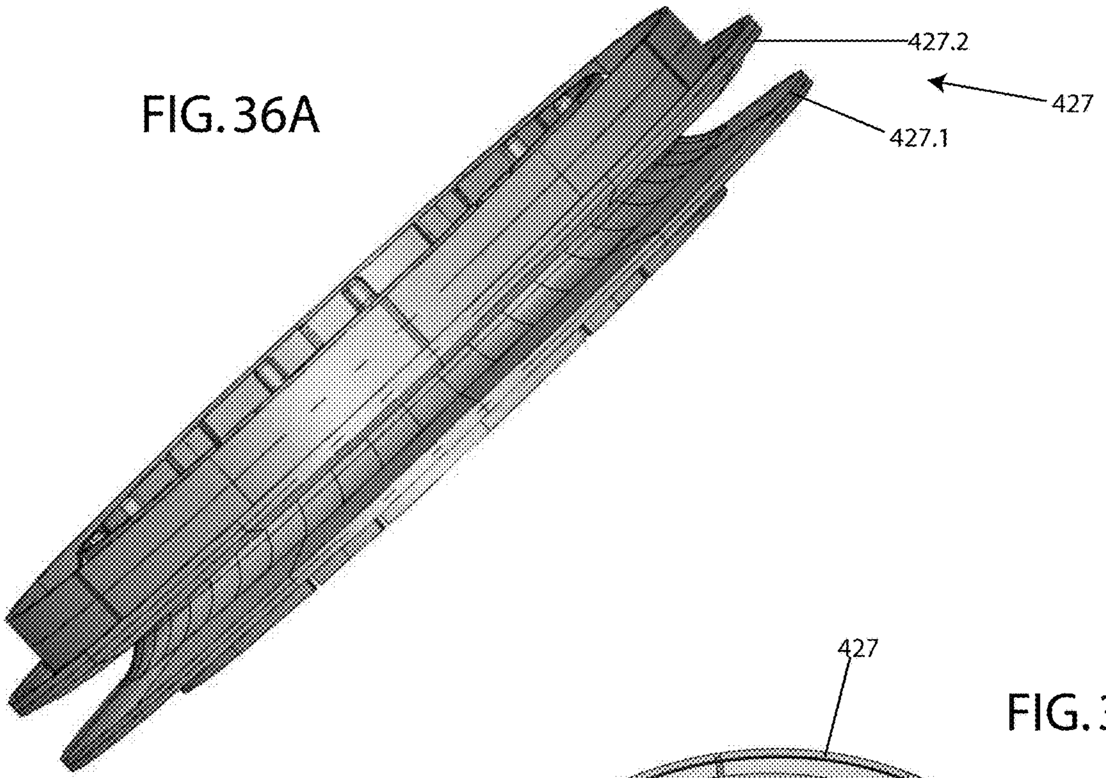
FIG. 36A is a side perspective view of an air inlet.
Figure 36B:
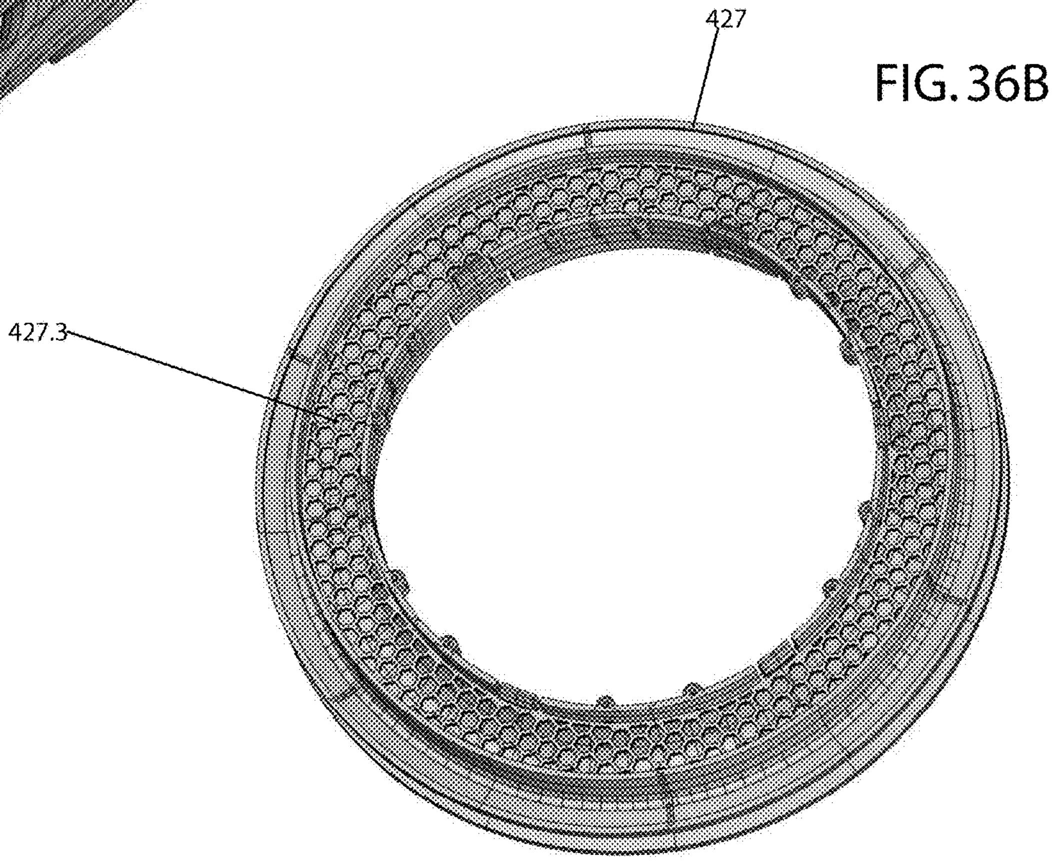
FIG. 36B is a bottom perspective view of an air inlet.

FIGS. 36A and 36B show a perspective and bottom view of an air inlet 427. Air inlet 427 includes a bottom section 427.1 and a top section 427.2. Both bottom section 427.1 and top section 427.2 have a curved interface configured to aerodynamically receive air intake into the system.

FIG. 37A shows a top view of the air inlet 427 which shows semen 427.3 housed within bottom section 427.1 FIG. 37B shows a side view of the air inlet 427 including both bottom section 427.1 and top section 427.2.

FIG. 37C is a view opposite FIG. 37A which shows an inner cylindrical surface 427.4 while also including bottom section 427.1 and top section 427.2. With this design air flows into the side of the air inlet 427 and through screen 427.3 and into the housing or main tank 450.

Figure 38A:
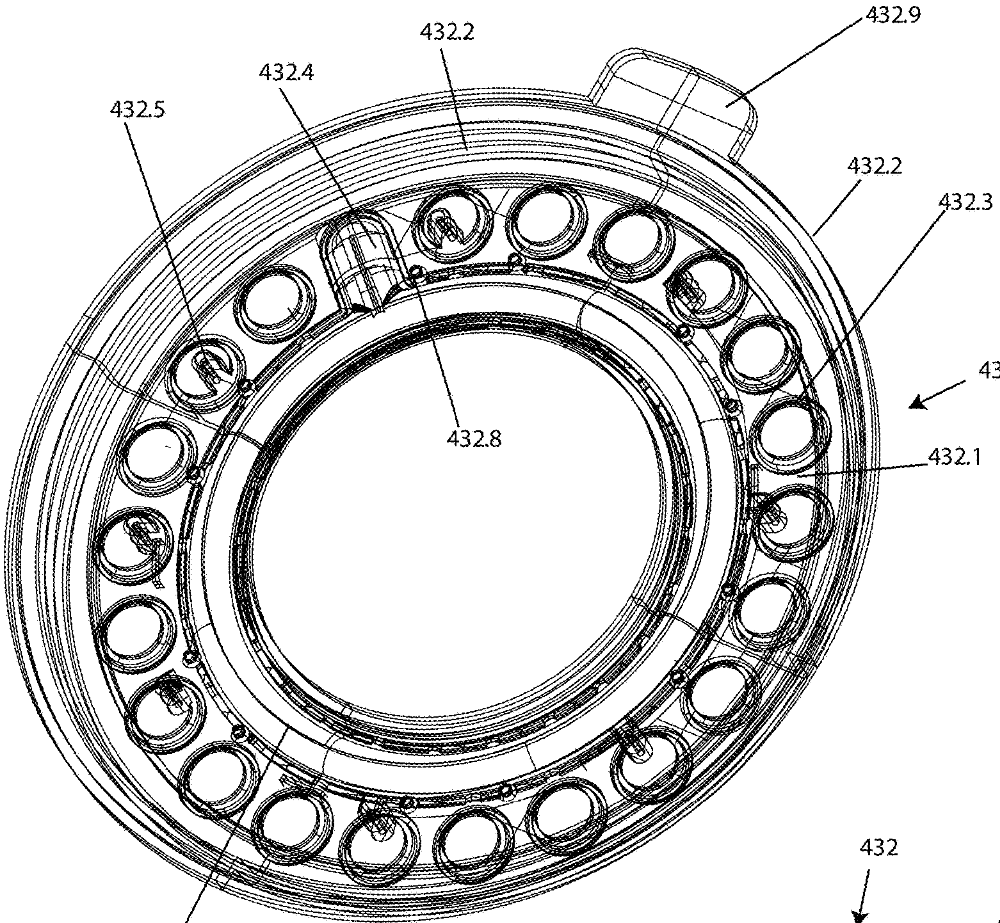
FIG. 38A is a top perspective view of a top tray.
Figure 38B:
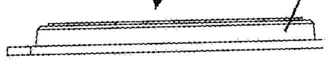
FIG. 38B is a side view of a top tray.
Figure 38C:
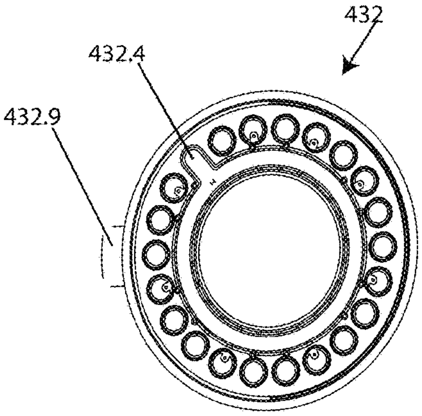
FIG. 38C is a top view of the top tray.
Figure 39:
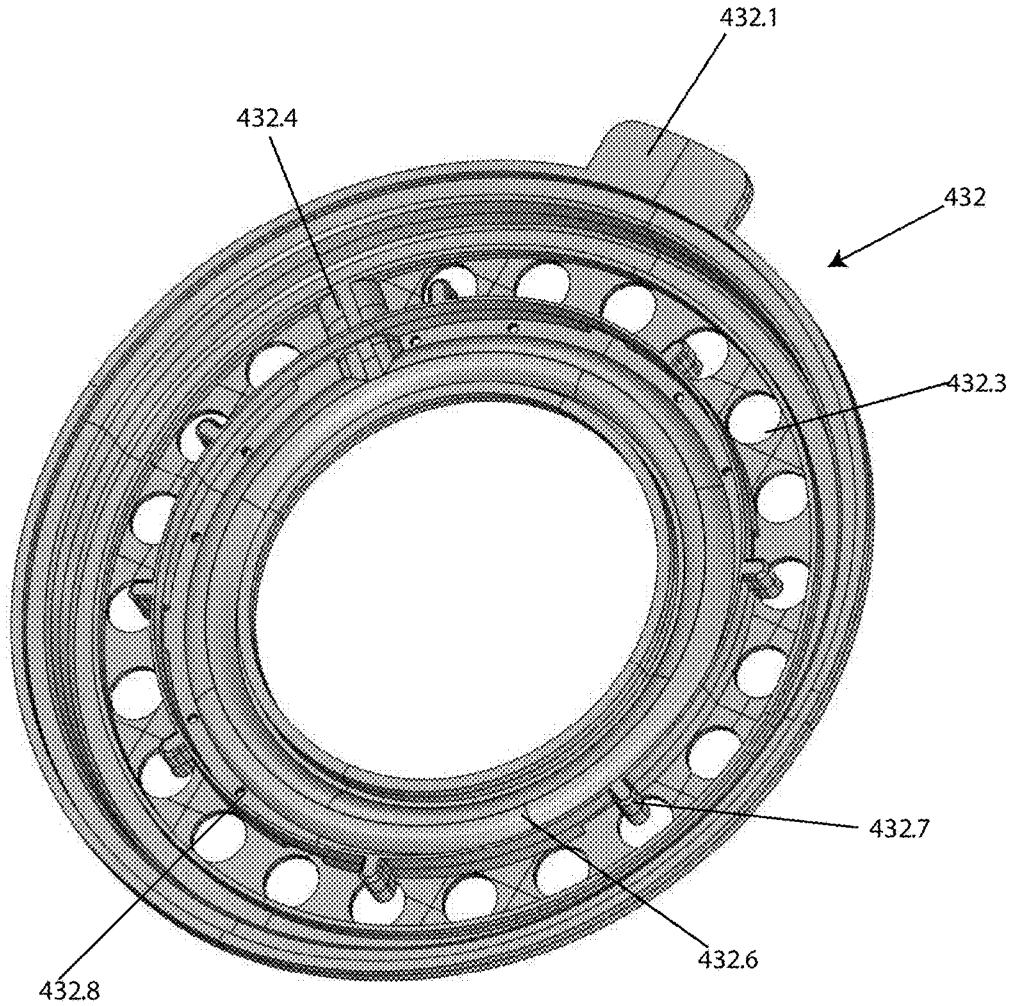
FIG. 39 is a perspective view of the top tray.

FIG. 38A shows a top-perspective view of top tray 432 while FIG. 38B shows a side view of top tray 432, and FIG. 38C shows a top view of top tray 432. FIG. 39 shows a perspective 3-D representation of this top tray. With these views there is shown a body section 432.1 a rim section 432.2 and air inlets 432.3 formed as circular holes interspersed around the body section 432.1. A fluid inlet 432.4 is configured to receive fluid therein. Screw connectors 432.5 extend into air inlets 432.3. In addition, a channel cover 432.6 which along with a corresponding channel cover on bottom tray 434 forms fluid paths 433.1 and 433.2. In addition, there are fluid openings 432.8 as well. A tab or flange on top tray 432 is configured to receive a top portion of outer pipe cover 480.

FIGS. 40A, 40B and 40C show bottom tray 434. Bottom tray 434 includes a rim section 434.1 a body section 434.2, air inlet 434.3 which match with air inlets 432.3 on top tray 432. Fluid opening 434.4 is configured to receive a feed pipe such as pipe 484. Fluid opening 434.4 sits opposite fluid inlet 432.4 when top tray 432 and bottom tray 434 are coupled together. Screw openings 434.5 extend into air inlets 432.3. Channel cover 434.6 sits opposite channel cover 434.6, an inner cylindrical shaft 434.7 extends substantially perpendicular to an extension of body section 434.2. Fluid holes 434.8 is positioned radially outside of channel cover 434.8. Fluid holes 434.9 is positioned radially inside of channel cover 434.6. Cylindrical shaft 434.7 includes a urn 434.10 and a plurality of screw holes configured to secure a fan such as fan 425.

The fluid sitting on top of bottom tray 434 is fed by pump 491 pumping fluid up through purification solution transfer system 490. Through pipe 493 and into fluid inlet 434.4. The fluid flows around the channel covers 434.6 and 432.6 along fluid paths 433.1 and 433.2 under moderate pressure. The fluid then spills out onto body section 432.2 and is covered by body section 432.1. The fluid flows over rim section 434.1 onto an Inner surface of main tank 450 as well as through hole 434.8 onto both an inner and outer surface of outer core pipe 460, and also through hole 434.9 along an outer surface of inner core pipe 470. With this design, bottom tray 434 distributes the fluid around the system on at least four (4) different walls or sides of the different tanks, or pipes 460 and 470.

Figure 41A:
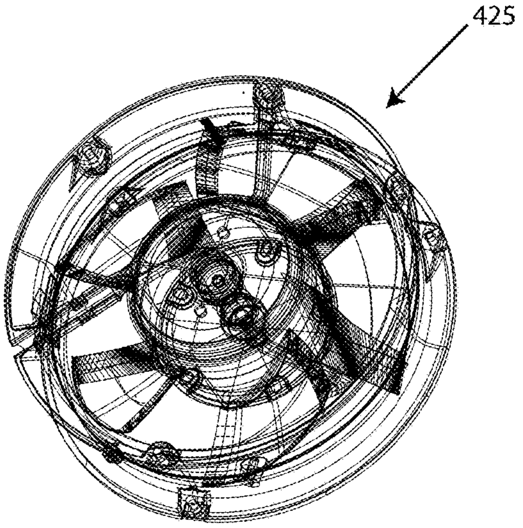
FIG. 41A is a top perspective view of the fan.
Figure 41B:
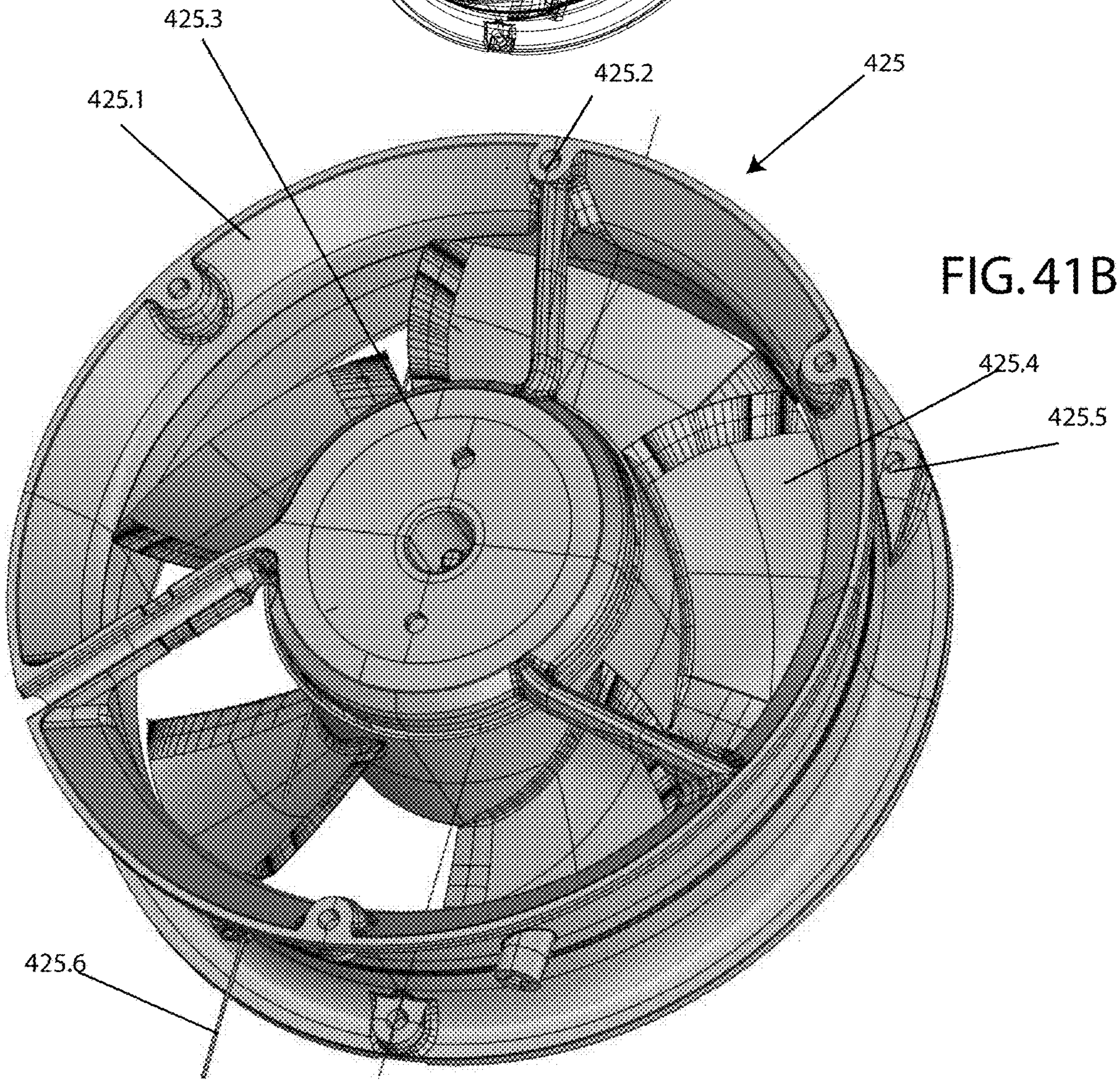
FIG. 41B is a top perspective view of the fan.

FIGS. 41A and 41B show fan 425 which includes a fan housing 425.1 Fan housing includes screw holes 425.2 are configured to couple to a bottom of PCB housing 422 via screws (not shown). Screw holes 425.5 are configured to couple the fan 425 to flange 434.10 with screws fitting into screw holes 434.1. Fan 425 includes motor 425.3 as well as contact pins 425.4. In addition, there is an electrical and control input in the form of line(s) 425.6.

Figure 42:
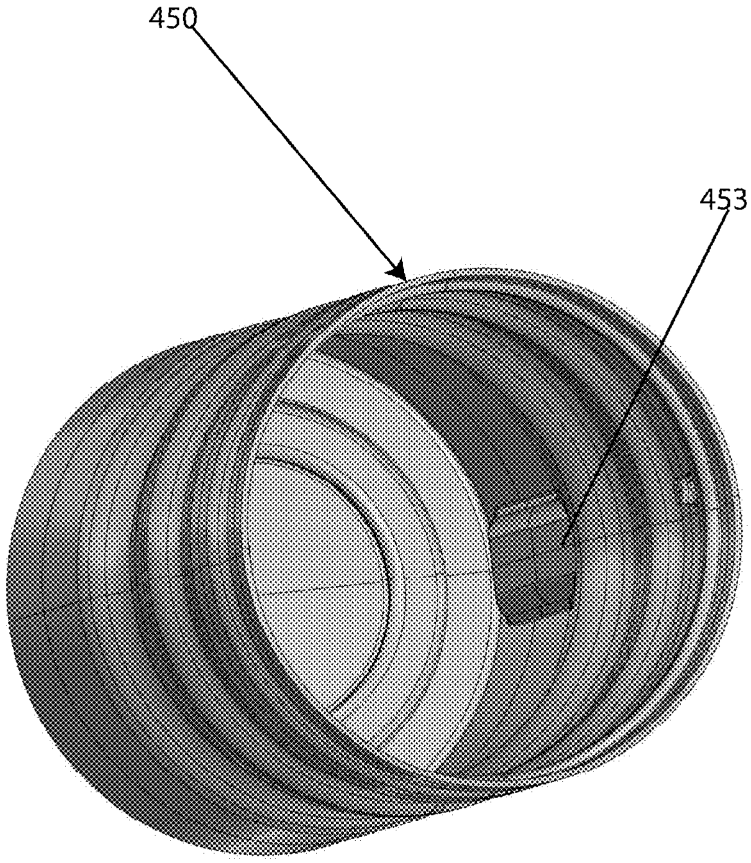
FIG. 42 is a top perspective view of the main tank.

FIG. 42 shews a perspective view of main tank 450 which includes recess or housing 453 configured to receive components from the water supply sub assembly 481. FIGS. 43A, 43B, 43C also show views of main tank 450 which shows inner and outer sections 451 and 452 as well as inner and outer surfaces 450.1 and 450.2. There is a hole 450.3 which is configured to receive water from water supply sub assembly 481. There is also a bottom portion 450.4 which is configured to mesh with bottom 499 as well.

Figure 44:
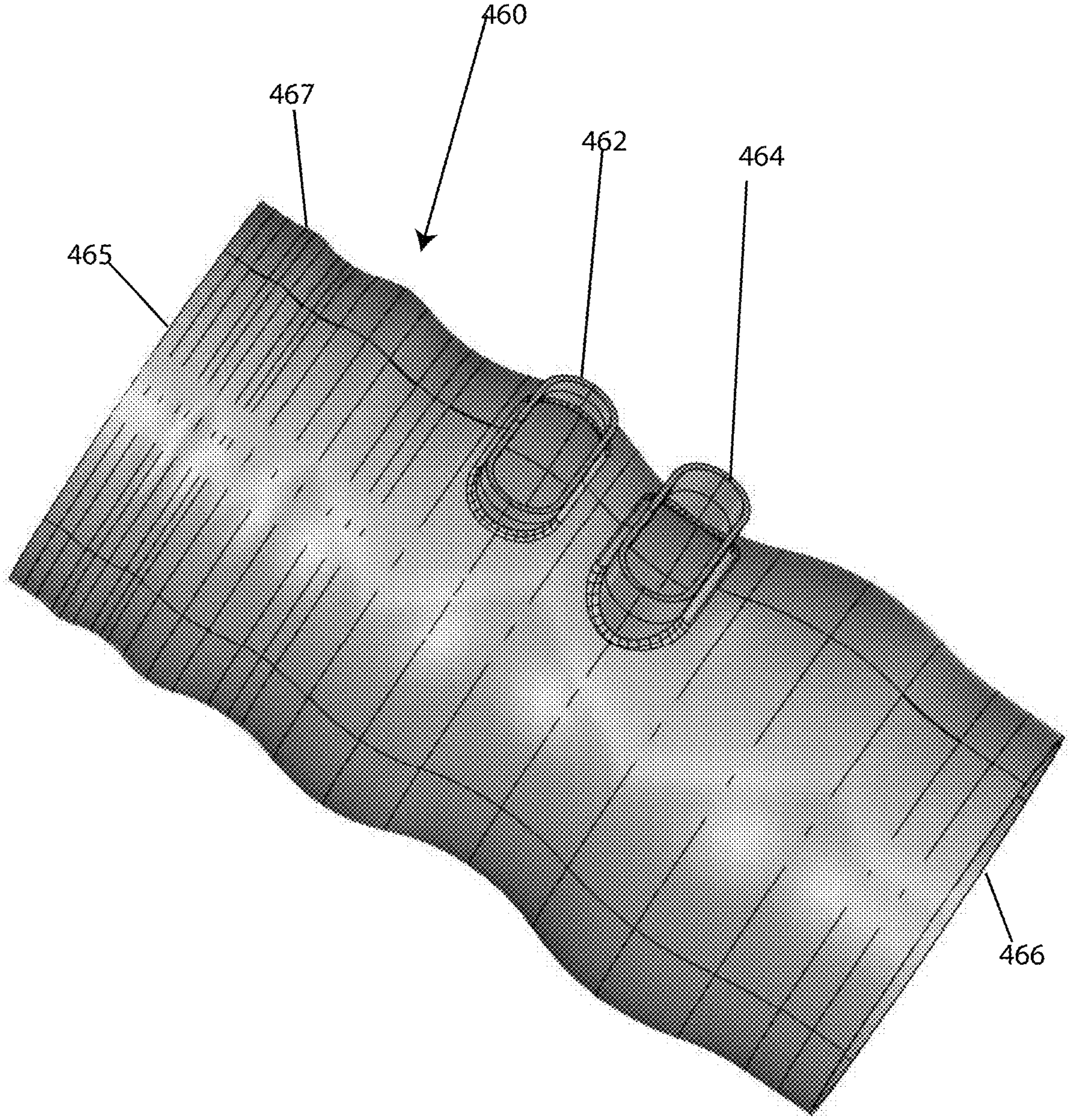
FIG. 44 is a side perspective view of the outer core pipe.
Figure 46:
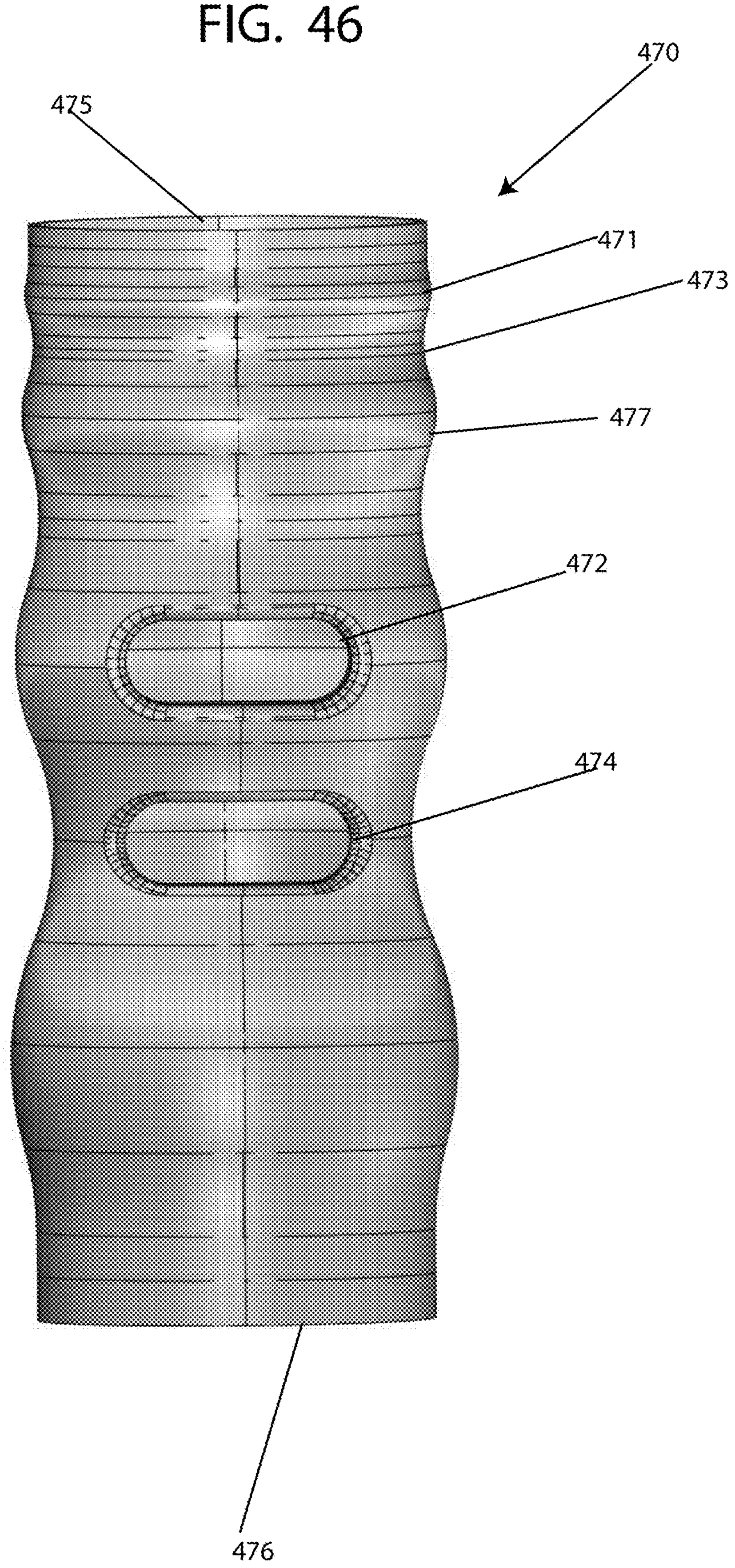
FIG. 46 is a side view of an inner core pipe.
Figure 47A:
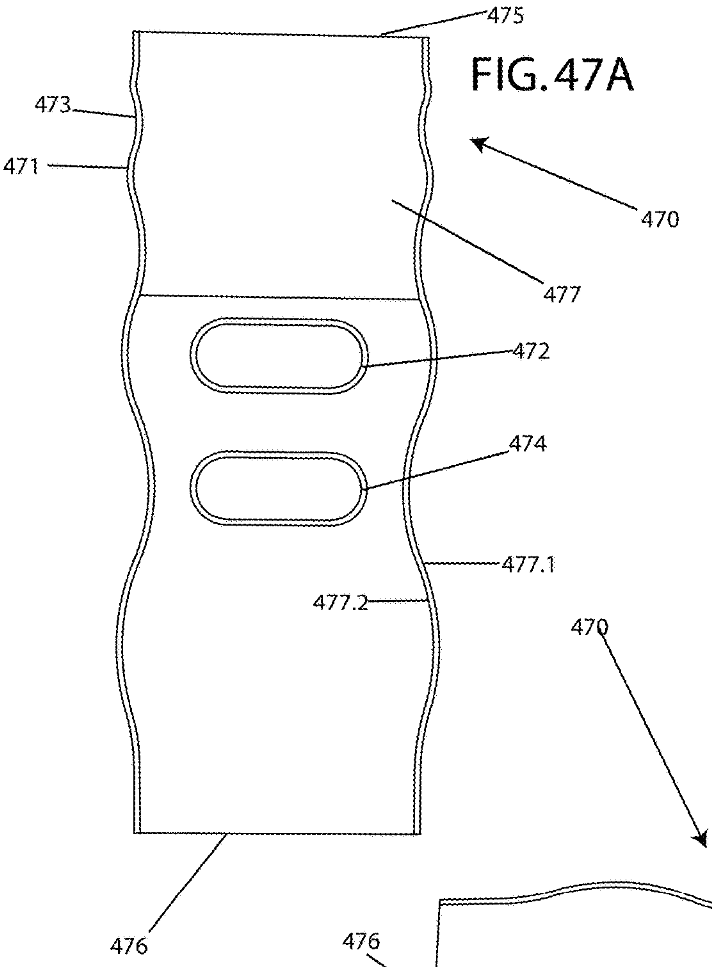
FIG. 47A is a side view of an inner core pipe.
Figure 47B:
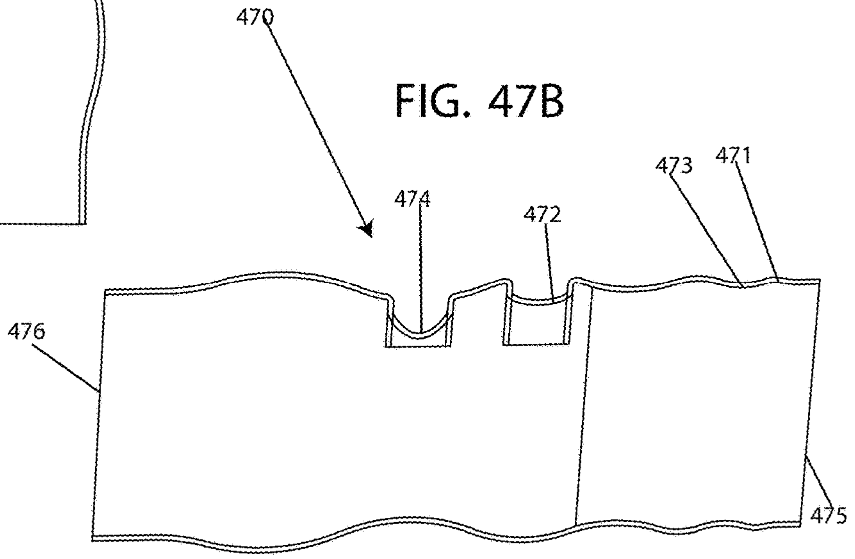
FIG. 47B is another side view of the inner core pipe.
Figure 47C:
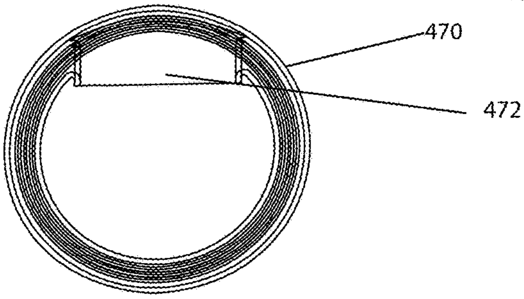
FIG. 47C is a top view of the inner core pipe.

FIG. 44 is a perspective view of outer core pipe 460 which includes a body section 467, air inlets 462 and 464 as well as outer sections 461 and inner section 463. There is also a top end 465 and a bottom end 466. Inner and outer surfaces 467.1 and 467.2 are also present on body section 467. Core pipe 460 also includes inner and outer sides 467.1 and 467.2 on body section 461. These features are also shown in greater detail in FIGS. 45A-45D.

FIGS. 46 and FIGS. 47A-47D show the inner core pipe 470 including a body section 477 with outer sections 471 and inner sections 473 as well as air inlets 472 and 474. Air inlets extend inward on inner core pipe 470. There is a top 475 and a bottom end 476 as well as a body section 477. There is also an outer surface 477.1 and an inner surface 477.2 of body section 477.

Figure 48:
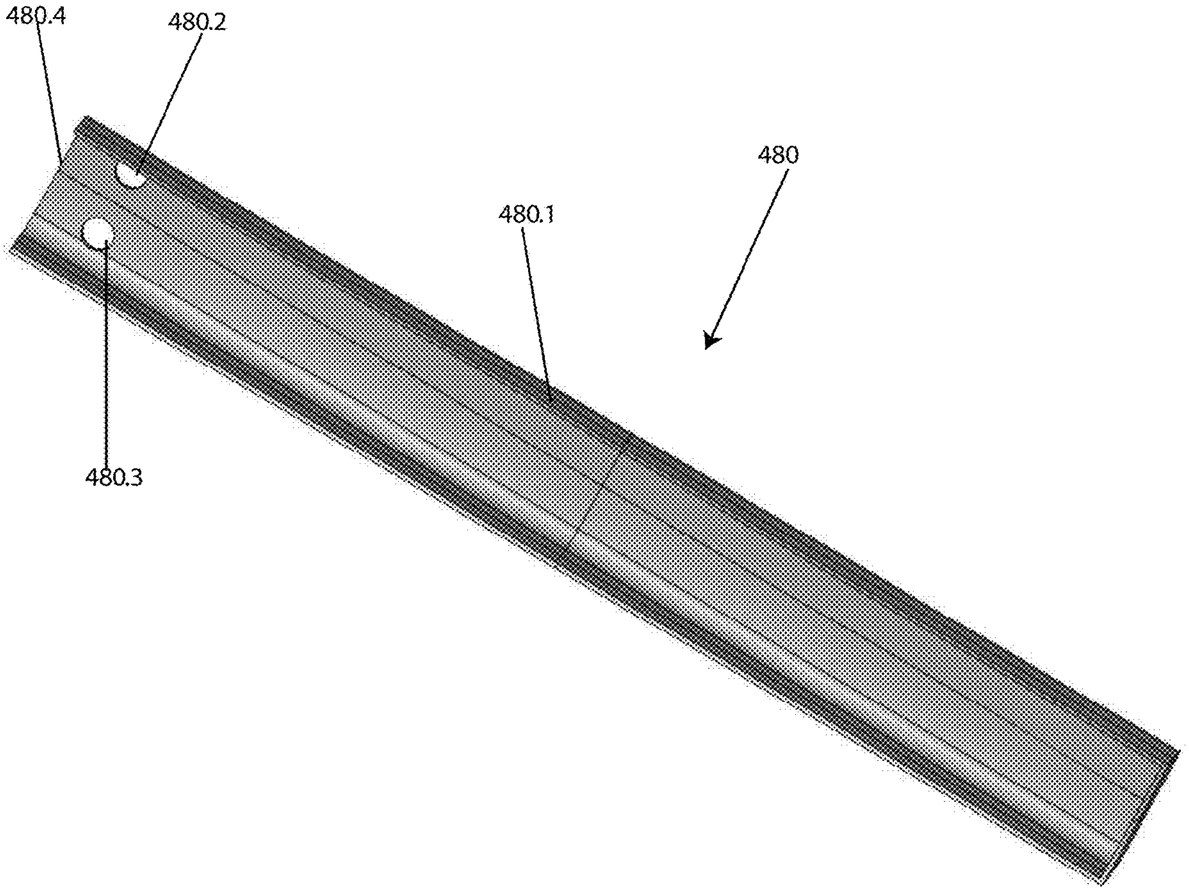
FIG. 48 is a perspective view of the outer pipe cover.

FIG. 48 is a view of the outer pipe cover 480 which includes a body section 480.1 water and electrical openings 480.2 and 480.3 respectively positioned adjacent to a bottom end 480.4

Figure 49:
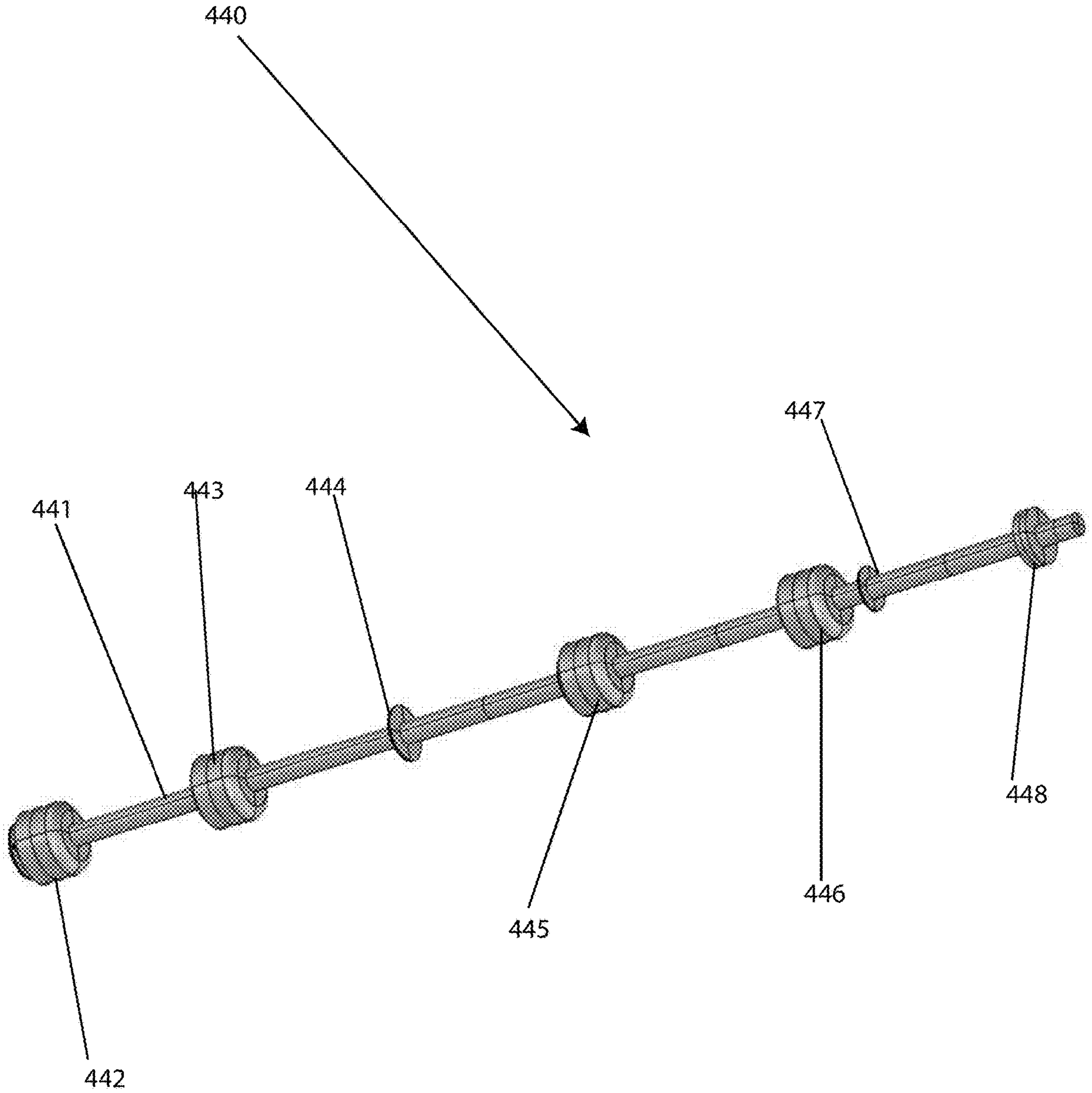
FIG. 49 is a perspective view of the fluid sensing system.

FIG. 49 is a perspective view of the fluid sensing system 440 which includes flotation sensors 442, 443, 445 and 446 positioned slidably along shaft 441. There are also stoppers 444 and 447 and 448 also positioned along these shafts. The stoppers 444, 447 and 448 can be in the form of sensors which when contacted by floats 442, 443, 445, and 446 this sends a signal that the fluid is at a predetermined height inside of the main tank. The fluid sensing system is configured to determine the height of the fluid inside of the main tank 450. While this is one type of fluid sensing system other types such as a capacitive sensor positioned along an outside of main tank 450 can also be used. This fluid sensing system 440 is in communication with PCB 424, in particular with microprocessor 424.5 of PCB 424 so that the computer components on PCB 424 is are configured to know the level of fluid in the system. This system can be programmed such that it allows the fluid levels to drop to a predetermined level and then be refilled periodically. Alternatively, the system can refill the tank repeatedly at shorter intervals.

Figure 50A:
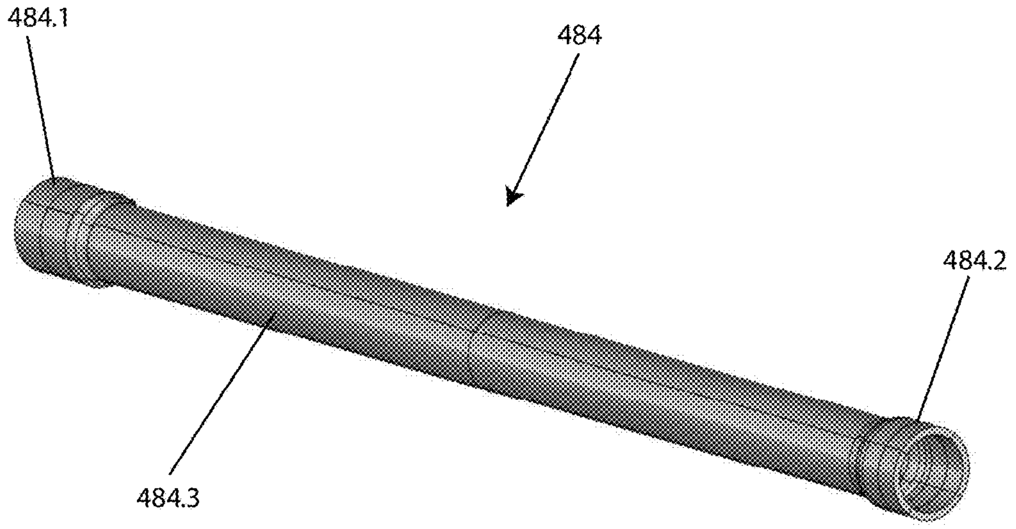
FIG. 50A is a side perspective view of the pipe.
Figure 50B:
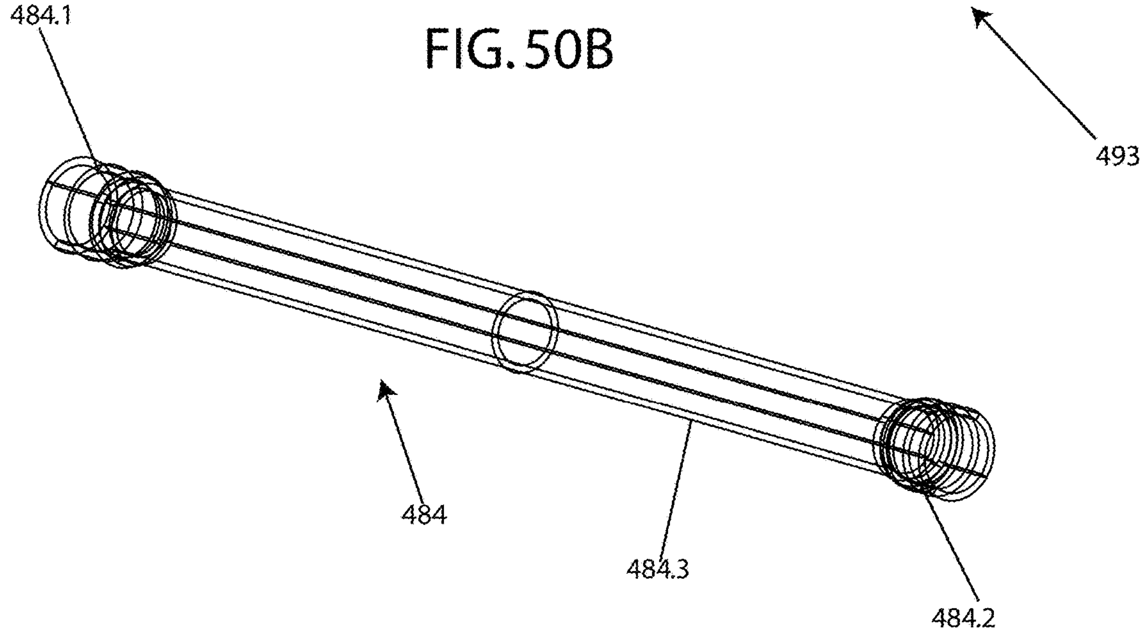
FIG. 50B is a side x-ray view of the pipe.

FIGS. 50A and 50B show side views of pipe 484 which includes ends 484.1 and 484.2 as well as a body section 484.3. Pipe 484 is used for the wafer supply sub assembly 481 while pipe 484 is the same in design as pipe 493 which is used for the purification solution transfer system 490 (FIG. 24).

Figure 51:
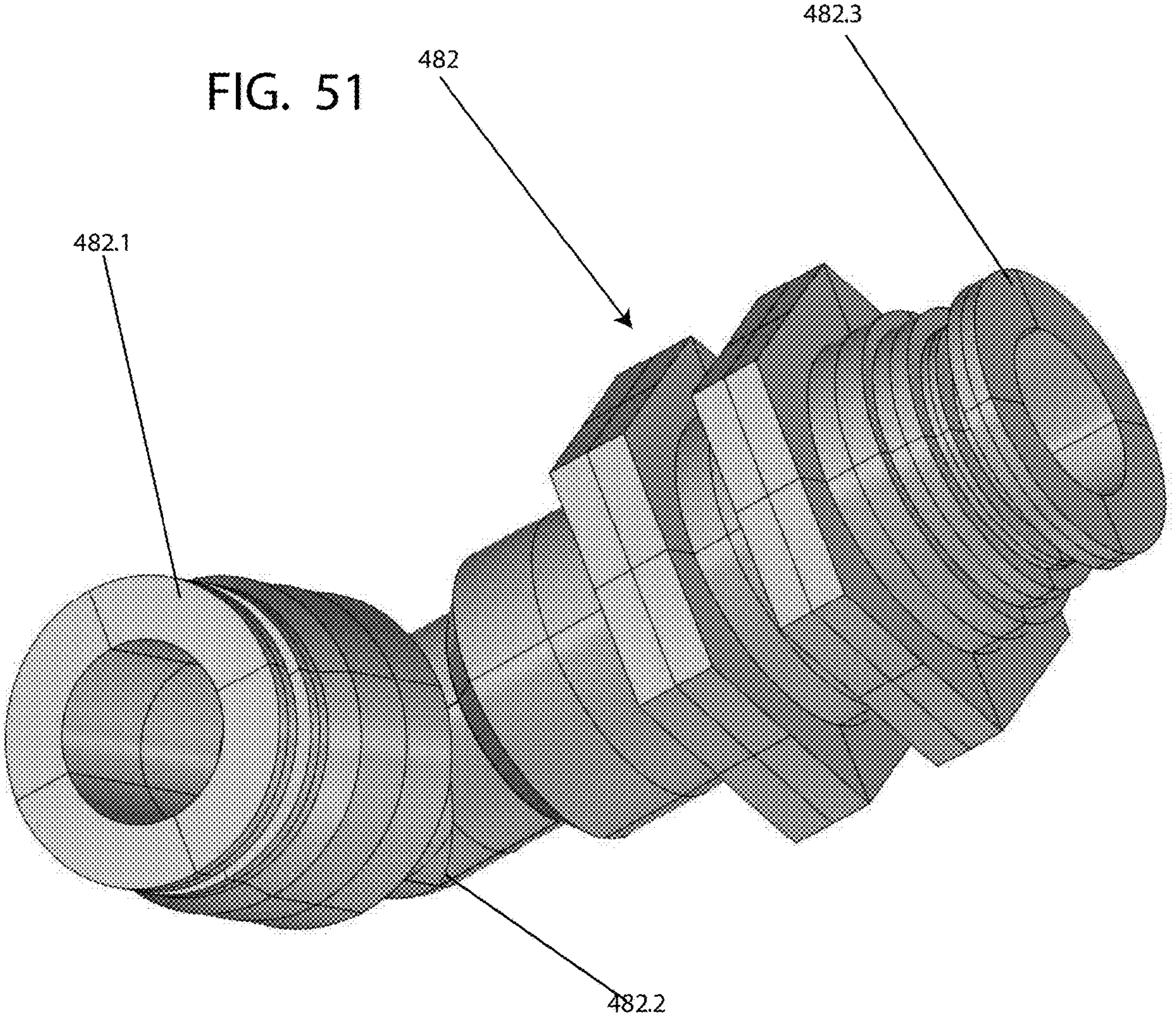
FIG. 51 is a side perspective view of a water intake.

FIG. 51 shows an elbow water intake 482 which includes a first intake end 482.1 an elbow section 482.2 and a top end 482.3 which is configured to connect to pipe 484. This water intake 482 is positioned at a bottom end of pipe 484. However, positioned along pipe 484 is also a solenoid 483. Solenoid 483 includes a plurality of solenoid elements 483.3 and 483.5 positioned along the water intake to selective restrict flow into the main tank 450. Solenoid elements 483.3 and 483.5 include respective solenoid actuators 483.2 and 483.4. Fluid flows in one end 483.1 and out an opposite end 483.6 to allow fluid to flow into the system.

Figure 53:
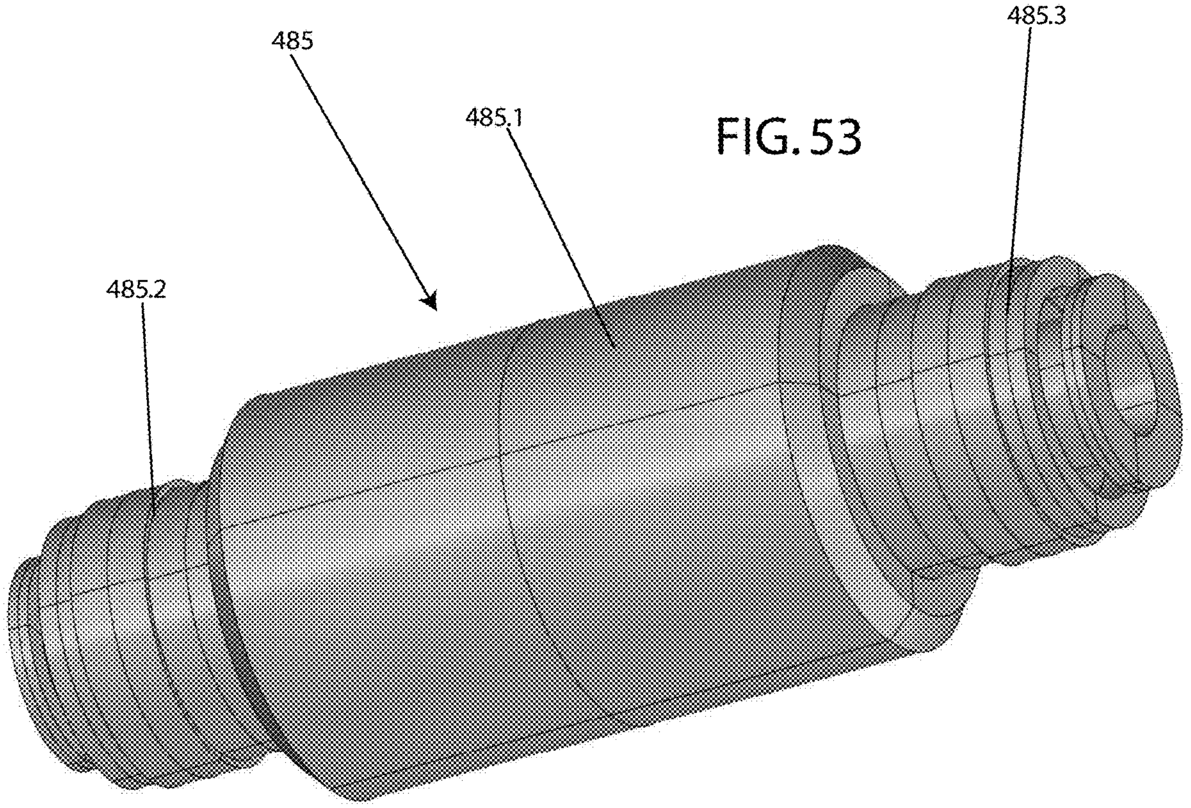
FIG. 53 is a side view of the flow restrictor.

FIG. 53 shows a side perspective view of a flow restrictor 485. Flow restrictor 485 has a body section 485.1 and two ends 485.2 and 485.3. This flow restrictor includes a choke valve in the body section 485.1 and is configured to selectively slow the flow of water into the system if the inflow is too high. Flow restrictor 485 is positioned above the solenoid valve(s) on the pipe 484.

Figure 54A:
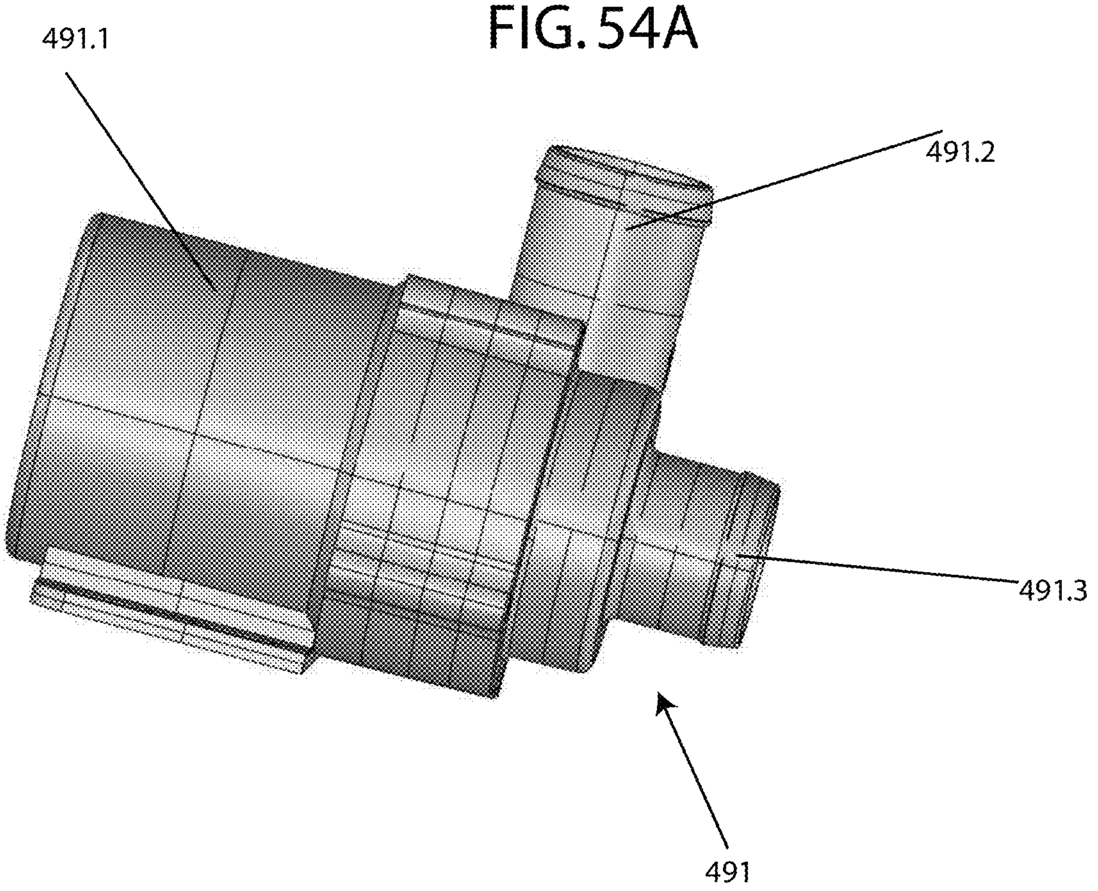
FIG. 54A is a side view of the pump.
Figure 54B:
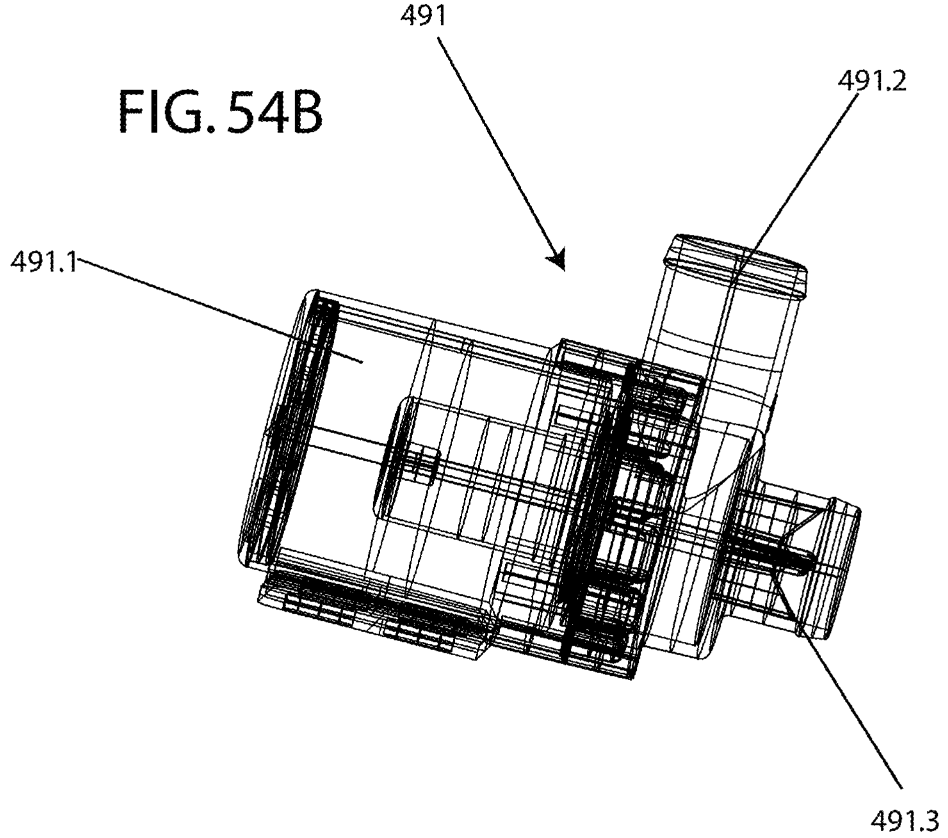
FIG. 54B is a side X-ray view of the pipe.

FIGS. 54A and 548 include a pump 491 which includes a pump body 491.1 an intake end 491.3 and an outflow end 491.2. Outflow end is configured to be coupled to an associated pipe 493. Pump 491 is structured similar to pump 492 which is a circulating pump positioned at a bottom region of main tank 450 and which is configured to selectively circulate fluid at the bottom of main tank 450. Pump 491 is configured to take in fluid and pump it up pipe 493 and onto the trays 432 and 434 for water distribution. Pump 492 is used to break up any coagulates in the fluid and to keep it circulating at a bottom region of main tank 450.

Figure 55:
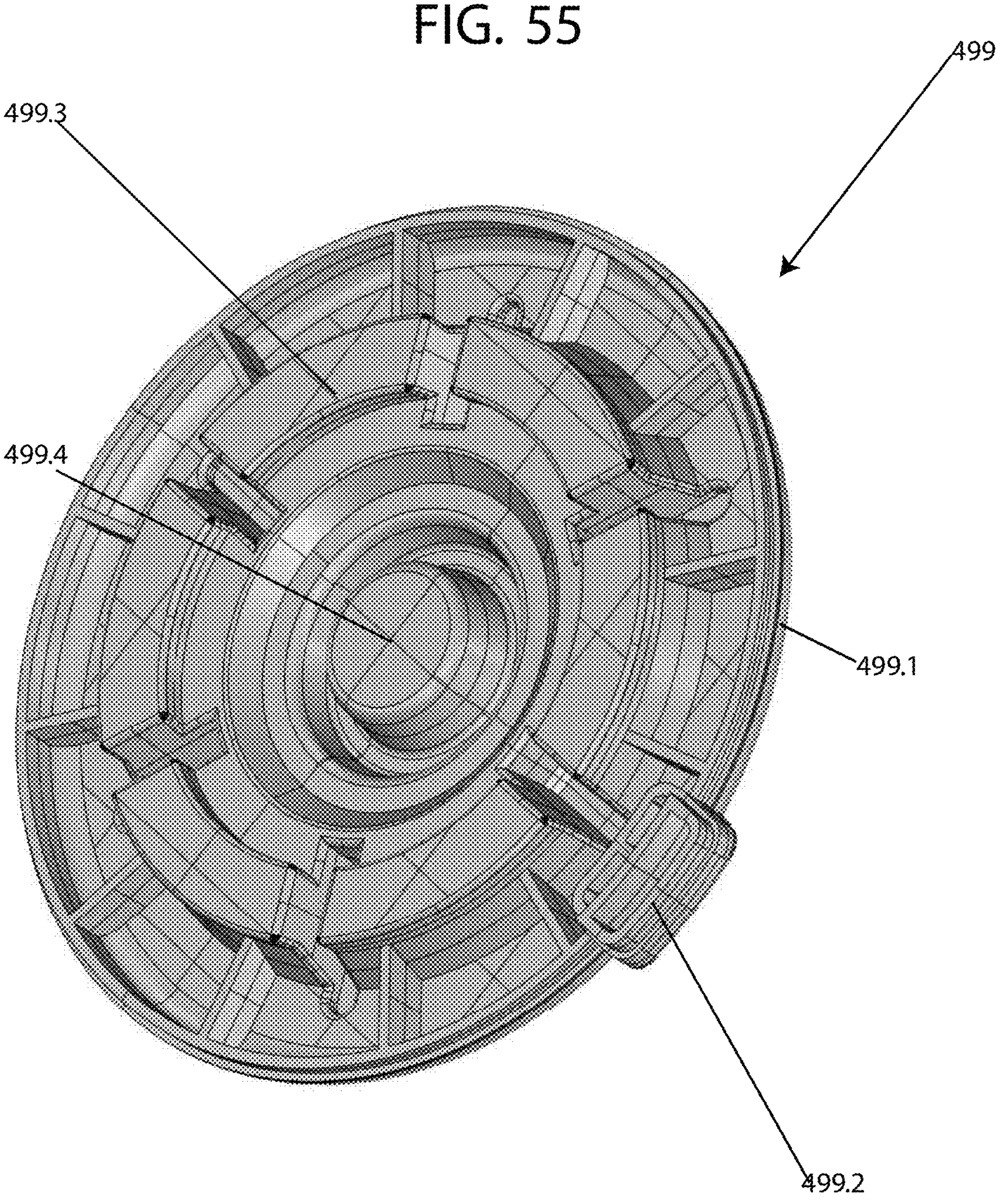
FIG. 55 is a perspective view of the bottom.

FIG. 55 is a perspective view of bottom 499. Bottom 499 includes an outer rim 499.1, a tab or flange 499.2, a base section 499.3 and a center region 499.4. Flange 499.2 is configured to receive outer pipe cover 480 which is seated therein.

Figure 56:
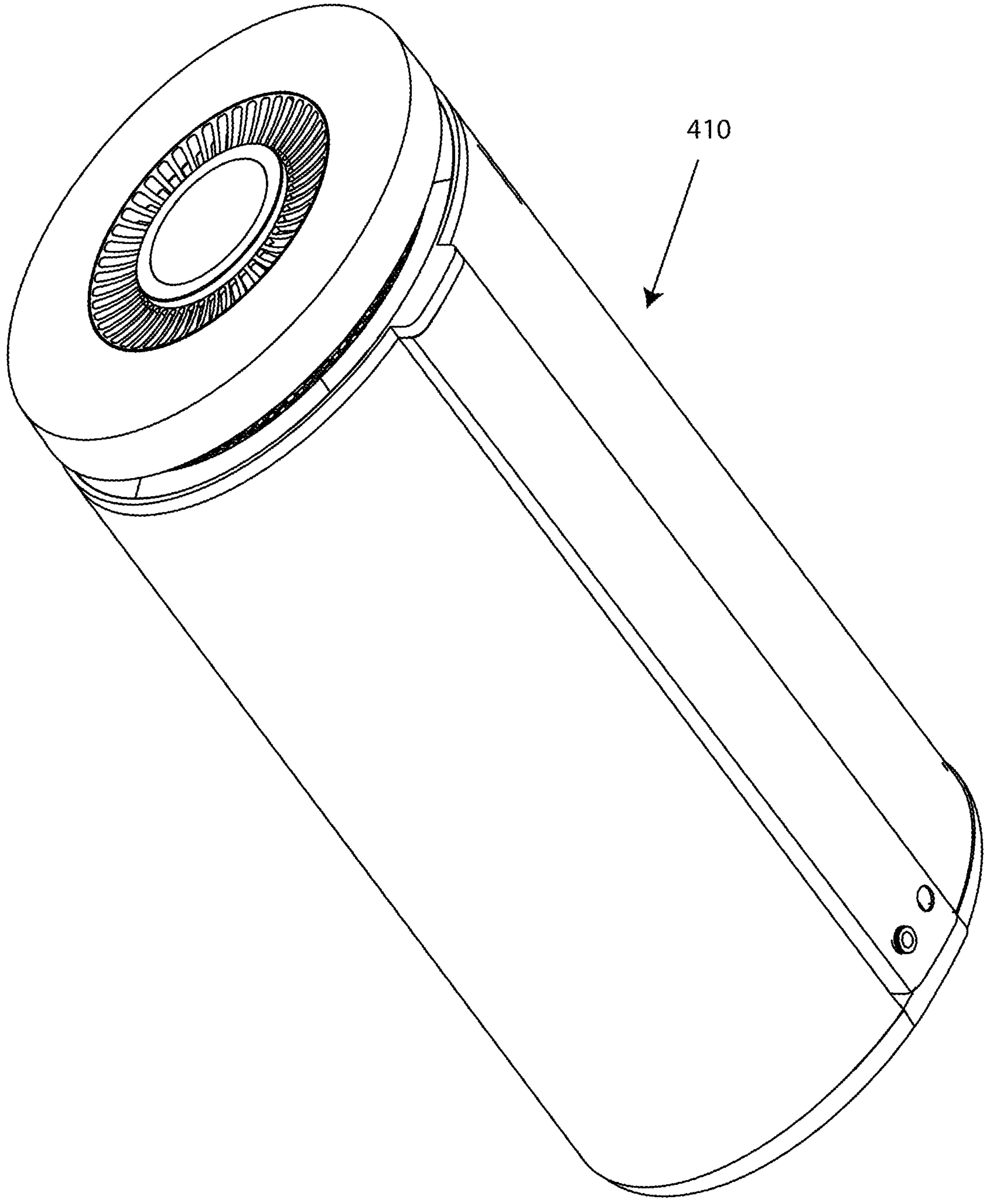
FIG. 56 is a perspective view of the device.
Figure 57:
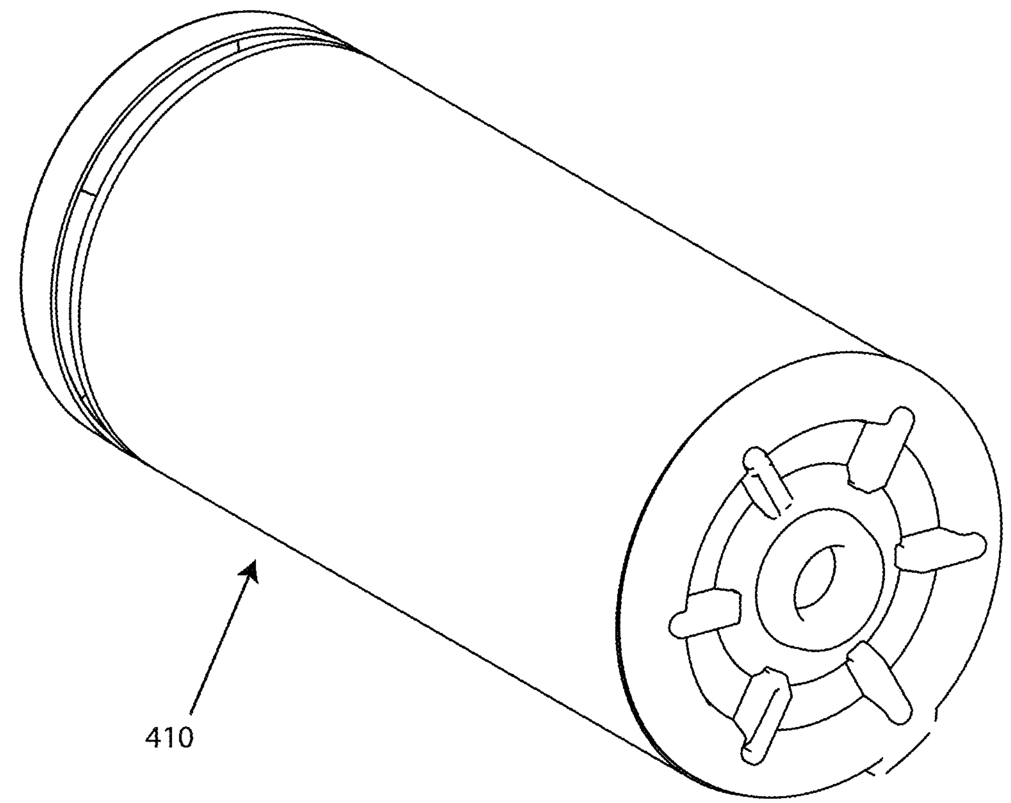
FIG. 57 is a bottom perspective view of the device.
Figure 58:
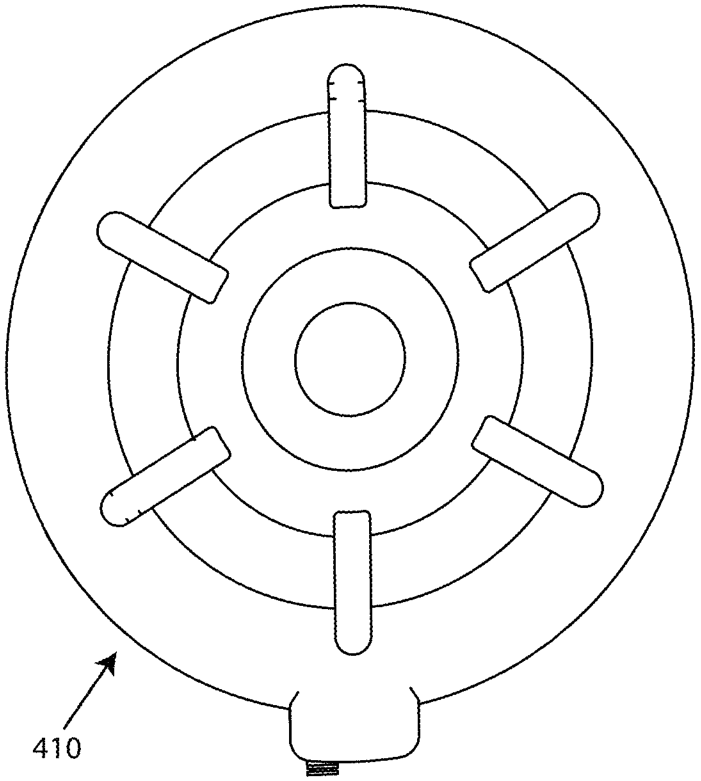
FIG. 58 is a bottom view of the device.
Figure 59:
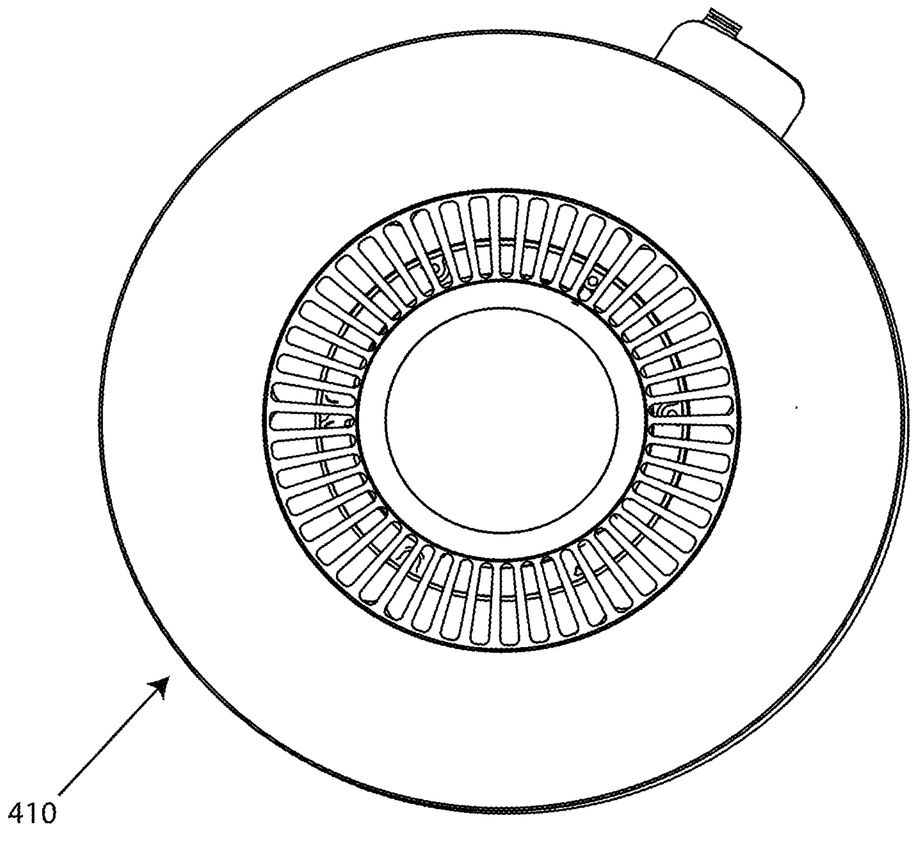
FIG. 59 is a top view of the device.
Figure 60:
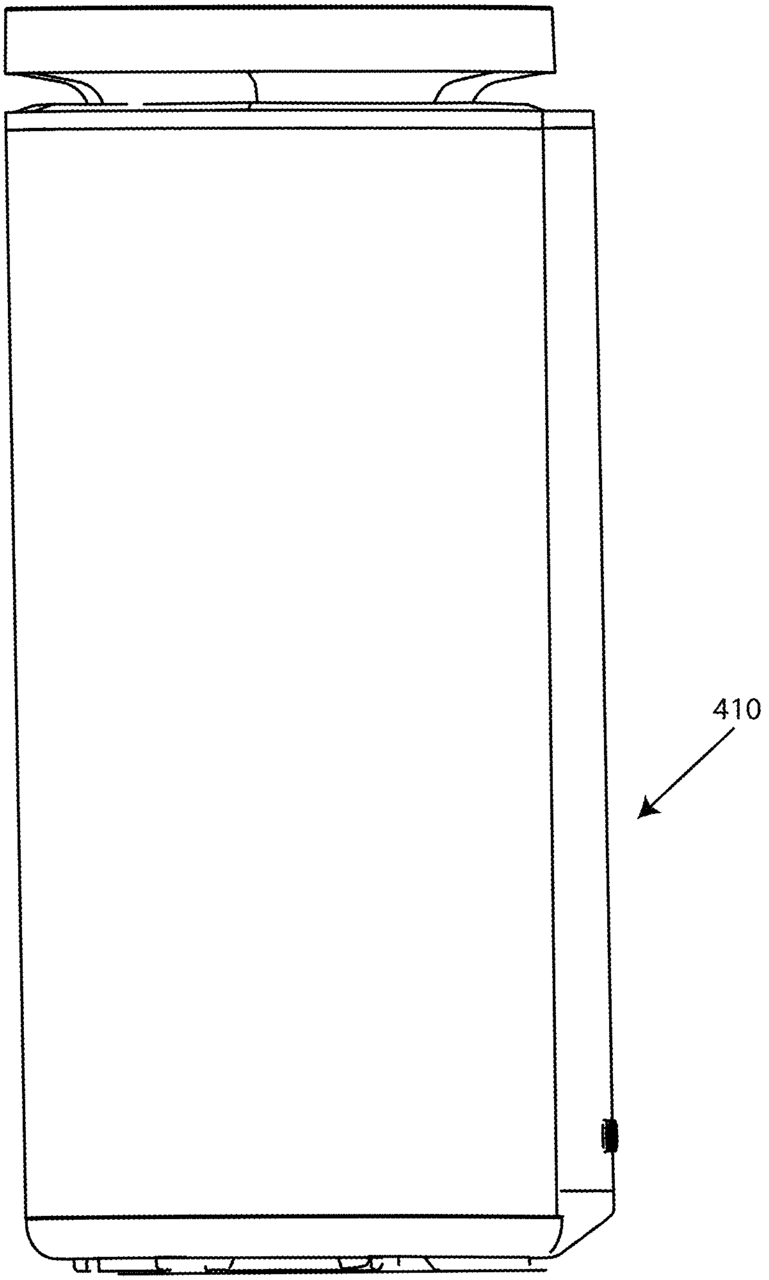
FIG. 60 is a side view of the device.
Figure 61:
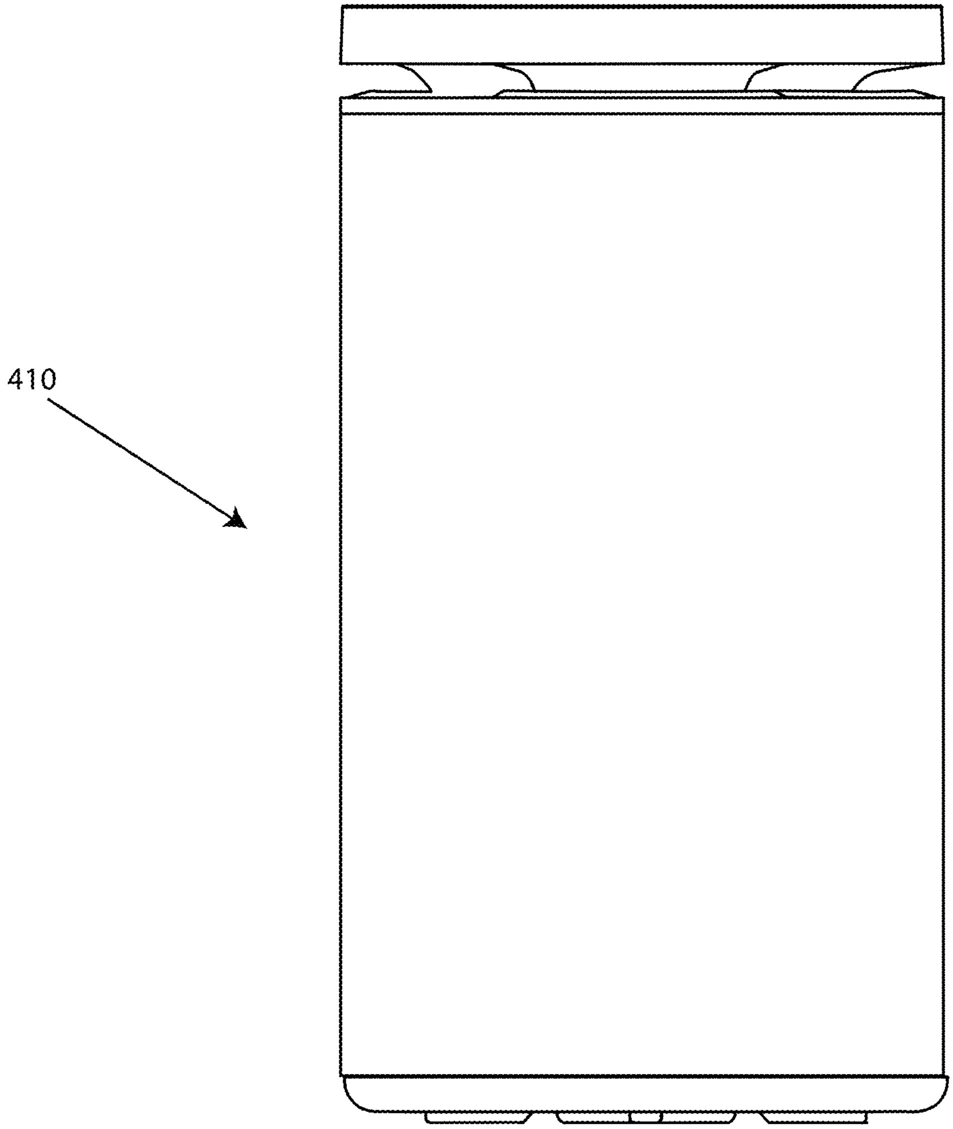
FIG. 61 is a second side view of the device.

FIG. 56 is a side-top perspective view of the device 410, while FIG. 57 is a side-bottom perspective view of the device 410. FIG. 58 is a bottom view of the device 410 while FIG. 59 is a top view of the device 410. FIG. 60 is a first side view of the device 410 with the opposite side being identical while FIG. 61 is another side view of the device 410.

Ultimately the system is designed to create as much interaction between the incoming and outflowing air and the water based purification solution so that the air is cleansed of particles, ions or other impurities and then the air is expelled from the device as clean as possible.

Figure 63:
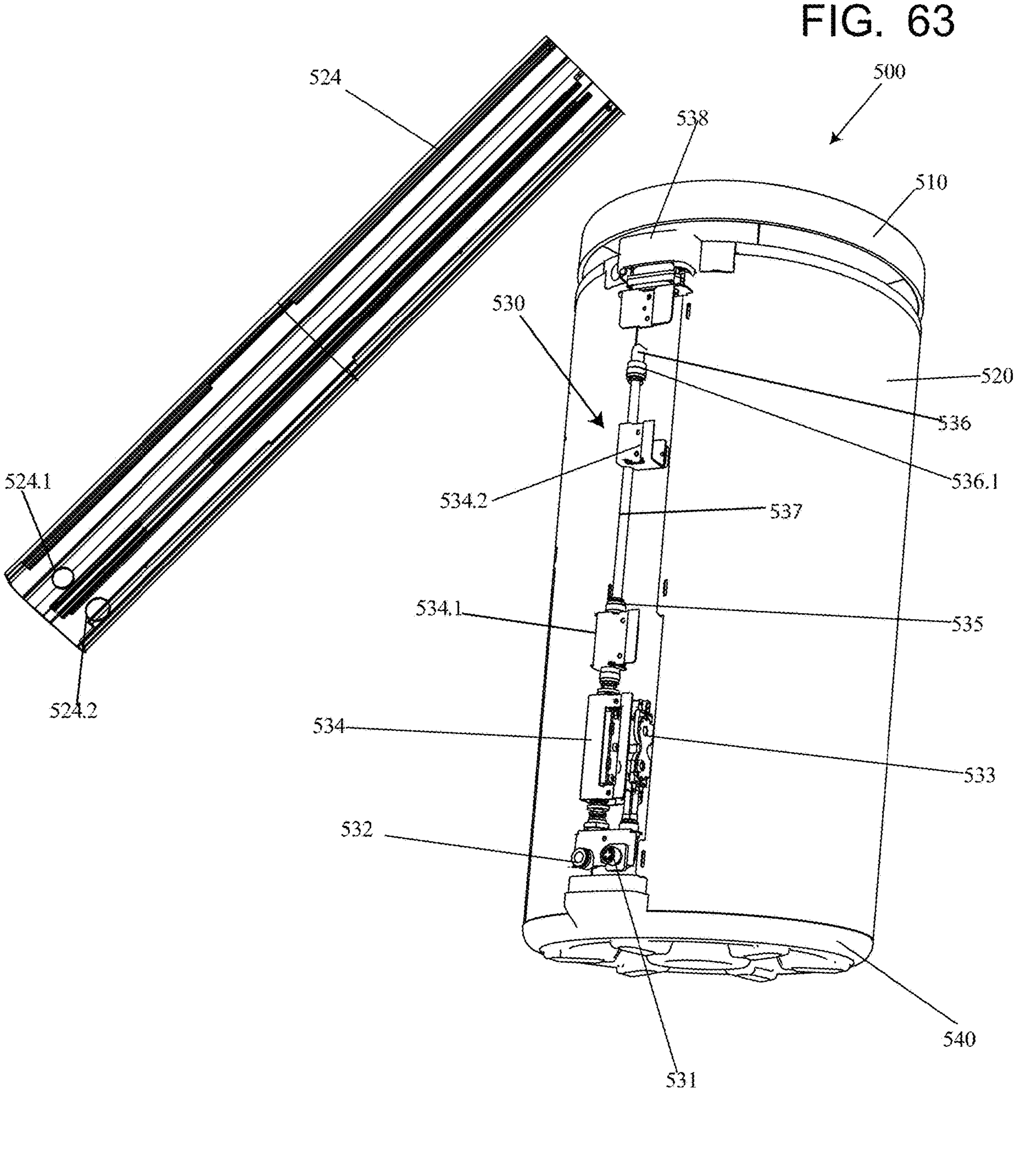
FIG. 63 is a side perspective view of the embodiment of FIG. 62A with a panel removed.

FIG. 62A is a side view of another embodiment while FIG. 62B is a bottom perspective view of the embodiment of FIG. 62A; FIG. 62C is a bottom view of the embodiment of FIG. 62A; and FIG. 62D is a side view of the embodiment of FIG. 62A. With this embodiment 500 there is a body section 520 a top 510 and a bottom 540 coupled together. This embodiment of an air filtration system also includes an air inlet 514 and a raised top cover 512. FIG. 63 is a side perspective view of this embodiment 500 wherein in the body section 520 there is a skin 522, and an elongated cover 524. The elongated cover 524 and the skin 522 form the outer shell for the device. Inside the elongated cover 524 is a water and electrical inlet system 530. This system 530 includes a water quick connect inlet 532, an electrical quick connect 531. Positioned adjacent to and above the water inlet 532 is a double solenoid stop valve 533. This valve 533 is secured to the body with a bracket 534. There is another bracket 534.1 covering over a water intake system. Another bracket 534.2 is used to couple the water inlet pipe 587 to the body as well as manage any electrical cabling introduced into the system.

Water inlet 532 is configured to be connected to a standard household or commercial building supply. Therefore, there is sufficient ambient pressure in the line or water inlet pipe 537 to drive the water up the side of the container and into the system if the double solenoid valves 533 are positioned in an open position. In addition, the electrical input into the system can be in the form of any suitable electrical input but in at least one embodiment is a DC low voltage Input sufficient to run the solenoid valves, the processing system, the fan as well as the one or more circulating pumps disposed inside of the system.

Figure 64:
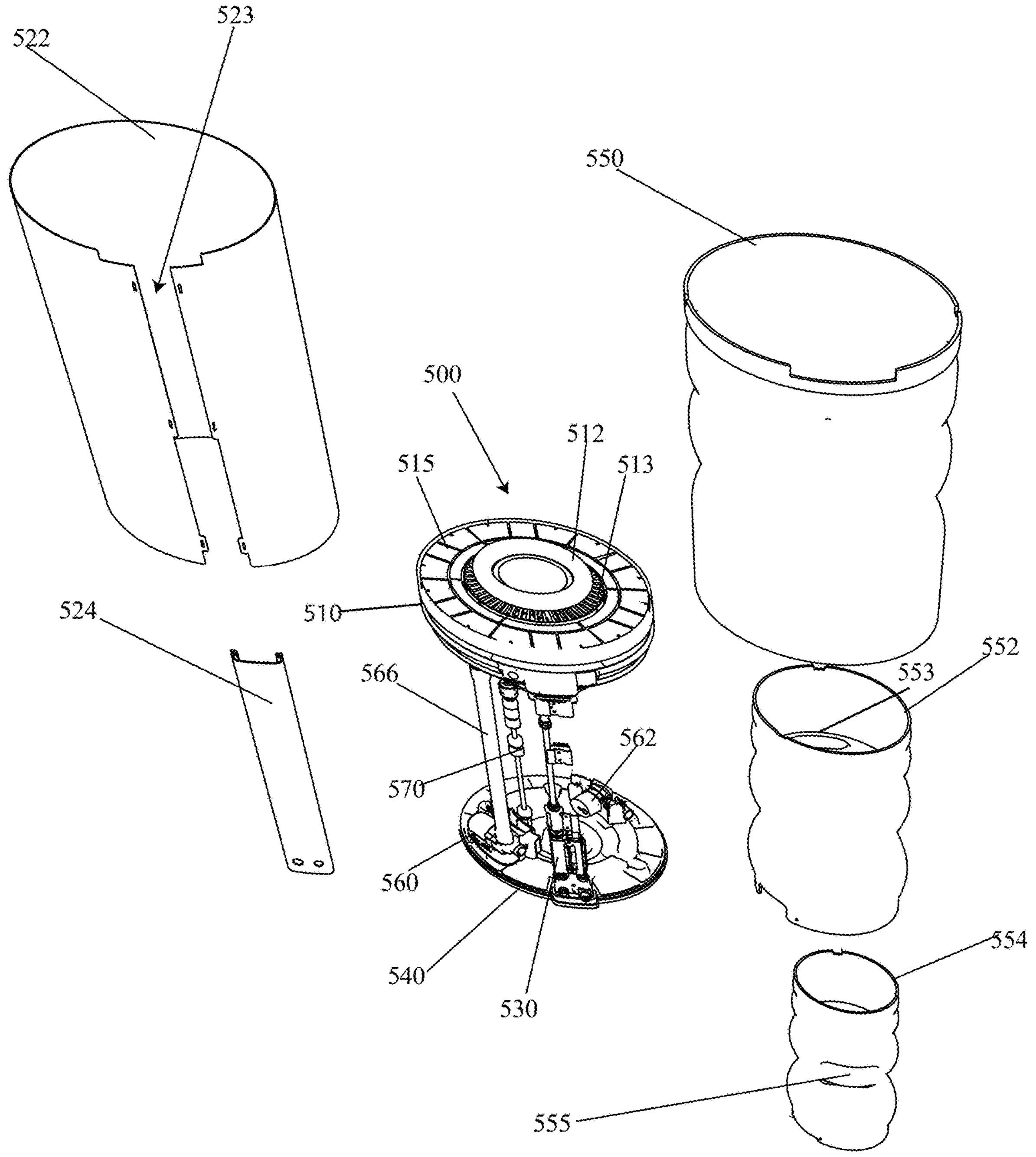
FIG. 64 is a perspective exploded view of the embodiment of FIG. 63.

FIG. 64 is a top exploded perspective view of the embodiment 500 with the skin 522 removed. This skin 522 has a slot opening 523 configured to receive the water and electrical inlet system. The elongated cover 524 fits over this slot opening 523. In addition, as shown in this exploded view there is a container 550 which has an undulating surface or corrugated surface with convex and concave surfaces extending vertically down when the device is positioned upright. Disposed concentrically inside of container 550 are cores 552 and 554. Core 552 has a wider diameter than core 554. While container 550 and these cores are substantially open at their top ends, container 550 is closed at its bottom end while cores 552 and 554 are open at their bottom ends. In addition, core 552 has an opening 553, while core 554 has an opening 555. In at least one embodiment, these cores do not extend all the way to the bottom, leaving a substantially open bottom end.

Disposed at either ends is a top 510 and a bottom 540. The top 510 and bottom 540 close the container 550 to keep fluid inside. Bottom 540 can be welded or coupled to container 550 via an adhesive and sealant. As shown, there is water and electrical inlet system 530 coupled to bottom 540, pumps 560 and 562 coupled to bottom 540 and a float level sensor 570 coupled to bottom 540 as well. Pump 560 is a riser circulating pump which circulates the aqueous solution from a bottom section of the container to a top section of the container essentially up to trays 580 (See FIG. 65). This pump 560 pumps the fluid through riser pipe 566 which is connected at one end to the pump 560 and at the other end to the trays 580. FIG. 62 is a circulating pump which circulates the fluid around the container in a radial or circular manner. In addition, there is a float level sensor 570 which includes a plurality of floats 572 which float to different levels and indicate the level of fluid inside of the container 550.

The fluid that is stored inside of the container can be in one embodiment simply water. However, in a preferred embodiment this fluid can be a water and proprietary biological solution as described above.

Figure 65:
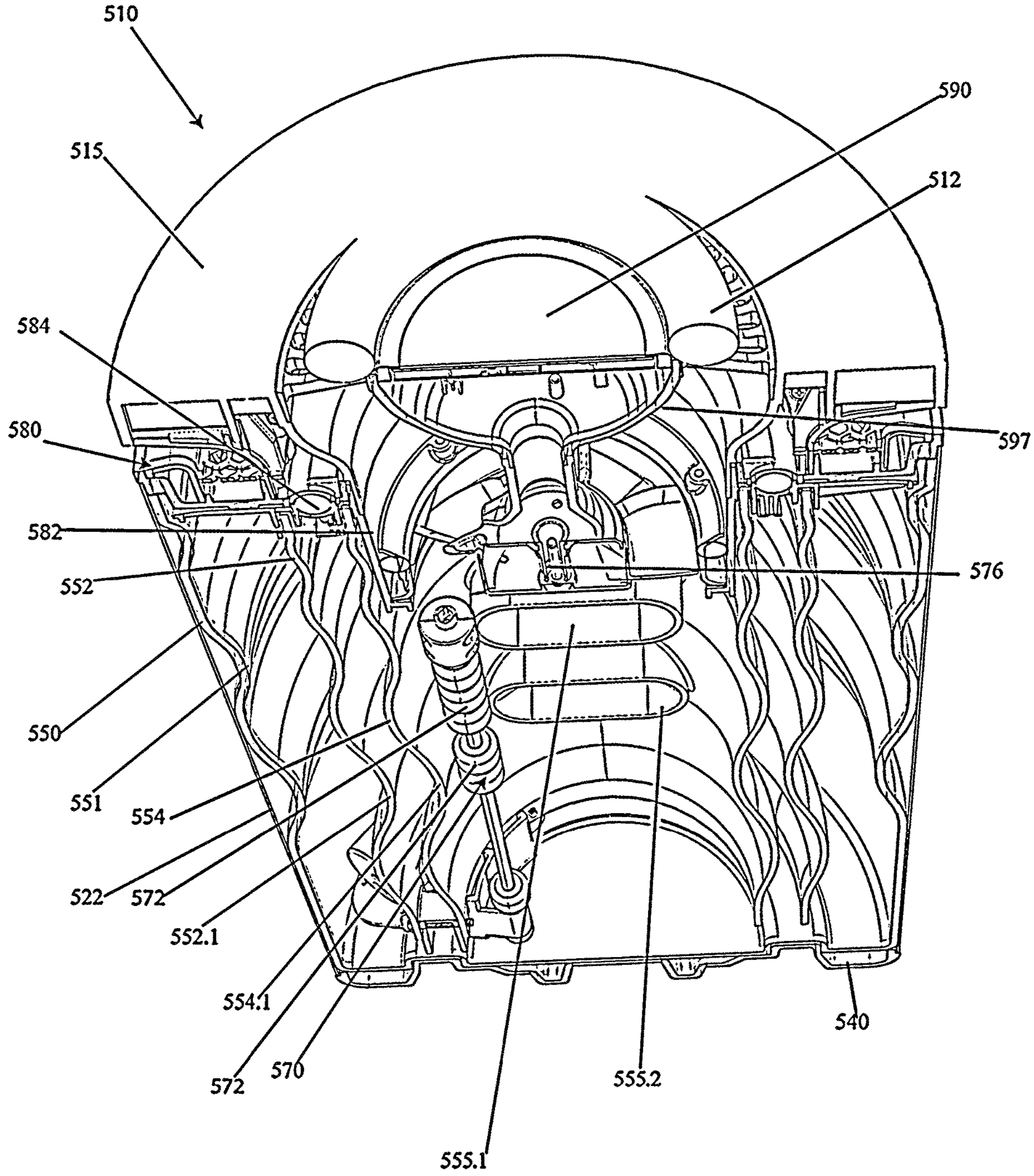
FIG. 65 is a top front perspective cross-sectional view of the embodiment of FIG. 63.

FIG. 65 is a top front cross-sectional perspective view of the embodiment of FIG. 63. In this view there is shown top 510 having a top surface 515, and a top covering 612 which surrounds a touch screen and other electrical components 590. Top cover ring 512 extends above top surface 515. This top cover ring 512 is configured to keep article from resting over the air exhaust 513. Disposed below the top cover. Below the top cover are trays 580. Trays 580 sit within the container 550 and inside of the skin but above cores 552, and 554. Each of container 550 and cores 552 and 554 have undulating surfaces such as respective surfaces 551, 552.1 and 554.1 which extend radially inward to catch falling solution. Core 554 has air inlets 555.1 and 555.2. These air inlets are designed to receive intake air which is fed through air inlet 514 through air intake grill 517 (See FIG. 69). A float level sensor device 570 has separate float level sensors 572 and 573. A fan 576 is positioned in a radially inner region, and coupled to a lower region 582.9 of tray 582. At the bottom of this view is shown bottom 540.

Figure 66:
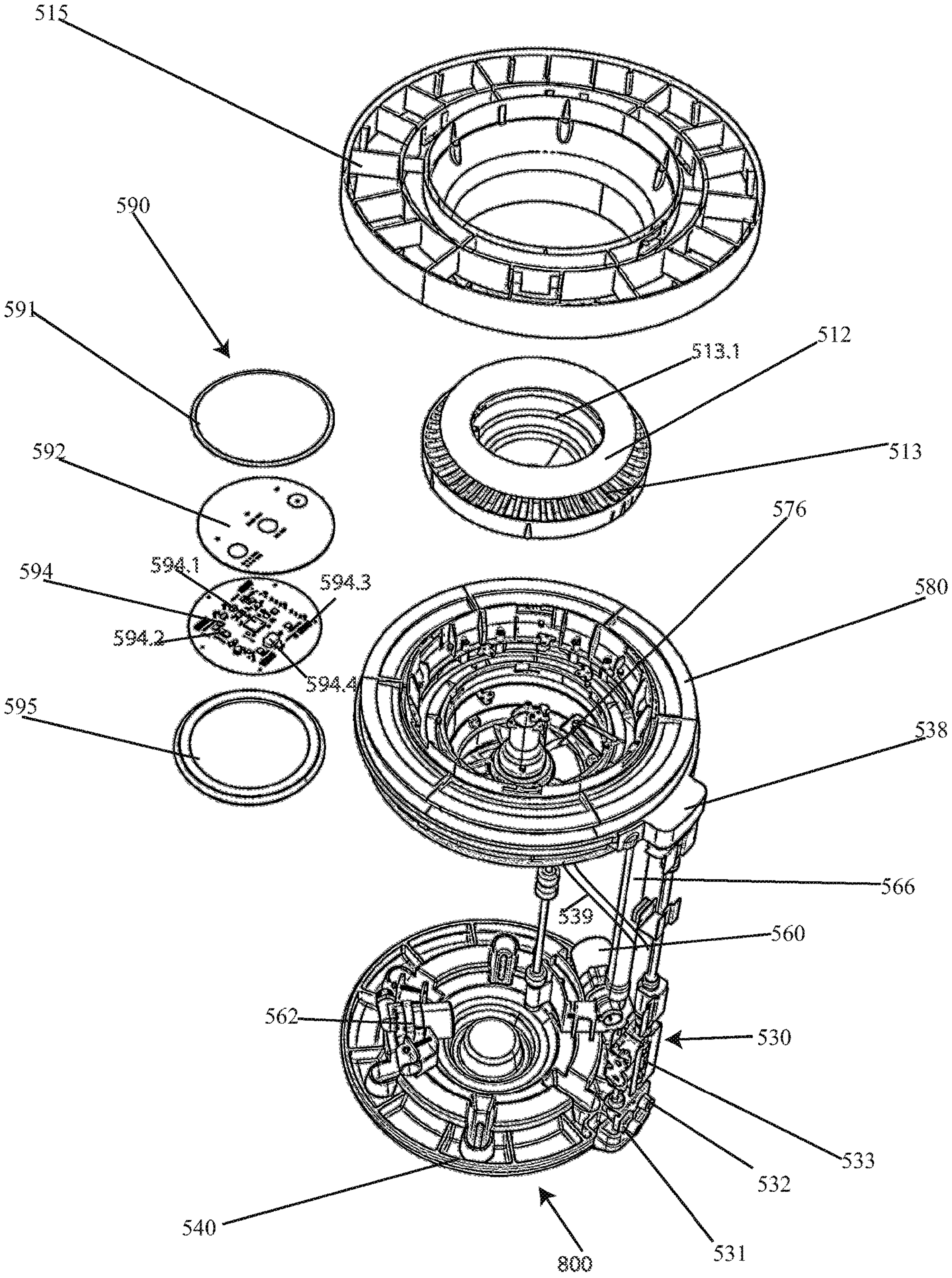
FIG. 66 is a top perspective exploded view of the embodiment of FIG. 63 with the skin and the cores removed.

FIG. 66 is an exploded view of the device which includes a top surface 515 which is configured to house both top ring 512 and air exhaust 513. Air exhaust 513 is configured to be angled up to prevent the placement of flat articles on it thereby preventing the exhaust of these materials. A plurality of electronic controlling components 590 including a touch screen 592 are configured to set the components inside of a central region 513.1. These electronic components can form a controller that at least in one embodiment includes a microprocessor such as microprocessor 594.1. There can be a touch screen 592, a motherboard 594 with at least one processor such as a microprocessor 594.1. In addition, coupled to the motherboard is a memory 594.2, a plurality of pins 594.3 which are configured to connect to at least one communication line and/or power line, as well as at least one transceiver 594.4 which is configured to communicate externally to a computer network. In addition, there is at least one additional ring 595 which is configured to encase these electronic components when they are stored in the central region 513.1. These components are fed by an electrical cable 539 that extends inward and which feed power from water and electrical inlet system 530 to the electrical controlling components 590. In addition, there are shown pumps 560 and 562 which are coupled to bottom 540. Thus, in at least one embodiment the controller can comprise the microprocessor 594.1, the memory 594.2, and at least one transceiver 594.4 to communicate with outside components such as pumps, sensors, fans and valves.

FIG. 67A is a top perspective view of the embodiment of FIG. 63 which shows top 510, along with top surface 515 as well as electrical components 590 and top ring 512. In addition there is riser pipe 566 as well as water and electrical inlet system 530. A the bottom is pump 560 coupled to bottom 540. Air inlets 553.1 and 553.2 are shown in core 552. In FIG. 67B there is shown double solenoid valve 533 as well as water inlet 532. In FIG. 67C there is shown circulating pump 562 while in FIG. 67D there is shown bottom 540.

FIGS. 68A and 68B show bottom 540 which shows pumps 560 and 562 along with at least a portion of water and electrical inlet system. These respective pumps are coupled to the bottom section 540 via brackets.

Figure 69:
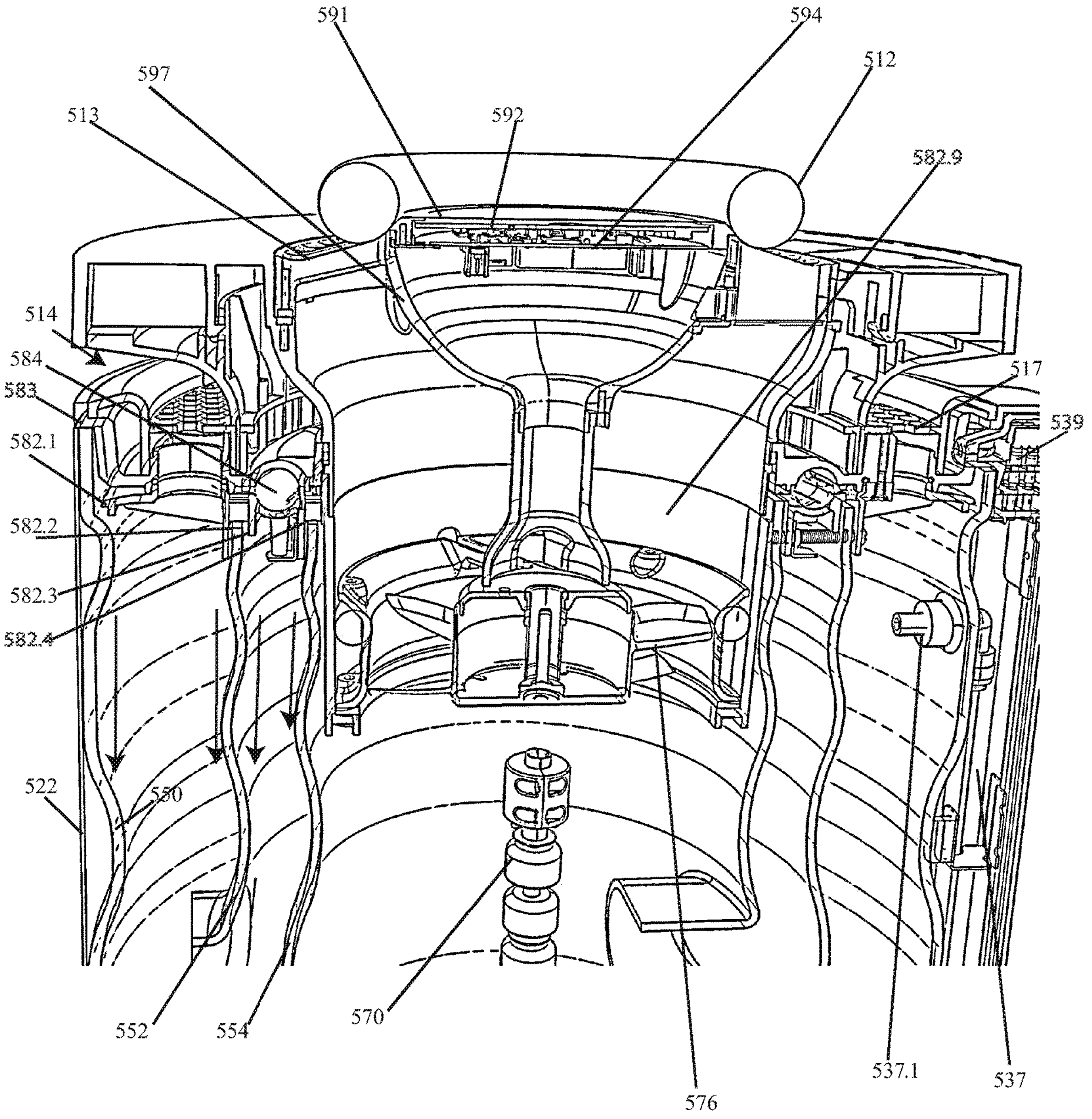
FIG. 69 is a front perspective cross-sectional view of the embodiment of FIG. 63.

FIG. 69 shows another side cross-sectional view of the device which shows cover plate 591, touch screen 592, and motherboard 594. There is raised top ring 512 also positioned adjacent to the components. The components sit within a bowl-shaped container 597 which sits adjacent to air outlet 513. Air outlet 513 is a raised grill which is configured to vent air dispersed by fan 576. Annular air intake 514 is shown wherein air flows in through a air inlet 517 having a grill. In addition, there is shown a cross sectional view of trays 580 including trays 582 and tray 583. There is also shown electrical coupling 539 which is positioned adjacent to air inlet 517. A water fill inlet 537.1 is shown extending through container 550. This water fill inlet 537.1 is extending in from water riser pipe 537. Fill level sensor 570 is disposed in a central region of container 550, inside of both cores 552 and 554. Positioned above fill level sensor 570 is fan 576. Fan 576 is seated in a central core section 582.9 which forms a cylindrical seat for fan 576. Trays 582 and 583 are seated within each other to form a central pipe or channel 584 which feeds water around in an annular ring around the container 550 between the inner core 554 and the outer core 552. The central pipe or channel 584 serves as a fluid feed which substantially evenly distributes the fluid solution comprising proprietary biological solution and water to the walls of the cores 852 and 854 as well as to an inner wall of the container 550. For example, in lower tray 582 there are different spillovers or openings including spillover 582.1 which spills over to the inner wall of container 550. Spillover 582.1 is an outer edge of lower fray 582. In addition, there is an opening in tray 582 which comprises opening 582.6 (see FIG. 76), wherein this opening 582.6 spills over outer core 552 forming spillover paths 582.2 and 582.3 which allow the fluid to flow respectively over the outer surface of outer core 552 and the inner surface of outer core 552 respectively. Furthermore, there is an additional spillover path 582.4 which spills over to an outer surface of inner core 554. This spillover path is formed by opening 582.7 shown in FIG. 76.

Figure 70:
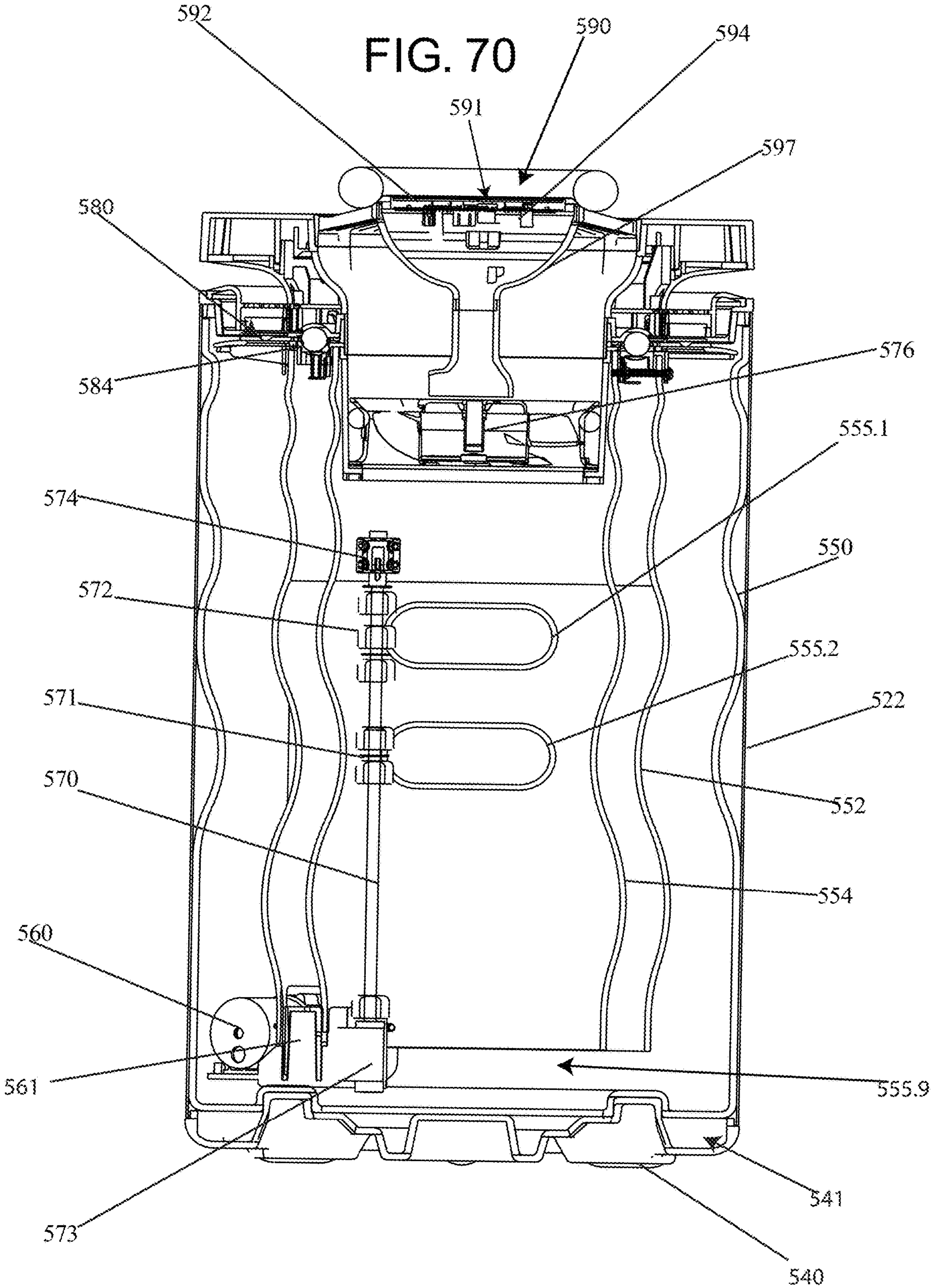
FIG. 70 is a front cross-sectional view of the embodiment of FIG. 63.

FIG. 70 shows a side cross-sectional view of the device which shows skin 522 sitting outside of container 550. Outer core 552 and inner core 554 are positioned concentric with each other inside of container 550. Inner core 554 has air vent openings 555.1 and 555.2. Pump 560 is positioned between container 550 and outer core 552. Fill level sensor 570 is positioned inside of inner core 554. Fill level sensor

570 includes sensors 571 and 572, a base 573 coupled to the bottom of container 550 and at least one electrical connection end 574 for connecting to an electronic cable or to the electronic components 590. The electronic components shown include a top cover 591, a touch screen 592 and a motherboard 594. At the bottom end of the container, there is an open area 555.9 which is open with respect to cores 552 and 554. In addition, positioned towards a bottom section of container 550 is a bracket 561 configured to space outer core 552 from inner core 554. Furthermore, positioned between bottom 540 and container 550 is a housing region configure to house a bearing (See FIG. 90.) wherein when the device is turned on it side if allows bottom 540 to rotate thereby forming a rotatable wheel rotating around below container 550.

Figure 71A:
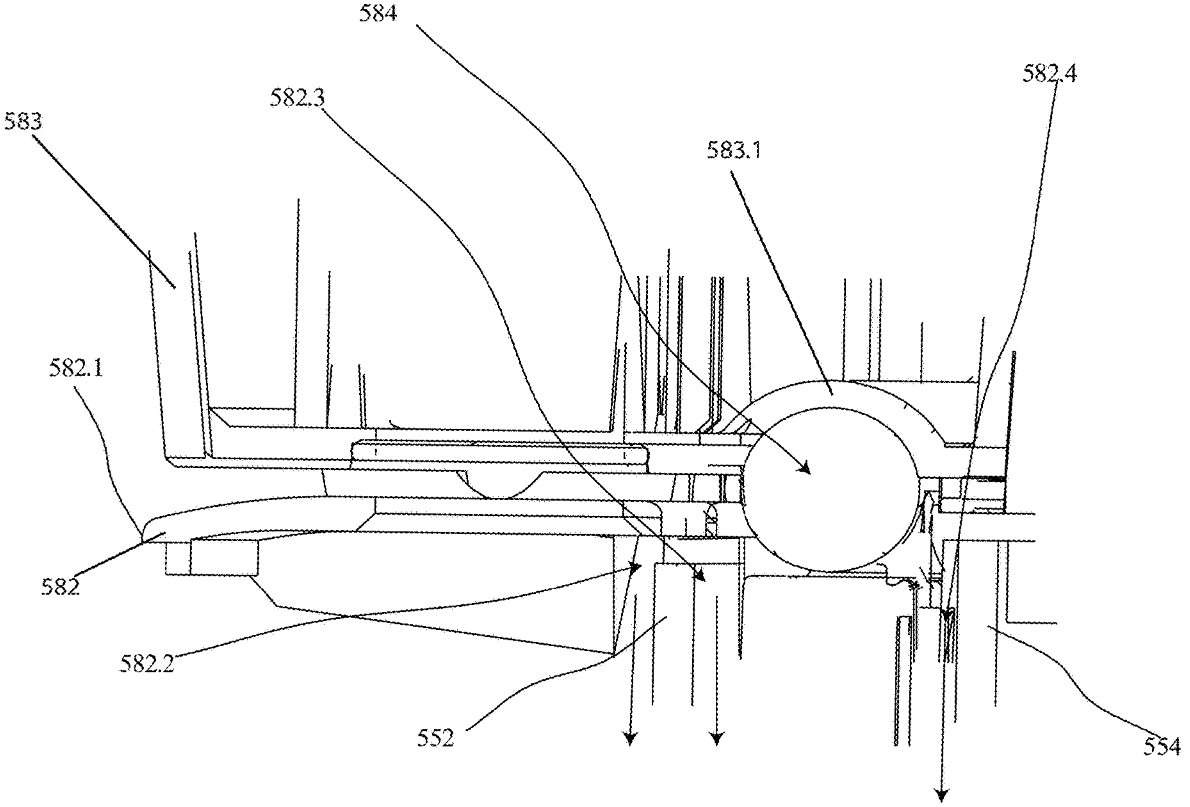
FIG. 71A is a close up view of a section of the view in FIG. 70.

FIG. 71A shows a side close up view of a section of the device which shows top tray 583, sitting above bottom tray 582. There is shown spillover 582.1 which allows fluid to flow off as well as spillovers 582.2., 582.3, and 582.4 as well as channel 584.

Figure 71B:
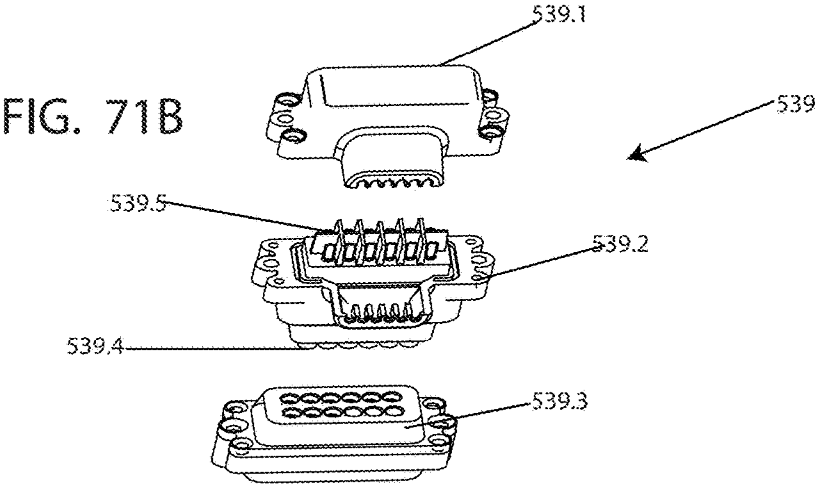
FIG. 71B is aa view of the quick connect electrical connection.

FIG. 71B shows a close up of the quick connect electrical connection 539. This quick connect electrical connection includes a pin-based connection base 539.3 which is configured to receive a pin harness 539.2 having pins 539.4 and opposite contact pins 539.5. Pins 539.4 are configured to fit inside the pin openings of connection base 539.3. These contact pins 539.5 are configured to connect to additional wiring inside of the container. This quick connection 539 allows a top cover such as top section 510 to be removed from the rest of the container without having to disconnect complicated wiring.

Figure 72A:
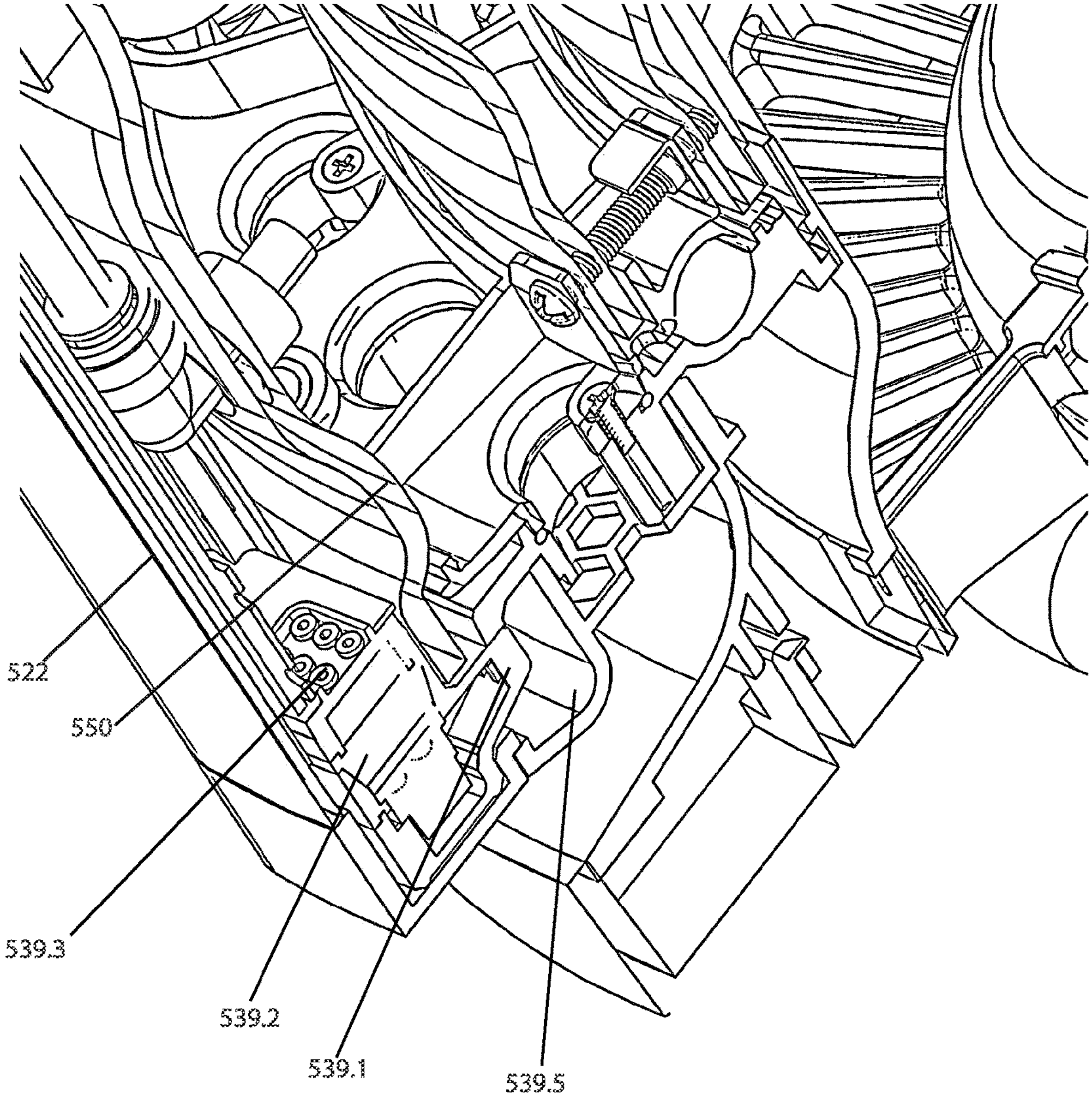
FIG. 72A is another side cross-sectional view of the embodiment of FIG. 63.

FIG. 72A shows an upside down cross-sectional view of the quick connect electrical connection situated inside of the container 550 wherein there is shown connection base 539.3, pin harness 539.2, and cover 539.1. There is shown an annular ring 539.5 which is configured to receive wiring from the quick connect 539. The wiring can then be distributed to the interior electrical components.

Figure 72B:
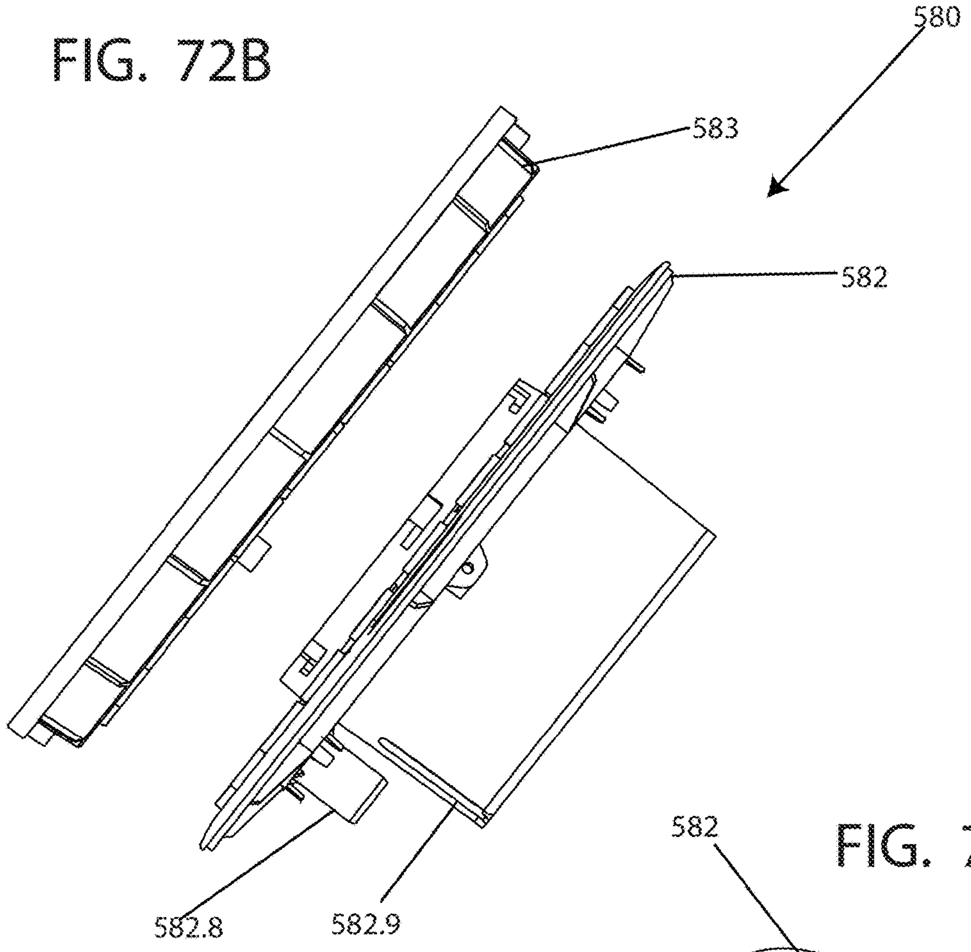
FIG. 72B is a side exploded view of the trays.

FIG. 72B shows trays 580 comprising top tray 583, and bottom tray 582. Bottom tray 582 has a fill connection 582.8 as well as a slit in a side wall 582.9. Top tray 583 fits over bottom tray 582 and is secured thereto by screws.

Figure 72C:
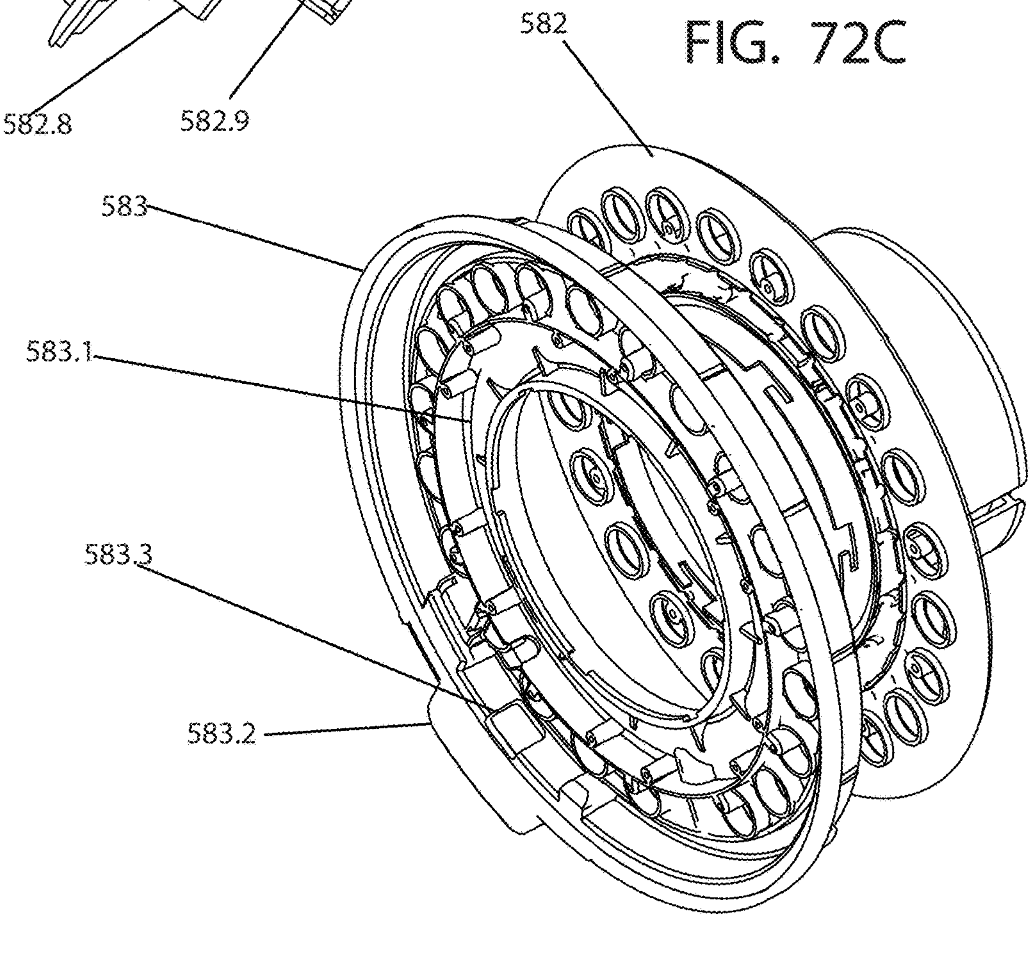
FIG. 72C is a perspective exploded view of the trays.

FIG. 72C shows a perspective view of the two trays 580 including top tray 583 and bottom tray 582. Top tray 583 has a channel cover 583.1 which covers over a corresponding bottom channel in bottom tray 582 to form channel 584. In addition, top tray 583 has a top cover 583.2 for receiving the quick connect electrical connection 539. Top tray 583 has an opening 583.3 which is configured to receive a cable when it extends in from the quick connect 538.

Figure 73:
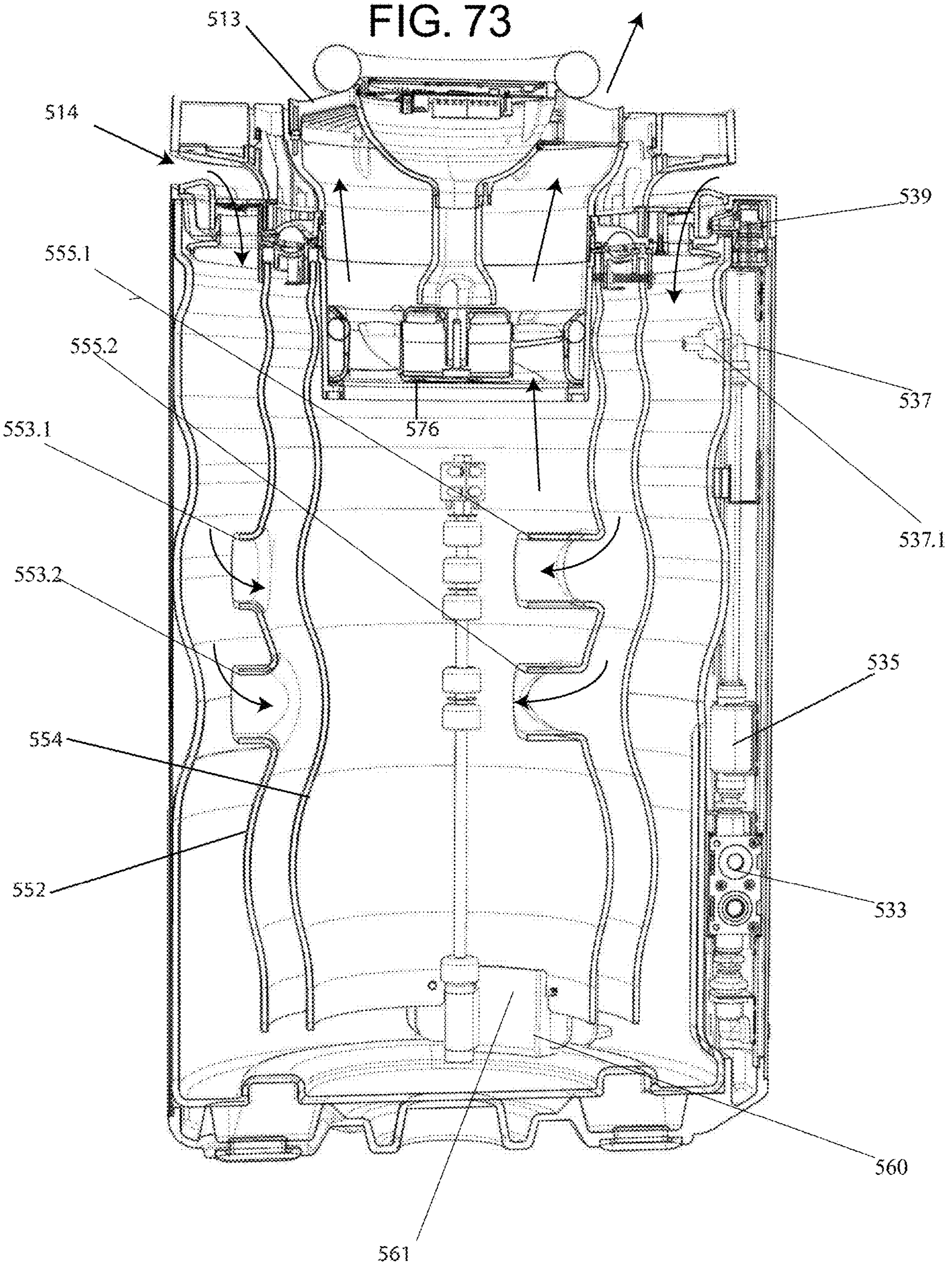
FIG. 73 is another side cross-sectional view of the embodiment of FIG. 63.

FIG. 73 shows a side cross-sectional view which includes container 550, outer core 552 and inner core 552. Air vents 553.1 and 553.2 are shown extending radially outward from outer core 552. In addition, air vents 555.1 and 555.2 are shown extending inward into a central region allowing air to flow therein. The arrows shown in this view show the pattern of air flow from the air inlet 514 into the region between container 550 and outer core 552, into vents 553.1 and 553.2, around inner core 554, and then through vents 555.1 and 555.2 into a central region. Next the air is drawn by fan 576 through the fan area and out of the air vents 513. As this air is drawn through the container it is interacting with the biological solution of water and proprietary biological solution or other biological reagent which is cascading or dripping down the walls of the container 550, the outer core 552 and the inner core 554. This interaction of the air with the biological reagent creates an ion-based cleansing effect drawing impurities from the air and then settling with the biological reagent. At the bottom of container 550 is a bracket 561 which is configured to couple to cores 552 and 554 to stabilize these cores above the bottom section of container 550.

Figure 74:
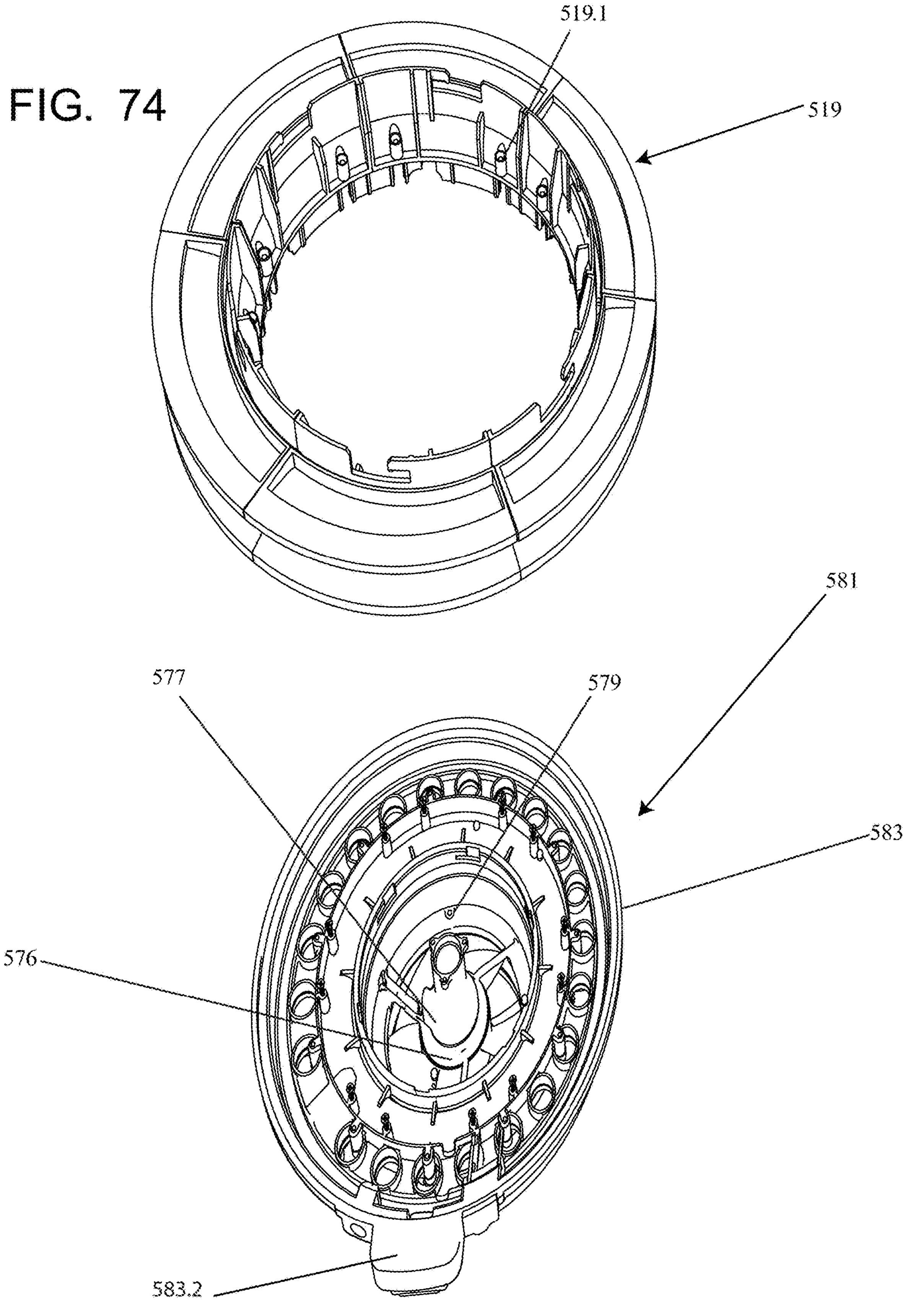
FIG. 74 is an exploded view of the cover and the trays.

FIG. 74 is an exploded view of the top cover 510 which includes a cover air vent section 519 which sits on top of trays 580, including top tray 583 and bottom tray 582. In addition, there is shown fan 576 which has a central channel 577 attached on top of it The central channel 577 can be used to receive any suitable cabling.

Figure 75:
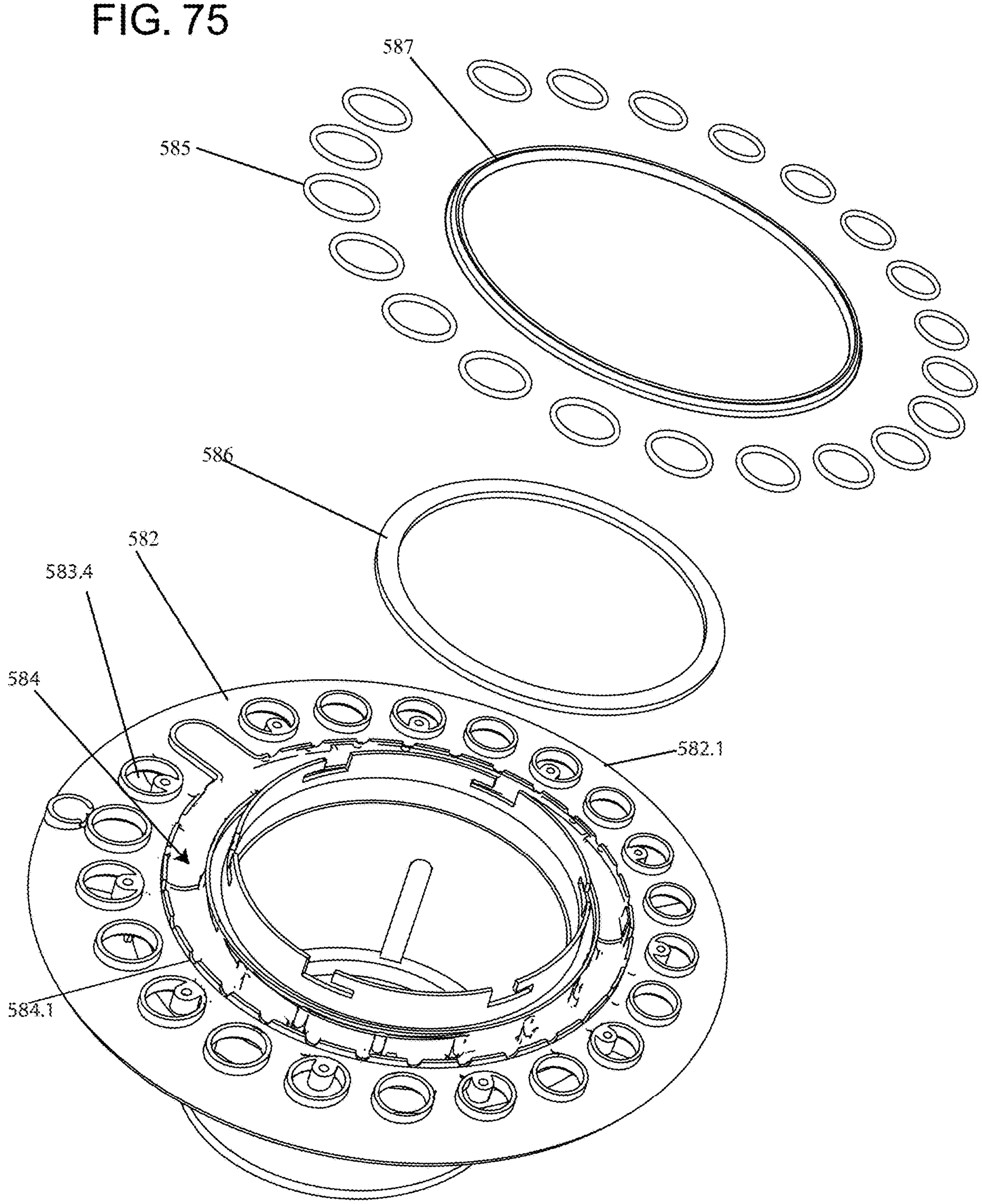
FIG. 75 is an exploded view of the trays and the gaskets associated with the trays.

FIG. 75 shows bottom tray 582 with gasket 586 as well as rings or gaskets 585 which fit between the air vent holes 583.4. The channel 584 is configured to distribute the biological reagent through holes 584.1 which allow the fluid biological reagent to flow along the top surface of the bottom tray 582 and ever an edge or spillover 582.1. Air vent holes 583.4 are sealed by gaskets 585 which serve as O-rings and sit between top tray 583 and bottom tray 582. An additional gasket 587 serves to allow the remainder of the top cover including the air vent section 519 (See FIG. 74) sit on top of top tray 583.

Figure 76:
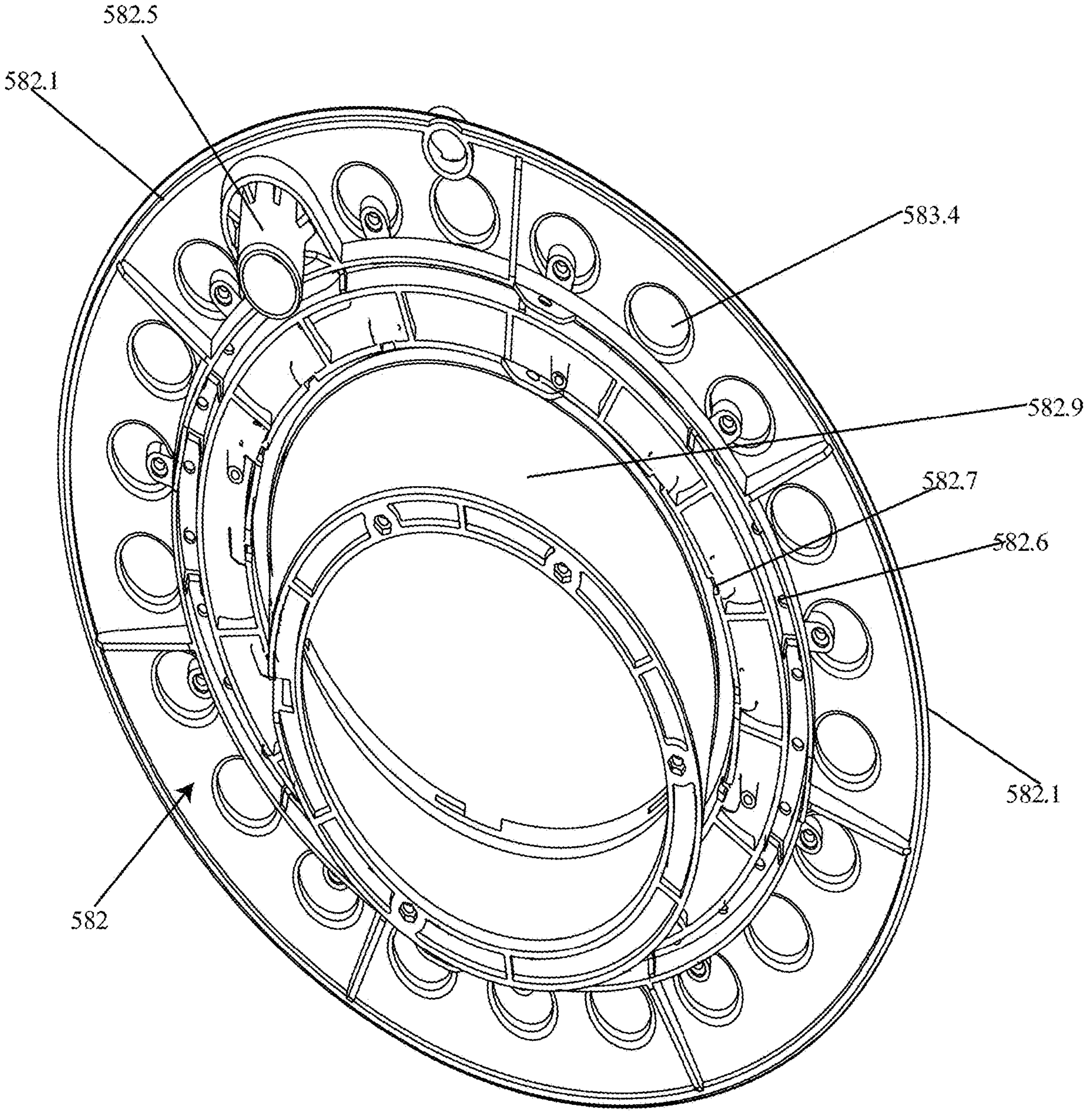
FIG. 76 is a bottom view of the trays.

FIG. 76 shows a bottom view of bottom tray 582. This bottom tray has a spillover 582.1 configured to allow the biological reagent to flow down the inner surface of container 550, as well as a plurality of holes 582.6 which are configured to allow the biological reagent to flow theredown around both the outer surface of outer core 552 and the inner surface of outer core 552 by spilling over the top of both sides of outer core 552. These holes are fluidly connected with channel 584. In addition, holes 582.7 are angled inward to allow fluid to flow down towards an outer surface of inner core 554 as well. These holes 582.7 are angled radially inward so that when the fluid flows, it splashes into a side region of the outer surface of the inner core.

Figure 77A:
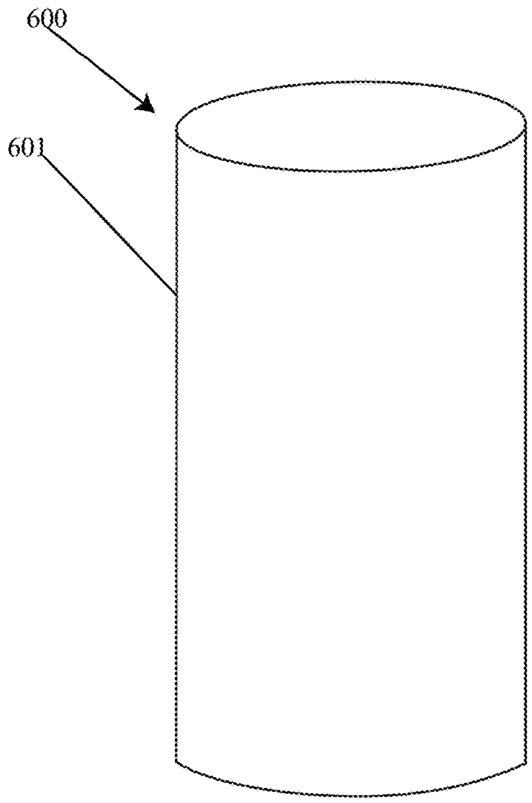
FIG. 77A is a side perspective view of a container of another embodiment of the invention.
Figure 77B:
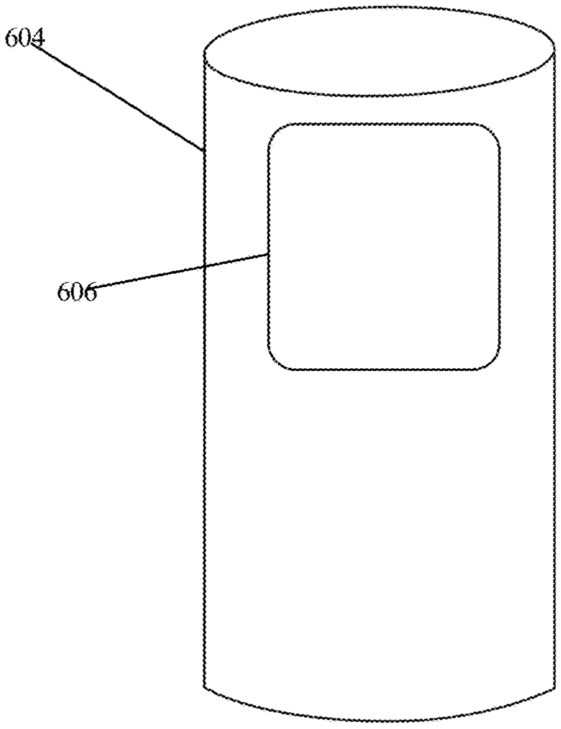
FIG. 77B is a side perspective view of & core of another embodiment of the invention.
Figure 77C:
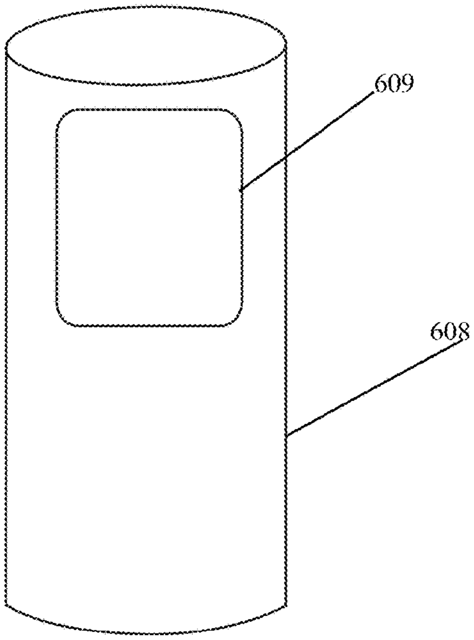
FIG. 77C is a side perspective view of another core.

FIG. 77A shows a side perspective view of another embodiment. In this embodiment there is an outer container 601 as well as an outer core 604 having an opening 606 as well as an inner core 608 having an opposite opening 609. This embodiment is similar to the above embodiments however this container and these cores are not undulating, rather they have substantially flat or straight sides extending along a cylindrical cross section.

Figure 78A:
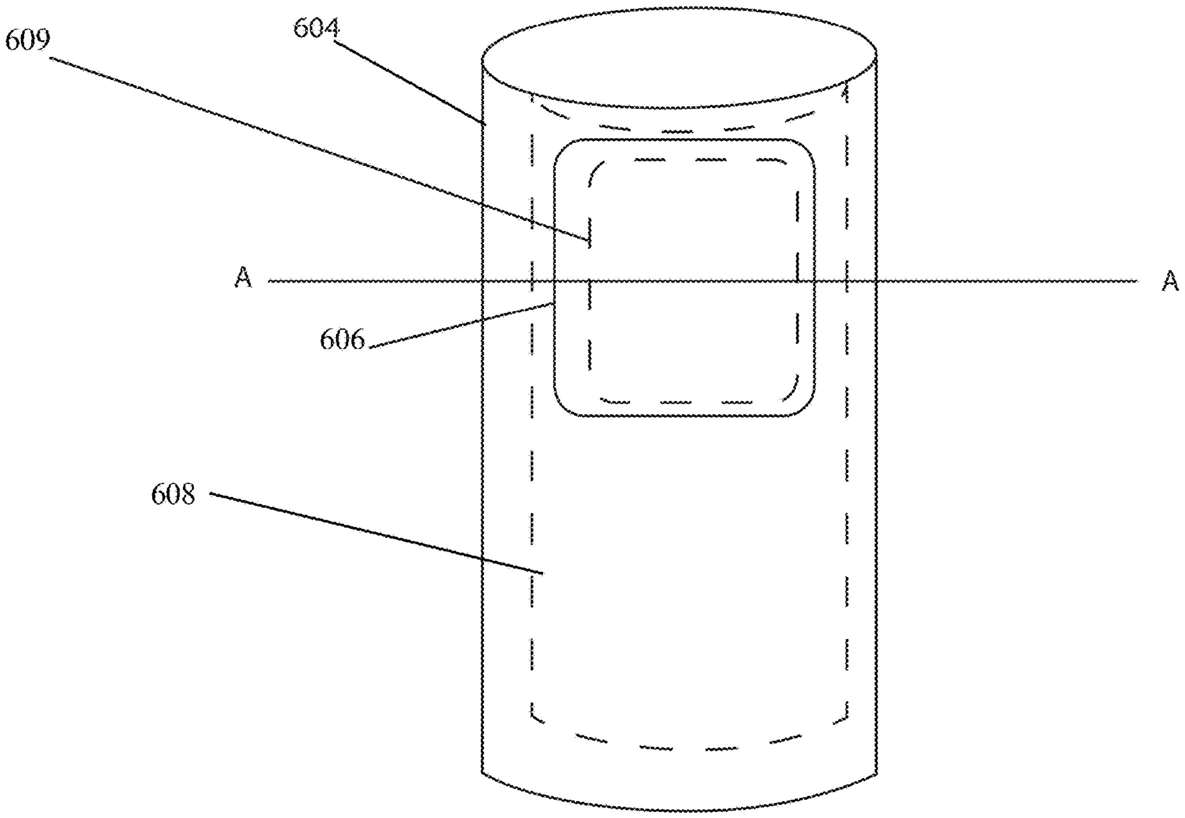
FIG. 78A shows a side perspective view of the cores placed one inside of the other.
Figure 78B:
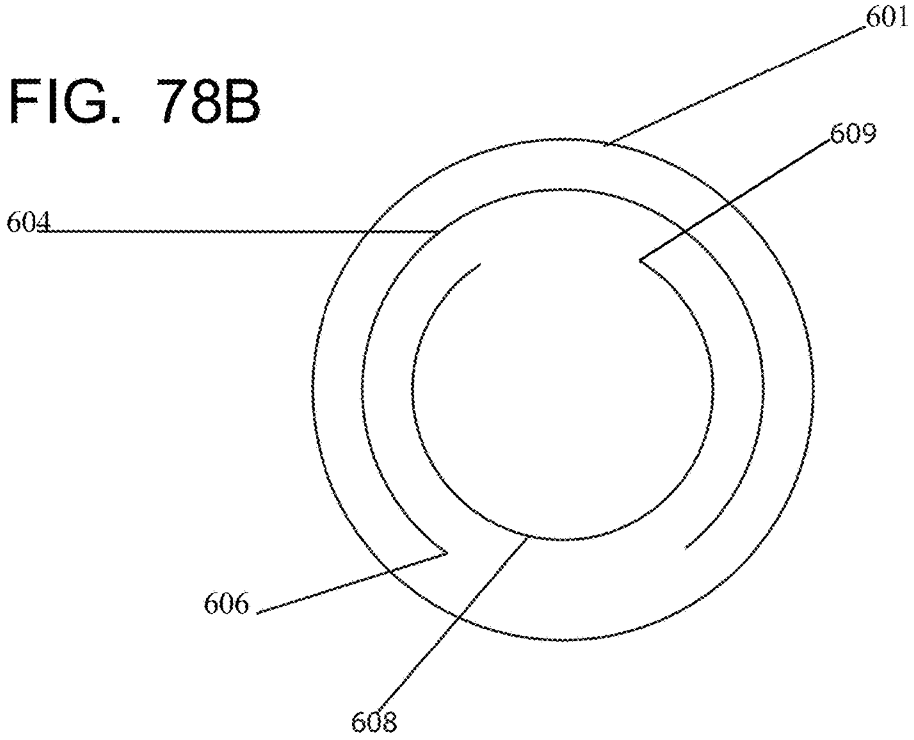
FIG. 78B shows a top view of the container and the cores placed inside of each other.

FIG. 78A shows a perspective view of the two cores including core 604 and core 608. Core 604 includes opening 606 while core 608 includes an oppositely positioned opening 609. FIG. 78B shows a top view of the outer container 601 with the two cores 604 and inner core 608. With the openings 606 and 609 spaced opposite each other this causes air flaw to flow around the cores such that air flows first through opening 606 and then around inner core 608 and then into opening 609 to reach a central region, wherein the air is drawn out by a fan (not shown).

Figure 79:
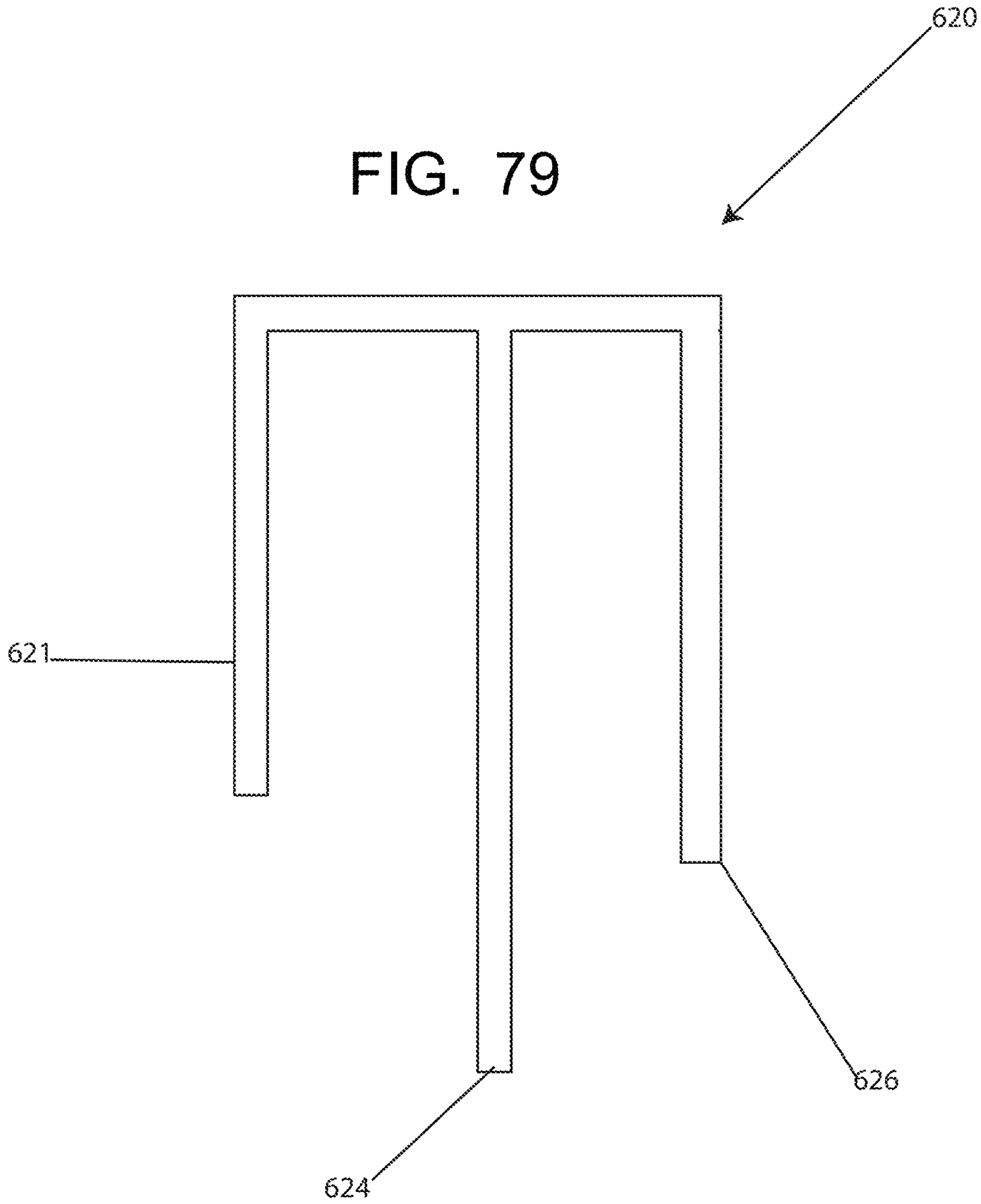
FIG. 79 shows a side view of the level sensor.
Figure 80:
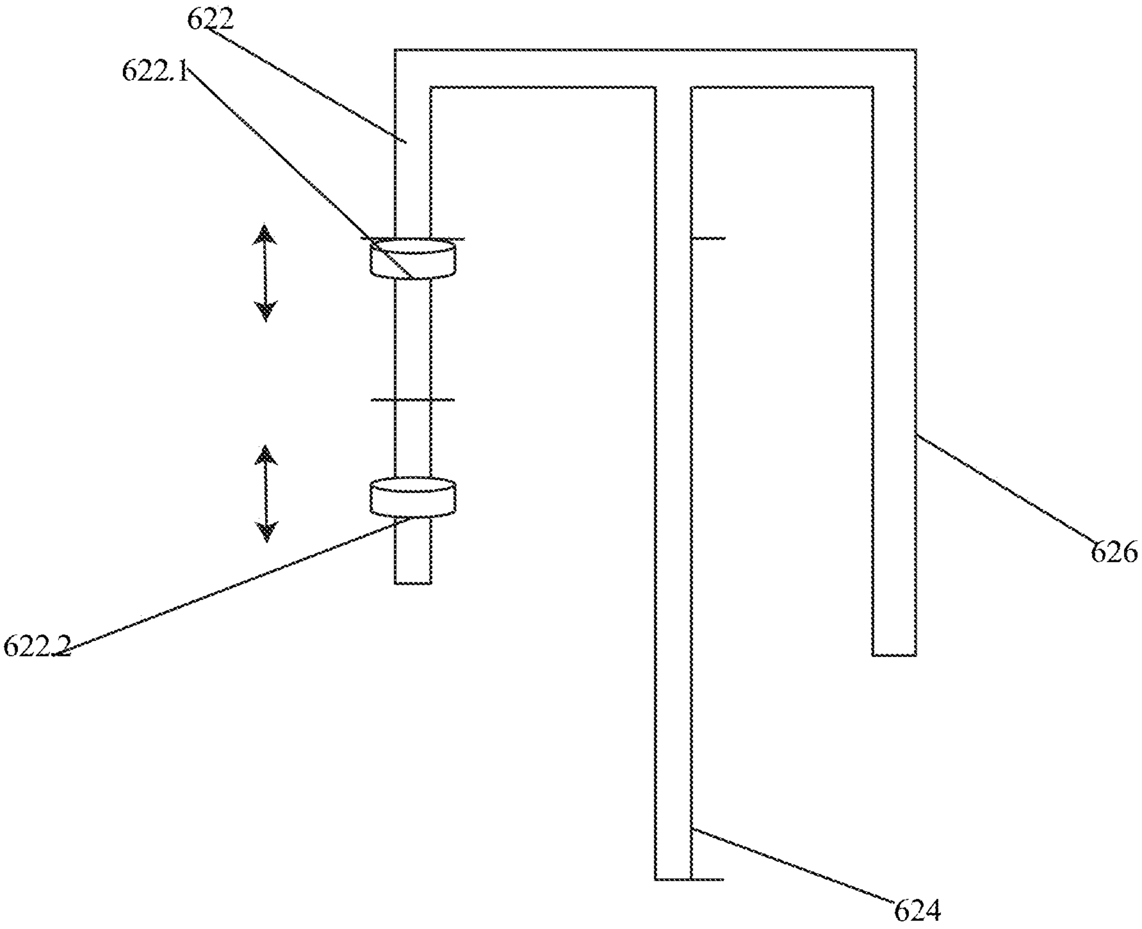
FIG. 80 shows another side view of the level sensor.
Figure 81:
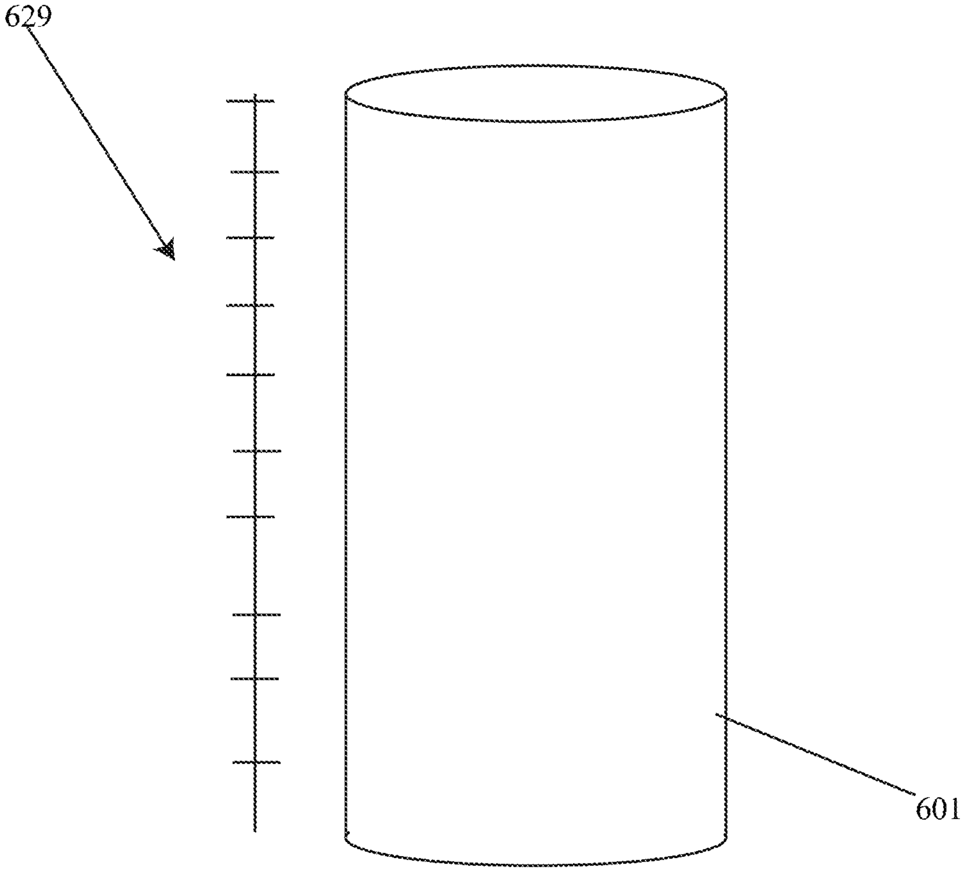
FIG. 81 is a side view of the different levels for the level sensor.

FIG. 79 shows a fill level sensor 620 which can include any one of a capacitive sensor 622, an inductive sensor 624, and or an optical sensor 626. FIG. 80 shows a float level sensor 622 which has different floaters 622.1 and 622.2 which float tip and down to different levels as indicated above. There can also be an inductive sensor 624 and/or an electrical or optical sensor 626 for further readings on a fail safe level. FIG. 81 shows the different levels that the sensors can read. For example, these different sensors can read at up to 10 different levels based upon a pre-set chart 629, to create a more accurate reading of whether to refill the tank with water or biological solution.

Figure 82A:
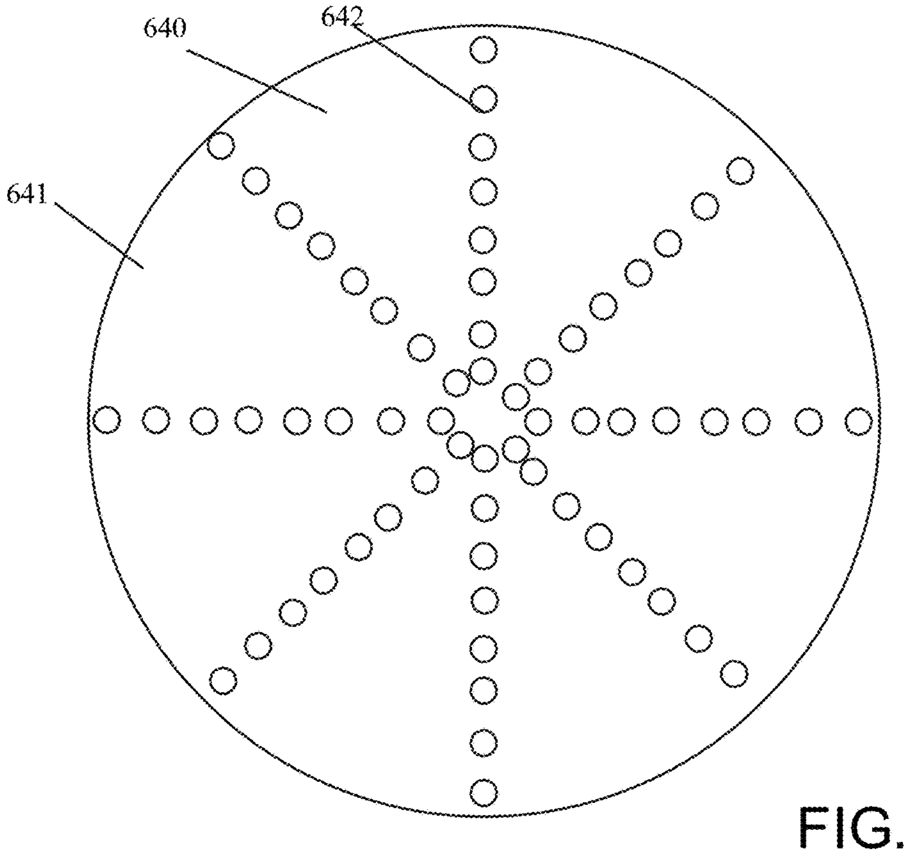
Figure 82B:
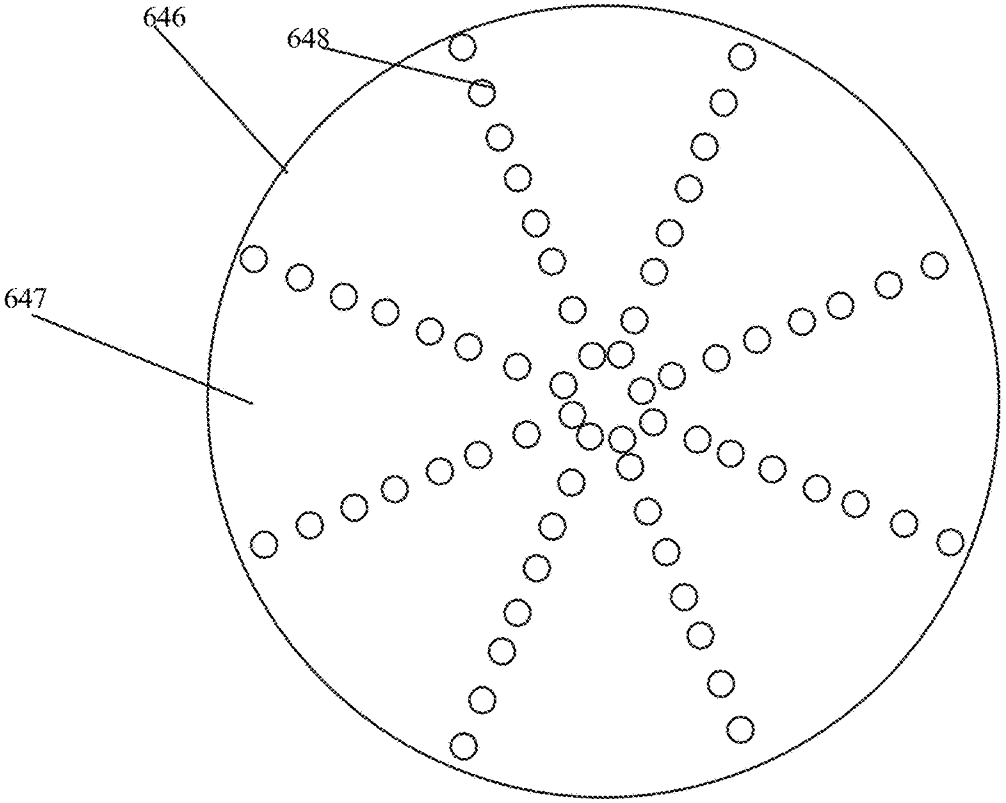
Figure 83:
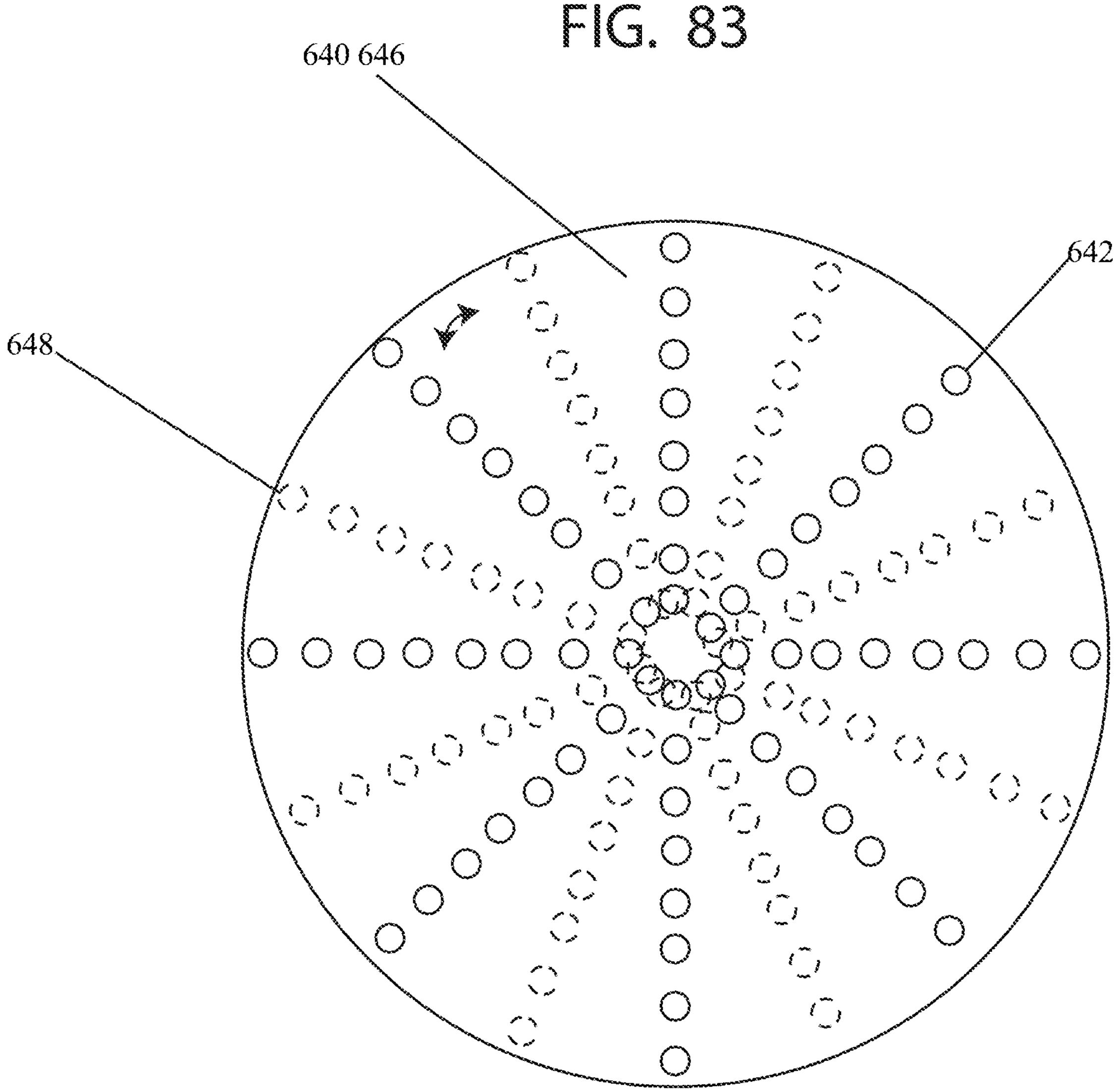

FIG. 82A shows a section tray 640 which includes a flat surface section 641 and a plurality of holes 642. This tray allows fluid to flow through the holes 642 and down into a lower level. This tray 640 sits above a second fray shown in FIG. 82B. Second tray 646 also includes a plurality of holes 648 and a surface 647. The holes in both tray 640 and tray 646 are shaped like spokes, radiating outwardly from a central region. FIG. 83 shows the two trays 640 and 646 laid one on top of the other with the holes offset from each other such that holes 642 is offset from holes 648 so that fluid flows down from one tray spilling onto the surface of the lower tray and then eventually running down through the holes of the lower tray.

Figure 84:
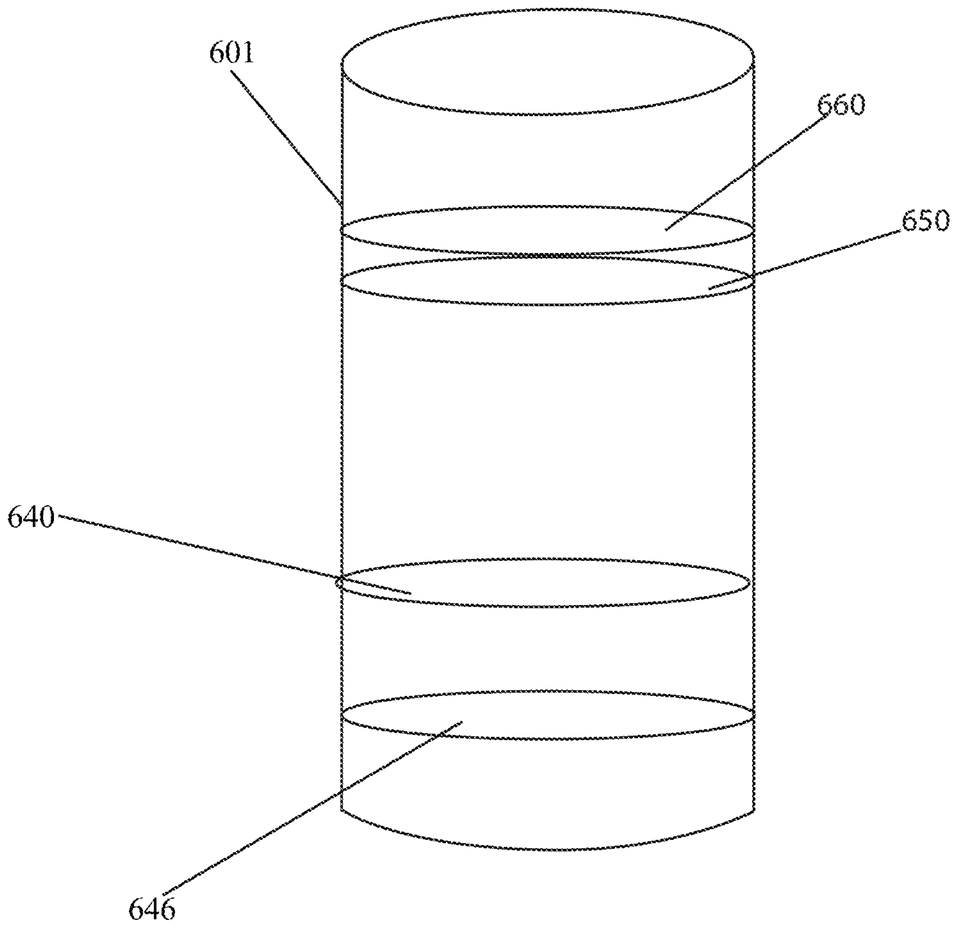

For example, as shown in FIG. 84 there is a top tray 660, and a lower tray 650 (See FIGS. 85A and 85B) which are positioned above trays 640 and 646. Biological reagent spills down the sides of the respective cores 604 and 608 such that biological reagent flows down both the outside surface and the inside surface of core 604, and the outside surface of core 608. As the reagent hits tray 640 it accumulates on the surface and then flow down through holes 642 before it hits surface 647 of tray 646. The reagent then sits on surface 647 until it accumulates enough to How through holes 648 to a lower level. These two different sets of trays allow for different levels of biological reagent to be kept substantially separate from each other. For example, even if the fill level of the biological reagent was above even tray 640, any particulates could then be separated from each other via the different levels formed by tray 640 and tray 646.

FIGS. 85A and 85B show bottom trays that can be used in this system to distribute biological reagent to the system. For example, in FIG. 85A there is shown a bottom tray 650 which includes a surface 651, with a plurality of air holes 642 for allowing air to flow therethrough. A cap 653 is shown to cover electrical cabling while there is also shown a water feed opening 654 configured to allow water to flow up and therethrough. There are a plurality of outer peripheral holes 656 which are configured to allow the biological reagent to flow down the inside surface of the outer container. A plurality of holes 657 are configured to allow the biological reagent to flow down both the inside and outside surfaces of the outer core 604. In addition openings 658 are configured to allow the biological reagent to flow down the outer surface of the inner core 606 as well. Thus, this tray is configured to distributed the biological reagent as it is fed into the tray in the manner disclosed above in the alternative embodiments.

FIG. 85B shows an alternative lower tray 670. This lower tray 670 includes an air intake hole 671 as well as fluid ports 672 for receiving the biological reagent. Outer fluid holes 675 are fed by the biological reagent flowing over the tray surface 674 to these outer holes. The outer holes then feed the inside surface of the associated container such as container 601. Another set of holes 676 are configured to feed the top of outer core 604, allowing the biological reagent to spill over the outer surface and the inner surface of the outer core 604. In addition, holes 603 are configured to allow the biological reagent to flow down the outer surface of the inner core 608. FIG. 85C shows a top tray or cover 660 which has air holes 662, a cover 663 and a raised cover section for receiving the fluid intake. Top tray or cover 660 is configured to fit over bottom tray 650.

Figure 86:
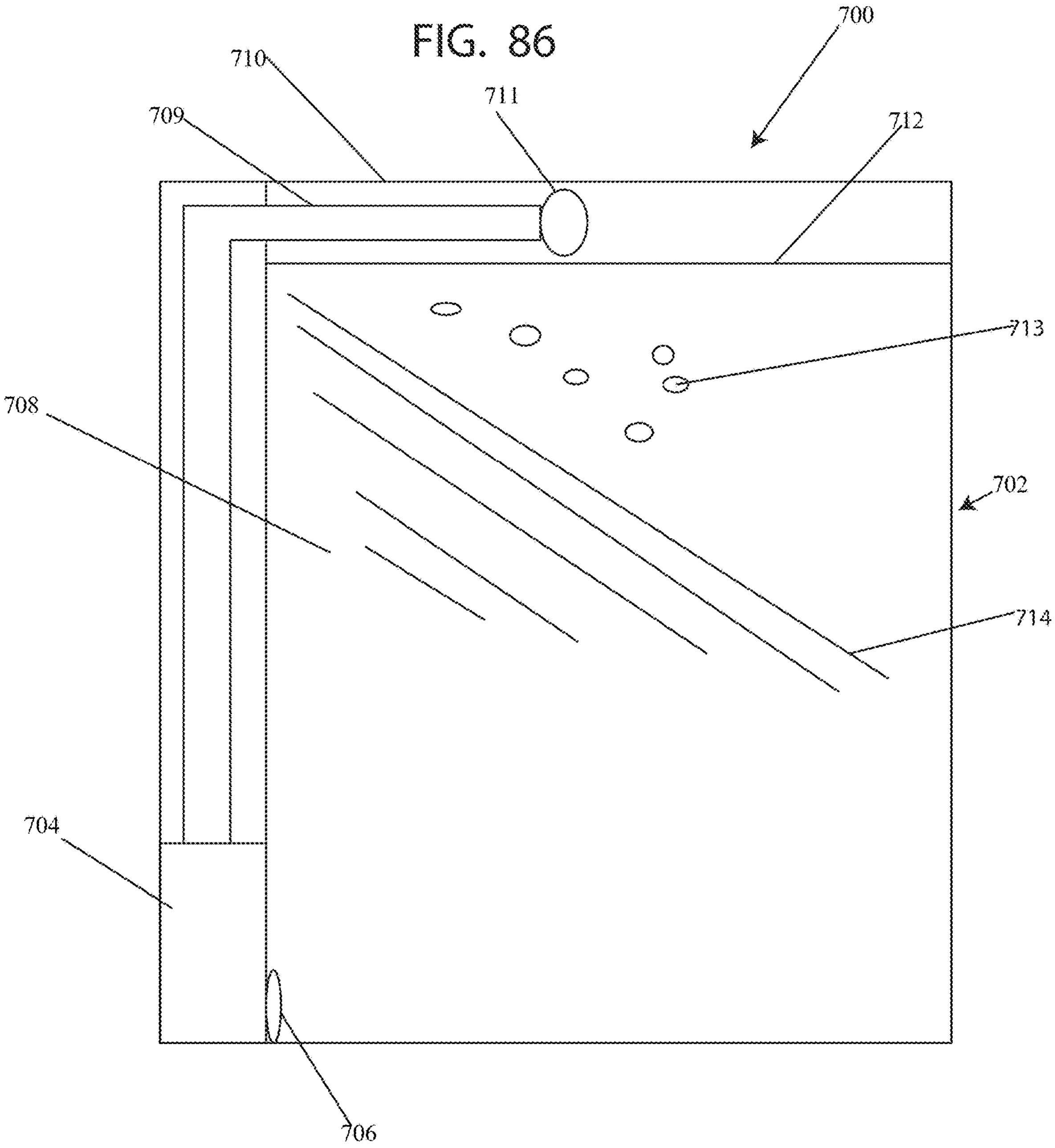
Figure 87:
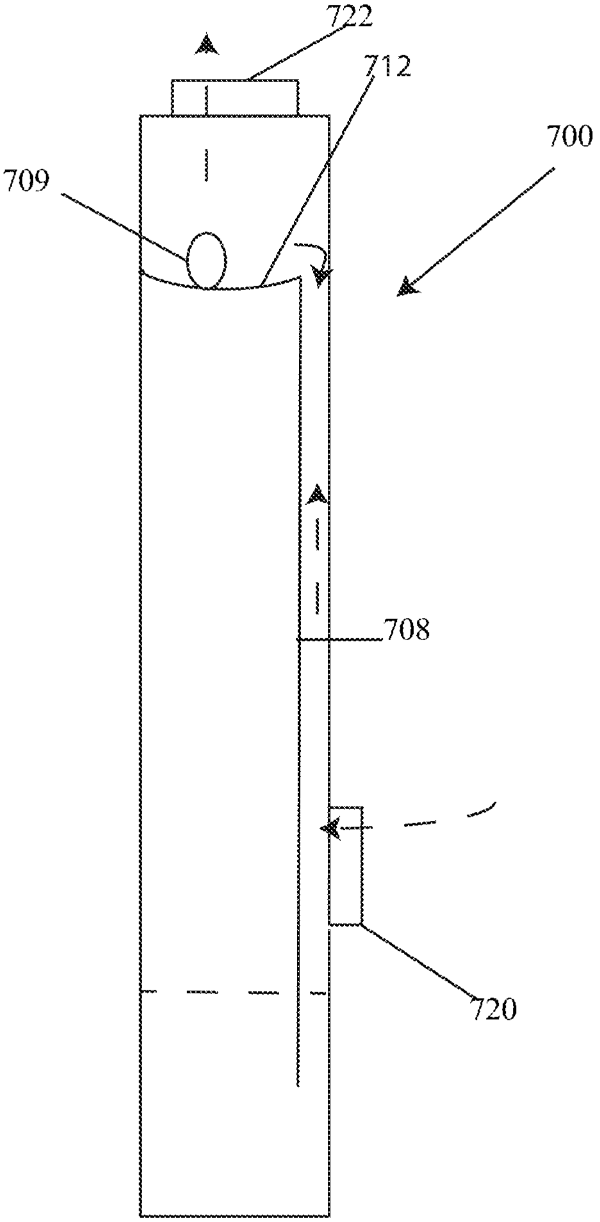

FIG. 86 shows a side cut away view of another embodiment. With this embodiment 700, there is disclosed a substantially rectangular or square shaped design which allows the device to be fit into smaller spaces such as apartments or different work environments. For example, there is shown a substantially rectangular housing 702. This housing 702 is configured to form a container for the biological reagent while providing space for a pump 704. There is a fluid intake 706 which is configured to receive the biological reagent, wherein the pump 704 is configured to pump the reagent up through pipe 700 and out through opening 711 in top section 710. The fluid then sits on tray section 712 (See FIG. 87), wherein the fluid biological reagent flows down front surface 708 (See FIGS. 86 and 87). This front surface can be a textured surface such as bumps 713 or contours 714 which create a contoured surface to disperse the water flow down the surface of wall 708. FIG. 87 shows the arrows of flow with the dotted line arrows pointing up signifying air flow with the solid line signifying the fluid flow down. In addition, there is show a fan 722 as well as an air intake opening for receiving air flow in the housing. With this design the air flow moves opposite the fluid flow thereby creating increased interaction between the air and the fluid flow.

Figure 88A:
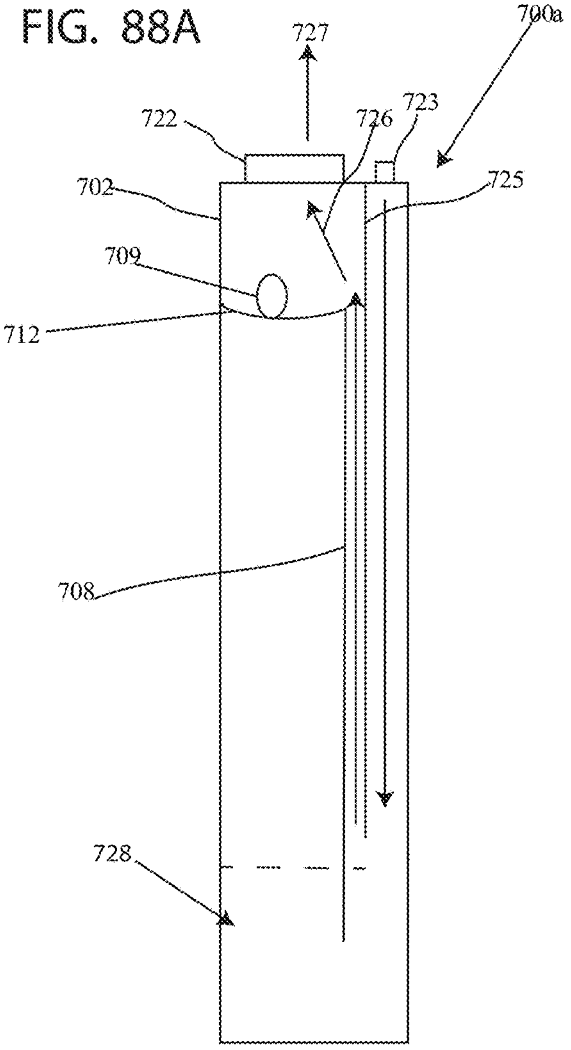
Figure 88B:
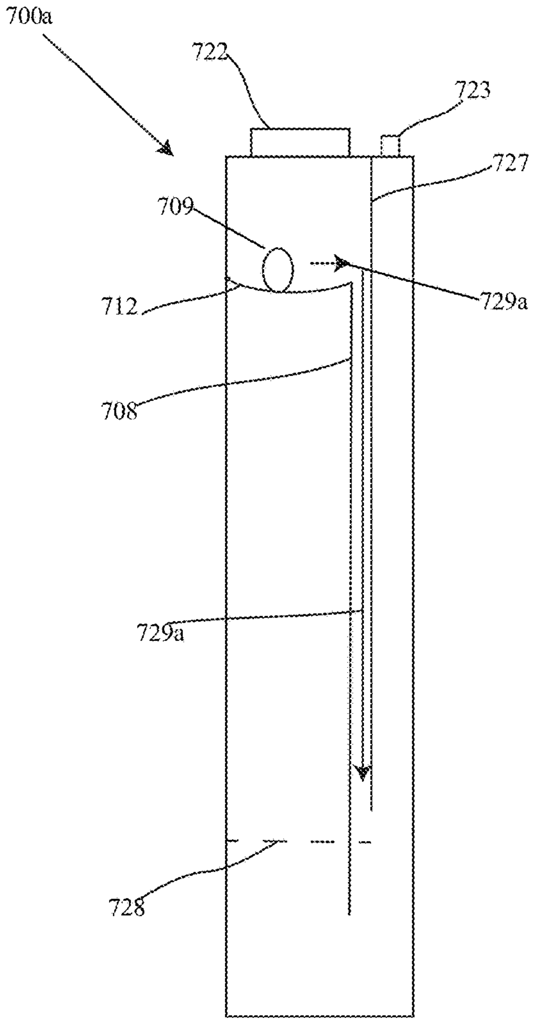

FIG. 88A shows a side view of another embodiment wherein with this view there is shown body or housing 702 which has an upper air intake 723 as well as an additional air flow wall 725. With this additional air flow wall, the air intake 723 allows air to flow in through a top section around wall 725 and then around wall 725 and then back up a channel between wall 725 and wall 708 with arrow 728 and 727 showing that the air flow is out of the container. Meanwhile fluid is pumped up to tray 712 where it then spills over down wall 708 and interacts with the oppositely moving air flowing through the housing. Reference numeral 728 designates a lower area where the fluid biological reagent collects at the bottom of the container. Similarly, FIG. 88B shows the components shown in FIG. 88A, however this view shows the fluid flow via arrows 729*a* and 729*b*.

Thus, with this design, there is substantial interaction between the incoming air flow and the cascading fluid flow which falls in a direction opposite the flow of air. The direct interaction between the air flow and the opposite moving biological reagent results in an interaction between the two which results in a cleansing of the air as it passes through the housing.

FIG. 89A shows a substantially rectangular design which shows a first embodiment having a housing 712*a* which has a pump 704*a*, a riser line 709*a*, and a distribution cutlet 711*a*. There are also a plurality of receiving trays 715*a* which slope in a first direction and a second set of receiving trays which slope in an opposite direction. The pump 704*a* pumps the biological reagent or purification solution up to distribution outlet 711*a*. The biological reagent flows down first trays 715*a* to second trays 715*b* cascading down to a bottom region of housing 712*a*, during this time of flow of the biological reagent, the air flow is moving in a transverse direction as shown by the transverse arrow which extends transverse to the fluid flow arrows extending down the different trays. This transverse air flow which moves transverse to the fluid flow of the biological reagent creates an interaction between the air and the fluid biological reagent resulting in a cleansing of the air.

FIG. 89B shows another embodiment which shows a housing 712*b* which has a vent 710*a* which allows air flow into the housing. The air is drawn from a fan 722 disposed in a top region of the housing 712*b*. The housing has a plurality of trays 715*a* and 715*b* which allow a cascading of biological reagent as described above. This embodiment however has the air flow moving in a substantially opposite direction to the flow of fluid biological reagent thereby causing interaction between the flowing air and the flowing water passing each other.

FIG. 90 discloses a substantially circular or annular bearing 800 which is configured to be coupled to a bottom section such as bottom section 540 in the housing region 541 between bottom section 540 and container 550 (See FIG. 70). FIG. 91 shows an exploded view of the bearing 800 which includes a rotary feet clamper 810, couplings 816 or screws which are configured to clamp hearing hold 820 to casing 830. Rotary clamper includes an outer raceway 812 which is configured to receive one or more ball hearings while bearing hold 820 also includes an inner raceway 822 which is configured to be formed opposite raceway 812 and to allow at least one ball bearing to move therein.

FIG. 92 shows a cross sectional view of this bearing 800 which includes clamper 810 camped to casing 830 thereby securing bearing hold 820 therein. In this view, the concave raceways 812 and 822 join to form a cylindrically cross sectioned raceway 818 which is configured to receive at least one ball bearing therein. FIG. 93 shows another exploded view of the bearing 800 which shows casing 830, rotary bearing hold 820 and clamp 810 having raceway 812 along with couplings 816 or screws and at least one ball bearing 840. With this design, when a container 550 is rotated onto its side such as onto an edge of bottom 540, with the device tilted at an angle offset approximately 20 degrees or more from vertical, the bearing allows bottom 540 to rotate vs. container 550 thereby allowing for easier transport of the device. This bearing 800 can be used with any of the above identified embodiments as well.

FIG. 94 shows atop view of a touch screen 592 wherein this touch screen has a plurality of different sections or components. For example, this surface 902 has a first region that is an indication region 904 that indicates whether the tank needs to be filled. Another region 906 is a lighted region which indicates whether the tank is full. Another region 908 functions as an on/off switch while regions 912 and 914 are for indicating fan speed levels. For example, region 912 indicates whether the fan is in a night mode and operating at a first level of speed while region 914 indicates whether the fan is at a second level of speed. The level of the fan can be selected using a fan select button 916. Region 910 can be used to select whether to auto fill the tank or whether to manually fill the tank. For example, with auto filling the tank selected it will only selectively open the double solenoid valves 533 if the float level sensor 570 indicates that the fill level is below a predetermined level. Region 918 indicates whether the device needs service while region 920 and 922 indicate whether the device is on the auto or manual fill mode. Region 824 is used as a BIOX indicator to tell the user to add more biological reagent to the aqueous solution. Region 926 is used as a pump indicator which is configured to indicate whether the pump is operating.

FIG. 95 shows the layout of the computer related components of the above embodiments. For example, there is shown motherboard 594 which includes microprocessor 594.1, memory 594.2, pins 594.3 and transceiver 594.4 wherein all of these components are coupled together on motherboard 594. Microprocessor 594.1 is configured to process the information relating to the predetermined fill level, the flow rate of the associated pumps 560 and 562 as well as the readings from external sensors. Predetermined values for the fill level as well as the temperature, and the flow rate of the pumps are stored in memory 594.2. Pins 594.3 allow for direct wired communication to external components as well as any power wired therein. A transceiver 594.4 is configured to communicate with external sensors 940 and 944 as well as sensor 946. These sensors can be in the form of a temperature sensor 940, a humidity sensor 944 and a VOC (volatile organic chemical) sensor 946. Other alternative sensors can be configured to communicate with the components on motherboard 594 as well. In addition, a server 950 is configured to communicate with the motherboard 594 either through wired communication (through communication via pins 594.3) or via wireless communication via transceiver 594.4 Data taken from the device and stored in memory 594.2 can then be transported to server 950 for later storage and processing. Multiple external computer components each associated with any one of the above air purification embodiments can be in communication with one or more servers 950 to register operating parameters, overall environmental air quality and performance of these devices.

FIG. 96A shows an alternative embodiment which includes the following components a motherboard 1001, a processor 1002 which can be in the form of a microprocessor. In addition, there is a memory 1004, which can be in the form of an EEPROM, RAM or ROM or flash type memory. Memory 1004 is configured to feed instructions into microprocessor 1002. A power supply 1006 is configured to provide power to motherboard 1001. The power supplied to motherboard 1001 is configured to power all of the other additional components. In addition, there is a communications device or chip 1008 which is configured is communicate wirelessly or in a wired manner to additional components such as to additional sensors or other additional computing devices. Communications chip 1008 can communicate via either WIFI or cellular communications. Furthermore, there is a GPS chip 1009 which is configured to locate the electronic device in a region. GPS chip 1009 allows for the location of each of these systems in a geographic location. The information obtained fey the sensors in this system can be communicated to microprocessor 1002 and this information as well as the location information of GPS chip 1009 can then be communicated to other servers such as any one of the PC 1030, smartphone 1032, and server 1034.

FIG. 96B shows a configuration of the computer system 1000 which is in communication with sensors such as a float level sensor. Other sensors can also be in communication with this computer system including a fluid or water temperature sensor 1020 which can be configured to read the water or fluid temperature. Another sensor 1022 can include an air sensor which is configured to read the air temperature. A further sensor 1024 can include a humidity sensor which is configured to measure the humidity of the air leaving the purifier.

FIG. 97 shows the distributed computing environment for computer 1000 as well as other remote servers as well. For example, computer 1000 is configured to communicate with local PC such as PC 1030, or with a local smart phone such as smart phone 1032 via Bluetooth. Alternatively, computer 1000 can also communicate directly with a server 1034, which can then process the information and communicate back with other devices such as a local personal computer (PC) 1030 or a smart phone 1032.

FIGS. 98A and 98B show how the system 210, 500 can be incorporated into a zoned or space HVAC system comprising an air handler 1100. For example, in one embodiment, the system 210, 500 can be placed adjacent to an intake of an air handler 1100 along intake pipe 1102. The air can then leave air handler 1100 via outflow pipe 1104. Alternatively, as shown in FIG. 98B the air handler 1100 can be positioned upstream from the system 210, 500 wherein the system 210, 500 is positioned adjacent to the outflow of air handler 1100 adjacent to outflow pipe 1104.

FIG. 99 shows another view of a clean in place (CIP) system. This clean in place system is used to clean commercial and industrial biological reactor units where relocating the unit to empty the contents is impractical. This may be due to the larger size of the unit, the location it is installed in or the local preferences and/or protocols of the facility.

The CIP assembly 1050 is designed to recirculate the bio solution and filter out any sludge or particulates that has been captured, thus providing an adequate cleaning of built up digested and non-digested matter.

The CIP comprises a plurality of components including a portable cart 1051 and bracket assembly 1052, a variable speed jet pump 1054, a bag filter assembly 1056, a suction line 1058, and a discharge hose 1059.

FIG. 100 is a flow chart for a basic determination of whether to fill a container with more fluid solution such as water. For example, in step 1 a microprocessor such as any one of the above-mentioned microprocessors 424.5, 594.1 or 1002 in coordination with any one of the above fill level sensors 240, 570 or 620 determines a water or fluid level in the container. Next, in step 2 if the fluid level is determined by the microprocessor to be too low then the microprocessor can then selectively open the solenoid valves 533 and allow fluid such as water to flow into the container. Next, in step 3 the microprocessor along with the fluid level sensor can determine the water level. If the water level has met or exceeded a predetermined level for fluid in the container, then the microprocessor can selectively close the solenoid valves in step 4. Next, in step 5 the controller such as microprocessor can then continue to monitor the water or solution level in the container and then revert bank to step 2 and open the solenoid valves if the controller determines that more fluid is needed in the container.

FIG. 101 shows a flow chart for the process for controlling the device including reading any peripheral sensors as well as controlling pumps and fans and the solenoid. For example, with this process the controller is controlled by a microprocessor such as microprocessor 424.5, 594.1 and 1002. Any one of these microprocessors can control any one of the fill level sensors 240, 570 or 520 or temperature sensors 940 or 1022 or humidity sensors 944 or 1024, or volatile oxygen compound sensors 946 or other harmful gas sensors.

For example in step 10 the system including the controller (microprocessor and any suitable memory) communicates with an appropriate fill level sensor to determine the water level. Next, in step 11 the controller determines the ambient air temperature using any one of the above temperature sensors. Next, the controller determines the presence and amount of volatile compounds in step 12 by communicating with the VOC sensor. Next, in step 13 the controller communicates with the humidity sensor to determine the humidity adjacent to the controller. Next, the controller communicates with at least one pump such as any one of pumps 491, 492, 560, 562, 704, and 704*a*. This controller reads any one or more of the following characteristics: the pump temperature, RPM of the motor and the flow rate. This is to determine if the pump is operating properly. If the pump is straining because the fluid is highly viscous or there are heavy particulates then the controller can shut down the pump to save the pump motor. The controller can then notify the user that the tank or container should be cleared of particulate matter before resuming the user of the pump. In addition the controller can read the RPM of the fan which can be any one of fan 225, 425, 576, or 722. Next, in step 16 the controller can selectively open one or more the associated solenoid valves 533 to allow water or other similar solutions or compounds to flow therein. These solenoid valves can be any one of solenoid valves 533 which selectively allow water to flow into the housing under ambient household pressure.

In addition depending on the presence of VOC's, ambient temperature, and possibly humidity, as read by an associated controller, the controller can in step 17 change the fan speed of an associated fan or in step 18 change the fluid pump rate to create more interaction between the air and the biological reagent solution or purification solution. If the change in the pump rate and the fan does not work sufficiently the controller can also signal to request additional biological reagent to increase the rate of interaction between the dissolved biological reagent and the air flowing past the liquid reagent.

If however the controller reads that the pumps are straining the controller can then signal to request that the container be cleaned and overhauled so that the additional accumulated particulate matter is cleaned from both the container and the pumps to allow the pumps to operate more effectively.

FIG. 102 shows the process for the clean in place system CIP. For example, the process involves the following steps: in step 101 the system determines the date and time for the cleaning this can be done using the microprocessor 1002. Next in step 102, a user can 24 hours before scheduled cleaning, add predetermined amount of coagulant to bioreactor. In at least one embodiment the coagulant can be Aluminum Sulfate. Next in step 103, the system can allow the unit to recirculate the coagulant with a pump such as pump 560 for 30-60 seconds.

Next, in step 104 the system can shut off Bioreactor, and allow Coagulant to coagulate contaminates and settle floc to the bottom of the tank.

Next, in step 105 the system is configured to allow 24 hours for Bioreactor to settle the floc. Furthermore, in step 106 a user can insert new bag filter into the CIP filter assembly. Next in step 107 the user can insert a suction pole to bottom of the tank. In step 108 the user can plug in the unit to 110V power. Next in step 109 the user can then turn on CIP unit. Next, in step 110 the user can allow CIP unit to recirculate water until all settled contaminants are removed and water is clear, moving suction pole around bottom of bioreactor tank to suction settled material. Furthermore, in step 111, the user can remove the filter and discard. This allows for a thorough cleaning of the system in one place without removing the device from operation for too long.

In all of these designs the size and shape of the machine can be varied, however the above processing can still be used. The processor/motherboard and electronic components can be adapted for use with other air purification machines using a biological reagent in combination with water that is configured to attract particles in the air.

Accordingly, while at least one embodiment of the present invention have been shown and described, it is to be understood that many changes and modifications may be made thereunto without departing from the spirit and scope of the invention as defined in the appended claims.

What is claimed is:

1. An air purification system comprising:

a housing:

at least one fan coupled to the housing;

at least one container coupled to the housing:

at least one purification solution disposed in the housing;

at least one tray disposed in an upper region of the container, said tray extending substantially horizontally and having openings allowing the purification solution to flow down from the tray and openings allowing air to flow up into the tray, at least one purification solution transfer system, wherein said purification solution transfer system is configured to transfer purification solution from one region in said housing to said tray so that said purification solution flows along an inner surface of said at least one container;

a plurality of cores disposed in said housing;

wherein said at least one tray has a channel having a channel cover forming a solid channel which radiates outward from a center region and which allows liquid purification solution to flow under pressure therein from an inner region to outer regions of the tray and down at least an inner surface of at least one core and an outer surface of at least one additional core of said plurality of cores.

2. The air purification system as in claim 1, wherein said at least one purification solution comprises water and a biological reagent.

3. The air purification system as in claim 1, further comprising at least one fill level sensor.

4. The air purification system as in claim 3, further comprising at least one controller comprising a microprocessor, at least one memory, and at least one transceiver, wherein said at least one controller is in communication with said at least one fill level sensor.

5. The air purification system as in claim 4, further comprising a water feed configured to selectively feed water into the container.

6. The air purification system as in claim 5, further comprising at least one valve, wherein said at least one valve is configured to selectively allow water from said water feed to be fed into the container.

7. The air purification system as in claim 6, wherein said at least one valve is in communication with said at least one controller, wherein said at least one controller is configured to selectively operate said at least one valve to selectively allow water into the container.

8. The air purification system as in claim 6, wherein said at least one valve comprises at least one dual solenoid valve.

9. The air purification system as in claim 8, wherein said fan is disposed adjacent to a central cylinder inside of said housing and wherein said fan is configured to create a negative pressure inside of said housing.

10. The air purification system as in claim 9, wherein said at least one fan is in communication with said at least one controller and wherein said at least one controller is configured to control a speed of said at least one fan.

11. The air purification system as in claim 5, wherein said purification solution transfer system comprises at least one pump, wherein said at least one pump is configured to pump purification solution up from a lower region in the container to an upper region in the container.

12. The air purification system as in claim 11, wherein said pump is in communication with said at least one controller, and wherein said at least one controller is configured to control a flow rate of said pump.

13. The air purification system as in claim 12, further comprising a plurality of cores, wherein said plurality of cores are substantially cylindrically shaped.

14. The air purification system as in claim 1, wherein said tray comprises a bottom portion and a top portion and wherein said bottom portion and said top portion form said channel, wherein said channel is configured to allow said purification solution to be pressurized therein.

15. The air purification system as in claim 14, wherein said tray comprises a plurality of holes.

16. A container comprising:

a body section;

a base, comprising a top portion forming an annular ring having an open center and fastened to said body section said top portion having a raceway;

a bottom portion forming an annular ring having an open center;

an intermediate section disposed between said top portion and said bottom portion said intermediate portion having a raceway; and a bearing disposed between said top portion and said bottom portion in said raceway of said top portion and said raceway of said intermediate section wherein said top portion sits radially inside of said bottom portion and wherein said bottom portion of said base is rotatably coupled to said top portion via said bearing and wherein said bottom portion has a beveled outer edge which is angled up such that when said body section is turned on an angle it can be rolled on said base with said bottom portion rotating around said top portion.

17. The container as in claim 16, wherein said container is cylindrical and said base is substantially circular.

18. The container as in claim 17, wherein said bottom portion is coupled to said body section.

19. The container as in claim 18, further comprising a plurality of ball bearings disposed inside of said raceway of said top portion and said raceway of said intermediate portion and wherein said plurality of ball bearings are laterally supported in said raceway of said top portion and said raceway of said intermediate portion.

20. The container as in claim 19, wherein when said container is rotated on its side, said base forms a rotatable wheel allowing said container to be rolled and wherein said ball bearing is braced laterally by said raceway of said top portion and said raceway of said intermediate portion.

* * * * *